US012791535B2

(12) United States Patent
Milburn et al.

(10) Patent No.: US 12,791,535 B2
(45) Date of Patent: *Nov. 10, 2026

(54) SMALL MOLECULE BIOCHEMICAL PROFILING OF INDIVIDUAL SUBJECTS FOR DISEASE DIAGNOSIS AND HEALTH ASSESSMENT

(71) Applicant: Metabolon, Inc., Morrisville, NC (US)

(72) Inventors: Michael V. Milburn, Apex, NC (US); John A. Ryals, Chapel Hill, NC (US); Lining Guo, Chapel Hill, NC (US); Andrea Eckhart, Durham, NC (US); Jacob Wulff, Morrisville, NC (US); Adam D. Kennedy, Durham, NC (US); Thomas J. Jönsson, Durham, NC (US); Ryan Douglas Michalek, Durham, NC (US); Bryan Wittmann, Rougemont, NC (US); Matthew Mitchell, Durham, NC (US)

(73) Assignee: Metabolon, Inc., Morrisville, NC (US)

( * ) Notice: Subject to any disclaimer, the term of this patent is extended or adjusted under 35 U.S.C. 154(b) by 1593 days.

This patent is subject to a terminal disclaimer.

(21) Appl. No.: 16/286,259

(22) Filed: Feb. 26, 2019

(65) Prior Publication Data

US 2020/0025729 A1 Jan. 23, 2020

Related U.S. Application Data

(63) Continuation of application No. 15/288,917, filed on Oct. 7, 2016, now Pat. No. 10,267,777, which is a continuation of application No. PCT/US2015/024907, filed on Apr. 8, 2015.

(60) Provisional application No. 62/118,338, filed on Feb. 19, 2015, provisional application No. 62/037,422, filed on Aug. 14, 2014, provisional application No. 61/976,886, filed on Apr. 8, 2014.

(51) Int. Cl.

| | |
|---|---|
| ***G01N 30/88*** | (2006.01) |
| ***G01N 30/72*** | (2006.01) |
| ***G01N 33/487*** | (2006.01) |
| ***G01N 33/50*** | (2006.01) |
| ***G16B 40/00*** | (2019.01) |
| ***G16B 40/10*** | (2019.01) |
| ***G16B 45/00*** | (2019.01) |
| ***H01J 49/00*** | (2006.01) |

(52) U.S. Cl.

CPC ............ *G01N 30/88* (2013.01); *G01N 30/72* (2013.01); *G01N 30/7206* (2013.01); *G01N 30/7233* (2013.01); *G01N 33/487* (2013.01); *G01N 33/50* (2013.01); *G16B 40/00* (2019.02); *G16B 40/10* (2019.02); *G16B 45/00* (2019.02); *H01J 49/0036* (2013.01); *G01N 2030/8813* (2013.01); *G01N 2800/00* (2013.01); *G01N 2800/04* (2013.01); *G01N 2800/52* (2013.01)

(58) Field of Classification Search

CPC ........ G16B 40/00; G16B 40/10; G16B 45/00; G01N 2800/00; G01N 2800/04

See application file for complete search history.

(56) References Cited

U.S. PATENT DOCUMENTS

| | | | |
|---|---|---|---|
| 4,511,659 | A | 4/1985 | Matson |
| 4,863,873 | A | 9/1989 | Matson |
| 5,104,639 | A | 4/1992 | Matson |
| 5,824,467 | A | 10/1998 | Mascarenhas |
| 6,087,090 | A | 7/2000 | Mascarenhas |
| 6,190,858 | B1 | 2/2001 | Persaud et al. |
| 6,194,217 | B1 | 2/2001 | Matson |
| 6,210,970 | B1 | 4/2001 | Matson |
| 6,258,605 | B1 | 7/2001 | Chace |

(Continued)

FOREIGN PATENT DOCUMENTS

| | | | |
|---|---|---|---|
| AU | 2015243857 | A1 | 10/2016 |
| EP | 1923806 | A1 | 5/2008 |

(Continued)

OTHER PUBLICATIONS

Koeberl et al. Evaluation of 3-methylcrotonyl-coA carbosylas deficiency detected by tandem mass spectrometry newborn screening. J Inherit Metab Dis 2003, vol. 26, pp. 25-35 (Year: 2003).*
Gika et al., Evaluation of the repeatability of ultra-performance liquid chromatography-TOF-MS for global metabolic profiling of human urine samples. J Chromatogr B Analyt Technol Biomed Life Sci. Aug. 15, 2008;871(2):299-305.
Hisu et al., Feasibility of identifying the tobacco-related global metabolome in blood by UPLC-QTOF-MS. J Proteome Res. Feb. 1, 2013;12(2):679-91.
Kirwan et al., Characterising and correcting batch variation in an automated direct infusion mass spectrometry (DIMS) metabolomics workflow. Anal Bioanal Chem. Jun. 2013;405(15):5147-57.

(Continued)

*Primary Examiner* — Janna Nicole Schultzhaus
(74) *Attorney, Agent, or Firm* — McCarter & English, LLP; Matthew R. Van Eman

(57) ABSTRACT

Methods and systems are described herein for small molecule biochemical profiling of an individual subject for diagnosis of a disease or disorder, facilitating diagnosis of a disease or disorder, and/or identifying an increased risk of developing a disease or disorder in the individual subject. Aberrant levels of small molecules present in a sample from an individual subject are identified and diagnostic information relevant to the individual subject is obtained based on the identified aberrant levels. The obtained diagnostic information includes one or more of an identification of at least one biochemical pathway associated with the identified subset of the small molecules having aberrant levels, an identification at least one disease or disorder associated with the identified subset of the small molecules having aberrant levels, and an identification of at least one recommended follow up test associated with the identified subset of the small molecules having aberrant levels.

19 Claims, 25 Drawing Sheets

(56) References Cited

U.S. PATENT DOCUMENTS

| | | | |
|---|---|---|---|
| 6,326,163 | B1 | 12/2001 | Forssmann et al. |
| 6,376,210 | B1 | 4/2002 | Yuan |
| 6,558,955 | B1 | 5/2003 | Kristal et al. |
| 6,677,160 | B1 | 1/2004 | Stockman et al. |
| 7,005,255 | B2 | 2/2006 | Kaddurah-Daouk et al. |
| 7,329,489 | B2 | 2/2008 | Kaddurah-Daouk et al. |
| 7,550,258 | B2 | 6/2009 | Kaddurah-Daouk et al. |
| 7,550,260 | B2 | 6/2009 | Kaddurah-Daouk et al. |
| 7,553,616 | B2 | 6/2009 | Kaddurah-Daouk et al. |
| 7,567,870 | B1 | 7/2009 | Hood et al. |
| 7,635,556 | B2 | 12/2009 | Kaddurah-Daouk et al. |
| 7,682,783 | B2 | 3/2010 | Kaddurah-Daouk et al. |
| 7,682,784 | B2 | 3/2010 | Kaddurah-Daouk et al. |
| 7,910,301 | B2 | 3/2011 | Kaddurah-Daouk et al. |
| 7,947,453 | B2 | 5/2011 | Kaddurah-Daouk et al. |
| 8,849,577 | B2 | 9/2014 | Ryals et al. |
| 10,267,777 | B2 | 4/2019 | Milburn et al. |
| 2004/0018500 | A1 | 1/2004 | Glassbrook et al. |
| 2004/0121305 | A1 | 6/2004 | Wiegand et al. |
| 2004/0143461 | A1 | 7/2004 | Watkins |
| 2009/0017464 | A1 | 1/2009 | Kaddurah-Daouk et al. |
| 2009/0318392 | A1 | 12/2009 | Oresic et al. |
| 2010/0174505 | A1 | 7/2010 | Abraham-Fuchs et al. |
| 2012/0122981 | A1 | 5/2012 | Hu et al. |
| 2014/0017706 | A1 | 1/2014 | Freitas Oliveira et al. |

FOREIGN PATENT DOCUMENTS

| | | | |
|---|---|---|---|
| JP | 3129250 | B2 | 1/2001 |
| JP | 2009-535644 | A | 10/2009 |
| JP | 2010-503840 | A | 2/2010 |
| JP | 2010-216981 | A | 9/2010 |
| JP | 2011-85427 | A | 4/2011 |
| JP | 2012-520078 | A | 9/2012 |
| JP | 2012-522989 | A | 9/2012 |
| JP | 2013-525801 | A | 6/2013 |
| JP | 2014-503220 | A | 2/2014 |
| WO | WO-1986/03006 | A1 | 5/1986 |
| WO | WO-1992/13273 | A1 | 8/1992 |
| WO | WO-1996/23075 | A1 | 8/1996 |
| WO | WO-1999/44062 | A1 | 9/1999 |
| WO | WO-2004/038381 | A2 | 5/2004 |
| WO | 2008/031917 | A1 | 3/2008 |
| WO | 2010/114897 | A1 | 10/2010 |
| WO | WO-2011/055820 | A1 | 5/2011 |
| WO | 2011/139914 | A1 | 11/2011 |
| WO | WO-2012/066057 | A1 | 5/2012 |
| WO | 2014/004539 | A1 | 1/2014 |

OTHER PUBLICATIONS

Loftus et al., Metabonomic investigation of liver profiles of non-polar metabolites obtained from alcohol-dosed rats and mice using high mass accuracy MSn analysis. J Proteome Res. Feb. 4, 2011;10(2):705-13.

Simon-Manso et al., Metabolite profiling of a NIST Standard Reference Material for human plasma (SRM 1950): GC-MS, LC-MS, NMR, and clinical laboratory analyses, libraries, and web-based resources. Anal Chem. Dec. 17, 2013;85(24):11725-31.

Baran et al., MathDAMP: a package for differential analysis of metabolite profiles. BMC ioinformatics. Dec. 13, 2006;7:530, 9 pages.

Beger, A review of applications of metabolomics in cancer. Metabolites. Jul. 5, 2013;3(3):552-74.

Blekhman et al., Comparative metabolomics in primates reveals the effects of diet and gene regulatory variation on metabolic divergence. Sci Rep. Jul. 28, 2014;4:5809, 8 pages.

Brindle et al., Rapid and noninvasive diagnosis of the presence and severity of coronary heart disease using 1H-NMR-based metabonomics. Nat Med. Dec. 2002;8(12):1439-44.

Buchholz et al., Metabolomics: quantification of intracellular metabolite dynamics. Biomol Eng. Jun. 2002;19(1):5-15.

Chace et al., Use of tandem mass spectrometry for multianalyte screening of dried blood specimens from newborns. Clin Chem. Nov. 2003;49(11):1797-817.

Denkert et al., Metabolomics of human breast cancer: new approaches for tumor typing and biomarker discovery. Genome Med. Apr. 30, 2012;4(4):37, 9 pages.

Di Pierro et al., An ion-pairing high-performance liquid chromatographic method for the direct simultaneous determination of nucleotides, deoxynucleotides, nicotinic coenzymes, oxypurines, nucleosides, and bases in perchloric acid cell extracts. Anal Biochem. Nov. 1, 1995;231(2):407-12.

Dietzen et al., National academy of clinical biochemistry laboratory medicine practice guidelines: follow-up testing for metabolic disease identified by expanded newborn screening using tandem mass spectrometry; executive summary. Clin Chem. Sep. 2009;55(9):1615-26.

Dunn et al., Procedures for large-scale metabolic profiling of serum and plasma using gas chromatography and liquid chromatography coupled to mass spectrometry. Nat Protoc. Jun. 30, 2011;6(7):1060-83.

Dunn et al., The importance of experimental design and QC samples in large-scale and MS-driven untargeted metabolomic studies of humans. Bioanalysis. Sep. 2012;4(18):2249-64.

Gamache et al., Metabolomic applications of electrochemistry/mass spectrometry. J Am Soc Mass Spectrom. Dec. 2004;15(12):1717-26.

Gerber et al., Cardiovascular and metabolic profile during intervention with urapidil in humans. Hypertension. Nov.-Dec. 1985;7(6 Pt 1):963-71.

Gika et al., Current practice of liquid chromatography-mass spectrometry in metabolomics and metabonomics. J Pharm Biomed Anal. Jan. 2014;87:12-25. Epub Jul. 17, 2013.

Giovane et al., New insights into cardiovascular and lipid metabolomics. J Cell Biochem. Oct. 15, 2008;105(3):648-54.

Glassbrook et al., Metabolic profiling on the right path. Nat Biotechnol. Nov. 2000;18(11):1142-3.

Gribbestad et al., Metabolite composition in breast tumors examined by proton nuclear magnetic resonance spectroscopy. Anticancer Res. May-Jun. 1999;19(3A):1737-46.

Gucciardi et al., A rapid UPLC-MS/MS method for simultaneous separation of 48 acylcarnitines in dried blood spots and plasma useful as a second-tier test for expanded newborn screening. Anal Bioanal Chem. Aug. 2012;404(3):741-51.

Harrington et al., Differences in cerebrospinal fluid proteins between patients with schizophrenia and normal persons. Clin Chem. May 1985;31(5):722-6.

HMDB, Showing metabocard for 2-Isopropylmalic acid (HMDB0000402). Retrieved online at: http://www.hmdb.ca/metabolites/HMDB0000402. 7 pages, (2017).

HMDB, Showing metabocard for D-Xylitol (HMDB0002917). Retrieved online at: http://www.hmdb.ca/metabolites/HMDB0002917. 8 pages, (2017).

HMDB, Showing metabocard for Pyroglutamic acid (HMDB0000267). Retrieved online at: http://www.hmdb.ca/metabolites/HMDB0000267. 14 pages, (2017).

Holmes et al., Metabonomic characterization of genetic variations in toxicological and metabolic responses using probabilistic neural networks. Chem Res Toxicol. Feb. 2001;14(2):182-91.

Jung et al., Tissue metabolite profiling identifies differentiating and prognostic biomarkers for prostate carcinoma. Int J Cancer. Dec. 15, 2013;133(12):2914-24.

Kell, Metabolomics and systems biology: making sense of the soup. Curr Opin Microbiol. Jun. 2004;7(3):296-307.

Kimura et al., Automated metabolic profiling and interpretation of GC/MS data for organic acidemia screening: a personal computer-based system. Tohoku J Exp Med. Aug. 1999;188(4):317-34.

Kristal et al., Simultaneous analysis of the majority of low-molecular-weight, redox-active compounds from mitochondria. Anal Biochem. Oct. 1, 1998;263(1):18-25.

Kuhara et al., Chemical Diagnosis of Metabolic Disorders of Fatty Acids, Amino Acids, Sugars, and Nucleic Acid Bases. Proc Jap Soc Biomed Mass Spectrom. 1997;22:119-124.

(56) References Cited

OTHER PUBLICATIONS

Kuhara et al., Pilot study of gas chromatographic-mass spectrometric screening of newborn urine for inborn errors of metabolism after treatment with urease. J Chromatogr B Biomed Sci Appl. Aug. 6, 1999;731(1):141-7.
Lindon et al., Direct coupling of chromatographic separations to NMR spectroscopy. Progress in Nuclear Magnetic Resonance Spectroscopy. Jun. 1996;29:1-49.
Lindon et al., Directly coupled HPLC-NMR and its application to drug metabolism. Drug Metab Rev. Aug. 1997;29(3):705-46.
Matsumoto et al., A new chemical diagnostic method for inborn errors of metabolism by mass spectrometry-rapid, practical, and simultaneous urinary metabolites analysis. Mass Spectrom Rev. 1996;15(1):43-57.
Matsumoto et al., Abnormal fatty acid metabolism in patients in hopantenate therapy during clinical episodes. J Chromatogr. Jan. 2, 1991;562(1-2):139-45.
Miyagi et al., Plasma free amino acid profiling of five types of cancer patients and its application for early detection. PLoS One. Sep. 2011;6(9):e24143. 12 pages.
Mizuno et al., Application of a gas chromatography mass spectrometry computer system for clinical diagnosis. Biomed Mass Spectrom. Dec. 1981;8(12):593-7.
Nicholson et al., 'Metabonomics': understanding the metabolic responses of living systems to pathophysiological stimuli via multivariate statistical analysis of biological NMR spectroscopic data. Xenobiotica. Nov. 1999;29(11):1181-9.
Ning et al., Gas chromatographic-mass spectrometric metabolic profiling of patients with fatal infantile mitochondrial myopathy with de Toni-Fanconi-Debré syndrome. Acta Paediatr Jpn. Dec. 1996;38(6):661-6.
Ott et al., Correcting ligands, metabolites, and pathways. BMC Bioinformatics. 2006;7:517, 15 pages.
Pourfarzam et al., Analysis of fatty acid oxidation intermediates in cultured fibroblasts to detect mitochondrial oxidation disorders. Clin Chem. Dec. 1994;40(12):2267-75.
Rashed et al., Screening blood spots for inborn errors of metabolism by electrospray tandem mass spectrometry with a microplate batch process and a computer algorithm for automated flagging of abnormal profiles. Clin Chem. Jul. 1997;43(7):1129-41.
Sangster et al., A pragmatic and readily implemented quality control strategy for HPLC-MS and GC-MS-based metabonomic analysis. Analyst. Oct. 2006;131(10):1075-8.
Schmidt, Metabolomics: What's Happening Downstream of DNA. Environ Health Perspect. May 2004;112(7):A410-A415.
Shah et al., Metabolomic profiling for the identification of novel biomarkers and mechanisms related to common cardiovascular diseases: form and function. Circulation. Aug. 28, 2012;126(9):1110-20.
Sheikh et al., Small molecule metabolite extraction strategy for improving LC/MS detection of cancer cell metabolome. J Biomol Tech. Apr. 2011;22(1):1-4.
Trethewey et al., Metabolic profiling: a Rosetta Stone for genomics? Curr Opin Plant Biol. Apr. 1999;2(2):83-5.
Vuckovic, Current trends and challenges in sample preparation for global metabolomics using liquid chromatography-mass spectrometry. Anal Bioanal Chem. Jun. 2012;403(6):1523-48.
Want et al., Global metabolic profiling procedures for urine using UPLC-MS. Nat Protoc. Jun. 2010;5(6):1005-18.
Zhang et al., Esophageal cancer metabolite biomarkers detected by LC-MS and NMR methods. PLoS One. Jan. 2012;7(1):e30181. 10 pages.
Zou et al., A comprehensive workflow of mass spectrometry-based untargeted metabolomics in cancer metabolic biomarker discovery using human plasma and urine. Metabolites. Sep. 11, 2013;3(3):787-819.
International Search Report and Written Opinion for Application No. PCT/US2015/024907, dated Jun. 25, 2015, 10 pages.
Notification of a Third-Party Submission of Information for Japanese Application No. 2016-561615 from the Japanese Patent Office, dated Feb. 25, 2019, and Third-Party Submission with English translation of the Notification. 35 pages.
Baumgartner et al., The molecular basis of human 3-methylcrotonyl-CoA carboxylase deficiency. J Clin Invest. Feb. 2001;107(4):495-504.
Grunert et al., 3-methylcrotonyl-CoA carboxylase deficiency: clinical, biochemical, enzymatic and molecular studies in 88 individuals. Orphanet J Rare Dis. May 29, 2012;7:31, 24 pages.

* cited by examiner

SMALL MOLECULE BIOCHEMICAL PROFILING OF INDIVIDUAL SUBJECTS FOR DISEASE DIAGNOSIS AND HEALTH ASSESSMENT

RELATED APPLICATIONS

This application is a continuation of U.S. application Ser. No. 15/288,917, filed on Oct. 7, 2016, which is a continuation under 35 U.S.C. § 111(a) of International Application No. PCT/US2015/024907, filed on Apr. 8, 2015, which claims priority to U.S. Provisional Application No. 61/976,886, filed on Apr. 8, 2014, U.S. Provisional Application No. 62/037,422, filed on Aug. 14, 2014, and U.S. Provisional Application No. 62/118,338, filed on Feb. 19, 2015, the contents of all of which are incorporated by reference herein in their entirety.

BACKGROUND

Metabolomics is a rapidly evolving field that aims to measure all small molecules (metabolites) in biological samples. Metabolites represent an intermediate biological process that bridges gene function, environmental impact, and health/disease endpoints (Suhre, K. & Gieger, C. Genetic variation in metabolic phenotypes: study designs and applications. *Nat Rev Genet* 13, 759-769 (2012)). Metabolic phenotypes in conjugation with genomics can generate novel insights into gene function, disease pathology, and biomarkers for disease diagnosis and prognosis (Suhre, K. et al. Human metabolic individuality in biomedical and pharmaceutical research. *Nature* 477, 54-60 (2011); Milburn, M. V. & Lawton, K. A. Application of metabolomics to diagnosis of insulin resistance. *Annu Rev Med* 64, 291-305 (2013)).

Since the early part of the century metabolomics has found its place in scientific research and discovery. The approach has been widely and successfully used to identify biomarkers for various indications. However, metabolomics has not been widely used for diagnosing disease in an individual patient.

Currently, clinical diagnostic tests measure at most 100 biochemical compounds from a single class of compound (e.g., urine organic acids) and typically only a single biochemical, which necessitates performing many diagnostic tests. The tests are typically run in sequence, and require a significant amount of sample (e.g., at least 0.5 mL per test), and in some cases, may require invasive methods to obtain said sample (e.g., tissue biopsy).

SUMMARY

Some embodiments described herein include systems, methods and apparatuses that employ metabolic profiling in a clinical setting of symptomatic individuals with unknown (or, as a control, known diseases) and of asymptomatic individuals. In some embodiments, the metabolomic profiling of a symptomatic individual aids in the diagnosis of the disease or disorder responsible for the symptoms observed in these individuals. In some embodiments, metabolomic profiling of a symptomatic individual determines the severity of the individual's disease. In some embodiments, the metabolomic profiling of an asymptomatic individual can uncover health risks enabling therapeutic intervention prior to symptom and disease onset or at an early stage of disease. In the examples described herein, a biological sample from an individual was surveyed for the changes (increases or decrease, presence or absence) of biochemicals and the associated biochemical pathways and detected changes in endogenous, dietary, microbial, xenobiotic small molecules (i.e., metabolites, biochemicals, chemicals, compounds) that indicted perturbations in biochemical sub-pathways and pathways that are associated with diseases and disorders and identified individuals who had or were at risk of having several diseases or disorders for each individual in a population of individuals. In the examples, for each individual in a population of individuals, a single biological sample from the individual was simultaneously surveyed for the presence of, absence of, or aberrant levels of endogenous, dietary, microbial, and xenobiotic small molecules. The simultaneous survey of the biological sample included automatically generating a biochemical profile of the biological sample and then automatically statistically analyzing the biochemical profile data to identify small molecules that are statistical outliers. The examples demonstrated that the generated biochemical profile of a sample from a symptomatic individual and automated statistical analysis of the generated biochemical profile uncovered perturbed or aberrant biochemical pathways and/or aberrant levels of small molecules that aid in the diagnosis of the symptomatic individual. In some embodiments, a visualization of the results of the automated statistical analysis of the generated biochemical profile may be provided to aid in identifying perturbed or aberrant biochemical pathways and/or aberrant levels of small molecule. In some embodiments, a list of one or more possible diagnoses associated with the identified perturbed or aberrant biochemical pathways and/or aberrant levels of small molecules is displayed. In some embodiments, a list of additional diagnostic tests and procedures associated with the identified perturbed or aberrant biochemical pathways and/or aberrant levels of small molecules is displayed. In some embodiments, systems, methods and apparatuses of the instant invention expands the ability to diagnose disease and improve clinical assessment of the health of an individual.

In one embodiment, methods are provided for aiding in the diagnosis of symptomatic individuals.

In an embodiment, said symptomatic individuals are newborns.

In an embodiment, methods are provided to identify at risk individuals in a "healthy" clinical cohort, (i.e., asymptomatic individuals).

In an embodiment, the asymptomatic individuals are newborns.

In one embodiment, the disease to be diagnosed is a rare disease.

An embodiment includes a method for facilitating diagnosis of a disease or disorder in an individual subject. The method includes obtaining a sample from the individual subject and generating a small molecule profile of the sample including information regarding presence or absence of and a level of each of a plurality of small molecules in the sample. The method also includes comparing the small molecule profile of the sample to a reference small molecule profile that includes a standard range for a level of each of the plurality of small molecules and identifying a subset of the small molecules in the sample each having an aberrant level. An aberrant level of a small molecule in the sample being a level falling outside the standard range for the small molecule. The comparison and identification are conducted using an analysis facility executing on a processor of a computing device. The method further includes obtaining diagnostic information from a database based on the aberrant levels of the identified subset of the small molecules.

The database holds information associating an aberrant level of one or more small molecules of the plurality of small molecules with information regarding a disease or disorder for each of a plurality of diseases and disorders. The method also includes storing the obtained diagnostic information. The stored diagnostic information including one or more of: an identification of at least one biochemical pathway associated with the identified subset of the small molecules having aberrant levels, an identification at least one disease or disorder associated with the identified subset of the small molecules having aberrant levels, and an identification of at least one recommended follow up test associated with the identified subset of the small molecules having aberrant levels.

In one embodiment, the disease or disorder to be diagnosed is any of a plurality of diseases and disorders. Said diseases and disorders include but are not limited to human genetic disorders of metabolism including urea cycle disorders, organic acidemias, disorders of amino acid metabolism and transport, fatty acid oxidation disorders, disorders of carbohydrate metabolism, nucleoside synthesis and recycling defects, disorders of metal transport, neurotransmitter & small peptide disorders, disorders of mitochondrial energy metabolism, lysosomal storage diseases, disorders of protein glycosylation, pentose phosphate metabolism disorders, disorders of glucose transport, disorders of ketogenesis & ketolysis, disorders of vitamin/cofactor synthesis and recycling, disorders of lipid and bile acid metabolism, and peroxisomal disorders.

Another embodiment includes a method of screening an individual subject for a plurality of diseases or disorders. The method includes obtaining a sample from the individual subject and generating a small molecule profile of the sample including information regarding presence or absence of and a level of each of a plurality of small molecules in the sample. The method further includes comparing the small molecule profile of the sample to a reference small molecule profile that includes a standard range for a level of each of the plurality of small molecules to determine if any of the plurality of small molecules have aberrant levels in the sample. An aberrant level of a small molecule in the sample being a level falling outside the standard range for the small molecule. For a small molecule profile having an aberrant level of any of the plurality of small molecules in the sample, a subset of the small molecules each having an aberrant level in the sample is identified. The comparison and identification is conducted using an analysis facility executing on a processor of a computing device. For a small molecule profile having an aberrant level of any of the plurality of small molecules in the sample, diagnostic information is obtained from a database based on the aberrant levels of the identified subset of the small molecules. The database includes information associating an aberrant level of one or more small molecules of the plurality of small molecules with information regarding a disease or disorder for each of a plurality of diseases and disorders. For a small molecule profile having an aberrant level of any of the plurality of small molecules in the sample, the obtained diagnostic information is stored. The stored diagnostic information includes one or more of: an identification of at least one biochemical pathway associated with the identified subset of the small molecules having aberrant levels, an identification of at least one disease or disorder associated with the identified subset of the small molecules having aberrant levels, and an identification of at least one recommended follow up test associated with the identified subset of the small molecules having aberrant levels. For a small molecule profile not having an aberrant level of any of the plurality of small molecules in the sample, information indicating that no aberrant levels were detected is stored.

An embodiment includes a method for screening an individual subject for an increased risk of developing a disease or disorder for a plurality of diseases or disorders. The method includes obtaining a sample from the individual subject and generating a small molecule profile of the sample including information regarding presence or absence of and a level of each of a plurality of small molecules in the sample. The method also includes comparing the small molecule profile of the sample to a reference small molecule profile that includes a standard range for a level of each of the plurality of small molecules to determine if any of the plurality of small molecules have aberrant levels in the sample. An aberrant level of a small molecule in the sample is a level falling outside the standard range for the small molecule. For a small molecule profile having an aberrant level of any of the plurality of small molecules in the sample, a subset of the small molecules each having an aberrant level in the sample is identified, the comparison and identification being conducted using an analysis facility executing on a processor of a computing device. For a small molecule profile having an aberrant level of any of the plurality of small molecules in the sample, diagnostic information is obtained from a database based on the aberrant levels of the identified subset of the small molecules. The database includes information associating an aberrant level of one or more small molecules of the plurality of small molecules with information regarding a disease or disorder for each of a plurality of diseases and disorders. For a small molecule profile having an aberrant level of any of the plurality of small molecules in the sample, the obtained diagnostic information is stored. The stored diagnostic information includes an identification of an increased risk for developing a disease or disorder associated with the identified subset of the small molecules having aberrant levels. For a small molecule profile not having an aberrant level of any of the plurality of small molecules in the sample, information indicating that no aberrant levels were detected is stored.

BRIEF DESCRIPTION OF THE DRAWINGS

In FIG. 9, 1-pentadecanoylglycerophosphocholin" means 1-pentadecanoylglycerophosphocholine (15:0), "15-methylpalmitate-isobar-with-2-meth" means 15-methylpalmitate (isobar with 2-methylpalmitate), and "3-carboxy-4-methyl-5-propyl-2-furanpro" means 3-carboxy-4-methyl-5-propyl-2-furanpropanoate (CMPF).

In FIG. 10, "Drug" refers to a xenobiotic drug metabolite, "Fatty.Acid.Metabolism.Also.BCAA.Meta . . . " means Fatty Acid Metabolism (also BCAA Metabolism), "Pyrimidine.Metabolism.Thymine.Conta . . . " means Pyrimidine Metabolism (Thymine containing).

In FIG. 11, "1-eicosapentaenoylglycerophosphoeth . . . " means 1-eicosapentaenoylglycerophosphoethanolamine and "2-arachidonoylglycerophosphoethanol . . . " means 2-arachidonoylglycerophosphoethanolamine.

In FIG. 12, "5-acetylamino-6-formylamino-3-methyl." means 5-acetylamino-6-formylamino-3-methyluracil, and "5alpha-androstan-3alpha,17beta-diol . . . " means 5alpha-androstan-3alpha,17beta-diol disulfate.

In FIG. 14, "3-carboxy-4-methyl-5-propyl-2-furanpro . . . " means 3-carboxy-4-methyl-5-propyl-2-furanpropanoate (CMPF).

FIG. 16A is a plot of altered trimethylamine N-oxide levels measured in patients undergoing treatment with supplemental carnitine divided or "binned" by IEM disorder of the patient. As shown by the plot supplemental carnitine increases trimethylamine N-oxide levels. FIG. 16B is a plot of altered phenylactylglutamine levels in patients undergoing ammonia scavenging phenylbutyrate therapy binned by IEM disorder of the patient. As shown by the plot, ammonia scavenging phenylbutyrate therapy causes an increase in phenylacetylglutamine. FIG. 16C is a plot of altered creatine levels measured in patients treated with supplemental creatine binned by IEM disorder of the patient. As shown by the plot, the creatine is directly measurable in plasma. "Other" refers to the remaining patients with an IEM not belonging to one of the binned classes shown.

DETAILED DESCRIPTION

Figure 1:
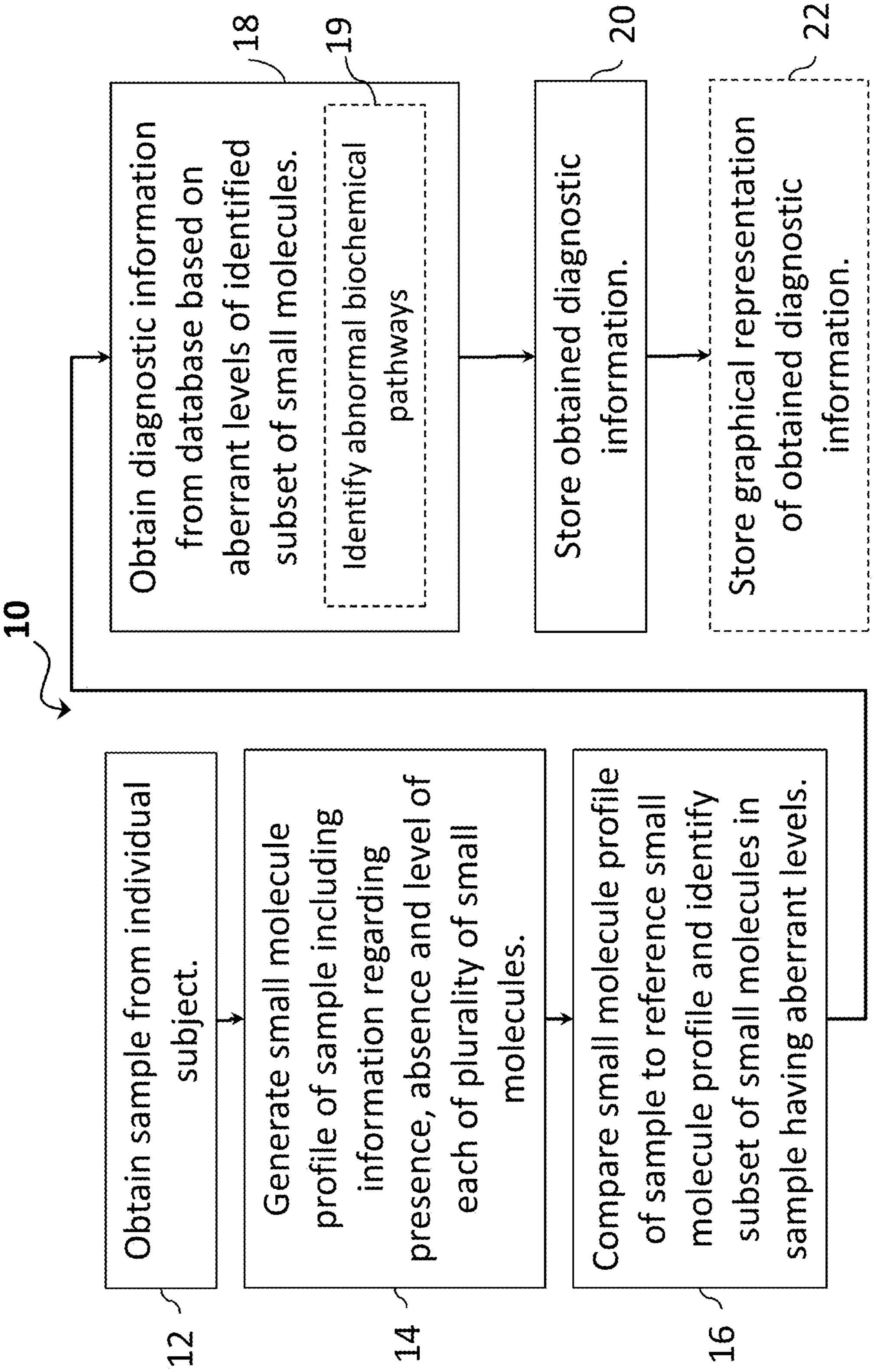
FIG. 1 is a block diagram of a method for facilitating diagnosis of a disease or disorder in an individual subject, in accordance with an embodiment.

It is desirable to have a single test that can measure hundreds of biochemicals in multiple biochemical classes and biochemical pathways using a small amount (e.g., 100 μl or less) of sample to diagnose or aid in the diagnosis of disease of an individual subject. Such a test may also be used to identify disease earlier than current clinical diagnostic tests, allowing for earlier treatment and/or intervention. Such a test may be useful in healthy or asymptomatic individuals to detect early metabolic indications of disease or as a health assessment. Such a test may be useful in symptomatic individuals for whom a diagnosis has not been made. Such a test may be particularly useful in newborns, where obtaining multiple samples of large volumes may be difficult.

In order to control escalating health care costs and maintain life quality, there are increased emphases to incorporate more advanced and informative technologies in clinical practices to guide disease prevention and early diagnosis. Some embodiments of the technology described herein employ an efficient and effective approach for obtaining a comprehensive metabolic phenotype of an individual, which can be useful to evaluate the health status of the individual and aid in the diagnosis of disease, based on a small sample size.

Definitions

"Sample" or "biological sample" or "specimen" means biological material isolated from a subject. The biological sample may contain any biological material suitable for detecting the desired biomarkers, and may comprise cellular and/or non-cellular material from the subject. The sample can be isolated from any suitable biological tissue or fluid such as, for example, blood, blood plasma, serum, skin, epidermal tissue, adipose tissue, aortic tissue, liver tissue, urine, cerebral spinal fluid, crevicular fluid, or cell samples. The sample can be, for example, a dried blood spot where blood samples are blotted and dried on filter paper.

"Subject" means any animal, but is preferably a mammal, such as, for example, a human, monkey, non-human primate, rat, mouse, cow, dog, cat, pig, horse, or rabbit. Said subject may be symptomatic (i.e., having one or more characteristics that suggest the presence of or predisposition to a disease, condition or disorder, including a genetic indication of same) or may be asymptomatic (i.e., lacking said characteristics). Said subject may be a newborn. Said subject may be an infant. Said subject may be a child or a juvenile. Said subject may be an adult.

"Human infant" means the young human child in the earliest period of life, especially before the child can walk, typically extending from the time of birth to one year of age.

"Human newborn infant" means the period beginning at birth of the human and lasting through the $28^{th}$ day following birth.

The "level" of one or more biomarkers means the absolute or relative amount or concentration of the biomarker in the sample.

"Small molecule", "metabolite", "biochemical" means organic and inorganic molecules which are present in a cell. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000). The small molecules of the cell are generally found free in solution in the cytoplasm or in other organelles, such as the mitochondria, where they form a pool of intermediates, which can be metabolized further or used to generate large molecules, called macromolecules. The term "small molecules" includes signaling molecules and intermediates in the chemical reactions that transform energy derived from food into usable forms. Non-limiting examples of small molecules include sugars, fatty acids, amino acids, nucleotides, intermediates formed during cellular processes, and other small molecules found within the cell.

"Endogenous small molecule" means a small molecule originating from or produced within the human subject.

"Dietary small molecule" means a small molecule originating from the diet that is typically plant derived and not produced endogenously by humans; for example, essential amino acids and essential fatty acids.

"Xenobiotic small molecule" or "Xenobiotic" means a small molecule found within an organism that is not normally naturally produced by or expected to be present within that organism. A xenobiotic small molecule as used herein refers to chemical agents such as drugs (e.g., antibiotics), toxins, toxicants or pollutants (e.g., dioxins, polychlorinated biphenyls)

"Microbial small molecule" means a small molecule originating from a microbe and is not produced by humans (e.g., 3-indoxyl sulfate).

"Aberrant" or "aberrant metabolite" or "aberrant level" refers to a metabolite or level of said metabolite that is either above or below a defined standard range. For example, for some metabolites, a log transformed level falling outside of at least 1.5*IQR (Inter Quartile Range) is aberrant. In another example, for some metabolites a log transformed level falling outside of at least 3.0*IQR is identified as aberrant. In some examples, data was analyzed assuming a log transformed level falling outside of at least 1.5*IQR is aberrant, and in some examples, data was analyzed assuming a log transformed level falling outside of at least 3.0*IQR is aberrant. In another example, for some metabolites, a metabolite having a log transformed level with a Z-score of >1 or <−1 is aberrant. In some embodiments, for some metabolites, a metabolite having a log transformed level with a Z-score of >1.5 or <−1.5 is aberrant. In some embodiments, for some metabolites, a metabolite having a log transformed level with a Z-score of >2.0 or <−2.0 is aberrant. In some embodiments, different ranges of Z-scores are used for different metabolites. In some embodiments, the defined standard range may be based on an IQR of a level, instead of an IQR of a log transformed level. In some embodiments, the defined standard range may be based on a Z-score of a level, instead of on a Z-score of a log transformed level. An aberrant metabolite may also include rare metabolites as defined below and/or missing metabolites. Any statistical method may be used to determine aberrant metabolites.

"Outlier" or "outlier value" refers to any biochemical that has a level either above or below the defined standard range. Any statistical method may be used to determine an outlier value. By way of non-limiting example the following tests may be used to identify outliers: t-tests, Z-scores, modified Z-scores, Grubbs' Test, Tietjen-Moore Test, Generalized Extreme Studentized Deviate (ESD), which can be performed on transformed data (e.g., log transformation) or untransformed data.

"Pathway" is a term commonly used to define a series of steps or reactions that are linked to one another. For example, a biochemical pathway whereby the product of one reaction is a substrate for a subsequent reaction. Biochemical reactions are not necessarily linear. Rather, the term biochemical pathway is understood to include networks of inter-related biochemical reactions involved in metabolism, including biosynthetic and catabolic reactions. "Pathway" without a modifier can refer to a "super-pathway" and/or to a "subpathway." "Super-pathway" refers to broad categories of metabolism. "Subpathway" refers to any subset of a broader pathway. For example, glutamate metabolism is a subpathway of the amino acid metabolism biochemical super-pathway. An "abnormal pathway" means a pathway to which one or more aberrant biochemicals have been mapped, or that the biochemical distance for that pathway for the individual was high as compared with an expected biochemical distance for that pathway in a population (e.g., the biochemical distance for the pathway for the individual is among the highest 10% as compared with a population of samples from reference subjects for a given pathway).

"Rare disease" or "orphan disease" is any disease that affects a small percentage of the population, typically fewer than 200,000 Americans at any given time according to the National Institutes of Health.

"Test sample" means the sample from the individual subject to be analyzed.

"Reference sample" means a sample used for determining a standard range for a level of small molecules. "Reference sample" may refer to an individual sample from an individual reference subject (e.g., a normal (healthy) reference subject or a disease reference subject), who may be selected to closely resemble the test subject by age and gender. "Reference sample" may also refer to a sample including pooled aliquots from reference samples for individual reference subjects.

"Anchor sample" refers to a sample that is run in multiple analyses and may be used to compare the results from any analysis in which the same anchor sample is run. In some cases, the reference sample may also serve as an anchor sample.

"Matrix sample" refers to a pooled sample designed to most closely resemble the general population by age and gender; it is prepared by taking aliquots from appropriate age and gender matched samples and combining them into a single pool of samples. These Matrix samples are injected throughout the platform run and serve as technical replicates, allowing variability in the quantitation of all consistently detected biochemicals to be determined and overall process variability and platform performance to be monitored.

"Rare metabolite" or "rare biochemical" refers to a biochemical that is present in the test sample but is rarely observed in the reference sample. The "rare" metabolite is not present or is below the limits of detection in the reference sample or is present or detected in only a small fraction of the reference samples (e.g., detected in less than 15% of the reference samples, or detected in less than 10% of the reference samples).

"Missing metabolite" or "missing biochemical" refers to a biochemical that is not detected in the profile of the test sample but is detected in the profile of the reference sample or is detected in more than 90% of the reference samples.

"Human Genetic Disorders of Metabolism" refers to inborn errors of metabolism including urea cycle disorders (e.g., argininosuccinic acid lyase deficiency, argininemia, citrullinemia, guanidinoacetate methyl transferase deficiency, ornithine transcarbamylase deficiency, hyperornithinemia-homocitrullinemia-hyperammonemia, citrin deficiency), organic acidemias (e.g., glutaric aciduria, methylmalonic academia, isovaleric academia, propionic academia), disorders of amino acid metabolism and transport (e.g., HMG Co Lyase Deficiency, maple syrup urine disease, PKU, cobalamin deficiency, CblA, CblC, 3-methylcrotonyl CoA carboxylase deficiency, homocystinuria, molybdenum cofactor, tyrosinemia, aromatic amino acid decarboxylase deficiency, 3-methylglutaconic aciduria, urocanase deficiency, 3-hydroxyisobutyryl-CoA hydrolase deficiency), fatty acid oxidation disorders (e.g., CPTII, MCAD deficiency, very long chain acyl CoA dehydrogenase deficiency, SCAD deficiency, LCHAD deficiency, carnitine transport defect, carnitine-acylcarnitine translocase deficiency, trimethyllysine hydroxylase epsilon deficiency, primary carnitine deficiency, γ-butyrobetaine hydroxylase deficiency), disorders of carbohydrate metabolism (e.g., galactosemia), nucleoside synthesis and recycling defects (e.g., dihydropyrimidine dehydrogenase deficiency, xanthinuria, thymidine phosphorylase deficiency, adenosine deaminase deficiency, succinyladenosine lyase deficiency) disorders of metal transport (e.g., atransferrinemia, aceruloplasminemia), disorders linked to central carbon metabolism (e.g., pyruvate dehydrogenase deficiency, citrate transporter deficiency, GLUT1 deficiency, hyperoxaluria), disorders linked to GABA metabolism (e.g., succinic semialdehyde dehydrogenase deficiency, 4-aminobutyrate aminotransferase deficiency), disorders of mitochondrial energy metabolism (e.g., cytochrome c oxidase deficiency), lysosomal storage diseases (e.g., cystinosis), disorders of protein glycosylation (e.g., congenital disorder of glycosylation), pentose phosphate metabolism disorders (e.g., ribose-5-phosphate isomerase deficiency, transaldolase deficiency), disorders of glucose transport (e.g., GLUT1 deficiency syndrome), disorders of ketogenesis & ketolysis (e.g., mitochondrial 3-hydroxy-3-methylglutaryl-CoA synthase deficiency, succinyl-CoA 3-oxoacid CoA transferase deficiency, mitochondrial acetoacetyl-CoA thiolase deficiency), disorders of vitamin/cofactor synthesis and recycling (e.g., biotinidase deficiency, holocarboxylase synthetase deficiency), disorders of lipid and bile acid metabolism (e.g., cholesterol 7α-hydroxylase, sterol 27-hydroxylase), peroxisomal disorders (e.g., Smith-Lemli-Opitz syndrome, Zellweger syndrome), and sarcosinemia.

Improvements Over Art and/or Current Clinical Practices

The global nature and breadth of analysis obtained from a single, small sample to simultaneously survey 7000+ compounds represents a major advance and improvement over current clinical practice. In the methods described in the Examples, more than 700 named metabolites were included in a report generated from analysis of an individual test sample for an individual subject. The interrogation and measurement of these metabolites allow for the simultaneous survey of metabolites across at least eight biochemical super-pathways and 41 biochemical subpathways.

The small amount of sample required to obtain the wealth of biochemical information is a major improvement over current clinical practice. The amount of sample typically used in this method is less than 100 uL of a bodily fluid (e.g., blood, plasma, serum, urine, cerebral spinal fluid, saliva, crevicular fluid, etc.). In some embodiments, the method represents savings in terms of time and cost by enabling the use of a small, non-invasive biological sample to simultaneously assess many biochemicals, subpathways and super-pathways. In some embodiments, the ability to analyze biochemicals in the context of super-pathways and subpathways offers an advantage over the current clinical tests. One output of the method is a list of recommended clinical diagnostic tests to perform, in accordance with some embodiments. Currently clinical diagnostic tests measure at most 100 biochemical compounds from a single class of compound (e.g., urine organic acids) and typically only a single biochemical, which limits the diagnosis to diseases or disorders affecting that biochemical or class and necessitates performing many diagnostic tests. The tests are typically run in sequence thus, it may take days to weeks to obtain test results, thereby delaying diagnosis. Further, the tests require a significantly larger amount of sample (0.5 mL), and, in some cases, may require invasive methods to obtain said sample (e.g., tissue biopsy). Since the current clinical diagnostic tests typically only report on a single biochemical or single class of compound, the diagnosis is necessarily limited to the diseases or disorders where that single biochemical or biochemical(s) from the single class of compound are altered. Some embodiments of the present method would aid in diagnosis by simultaneously surveying a single, small volume, non-invasive or minimally invasive biological sample for thousands of small molecules from multiple biochemical classes and biochemical pathways and automatically providing a 'short list' of the number of necessary diagnostic tests for follow-up. In some embodiments, the methods described herein represent an improvement over current clinical practice by reducing the number of tests required to determine a diagnosis. In current clinical practice, multiple different tests including targeted panel assays for amino acids, acylcarnitines, organic acids, purines, pyrimidines, acylglycines, bile acids, orotic acid, and carnitine biosynthesis intermediates would need to be performed to achieve the same diagnostic utility as the methods described herein. Even within a single disease or disorder, such as, for example, cobalamin synthesis disorders or propionic acidemia, multiple different tests are necessary to differentiate these disorders one from another, and to determine the therapeutic regimen. In some embodiments, the methods described herein represent an improvement over current clinical practice by analyzing additional metabolites that are not currently accessible using current diagnostic panels. By one estimate, over 400 endogenous human analytes that were positively identified in the examples described herein could not be detected in a clinical biochemical genetics laboratory, even when using all available tests including: urine organic acid analysis, plasma amino acid analysis, or any of the other myriad smaller targeted test panels. In some embodiments, surveying a single, small volume, non-invasive sample for the presence, absence or altered levels of thousands of small molecules aids in the diagnosis of tens, hundreds, thousands, or tens of thousands of diseases or disorders, which represents an improvement over current clinical practice of obtaining multiple samples, a large volume sample, or an invasive sample from a subject and performing multiple tests. Further, based on recommendations provided in some example methods described herein, several follow-up diagnostic tests could be run in parallel which would save time to diagnosis. Further, in some embodiments, the method relies on a single sample type. Current clinical diagnostic methods measure some metabolites in serum, plasma or blood (e.g., homocysteine), while other diagnostic methods measure metabolites in urine (e.g., organic acids) and others measure biochemicals in CSF (e.g., gamma-aminobutyric acid). The methods described herein include the use of reference samples. Statistical analysis of small molecule profiles of the reference samples provide the standard range for a level of each small molecule.

In some embodiments, the reference samples are designed to closely resemble the test sample by age and gender. For example, an ethylenediaminetetraacetic acid-plasma (EDTA-plasma) test sample from a symptomatic newborn female, is compared to a reference sample generated from a pool of EDTA-plasma samples from newborn females.

In some embodiments, the reference samples may be run simultaneously with test samples. In these embodiments, one or more of the reference samples may also serve as an anchor sample. In some embodiments, the test sample may also serve as one of the reference samples. In some embodiments, the reference samples are analyzed in separate runs from the test sample. In these embodiments, a separate anchor sample analyzed in the same run with the test sample may be used to relate the data from the run with the test sample to the data from the run(s) with the reference samples.

In some embodiments, the methods described herein also include the use of anchor samples that are run simultaneously (i.e., in a same run) with test samples. Experimental techniques employed in some embodiments (e.g., LC/MS, GC/MS) provide relative, not absolute, values for levels of small molecules in a sample, which vary from run to run. An anchor sample that is analyzed in a same experimental run can be used to control for the run to run variability. For example, after a reference sample is run one time, an aliquot of the reference sample may be run subsequent times as an anchor sample with new samples enabling correction for run to run variability so that the results of subsequent analyses may be compared to previous analyses. As another example, a test sample(s) is analyzed once and results are reported. Then, the same test sample(s) is analyzed a second time as an anchor sample along with new test samples enabling correction for the run to run variability so that the results of the second analysis can be compared to the results of the first analysis.

In embodiments in which the reference samples are run separately from the test samples, one or more additional anchor samples are used to correct for the run to run variability when comparing the test samples to the reference small molecule profile generated from statistical analysis of the reference samples. For example, in some embodiments, one or more anchor samples are created from pooled aliquots of the references samples from the reference subjects and run simultaneously with test samples. The one or more anchor samples, which are created from the pooled reference samples, enable correction of the run to run variability for comparison of test sample data with the prior statistical analysis of the reference samples from the plurality of reference subjects. Results of the statistical analysis of the reference samples may be stored in a database for comparison. In some embodiments, the reference samples may be run before the test samples. In some embodiments, the reference samples may be run after the test samples.

In some embodiments, data from the reference samples from a plurality of reference subjects is statistically analyzed to determine a reference small molecule profile including a standard range for a level of each small molecule. In some embodiments, one or more anchor samples are created from pooled aliquots of the reference samples and run simultaneously with test samples. The one or more anchor samples, which are created from the pooled reference samples, enable correction of the run to run variability for comparison of test sample data with the prior statistical analysis of the samples from the plurality of reference subjects.

Comparison of the test sample with the reference small molecule profile, after correction for run to run variability, as needed, identifies the aberrant or outlier small molecules. In some embodiments, for each individual, the aberrant or "outlier" metabolites, super-pathways and subpathways are automatically identified by automated statistical analyses that are based on Euclidian distances and automatically reported, and may be visualized automatically. In some embodiments, the outlier metabolites are defined as those metabolites with a log transformed level of at least 1.5*IQR. The outlier metabolites may also be defined as those metabolites with a selected log transformed Z-score range (e.g., a Z-score of >1 or <−1, a Z-score of >1.5 or <−1.5, or a Z-score of >2.0 or <−2.0). In some embodiments, a Z-score range used to define the outlier metabolite levels may be different for some metabolites than for others (e.g., a Z-score of >1 or <−1 may be used for some metabolites and a Z-score of >1.5 or <−1.5 may be used for others). In some embodiments, a report is automatically generated, the report listing all rarely observed metabolites as well as common metabolites missing from the profile. In some embodiments, the metabolites are automatically sorted into subpathways and super-pathways. In some embodiments, an automated visualization of results showing super-pathways, subpathways and individual small molecules is generated. In some embodiments, abnormal biochemical pathways (i.e., abnormal super-pathways and/or abnormal subpathways) are identified. Thus, in some embodiments, the method analyzes and reports the information obtained from the entire biochemical profile and identifies aberrant metabolites, biochemical super-pathways and subpathways (e.g., normal pathways and/or abnormal pathways) to determine diagnosis or aid in the diagnosis of disease or disorders, and assesses the health of an individual without relying on specific diagnostic tests comprised of a single biomarker or sets of biomarkers (e.g., panels of biomarkers) for specific diseases.

Further, in an embodiment including the generation of reports, the reports are provided for an individual rather than a group of individuals. This is in contrast with current biochemical profiling or metabolomics-based methods of disease diagnosis. Typically in a metabolomics/biochemical profiling experiment, groups of subjects are classified with individuals classified only based on membership in a group and not on an individual basis. This is especially true for those individuals whose biochemical profile or measurements are regarded as 'outliers'; these outliers are usually ignored, removed from the dataset, or regarded as errors in the classification in a typical metabolomics biochemical profiling experiment. In contrast, embodiments of the methods presented herein seek to identify outliers and use this information to diagnose or aid in the diagnosis of disease.

Embodiments

In one embodiment a method is provided for the diagnosis or to aid in diagnosis of a disease or disorder in a symptomatic subject by surveying a biological sample from said subject for the presence, absence or aberrant level(s) of endogenous, dietary, microbial, and xenobiotic small molecules by statistical analysis to identify outlier values for said small molecules indicating the small molecule is aberrant in said sample and listing aberrant small molecules.

In an additional embodiment, the aberrant small molecules are visually displayed. The visualization may display each pathway (e.g., super-pathway or subpathway) with indicators of each of said pathways as being normal/typical or abnormal, including indicators for rare or missing values for said pathways. Any number of pathways may be listed in the display, and any number of graphic illustrations may be used to present the results. In an embodiment, the graphic illustration displays each aberrant biochemical classified according the level of the biochemical in the sample. Any number of biochemicals may be displayed in the graphic illustration. For example, all biochemicals measured in the sample may be displayed, or only biochemicals meeting a certain statistical cutoff may be displayed. The biochemicals may be ordered in any way in the display, for example, alphabetically, by significance, by disease relatedness, by biochemical super-pathway and/or subpathway, etc.

In one embodiment, a method is provided for the diagnosis or to aid in diagnosis of a disease or disorder in symptomatic subject by surveying a biological sample from said subject for the presence, absence, or aberrant level(s) of endogenous, dietary, microbial, and xenobiotic small molecules by statistical analysis to identify outlier values for said small molecules indicating the small molecule is aberrant in said sample, visualizing and listing aberrant small molecules, mapping aberrant small molecules to pathways (e.g., biochemical super-pathways and/or subpathways) to diagnose or aid in the diagnosis of disease or disorder. The small molecules may be categorized in any manner including categorization by disease relatedness, biochemical association, chemical structure, etc. Any number of categories may be used. For example 1 or more, 2 or more, 3 or more 5 or more, 10 or more, 15 or more, 20 or more, 50 or more, 100 or more categories may be used to categorize the small molecules. Any number of sub categories may be used. For example, 1 or more, 2 or more, 3 or more 5 or more, 10 or more, 15 or more, 20 or more, 50 or more, 100 or more may be used to subcategorize the small molecules. In one embodiment, aberrant small molecules may be categorized by one or more biochemical super-pathways, the said super-pathways including: Amino Acid; Peptide; Carbohydrate; Energy; Lipid; Complex Lipids; Nucleotide; Cofactors and Vitamins; and Xenobiotics. In one embodiment, aberrant small molecules may be mapped to one or more biochemical subpathways, the said subpathways including: Glycine, Serine and Threonine Metabolism; Alanine and Aspartate Metabolism; Glutamate Metabolism; Histidine Metabolism; Lysine Metabolism; Phenylalanine and Tyrosine Metabolism; Tryptophan Metabolism; Leucine, Isoleucine and Valine Metabolism; Methionine, Cysteine, SAM and Taurine Metabolism; Urea cycle; Arginine and Proline Metabolism; Creatine Metabolism; Polyamine Metabolism; Guanidino and Acetamido Metabolism; Glutathione Metabolism; Felinine Metabolism; Gamma-glutamyl Amino Acid; Dipeptide Derivative; Dipeptide; Polypeptide; Fibrinogen Cleavage Peptide; Glycolysis, Gluconeogenesis, and Pyruvate Metabolism; Glycolysis, Gluconeogenesis, and Pyruvate Metabolism; Pentose Phosphate Pathway; Pentose Metabolism; Glycogen Metabolism; Disaccharides and Oligosaccharides; Fructose, Mannose and Galactose Metabolism; Nucleotide Sugar; Aminosugar Metabolism; Advanced Glycation End-product; TCA Cycle; Oxidative Phosphorylation; Short Chain Fatty Acid; Medium Chain Fatty Acid; Long Chain Fatty Acid; Polyunsaturated Fatty Acid (n3 and n6); Quantitative Free Fatty Acid; Fatty Acid, Branched; Fatty Acid, Dicarboxylate; Fatty Acid, Methyl Ester; Fatty Acid, Ester; Fatty Acid, Amide; Fatty Acid, Keto; Fatty Alcohol, Long Chain; Fatty Acid Synthesis; Fatty Acid Metabolism; Fatty Acid Metabolism (also BCAA Metabolism); Fatty Acid Metabolism(Acyl Glycine); Fatty Acid Metabolism(Acyl Carnitine); Carnitine Metabolism; Ketone Bodies; Neurotransmitter; Fatty Acid, Monohydroxy; Fatty Acid, Dihydroxy; Fatty Acid, Oxidized; Eicosanoid; Endocannabinoid; Inositol Metabolism; Phospholipid Metabolism; Lysolipid; Glycerolipid Metabolism; Monoacylglycerol; Diacylglycerol; Sphingolipid Metabolism; Mevalonate Metabolism; Sterol; Steroid; Primary Bile Acid Metabolism; Secondary Bile Acid Metabolism; Diacylglycerol; Triacylglycerol; Lysophosphatidylcholine; Phosphatidylcholine; Phosphatidylethanolamine; Phosphatidylserine; Sphingomyelin; Sphingolipid Metabolism; Cardiolipin; Cholesterol Ester; Phospholipids; Purine Metabolism, (Hypo)Xanthine/Inosine containing; Purine Metabolism, Adenine containing; Purine Metabolism, Guanine containing; Pyrimidine Metabolism, Orotate containing; Pyrimidine Metabolism, Uracil containing; Pyrimidine Metabolism, Cytidine containing; Pyrimidine Metabolism, Thymine containing;

Purine and Pyrimidine Metabolism; Nicotinate and Nicotinamide Metabolism; Riboflavin Metabolism; Pantothenate and CoA Metabolism; Ascorbate and Aldarate Metabolism; Tocopherol Metabolism; Biotin Metabolism; Folate Metabolism; Tetrahydrobiopterin Metabolism; Pterin Metabolism; Hemoglobin and Porphyrin Metabolism; Lipoate Metabolism; Thiamine Metabolism; Vitamin K Metabolism; Vitamin A Metabolism; Vitamin B12 Metabolism; Vitamin B6 Metabolism; Benzoate Metabolism; Xanthine Metabolism; Tobacco Metabolite; Food Component/Plant; Bacterial; Drug; Phthalate; and Chemical.

In one embodiment, a method is provided for the diagnosis or to aid in diagnosis of a disease or disorder in a symptomatic subject by surveying a biological sample from said subject for the presence, absence, or aberrant level(s) of endogenous, dietary, microbial, and xenobiotic small molecules by statistical analysis to identify outlier values for said small molecules indicating the small molecule is aberrant in said sample, listing aberrant small molecules, mapping aberrant small molecules to biochemical pathways (e.g., biochemical super-pathways and/or subpathways) and visualizing the maps and, further, providing a list of recommended follow-on clinical diagnostic tests.

In one embodiment a method is provided for the diagnosis or to aid in diagnosis of a disease or disorder in a symptomatic subject by surveying a biological sample from said subject for the presence, absence or aberrant level(s) of endogenous, dietary, microbial, and xenobiotic small molecules by statistical analysis to identify outlier values for said small molecules indicating the small molecule is aberrant in said sample, listing aberrant small molecules, mapping aberrant small molecules to pathways (e.g., biochemical super-pathways and/or subpathways) and visualizing the maps and providing a list of possible/probable diseases or disorders.

In one embodiment a method is provided for the diagnosis or aid in diagnosis of disease or disorder in symptomatic subject by surveying a biological sample from said subject for the presence, absence or aberrant level(s) of endogenous, dietary, microbial, and xenobiotic small molecules by statistical analysis to identify outlier values for said small molecules indicating the small molecule is aberrant in said sample, listing aberrant small molecules, mapping aberrant small molecules to pathways (e.g., biochemical super-pathways and/or subpathways) and visualizing the maps and, further, providing a list of possible/probable diseases or disorders and further providing a list of recommended follow-on clinical diagnostic tests.

FIG. 1 is a block diagram of a method 10 for diagnosis of, or facilitating diagnosis of, a disease or disorder in an individual subject, in accordance with some embodiments. A sample is obtained from an individual subject (step 12). A small molecule profile of the sample is generated including information regarding presence of, absence of, and a level of each of a plurality of small molecules in the sample (step 14). The small molecule profile of the sample is compared to a reference small molecule profile that includes a standard range for a level of each of a plurality of small molecules and a subset of the small molecules in the sample having an aberrant level is identified (step 16). Diagnostic information is obtained from a database based on the aberrant levels of the identified subset of the small molecules (step 18). In some embodiments, obtaining diagnostic information based on the aberrant levels of the identified subset of the small molecules includes identifying one or more abnormal biochemical pathways (step 19). The database includes information associating an aberrant level of one or more small molecules of the plurality of small molecules with information regarding a disease or disorder for each of a plurality of diseases and disorders. In some embodiments, the method includes generating a disease or disorder-specific composite score based on a weighted combination of data from one or more of the subset of small molecules identified as having aberrant levels, and obtaining diagnostic information from the database based on the aberrant levels of the identified subset of the small molecules includes obtaining diagnostic information from the database based on the generated disease or disorder-specific composite score. The obtained diagnostic information is stored (step 20). The stored diagnostic information includes one or more of an identification of at least one biochemical pathway associated with the identified subset of the small molecules having aberrant levels, an identification at least one disease or disorder associated with the identified subset of the small molecules having aberrant levels, and an identification of at least one recommended follow up test associated with the identified subset of the small molecules having aberrant levels. Thus, the stored diagnostic information facilitates diagnosis of a disease or a disorder in the individual subject. In some embodiments, the method further includes storing a graphical representation of the obtained diagnostic information (step 22). The dashed lines around the boxes for steps 19 and 22 in FIG. 1 indicate that these need not be present in all embodiments.

In some embodiments of methods described herein, the individual subject is symptomatic for one or more of the plurality of diseases and disorders. In some embodiments, method 10 is a method for diagnosis of or facilitating diagnosis of a disease or disorder in a symptomatic individual subject.

In some embodiments of methods described herein, the individual subject is asymptomatic for all of the plurality of diseases and disorders. In some embodiments, method 10 is a method for diagnosis of or facilitating diagnosis of a disease or disorder in an asymptomatic individual subject. In some embodiments of methods described herein, the individual subject is a human newborn. In some embodiments of methods described herein, the individual subject is a human infant.

In step 12, the sample obtained from an individual subject is a biological sample. As explained in the definitions section, in various embodiments, the biological sample may be any biological material isolated from a subject. The biological sample may contain any biological material suitable for detecting the desired biomarkers, may comprise cellular and/or non-cellular material from the subject, and may be isolated from any suitable biological tissue or fluid. In some embodiments, the individual subject is a human newborn and the biological sample is blood or urine. In some embodiments, the individual is a human newborn or a human infant and the biological sample is urine obtained from a diaper.

In some embodiments, the sample obtained from the individual subject has a volume of less than 500 μL, of less than 400 μL, of less than 300 μL, of less than 200 μL, of less than 100 μL, of less than 90 μL, of less than 80 μL, of less than 70 μL, of less than 60 μL, of less than 50 μL, of less than 40 μL, or of less than 30 μL. In some embodiments, the sample obtained from the individual subject has a volume in a range of 20 to 500 μL, of 20 to 400 μL, of 20 to 300 μL, of 20 to 200 μL, of 20 to 100 μL, of 20 to 90 μL, of 20 to 80 μL, of 20 to 70 μL, of 20 to 60 μL, of 20 to 50 μL, of 20 to 40 μL, or of 15 μL to 30 μL. As explained above, small biological sample sizes may be particularly beneficial when testing biological samples obtained from a newborn human.

Generating the small molecule profile of the sample (step 14) includes generating information regarding the presence, absence and a level of each of a plurality of small molecules. This may also be described as surveying the biological sample herein. A small molecule profile of the sample is generated including information regarding presence of, absence of, and a level of each of a plurality of small molecules in the sample (step 14).

In some embodiments a plurality of small molecules includes two or more of endogenous, dietary, microbial, and xenobiotic small molecules (e.g., endogenous and microbial small molecules; endogenous and xenobiotic small molecules; endogenous and dietary small molecules). In some embodiments the plurality of small molecules includes three or more of endogenous, dietary, microbial, and xenobiotic small molecules (e.g., endogenous, microbial, and dietary small molecules; endogenous, microbial, and xenobiotic small molecules). In some embodiments, the plurality of small molecules includes endogenous, dietary, microbial, and xenobiotic small molecules.

The plurality of small molecules includes small molecules from various classes or super-pathways such as Amino Acid; Peptide; Carbohydrate; Energy; Lipid; Complex Lipids; Nucleotide; Cofactors and Vitamins; and Xenobiotics. In some embodiments, the plurality of small molecules includes two or more of sugars, fatty acids, amino acids, nucleotides, and products of catabolism. In some embodiments, the plurality of small molecules includes three or more of sugars, fatty acids, amino acids, nucleotides, and products of catabolism. In some embodiments, the plurality of small molecules includes four or more of sugars, fatty acids, amino acids, nucleotides, and products of catabolism. In some embodiments, the plurality of small molecules includes sugars, fatty acids, amino acids, nucleotides, and products of catabolism.

In some embodiments, the plurality of small molecules includes more than 25 small molecules, more than 50 small molecules, more than 100 small molecules, more than 200 small molecules, more than 300 small molecules, more than 400 small molecules, more than 500 small molecules, more than 600 small molecules, more than 700 small molecules, more than 800 small molecules, more than 900 small molecules, more than 1000 small molecules, more than 1100 small molecules, more than 1200 small molecules more than 1300 small molecules, more than 1400 small molecules, more than 1500 small molecules, more than 2000 small molecules, more than 3000 small molecules, more than 4000 small molecules more than 5000 small molecules, more than 6000 small molecules, or more than 7000 small molecules.

In some embodiments, the plurality of small molecules includes 25-2500 small molecules, 50-2500 small molecules, 100-2500 small molecules, 200-2500 small molecules, 300-2500 small molecules, 400-2500 small molecules, 500-2500 small molecules, 600-2500 small molecules, 700-2500 small molecules, 800-2500 small molecules, 900-2500 small molecules, or 1000-2500 small molecules.

In some embodiments, the plurality of small molecules includes 25-25,000 small molecules, 50-25,000 small molecules, 100-25,000 small molecules, 200-25,000 small molecules, 300-25,000 small molecules, 400-25,000 small molecules, 500-25,000 small molecules, 600-25,000 small molecules, 700-25,000 small molecules, 800-25,000 small molecules, 900-25,000 small molecules, 1000-25,000 small molecules, 1100-25,000 small molecules, 1200-25,000 small molecules, or 1300-25,000 small molecules.

Generation of the small molecule profile of a sample requires analysis of its constituent biochemical small molecules. The analysis may include extracting at least some of the plurality of small molecules from the sample. The analysis may be conducted using one or more different analytical techniques known in the art, for example, liquid chromatography (LC), high performance liquid chromatography (HPLC) (see Kristal, et al. *Anal. Biochem.* 263:18-25 (1998)), gas chromatography (GC), thin layer chromatography (TLC), electrochemical separation techniques (see, WO 99/27361, WO 92/13273, U.S. Pat. Nos. 5,290,420, 5,284,567, 5,104,639, 4,863,873, and U.S. RE32,920), refractive index spectroscopy (RI), ultra-violet spectroscopy (UV), fluorescent analysis, radiochemical analysis, near-infrared spectroscopy (Near-IR), nuclear magnetic resonance spectroscopy (NMR), light scattering analysis (LS), mass spectrometry (MS), tandem mass spectrometry ($MS/MS^2$), and combined methods such as gas-chromatography/mass spectrometry (GC-MS), liquid chromatography/mass spectrometry (LC-MS), ultrahigh performance liquid chromatography/tandem mass spectrometry ($UHLC/MS/MS^2$) and gas-chromatography/tandem mass spectrometry ($GC/MS/MS^2$).

U.S. Pat. No. 7,884,318, discloses systems, methods and computer-readable media for determining a composition of chemical constituents in a complex mixture, which may be employed for generating the small molecule profile of the sample, in accordance with some embodiments. U.S. Pat. No. 7,884,318 is incorporated by reference herein in its entirety. As described in U.S. Pat. No. 7,884,318, separation data and mass spectroscopy data are generated for a sample, and the generated separation and mass spectroscopy data is compared with a library of chemical information (a "chemical library") to determine small molecule chemical constituents of the sample.

U.S. Pat. Nos. 7,561,975 and 7,949,475, each of which is incorporated by reference herein in its entirety, provide additional disclosure regarding analysis for identification of small molecule constituents of a biological sample for multiple biological samples.

In some embodiments, multiple aliquots (e.g., two, three, four, five, six, etc.) of a single test sample may be tested. In some embodiments, data analysis for generation of the small molecule profile is fully automated, and the information derived from each analysis for the test sample is recombined after appropriate quality control (QC). In some embodiments, one or more additional control or standard samples (e.g., an anchor sample, a quality control sample) are analyzed in the same run as one or more aliquots from the single test sample. In some embodiments, aliquots from test samples from multiple different individuals are analyzed in the same run. In one embodiment, the test samples may be run as individual samples, in duplicate, triplicate, quadruplicate, or etc.

In some embodiments, data analysis for generation of the small molecule profile is partially automated (e.g., with a person manually verifying the identifications some or all small molecules based on the generated data). In some embodiments, data analysis for generation of the small molecule profile is fully automated.

The small molecule profile of the sample includes information regarding a presence of, an absence of, and a level of many different small molecules. For some small molecules, the information may indicate the specific chemical composition or specific chemical structure of the small molecule (see discussion of "named" small molecules below). For some small molecules, the information may indicate the properties or behavior of the small molecule obtained from the analysis method without indicating the specific chemical composition or structure of the small molecule (see discussion of "unnamed" small molecules below).

In some embodiments, the small molecule profile explicitly identifies small molecules determined to be present in the sample, a level associated with each small molecule present, and small molecules that are determined to be absent from the sample. The small molecule profile need not explicitly identify small molecules determined to be absent from the sample as long as information regarding small molecules determined to be absent from the sample can be inferred. For example, in some embodiments, the small molecule profile identifies small molecules present in the sample and a level of each small molecule present in the sample. The small molecules determined to be absent can be inferred from comparison with a listing of small molecules that would be detected if present based on the experimental techniques employed.

The small molecule profile is compared to a reference small molecule profile to identify a subset of the plurality of small molecules each having an aberrant level in the sample (step 16). The reference small molecule profile includes a standard range for a level of each of a plurality of small molecules. An aberrant level of a small molecule in the sample is a level falling outside the standard range for the small molecule. An aberrant level of a small molecule in the sample includes a small molecule absent from the sample for a standard range indicating that the small molecule should be present (e.g., a missing biochemical), a small molecule present in the sample for a standard range indicating that the small molecule should be absent (e.g., a rare biochemical), and a small molecule present in the sample in a concentration that falls outside a concentration predicted by the standard range (e.g., an outlier).

In some embodiments, the reference small molecule profile is determined, at least in part, from statistical analysis of small molecules profiles generated for reference samples from a population of reference subjects. As noted above, in some embodiments, the reference samples are selected to resemble the test sample (i.e., the sample from the individual subject) by age and/or by gender. In some embodiments, the reference samples are selected to be asymptomatic for the plurality of diseases and disorders. In some embodiments, the reference samples are not selected based on whether they are asymptomatic or symptomatic.

Similar to the test sample, each reference sample may be divided into multiple aliquots for analysis and may be analyzed in parallel, simultaneously or sequentially in various runs, with the resulting data combined after appropriate quality control.

As noted above, in some embodiments the reference samples are analyzed in a same experimental run as the test sample serving as anchor samples. In some embodiments, the reference samples are analyzed in a separate run from the test sample and additional anchor samples are used to correct for run to run variability. In some embodiments, the anchor samples are pooled aliquots of reference samples or pooled aliquots of test samples from previous runs.

Statistical analysis of the reference samples is used to generate the reference small molecule profile including a standard range for each of the plurality of small molecules. In some embodiments, the standard range for a small molecule is based on an inter quartile range (IQR) of the log transformed concentration data for the small molecule in the reference samples (e.g., <1.5*IQR). In some embodiments, the standard range for a small molecule is based on a number of standard deviations from the mean (i.e., the Z-score) of the log transformed concentration data for the small molecule in the reference samples.

Diagnostic information is obtained from a database based on the aberrant levels of the identified subset of the small molecules (step 18). The database includes information associating an aberrant level of one or more small molecules of the plurality of small molecules with information regarding a disease or disorder for each of the plurality of diseases and disorders. In methods in which a disease or disorder-specific composite score is generated based on a weighted combination of data from one or more of the subset of small molecules identified as having aberrant levels, the database further includes information associating a range of disease or disorder-specific composite scores with information regarding the disease or disorder for one or more of the diseases or disorders.

In some embodiments, diagnostic information in the database associates aberrant levels of small molecules with one or more biochemical pathways, and the obtained diagnostic information identifies one or more biochemical pathways associated with the subset of small molecules having aberrant levels. In some embodiments, diagnostic information in the database associates aberrant levels of small molecules with biochemical super-pathway and biochemical subpathways, and the obtained diagnostic information identifies biochemical super-pathways and biochemical subpathways associated with the subset of small molecules having aberrant levels. As used herein, obtaining information regarding biochemical pathways (e.g., biochemical super-pathways and/or subpathways) related to the subset of small molecules having aberrant levels in the sample is referred to as mapping the small molecules with aberrant levels to pathways. Information indicating biochemical pathways associated with the subset of small molecules having aberrant levels is considered diagnostic information because it indicates biochemical pathways that may not be functioning normally in the individual subject (abnormal pathways), which facilitates diagnosis.

In some embodiments, pathways associated with the subset of small molecules having aberrant levels are identified as abnormal pathways. In some embodiments, one or more abnormal biochemical pathways are identified by determining that the biochemical distance for that pathway for the individual is high as compared with an expected biochemical distance for that pathway in a reference population (e.g., the biochemical distance for the pathway for the individual is among the highest 10% as compared with a population of samples from reference subjects for a given pathway). The biochemical distance may be calculated from the Euclidean distance from the geometric mean for each small molecule in the pathway. In some embodiments, a standard range for a biochemical distance may be determined for each pathway from a population of reference samples, and the abnormal pathways identified by comparing the biochemical distance for each pathway for the sample with the corresponding standard range for the biochemical distance for that pathway (e.g., the standard range for the biochemical distance could be the range of biochemical distance that includes 90% of the reference samples, such that a distance falling beyond that range, or in the top 10% of the reference samples, would identify an abnormal pathway). In some embodiments, a combination of the aforementioned is used to identify abnormal pathways (e.g., a pathway is abnormal if it is associated with any of the subset or small molecules having aberrant levels or if the biochemical distance for the pathway is high as compared with an expected biochemical distance for that pathway in a population).

In some embodiments, information in the database associates small molecules having aberrant levels with an identification of a disease or a disorder, and the obtained information includes an identification of at least one disease or disorder associated with the identified subset of the small molecules having aberrant levels. In some embodiments, information in the database associates a range of disease or disorder-specific composite scores with an identification of at least one disease or disorder. In some embodiments, the identification is a possible or probable diagnosis of one or more diseases or disorders associated with the identified subset of the small molecules having aberrant levels. In some embodiments, the identification is a listing of one or more possible diseases or diagnosis associated with the identified subset of the small molecules having aberrant levels.

In some embodiments, diagnostic information in the database associates small molecules having aberrant levels with an identification of at least one follow up test, and the obtained information includes an identification of at least one follow up test associated with the identified subset of the small molecules having aberrant levels.

In some embodiments, the diagnostic information in the database includes information associating aberrant levels of small molecules with one or more biochemical pathways, information associating aberrant levels of small molecules with an identification of at least one disease or disorder, and information associating aberrant levels of small molecules with an identification of at least one follow up test. In some embodiments, the diagnostic information may be stored in multiple databases (e.g., the pathway information may be stored in one database and the information with an identification of a disease or disorder and information regarding follow up tests may be stored in another database).

The obtained diagnostic information is stored (step 20). The stored diagnostic information includes one or more of: an identification of at least one biochemical pathway associated with the identified subset of the small molecules having aberrant levels, an identification at least one disease or disorder associated with the identified subset of the small molecules having aberrant levels, and an identification of at least one follow up test associated with the identified subset of the small molecules having aberrant levels. In some embodiments, the stored diagnostic information includes an identification of at least one biochemical pathway associated with the identified subset of the small molecules having aberrant levels and one or more of: an identification at least one disease or disorder associated with the identified subset of the small molecules having aberrant levels, and an identification of at least one follow up test associated with the identified subset of the small molecules having aberrant levels.

Aberrant levels of one or more small molecules in a sample that indicate the presence of a disease or disorder is described herein as a signature for that disease or disorder. The signatures may be specific to the methods used to test the samples. In some embodiments, the database includes signatures for a plurality of diseases or disorders.

In some embodiments of methods described herein, the plurality of diseases and disorders includes more than 2 diseases or disorders, more than 10 diseases or disorders, more than 20 diseases or disorders, more than 30 diseases or disorders, more than 50 diseases or disorders, more than 100 diseases or disorders, more than 200 diseases or disorders, more than 300 diseases or disorders, more than 400 diseases or disorders, more than 500 diseases or disorders, more than 600 diseases or disorders, more than 700 diseases or disorders, more than 800 diseases or disorders, more than 900 diseases or disorders, more than 1000 diseases or disorders, more than 1100 diseases or disorders, more than 1200 diseases or disorders, more than 1300 diseases or disorders, more than 1400 diseases or disorders, more than 1500 diseases or disorders more than 2000 diseases or disorders, more than 3000 diseases or disorders, more than 4000 diseases or disorders, more than 5000 diseases or disorders, more than 6000 diseases or disorders, or more than 7000 diseases or disorders.

In some embodiments of methods described herein, the plurality of diseases and disorders includes between 2 and 10,000 diseases or disorders, between 10 and 10,000 diseases or disorders, between 20 and 10,000 diseases or disorders, between 30 and 10,000 diseases or disorders, between 50 and 10,000 diseases or disorders, between 100 and 10,000 diseases or disorders, between 200 and 10,000 diseases or disorders, between 300 and 10,000 diseases or disorders, between 400 and 10,000 diseases or disorders, between 500 and 10,000 diseases or disorders, more than between 600 and 10,000 diseases or disorders, between 700 and 10,000 diseases or disorders, between 800 and 10,000 diseases or disorders, between 900 and 10,000 diseases or disorders, between 1000 and 10,000 diseases or disorders, between 1100 and 10,000 diseases or disorders, between 1200 and 10,000 diseases or disorders, between 1300 and 10,000 diseases or disorders, between 1400 and 10,000 diseases or disorders, between 1500 and 10,000 diseases or disorders, between 2000 and 10,000 diseases or disorders, between 3000 and 10,000 diseases or disorders, between 4000 and 10,000 diseases or disorders, between 5000 and 15,000 diseases or disorders, between 6000 and 15,000 diseases or disorders, or between 7000 and 15,000 diseases or disorders.

Some embodiments include storing a graphical representation of some or all of the obtained diagnostic information (step 22). In some embodiments, a graphical representation of the one or more biochemical pathways associated identified subset of the small molecules having aberrant levels is stored. In some embodiments, the graphical representation includes graphical representation of super-pathways with indicators showing which super-pathways are associated with the identified subset of the small molecules having aberrant levels (e.g., see FIG. 4 and associated description in the Examples section below). In some embodiments, the graphical representation includes a graphical representation of the subpathways associated with the identified subset of the small molecules having aberrant levels (e.g., see FIG. 6 and associated description in the Examples section below). In some embodiments, the graphical representation includes a graphical representation of all biochemical subpathways with graphical indications of which are associated with the identified subset of the small molecules having aberrant levels (e.g., see FIG. 5 and associated description in the Examples section below). In some embodiments, the graphical representation further includes a graphical representation of the identified subset of the small molecules having aberrant levels and a graphical indication of a level of each (e.g., see FIGS. 7-9, 11-14, and 19-21 and associated descriptions in the Examples section below). As used herein, generation, storage and/or display of a graphical representation of some or all of the obtained diagnostic information is also referred to as visualization of the information or visualization of the results.

The graphical representation may be stored in any known format for electronic storage of images (e.g., JPEG/JFIF, JPEG 2000, Exif, TIFF, RAW, GIF, BMP, PNG, PPM, PGM, PNM, WEBP, CGM, SVG, etc.) In some embodiments, the graphical representation(s) may be incorporated into a document and stored in a document file format (e.g., PDF, .ps, .doc, .docx, .ppt, .odt, .htm, .html, etc.)

In some embodiments, multiple types of diagnostic information for the individual subject may be compiled into a single document, which is referred to as a report herein. The report may include information regarding any or all of: a total number of different small molecule biochemicals detected; identification of biochemical pathways (e.g., super-pathways and/or subpathways) associated with small molecules having aberrant levels; identification of which small molecules in the identified subpathways were present in aberrant levels, identification of biochemical small molecules present in aberrant levels and an indication of the levels, an identification of rare biochemicals, an indication of missing biochemicals, an indication of whether each outlier biochemical is present at a level higher or lower than the standard range; a list of possible or probable diagnoses, a list of recommended confirmatory tests, and a list of recommended follow up tests. The report may be stored in a suitable electronic file format. In some embodiments, the report of the results is provided to a health care provider and/or to the individual subject in any suitable electronic or non-electronic (e.g., paper) form.

Figure 2:
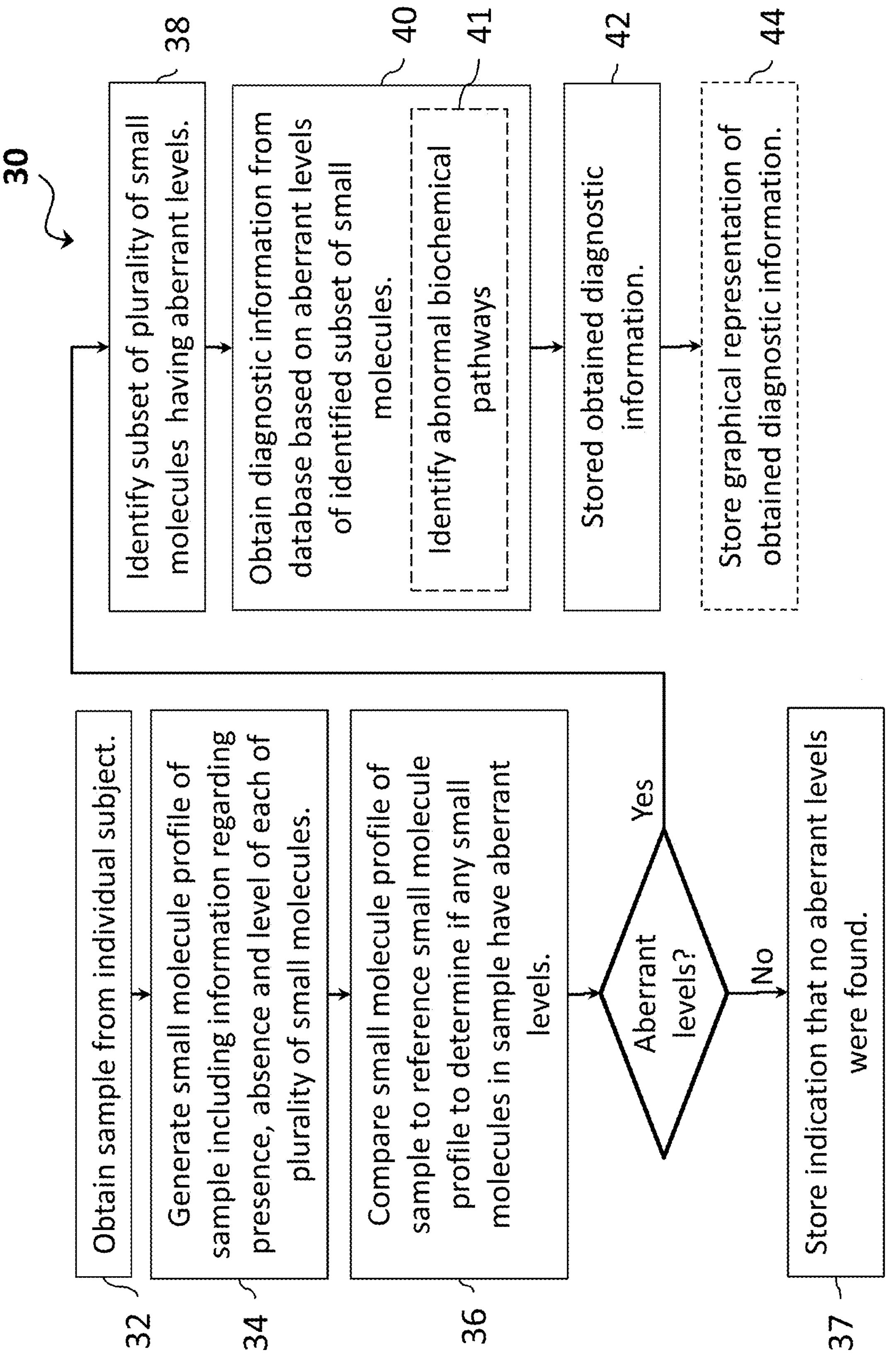
FIG. 2 is a block diagram of a method for screening an individual subject for plurality of diseases or disorders, in accordance with an embodiment.

FIG. 2 is a block diagram of a method 30 for screening an individual subject for a plurality of diseases or disorders, in accordance with an embodiment. A sample is obtained from the individual subject (step 32). A small molecule profile of the sample is generated including information regarding presence of, absence of, and a level of each of a plurality of small molecules in the sample (step 34). The small molecule profile of the sample is compared to a reference small molecule profile that includes a standard range for a level of each of a plurality of small molecules to determine if any of the small molecules in the profile have an aberrant level in the sample (step 36). As explained above, an aberrant level of a small molecule in the sample includes a small molecule absent from the sample for a standard range indicating that the small molecule should be present (e.g., a missing biochemical), a small molecule present in the sample for a standard range indicating that the small molecule should be absent (e.g., a rare biochemical), and a small molecule present in the sample in a concentration that falls outside a concentration predicted by the standard range (e.g., an outlier).

If none of the small molecules in the small molecule profile of the sample has an aberrant level, information is stored indicating that no aberrant levels were detected (step 37).

If any aberrant levels are detected, a subset of the plurality of small molecules having aberrant levels is identified (step 38). Diagnostic information is obtained from a database based on the identified subset of small molecules (step 40). In some embodiments, the method includes generating a disease or disorder-specific composite score based on a weighted combination of data from one or more of the subset of small molecules identified as having aberrant levels, and obtaining diagnostic information from the database based on the aberrant levels of the identified subset of the small molecules includes obtaining diagnostic information from the database based on the generated disease or disorder-specific composite score. In some embodiments, obtaining diagnostic information based on the aberrant levels of the identified subset of the small molecules includes identifying one or more abnormal biochemical pathways (step 41). The database includes information associating an aberrant level of one or more of the plurality of small molecules with information regarding a disease or disorder for each of a plurality of diseases or disorders. The obtained diagnostic information is stored (step 42). The stored diagnostic information includes one or more of: an identification of at least one biochemical pathway associated with the identified subset of the small molecules having aberrant levels, an identification of at least one disease or disorder associated with the identified subset of the small molecules having aberrant levels, and an identification of at least one follow up test associated with the identified subset of the small molecules having aberrant levels. In some embodiments, the method also includes storing a graphical representation of the obtained diagnostic information (step 44). The dashed line around the boxes for steps 41 and 44 in FIG. 2 indicates that these steps need not be present in all embodiments.

In some embodiments, the individual subject is asymptomatic for the plurality of diseases and disorders and method 30 is a method for screening the asymptomatic individual subject for plurality of diseases or disorders.

In some embodiments, the individual subject is symptomatic and method 30 is a method for screening the symptomatic individual subject for plurality of diseases or disorders.

In some embodiments, the individual subject is a human newborn and method 30 is a method for screening the human newborn for plurality of diseases or disorders. In some embodiments, the individual subject is a human infant and method 30 is a method for screening the human infant for plurality of diseases or disorders.

Figure 3:
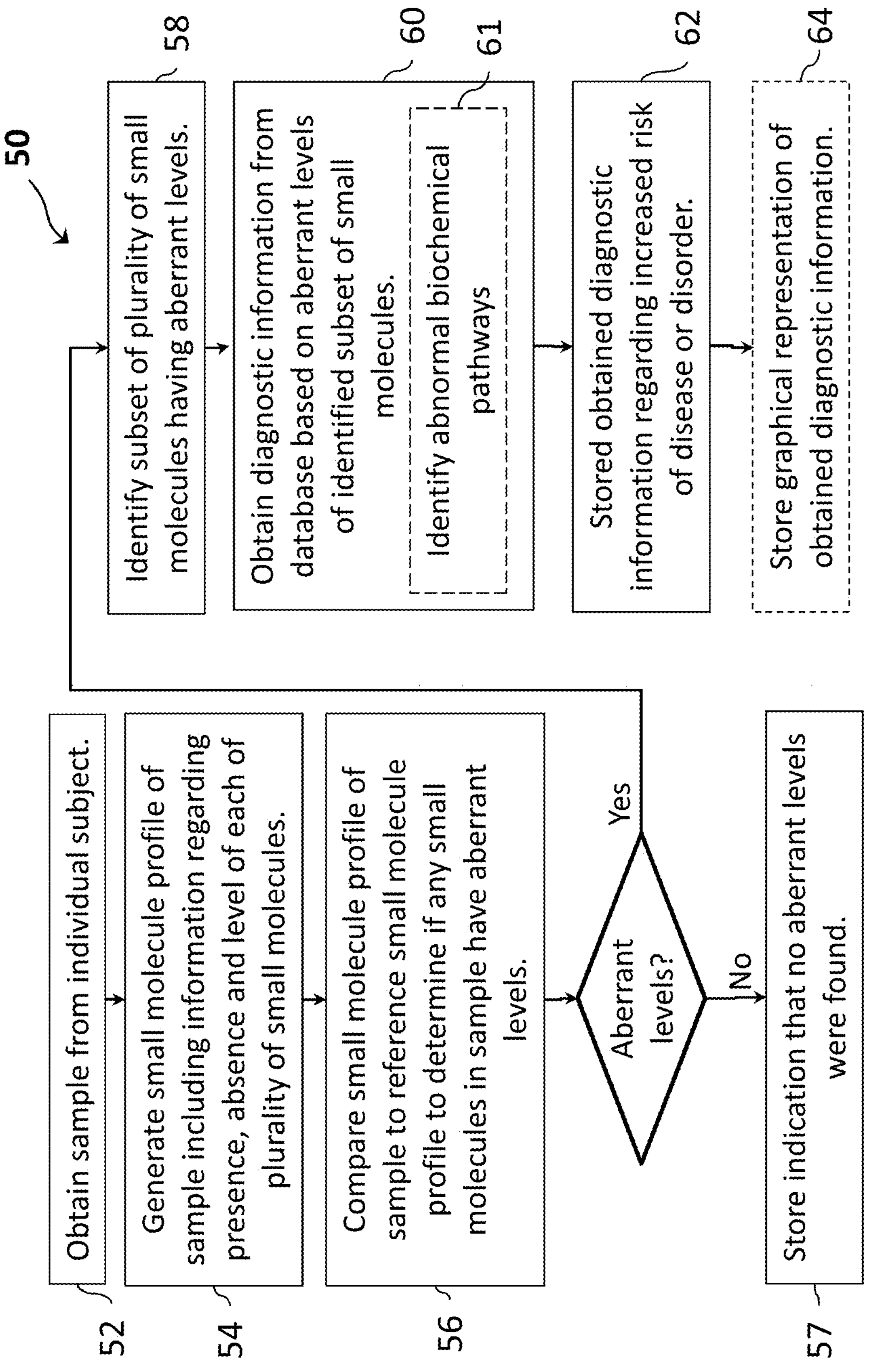
FIG. 3 is a block diagram of a method for screening an individual subject for an increased risk of developing a disease or disorder, in accordance with an embodiment.

FIG. 3 is a block diagram of a method 50 for screening an individual subject for an increased risk of developing one of the plurality of diseases or disorders, in accordance with an embodiment. A sample is obtained from the individual subject (step 52). A small molecule profile of the sample is generated including information regarding presence of, absence of, and a level of each of a plurality of small molecules in the sample (step 54). The small molecule profile of the sample is compared to a reference small molecule profile that includes a standard range for a level of each of a plurality of small molecules to determine if any of the small molecules in the profile have an aberrant level in the sample (step 56). If none of the small molecules in the small molecule profile of the sample has an aberrant level, information is stored indicating that no aberrant levels were detected (step 57).

If any aberrant levels are detected, a subset of the plurality of small molecules having aberrant levels is identified (step 58). Diagnostic information is obtained from a database based on the identified subset of small molecules (step 60). In some embodiments, obtaining diagnostic information based on the aberrant levels of the identified subset of the small molecules includes identifying one or more abnormal biochemical pathways (step 61). The database includes information associating an aberrant level of one or more of the plurality of small molecules with information regarding a disease or disorder for each of a plurality of diseases or disorders. The obtained diagnostic information, which includes an identification of an increased risk for developing a disease or disorder associated with the identified subset of small molecules having aberrant levels, is stored (step 62). In some embodiments, the method also includes storing a graphical representation of the obtained diagnostic information (step 64).

Aberrant levels of one or more small molecules in a sample that indicate an increased risk of developing a disease or disorder is described herein as a signature for increased risk of the disease or disorder. In method 50, the database includes signatures for the plurality of diseases or disorders. The dashed lines around the boxes for steps 61 and 64 in FIG. 3 indicate that these need not be present in all embodiments.

In further embodiments, a method is provided to diagnose or aid in diagnosis of a disease or disorder in a newborn or an infant.

In further embodiments, a method is provided for diagnosis or aid in diagnosis of a disease or disorder in an asymptomatic subject.

In one embodiment, a method is provided for the diagnosis or aiding in the diagnosis of a disease or disorder in a symptomatic subject. The method may include determining diagnostic information including a listing of one more possible diseases and/or one or more recommend additional tests.

In one embodiment, the detection of rare metabolites may be used to diagnose or aid in the diagnosis of a disease or disorder.

In one embodiment, the identification of missing metabolites may be used to diagnose or aid in the diagnosis of a disease or disorder.

In one embodiment, the biological sample is a urine sample and may be obtained from a material such as a diaper.

In one embodiment, generation of a small molecule profile of the sample include use of a matrix sample to aid in the identification of biochemicals in the test sample.

The steps of generating the small molecule profile of the sample, comparing the small molecules profile of the sample to a reference small molecule profile to determine if any small molecules in the sample have aberrant levels, identifying a subset of plurality of small molecules having aberrant levels, obtaining diagnostic information from a database based on aberrant levels of the identified subset of the small molecules, storing an indication that no aberrant levels were found, storing obtained diagnostic information, storing a graphical representation of obtained diagnostic information may be performed in part or in whole using instructions executing on one or processors of one or more computing systems.

Some embodiments include storage holding computer-executable code with instructions for performing various steps of methods described herein.

Figure 22:
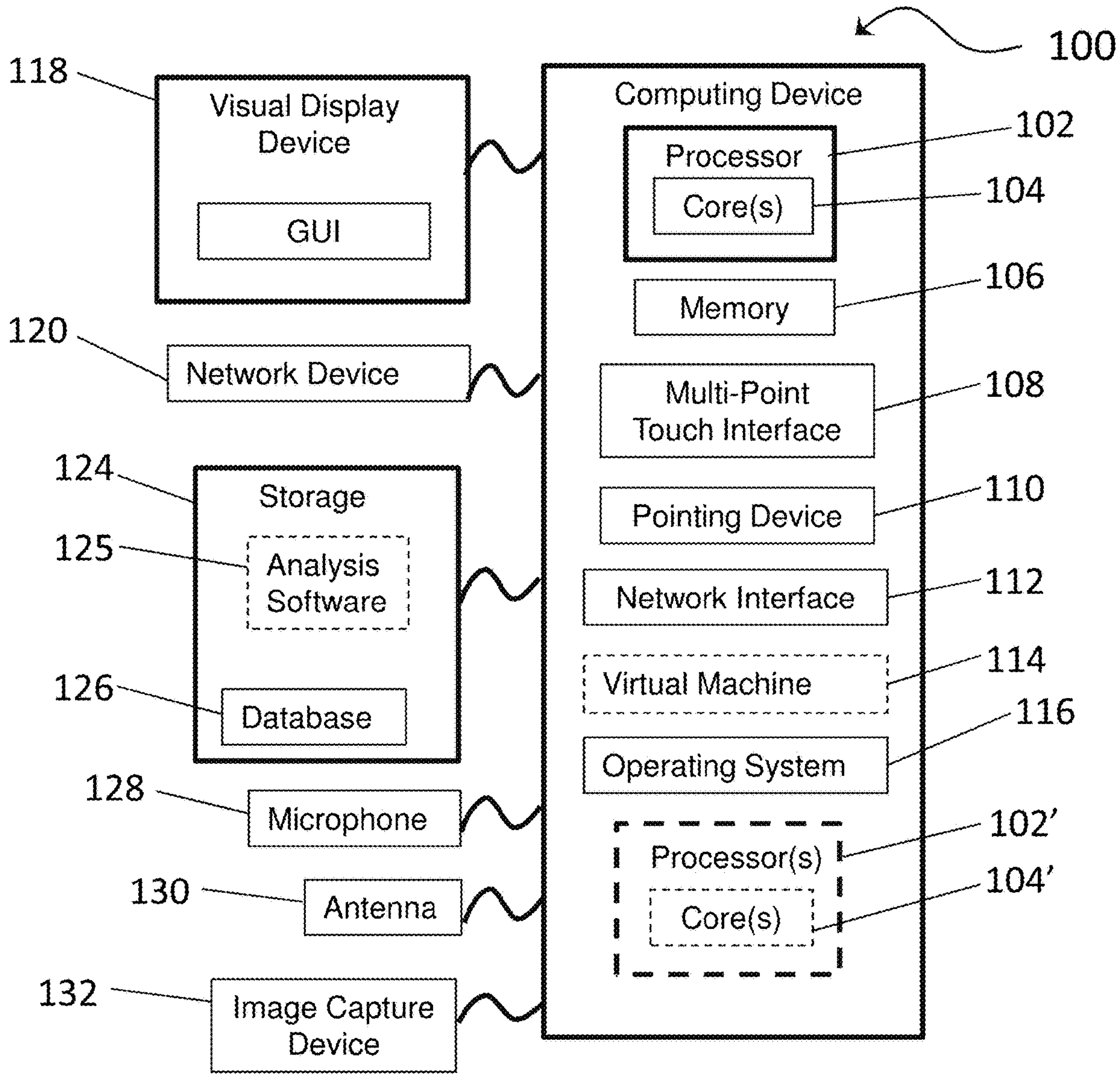
FIG. 22 is a block diagram of a computing device for use in implementing some steps of some exemplary methods, in accordance with some embodiments.

FIG. 22 is a block diagram of an exemplary computing device 100 that may be used to implement various steps of exemplary methods described herein. The computing device 100 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives), and the like. For example, memory 106 included in the computing device 100 may store computer-readable and computer-executable instructions or software for implementing all or part of steps or methods described herein. The computing device 100 also includes a configurable and/or programmable processor 102 and associated core 104, and optionally, one or more additional configurable and/or programmable processor(s) 102' and associated core(s) 104' (for example, in the case of computer systems having multiple processors/cores), for executing computer-readable and computer-executable instructions or software stored in the memory 106 and other programs for controlling system hardware. Processor 102 and processor(s) 102' may each be a single core processor or multiple core (104 and 104') processor.

Virtualization may be employed in the computing device 100 so that infrastructure and resources in the computing device may be shared dynamically. A virtual machine 114 may be provided to handle a process running on multiple processors so that the process appears to be using only one computing resource rather than multiple computing resources. Multiple virtual machines may also be used with one processor.

Memory 106 may include a computer system memory or random access memory, such as DRAM, SRAM, EDO RAM, and the like. Memory 106 may include other types of memory as well, or combinations thereof.

A user may interact with the computing device 100 through a visual display device 118, such as a computer monitor, which may display one or more graphical user interfaces that may be provided in accordance with exemplary embodiments. The computing device 100 may include other I/O devices for receiving input from a user, for example, a keyboard or any suitable multi-point touch interface 108, a pointing device 110 (e.g., a mouse), a microphone 128, and/or an image capturing device 132 (e.g., a camera or scanner). The multi-point touch interface 108 and the pointing device 110 may be coupled to the visual display device 118. The computing device 100 may include other suitable conventional I/O peripherals.

The computing device 100 may also include one or more storage devices 124, such as a hard-drive, CD-ROM, or other computer readable media, for storing data and computer-readable instructions and/or software for implementing exemplary embodiments described herein. Exemplary storage device 124 may also store one or more databases for storing any suitable information required to implement exemplary embodiments. For example, exemplary storage device 124 can store one or more databases 126 that include any or all of a chemical library, a reference small molecule profile, small molecules profiles of one or more reference samples, small molecule profiles of one or more test samples, diagnostic information associated with one or more aberrant small molecules for a plurality of diseases and disorders, information associating pathways with one or more aberrant small molecules, information associating a disease or disorder with one or more aberrant small molecules levels for a plurality of diseases or disorders, and an identification of at least one recommended follow up test associated with one or more aberrant small molecule levels. In other embodiments, different databases for different steps may be associated with different computing devices.

The one or more storage devices 124 may be used to store any or all of obtained diagnostic information, graphical representations of obtained diagnostic information, reports for an individual subject, etc.

The one or more storage devices 124 and or the memory 106 may hold software 125 executable on the processor 102 for implementing an analysis facility that compares the small molecule profile of the sample to a reference small molecule profile that includes a standard range for a level of each of the plurality of small molecules and identifies a subset of the small molecules in the sample each having an aberrant level.

The computing device 100 can include a network interface 112 configured to interface via one or more network devices 120 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. In exemplary embodiments, the computing device 100 can include one or more antennas 130 to facilitate wireless communication (e.g., via the network interface) between the computing device 100 and a network. The network interface 112 may include a built-in network adapter, network interface card, PCMCIA network card, card bus network adapter, wireless network adapter, USB network adapter, modem or any other device suitable for interfacing the computing device 100 to any type of network capable of communication and performing the operations described herein. Moreover, the computing device 100 may be any computer system, such as a workstation, desktop computer, server, laptop, handheld computer, tablet computer (e.g., the iPad™ tablet computer), mobile computing or communication device (e.g., the iPhone™ communication device), or other form of computing or telecommunications device that is capable of communication and that has sufficient processor power and memory capacity to perform the operations described herein. In some embodiments, the computing device 100 may communicate via a network with one or more computing devices used to obtain experimental data (e.g., a computing device associated with an LC/MS system, a computing device associated with a GC/MS system).

The computing device 100 may run any operating system 116, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the computing device and performing the operations described herein. In exemplary embodiments, the operating system 116 may be run in native mode or emulated mode. In an exemplary embodiment, the operating system 116 may be run on one or more cloud machine instances.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art shall understand that various substitutions and alterations in form and detail may be made therein without departing from the scope of the invention. Further still, other embodiments, functions and advantages are also within the scope of the invention.

Exemplary block diagrams/flowcharts are provided herein for illustrative purposes and are non-limiting examples of methods. One of ordinary skill in the art will recognize that exemplary methods may include more or fewer steps than those illustrated in the exemplary block diagrams/flowcharts, and that the steps in the exemplary block diagrams/flowcharts may be performed in a different order than the order shown in the illustrative block diagrams/flowcharts.

In some embodiments, the results of the methods described herein may be used in combination with other methods (e.g., whole exome sequencing).

Biomarkers Indicative of Disease Status

Novel biomarkers characteristic of particular disorders were identified using the metabolomic profiling techniques described herein. Generally, metabolomic profiles were determined for biological samples obtained from subjects diagnosed with one or more disorders, as well as from other subjects not diagnosed with said disorders (e.g., healthy control subjects). The metabolomic profile for biological samples from a subject having a given disorder was compared to the metabolomic profile for biological samples from healthy control subjects. Those molecules differentially present (e.g., those molecules differentially present at a level that is statistically significant) in the metabolomic profile of samples from subjects with a given disorder as compared to healthy control subjects were identified as biomarkers to distinguish those groups. Detection of a level of one or more biomarkers identified in this manner can be used to diagnose or facilitate diagnosis of an individual subject. Said biomarkers can be detected in a subject individually or in combination with other biomarkers (e.g., as part of a profile)
.

Biological samples suitable for the detection of biomarkers include biological material isolated from a subject. In exemplary embodiments, the sample can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

Any suitable method may be used to analyze the biological sample in order to determine the level(s) of the one or more biomarkers in the sample. Suitable methods include, but are not limited to, chromatography (e.g., HPLC, gas chromatography, liquid chromatography), mass spectrometry (e.g., MS, MS-MS), enzyme-linked immunosorbent assay (ELISA), antibody linkage, other immunochemical techniques, and combinations thereof. Further, the level(s) of the one or more biomarkers may be measured indirectly, for example, by using an assay that measures the level of a compound (or compounds) that correlates with the level of the biomarker(s) that are desired to be measured. The level(s) of the one or more biomarkers may also be determined as part of a biomarker profile, e.g., a metabolomic profile, using, for example, the methods set forth herein.

After the level(s) of the one or more biomarkers in a biological sample obtained from a subject are determined, the level(s) are compared to reference levels characteristic of a subject having the disorder (i.e., "positive" for the disorder), and/or reference levels characteristic of a subject not having the disorder (i.e., "negative" for the disorder). Levels of the one or more biomarkers matching the reference levels characteristic of a subject positive for a given disorder (e.g., levels that are the same as the reference levels, substantially the same as the reference levels, not statistically different from the reference levels, within an established range of the reference levels, etc.) are indicative of a positive diagnosis of the disorder in the subject. Levels of the one or more biomarkers matching the reference levels characteristic of a subject negative for a given disorder (e.g., levels that are the same as the reference levels, substantially the same as the reference levels, not statistically different from the reference levels, within an established range of the reference levels, etc.) are indicative of a negative diagnosis of the disorder in the subject. In addition, levels of the one or more biomarkers that are differentially present (e.g., at a level that is statistically significant) in the sample obtained from the subject, as compared to reference levels characteristic of a subject positive for a given disorder, are indicative of a negative diagnosis of the disorder in the subject. Levels of the one or more biomarkers that are differentially present (e.g., at a level that is statistically significant) in the sample obtained from the subject, as compared to reference levels characteristic of a subject negative for a given disorder, are indicative of a positive diagnosis of the disorder in the subject.

The level(s) of the one or more biomarkers may be compared to disorder-positive and/or disorder-negative reference levels using various techniques, including a simple comparison of the level(s) of the one or more biomarkers in the biological sample to disorder-positive and/or disorder-negative reference levels. The level(s) of the one or more biomarkers in the biological sample may also be compared to disorder-positive and/or disorder-negative reference levels using one or more statistical analyses (e.g., t-test, Welch's T-test, Wilcoxon's rank sum test, random forest). In various embodiments, such comparisons may be made manually, by an automated system, or by an automated system with manual verification.

A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype. A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). Such reference levels may also be tailored to specific techniques that are used to measure levels of biomarkers in biological samples (e.g., LC-MS, GC-MS, etc.), where the levels of biomarkers may differ based on the specific technique that is used.

In one embodiment, the novel biomarkers characteristic of particular disorders may be biochemically related to currently used diagnostic metabolites. In other embodiments, the novel biomarkers are unrelated to any currently used diagnostic metabolites for a given disorder. Novel biomarkers are listed in the last column of Table 2 and in the last column of Table 3. The level(s) of one or more biomarkers shown in Table 2 and Table 3 may be used to diagnose or facilitate diagnosis of a disorder in an individual subject. For example, the level of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers, etc., including a combination of all of the biomarkers in Table 2 and/or Table 3 or any fraction thereof, may be determined and used in such methods. Determining the level(s) of combinations of the biomarkers may allow greater sensitivity and specificity in the diagnosis of particular disorders, and may allow better differentiation from other disorders. In one embodiment, the level(s) of one or more novel biomarkers characteristic of a particular disorder may be assessed in combination with the level(s) of one or more currently used diagnostic metabolites indicative of the disorder. Currently used diagnostic metabolites indicative of particular disorders are set forth in Table 2, column 5 and in Table 3, column 5. Some biomarkers may be currently used diagnostic metabolites with respect to one type of sample (e.g., plasma), but novel with respect to another type of sample (e.g., urine).

The identification of novel metabolic biomarkers for particular disorders also allows treatment of the disorders. Accordingly, in exemplary embodiments, an effective amount of a therapeutic agent can be administered to a subject diagnosed with a particular disease or disorder using the biomarkers set forth herein.

Biomarkers which can be used to diagnose or facilitate diagnosis of particular disorders are described below.

3-Methylcrotonyl CoA Carboxylase Deficiency

Novel metabolic biomarkers indicative of 3-methylcrotonyl CoA carboxylase deficiency include beta-hydroxyisovaleroylcarnitine, glutarylcarnitine (C5), 3-methylcrotonylglycine, adipate, glutarate (pentanedioate), octadecanedioate (C18), hexadecanedioate (C16), tetradecanedioate (C14), dodecanedioate (C12), isovalerate, leucine, isovalerylglycine, alpha-hydroxyisovalerate, succinylcarnitine, 3-methylglutarylcarnitine, isovalerylcarnitine, alanylalanine, pyroglutamylvaline, ethylmalonate, N-acetylleucine, X-12007, X-12814, and combinations thereof. Accordingly, diagnosis of 3-methylcrotonyl CoA carboxylase deficiency in a subject can be made or facilitated by analyzing a biological sample obtained from the subject to determine the level of one or more metabolites including beta-hydroxyisovaleroylcarnitine, glutarylcarnitine (C5), 3-methylcrotonylglycine, adipate, glutarate (pentanedioate), octadecanedioate (C18), hexadecanedioate (C16), tetradecanedioate (C14), dodecanedioate (C12), isovalerate, leucine, isovalerylglycine, alpha-hydroxyisovalerate, succinylcarnitine, 3-methylglutarylcarnitine, isovalerylcarnitine, alanylalanine, pyroglutamylvaline, ethylmalonate, N-acetylleucine, X-12007, and X-12814, and comparing the level(s) of the metabolites in the sample to 3-methylcrotonyl CoA carboxylase deficiency-positive and/or 3-methylcrotonyl CoA carboxylase deficiency-negative reference levels of the metabolites.

Optionally, diagnosis of 3-methylcrotonyl CoA carboxylase deficiency in a subject can be made or facilitated by analyzing the level(s) of one or more currently used diagnostic metabolites in combination with the foregoing novel metabolic biomarkers. Currently used diagnostic metabolites indicative of 3-methylcrotonyl CoA carboxylase deficiency include 3-methylcrotonylglycine and beta-hydroxyisovalerate. Accordingly, methods of diagnosing or facilitating diagnosis of 3-methylcrotonyl CoA carboxylase deficiency may further include analyzing a biological sample obtained from the subject to determine the level of one or more additional metabolites including 3-methylcrotonylglycine, beta-hydroxyisovalerate, and combinations thereof.

In one embodiment, one or more biomarkers selected from the group consisting of 3-hydroxyisovaleroylcarnitine, β-hydroxyisovalerate, isovalerylglycine, leucine, 3-methylcrotonylglycine, isovalerate, and 3-hydroxyisovalerate may be used in diagnosing or aiding in the diagnosis of 3-methylcrotonyl CoA carboxylase deficiency in a subject.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of 3-methylcrotonyl CoA carboxylase deficiency in a subject can be made or facilitated by analyzing a biological sample derived from urine from the subject to determine the level of one or more metabolites including any of ethylmalonate, N-acetylleucine, and combinations thereof.

Adenosine Deaminase Deficiency

Novel metabolic biomarkers indicative of adenosine deaminase deficiency include 2'-deoxyinosine, adenine, N2-methylguanosine, 2'-deoxyguanosine, urate, N1-methyladenosine, adenosine, allantoin, xanthine, guanosine, hypoxanthine, N2,N2-dimethylguanosine, 7-methylguanosine, and combinations thereof. Accordingly, diagnosis of adenosine deaminase deficiency in a subject can be made or facilitated by analyzing a biological sample obtained from the subject to determine the level of one or more metabolites including 2'-deoxyinosine, adenine, N2-methylguanosine, 2'-deoxyguanosine, urate, N1-methyladenosine, adenosine, allantoin, xanthine, guanosine, hypoxanthine, N2,N2-dimethylguanosine, and 7-methylguanosine, and comparing the level(s) of the metabolites in the sample to adenosine deaminase deficiency-positive and/or adenosine deaminase deficiency-negative reference levels of the metabolites.

Optionally, diagnosis of adenosine deaminase deficiency in a subject can be made or facilitated by analyzing the level(s) of one or more currently used diagnostic metabolites in combination with the foregoing novel metabolic biomarkers. Currently used diagnostic metabolites indicative of adenosine deaminase deficiency include deoxyadenosine and S-adenosylhomocysteine. Accordingly, methods of diagnosing or facilitating diagnosis of adenosine deaminase deficiency may further include analyzing a biological sample obtained from the subject to determine the level of one or more additional metabolites including deoxyadenosine and S-adenosylhomocysteine.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of adenosine deaminase deficiency in a subject can be made or facilitated by analyzing a biological sample derived from urine from the subject to determine the level of one or more metabolites including any of 2'-deoxyinosine, adenine, N2-methylguanosine, 2'-deoxyguanosine, urate, N1-methyladenosine, adenosine, allantoin, xanthine, guanosine, hypoxanthine, N2,N2-dimethylguanosine, 7-methylguanosine, and combinations thereof.

Argininosuccinic Acid Lyase Deficiency

Novel metabolic biomarkers indicative of argininosuccinic acid lyase deficiency include N-delta-acetylornithine, uracil, arginine, aspartate, sorbose, fructose, citrulline, methyl-4-hydroxybenzoate, isoleucylaspartate, ornithine, uridine, homocitrulline, orotate, homoarginine, O-sulfo-L-tyrosine, palmitoyl sphingomyelin, X-13507, X-15245, X-15664, X-15454, and combinations thereof. Accordingly, diagnosis of argininosuccinic acid lyase deficiency in a subject can be made or facilitated by analyzing a biological sample obtained from the subject to determine the level of one or more metabolites including N-delta-acetylornithine, uracil, arginine, aspartate, sorbose, fructose, citrulline, methyl-4-hydroxybenzoate; isoleucylaspartate, ornithine, uridine, homocitrulline, orotate, homoarginine, O-sulfo-L-tyrosine, palmitoyl sphingomyelin, X-13507, X-15245, X-15664, and X-15454, and comparing the level(s) of the metabolites in the sample to argininosuccinic acid lyase deficiency-positive and/or argininosuccinic acid lyase deficiency-negative reference levels of the metabolites.

Optionally, diagnosis of argininosuccinic acid lyase deficiency in a subject can be made or facilitated by analyzing the level(s) of one or more currently used diagnostic metabolites in combination with the foregoing novel metabolic biomarkers. Currently used diagnostic metabolites indicative of argininosuccinic acid lyase deficiency include arginosuccinate. Accordingly, methods of diagnosing or facilitating diagnosis of argininosuccinic acid lyase deficiency may further include analyzing a biological sample obtained from the subject to determine the level of one or more additional metabolites including argininosuccinate.

In one embodiment, one or more biomarkers selected from the group consisting of argininosuccinate, citrulline, uracil, arginine, and aspartate may be used in diagnosing or aiding in the diagnosis of argininosuccinic acid lyase deficiency in a subject.

Argininemia

Novel metabolic biomarkers indicative of Argininemia include homoarginine, N-acetylarginine, ornithine, urea, homocitrulline, uracil, aspartate, argininosuccinate, proline, orotate, creatinine, uridine, 3-ureidopropionate, creatine, betaine, leucine, isoleucine, gamma-glutamylleucine, X-12339, X-12681, and combinations thereof. Accordingly, diagnosis of Argininemia in a subject can be made or facilitated by analyzing a biological sample obtained from the subject to determine the level of one or more metabolites including homoarginine, N-acetylarginine, ornithine, urea, homocitrulline, uracil, aspartate, argininosuccinate, proline, orotate, creatinine, uridine, 3-ureidopropionate, creatine, betaine, leucine, isoleucine, gamma-glutamylleucine, X-12339, and X-12681, and comparing the level(s) of the metabolites in the sample to Argininemia-positive and/or Argininemia-negative reference levels of the metabolites.

Optionally, diagnosis of Argininemia in a subject can be made or facilitated by analyzing the level(s) of one or more currently used diagnostic metabolites in combination with the foregoing novel metabolic biomarkers. Currently used diagnostic metabolites indicative of Argininemia include arginine, and 4-guanidinobutanoate. Accordingly, methods of diagnosing or facilitating diagnosis of Argininemia may further include analyzing a biological sample obtained from the subject to determine the level of one or more additional metabolites including arginine, 4-guanidinobutanoate, and combinations thereof.

In one embodiment, one or more biomarkers selected from the group consisting of argininosuccinate, 4-guanidinobutanoate, uridine, arginine, homocitrulline, N-acetylarginine, orotate, uracil, aspartate, creatinine, urea, proline, ornithine, X-12681, and X-12339 may be used in diagnosing or aiding in the diagnosis of Argininemia in a subject.

Biotinidase Deficiency

Novel metabolic biomarkers indicative of biotinidase deficiency include biotin, xylitol, 3-methylcrotonylglycine, propionylcarnitine (C3), and combinations thereof. Accordingly, diagnosis of biotinidase deficiency in a subject can be made or facilitated by analyzing a biological sample obtained from the subject to determine the level of one or more metabolites including xylitol, biotin, 3-methylcrotonylglycine, and propionylcarnitine (C3), and comparing the level(s) of the metabolites in the sample to biotinidase deficiency-positive and/or biotinidase deficiency-negative reference levels of the metabolites.

Cbl (Cobalamin Deficiency)

Novel metabolic biomarkers indicative of cobalamin deficiency include 2-methylmalonyl carnitine, propionylcarnitine, X-12749, and combinations thereof. Accordingly, diagnosis of cobalamin deficiency in a subject can be made or facilitated by analyzing a biological sample obtained from the subject to determine the level of one or more metabolites including 2-methylmalonyl carnitine, propionylcarnitine, and X-12749, and comparing the level(s) of the metabolites in the sample to cobalamin deficiency-positive and/or cobalamin deficiency-negative reference levels of the metabolites.

Optionally, diagnosis of cobalamin deficiency in a subject can be made or facilitated by analyzing the level(s) of one or more currently used diagnostic metabolites in combination with the foregoing novel metabolic biomarkers. Currently used diagnostic metabolites indicative of cobalamin deficiency include methylmalonic acid, homocysteine, 2-methylcitrate, and cystathionine. Accordingly, methods of diagnosing or facilitating diagnosis of cbl (cobalamin deficiency) may further include analyzing a biological sample obtained from the subject to determine the level of one or more additional metabolites including methylmalonic acid, homocysteine, 2-methylcitrate, cystathionine, and combinations thereof.

In one embodiment, one or more biomarkers selected from the group consisting of 2-methylmalonylcarnitine, tiglyl carnitine, 2-methylbutyrylcarnitine, and 2-methylcitrate may be used in diagnosing or aiding in the diagnosis of cobalamin deficiency in a subject.

Cbl A

Novel metabolic biomarkers indicative of Cbl A include 2-methylmalonyl carnitine, tiglyl carnitine, 2-methylbutyrylcarnitine, propionylcarnitine, X-12749, and combinations thereof. Accordingly, diagnosis of Cbl A in a subject can be made or facilitated by analyzing a biological sample obtained from the subject to determine the level of one or more metabolites including 2-methylmalonyl carnitine and tiglyl carnitine, 2-methylbutyrylcarnitine, propionylcarnitine, and X-12749, and comparing the level(s) of the metabolites in the sample to Cbl A-positive and/or Cbl A-negative reference levels of the metabolites.

Optionally, diagnosis of Cbl A in a subject can be made or facilitated by analyzing the level(s) of one or more currently used diagnostic metabolites in combination with the foregoing novel metabolic biomarkers. Currently used diagnostic metabolites indicative of Cbl A include methylmalonic acid, homocysteine, 2-methylcitrate, and cystathionine. Accordingly, methods of diagnosing or facilitating diagnosis of Cbl A may further include analyzing a biological sample obtained from the subject to determine the level of one or more additional metabolites including methylmalonic acid, homocysteine, 2-methylcitrate, cystathionine, and combinations thereof.

Cbl C

Novel metabolic biomarkers indicative of Cbl C include 2-methylmalonyl carnitine, propionylcarnitine, X-17677, X-12749, and combinations thereof. Accordingly, diagnosis of Cbl C in a subject can be made or facilitated by analyzing a biological sample obtained from the subject to determine the level of one or more metabolites including 2-methylmalonyl carnitine, propionylcarnitine, X-12749, and X-17677, and comparing the level(s) of the metabolites in the sample to Cbl C-positive and/or Cbl C-negative reference levels of the metabolites.

Optionally, diagnosis of Cbl C in a subject can be made or facilitated by analyzing the level(s) of one or more currently used diagnostic metabolites in combination with the foregoing novel metabolic biomarkers. Currently used diagnostic metabolites indicative of Cbl C include methylmalonic acid, homocysteine, 2-methylcitrate, and cystathionine. Accordingly, methods of diagnosing or facilitating diagnosis of Cbl C may further include analyzing a biological sample obtained from the subject to determine the level of one or more additional metabolites including methylmalonic acid, homocysteine, 2-methylcitrate, cystathionine, and combinations thereof.

Citrullinemia

Novel metabolic biomarkers indicative of Citrullinemia include homocitrulline, 3-ureidopropionate, N-acetylalanine, phenylacetylglutamine, phenylacetate, 4-ureidobutyrate, N-carbamoylaspartate, guanidinoacetate, urea, 4-guanidinobutanoate, N-acetylarginine, hippurate, ornithine, 2-methylhippurate, phenylacetylglycine, 4-phenylbutyrate, creatinine, orotate, 3,4-dihydroxyphenylacetate, homoarginine, guanidinosuccinate, gamma-glutamylphenylalanine, gamma-glutamylisoleucine, tryptophan, 1,5-anhydroglucitol (1,5-AG), N-acetyl-citrulline (previously X-12386), X-19684, X-12681, X-20598, X-18446, X-20588, and combinations thereof. Accordingly, diagnosis of Citrullinemia in a subject can be made or facilitated by analyzing a biological sample obtained from the subject to determine the level of one or more metabolites including homocitrulline, 3-ureidopropionate, N-acetylalanine, phenylacetylglutamine, phenylacetate, 4-ureidobutyrate, N-carbamoylaspartate, guanidinoacetate, urea, 4-guanidinobutanoate, N-acetylarginine, hippurate, ornithine, 2-methylhippurate, phenylacetylglycine, 4-phenylbutyrate, creatinine, orotate, 3,4-dihydroxyphenylacetate, homoarginine, guanidinosuccinate, gamma-glutamylphenylalanine, gamma-glutamylisoleucine, tryptophan, 1,5-anhydroglucitol (1,5-AG), N-acetyl-citrulline (previously X-12386), X-19684, X-12681, X-20598, X-18446, and X-20588, and comparing the level(s) of the metabolites in the sample to Citrullinemia-positive and/or Citrullinemia-negative reference levels of the metabolites.

Optionally, diagnosis of Citrullinemia in a subject can be made or facilitated by analyzing the level(s) of one or more currently used diagnostic metabolites in combination with the foregoing novel metabolic biomarkers. Currently used diagnostic metabolites indicative of Citrullinemia include citrulline and argininosuccinic acid. Accordingly, methods of diagnosing or facilitating diagnosis of Citrullinemia may further include analyzing a biological sample obtained from the subject to determine the level of one or more additional metabolites including citrulline, argininosuccinic acid, and combinations thereof.

In one embodiment, one or more biomarkers selected from the group consisting of 3-ureidopropionate, homocitrulline, citrulline, and N-acetyl-citrulline (previously X-12386) may be used in diagnosing or aiding in the diagnosis of Citrullinemia in a subject.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of citrullinemia in a subject can be made or facilitated by analyzing a biological sample derived from urine from the subject to determine the level of one or more metabolites including any of 4-ureidobutyrate, N-carbamoylaspartate, guanidinoacetate, 4-guanidinobutanoate, N-acetylarginine, hippurate, ornithine, 2-methylhippurate, 4-phenylbutyrate, creatinine, orotate, 3,4-dihydroxyphenylacetate, and combinations thereof.

Carnitine Palmitoyltransferase 2 Deficiency (CPTII)

Novel metabolic biomarkers indicative of Carnitine palmitoyltransferase 2 deficiency (CPTII) include N-octanoylglycine (C8 ester), sebacate (C8), caprate (C10), caprylate (C8), octanoylcarnitine, hexanoylcarnitine, and combinations thereof. Accordingly, diagnosis of CPTII in a subject can be made or facilitated by analyzing a biological sample obtained from the subject to determine the level of one or more metabolites including N-octanoylglycine (C8 ester), sebacate (C8), caprate (C10), caprylate (C8), octanoylcarnitine, and hexanoylcarnitine, and comparing the level(s) of the metabolites in the sample to CPTII-positive and/or CPTII-negative reference levels of the metabolites.

Optionally, diagnosis of CPTII in a subject can be made or facilitated by analyzing the level(s) of one or more currently used diagnostic metabolites in combination with the foregoing novel metabolic biomarkers. Currently used diagnostic metabolites indicative of CPTII include carnitine and acylcarnitines. Accordingly, methods of diagnosing or facilitating diagnosis of CPTII may further include analyzing a biological sample obtained from the subject to determine the level of one or more additional metabolites including carnitine, acylcarnitines, and combinations thereof.

In one embodiment, one or more biomarkers selected from the group consisting of sebacate (decanedioate), decanoylcarnitine, caprylate, caprate, octanoylcarnitine, hexanoylcarnitine, and N-octanoylglycine may be used in diagnosing or aiding in the diagnosis of CPTII in a subject.

Cystinosis

Novel metabolic biomarkers indicative of Cystinosis include cys-gly (oxidized), 1,5-anhydroglucitol (1,5-AG), glycocholenate sulfate, 4-acetylphenol sulfate, cresol glucuronide (previously X-11837), erythritol, vanillylmandelate, N2,N2-dimethyl-guanosine, phenylacetylglutamine, X-12846, X-12303, X-19145, X-12216, X-17717, X-15667, X-12119, X-11315, X-12731, X-12705, X-17685, X-18371, and combinations thereof. Accordingly, diagnosis of Cystinosis in a subject can be made or facilitated by analyzing a biological sample obtained from the subject to determine the level of one or more metabolites including cys-gly (oxidized), 1,5-anhydroglucitol (1,5-AG), glycocholenate sulfate, 4-acetylphenol sulfate, cresol glucuronide (previously X-11837), erythritol, vanillylmandelate, N2,N2-dimethylguanosine, phenylacetylglutamine, X-12846, X-12303, X-19145, X-12216, X-17717, X-15667, X-12119, X-11315, X-12731, X-12705, X-17685, and X-18371, and comparing the level(s) of the metabolites in the sample to Cystinosis-positive and/or Cystinosis-negative reference levels of the metabolites.

Optionally, diagnosis of Cystinosis in a subject can be made or facilitated by analyzing the level(s) of one or more currently used diagnostic metabolites in combination with the foregoing novel metabolic biomarkers. Currently used diagnostic metabolites indicative of Cystinosis include cystine. Accordingly, methods of diagnosing or facilitating diagnosis of Cystinosis may further include analyzing a biological sample obtained from the subject to determine the level of one or more additional metabolites including cystine.

Dihydropyrimidine Dehydrogenase Deficiency

Novel metabolic biomarkers indicative of dihydropyrimidine dehydrogenase deficiency include cytidine, 5,6-dihydrouracil, 4-ureidobutyrate, 3-ureidopropionate, uridine, orotate, N-carbamoylaspartate, and combinations thereof. Accordingly, diagnosis of dihydropyrimidine dehydrogenase deficiency in a subject can be made or facilitated by analyzing a biological sample obtained from the subject to determine the level of one or more metabolites including cytidine, 5,6-dihydrouracil, 4-ureidobutyrate, 3-ureidopropionate, uridine, orotate, and N-carbamoylaspartate, and comparing the level(s) of the metabolites in the sample to dihydropyrimidine dehydrogenase deficiency-positive and/or dihydropyrimidine dehydrogenase deficiency-negative reference levels of the metabolites.

Optionally, diagnosis of dihydropyrimidine dehydrogenase deficiency in a subject can be made or facilitated by analyzing the level(s) of one or more currently used diagnostic metabolites in combination with the foregoing novel metabolic biomarkers. Currently used diagnostic metabolites indicative of dihydropyrimidine dehydrogenase deficiency include uracil and thymine. Accordingly, methods of diagnosing or facilitating diagnosis of dihydropyrimidine dehydrogenase deficiency may further include analyzing a biological sample obtained from the subject to determine the level of one or more additional metabolites including uracil, thymine, and combinations thereof.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of dihydropyrimidine dehydrogenase deficiency in a subject can be made or facilitated by analyzing a biological sample derived from urine from the subject.

Glutaric Aciduria Type 1

Novel metabolic biomarkers indicative of glutaric aciduria type 1 include 3-methylglutarylcarnitine, 2-aminoadipate, X-12364, X-15674, and combinations thereof. Accordingly, diagnosis of glutaric aciduria type 1 in a subject can be made or facilitated by analyzing a biological sample obtained from the subject to determine the level of one or more metabolites including 3-methylglutarylcarnitine, 2-aminoadipate, X-12364 and X-15674, and comparing the level(s) of the metabolites in the sample to glutaric aciduria type 1-positive and/or glutaric aciduria type 1-negative reference levels of the metabolites.

Optionally, diagnosis of glutaric aciduria type 1 in a subject can be made or facilitated by analyzing the level(s) of one or more currently used diagnostic metabolites in combination with the foregoing novel metabolic biomarkers. Currently used diagnostic metabolites indicative of glutaric aciduria type 1 include glutarate (pentanedioate), glutarylcarnitine (C5), 3-hydroxyglutarate, and glutaconate. Accordingly, methods of diagnosing or facilitating diagnosis of glutaric aciduria type 1 may further include analyzing a biological sample obtained from the subject to determine the level of one or more additional metabolites including glutarate (pentanedioate), glutarylcarnitine (C5), 3-hydroxyglutarate, glutaconate, and combinations thereof.

In one embodiment, one or more biomarkers selected from the group consisting of glutarylcarnitine and glutarate (pentanedioate) may be used in diagnosing or aiding in the diagnosis of glutaric aciduria type 1 in a subject.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of glutaric aciduria type 1 in a subject can be made or facilitated by analyzing a biological sample derived from urine from the subject to determine the level of one or more metabolites including one or more of 3-methylglutarylcarnitine, 2-aminoadipate, and combinations thereof.

Guanidinoacetate Methyl Transferase (GAMT) Deficiency

Novel metabolic biomarkers indicative of guanidinoacetate methyl transferase deficiency include creatine, 3-(4-hydroxyphenyl)lactate, 1,3-dipalmitoylglycerol, guanidinoacetate, creatinine, cysteine s-sulfate, X-19602, X-12906, X-13007, X-10458, and combinations thereof. Accordingly, diagnosis of guanidinoacetate methyl transferase deficiency in a subject can be made or facilitated by analyzing a biological sample obtained from the subject to determine the level of one or more metabolites including creatine, 3-(4-hydroxyphenyl)lactate, 1,3-dipalmitoylglycerol, guanidinoacetate, creatinine, cysteine s-sulfate, X-19602, X-12906, X-13007, X-10458 and comparing the level(s) of the metabolites in the sample to guanidinoacetate methyl transferase deficiency-positive and/or guanidinoacetate methyl transferase deficiency-negative reference levels of the metabolites. As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of guanidinoacetate methyl transferase deficiency in a subject can be made or facilitated by analyzing a biological sample derived from urine from the subject to determine the level of one or more metabolites including guanidinoacetate.

3-Hydroxy-3-Methylglutaric Aciduria (HMG CoA Lyase Deficiency)

Novel metabolic biomarkers indicative of 3-hydroxy-3-methylglutaric aciduria (HMG CoA Lyase deficiency) include beta-hydroxyisovalerate, beta-hydroxyisovaleroylcarnitine, glutarylcarnitine (C5), arginylproline, 1-stearoylglycerophosphoethanolamine, o-cresol sulfate, 3-methylcrotonylglycine, adipate, glutarate (pentanedioate), octadecanedioate (C18), hexadecanedioate (C16), tetradecanedioate (C14), dodecanedioate (C12), isovalerate, acetylcarnitine, palmitoylcarnitine, hexanoylcarnitine, myristoylcarnitine, hexenedioylcarnitine (previously X-17001), X-17715, X-12741, X-16134, X-10593, X-12688, and combinations thereof. Accordingly, diagnosis of HMG CoA Lyase deficiency in a subject can be made or facilitated by analyzing a biological sample obtained from the subject to determine the level of one or more metabolites including beta-hydroxyisovalerate, beta-hydroxyisovaleroylcarnitine, glutarylcarnitine (C5), arginylproline, 1-stearoylglycerophosphoethanolamine, o-cresol sulfate, 3-methylcrotonylglycine, adipate, glutarate (pentanedioate), octadecanedioate (C18), hexadecanedioate (C16), tetradecanedioate (C14), dodecanedioate (C12), isovalerate, acetylcarnitine, palmitoylcarnitine, hexanoylcarnitine, myristoylcarnitine, hexenedioylcarnitine (previously X-17001), X-17715, X-12741, X-16134, X-10593, and X-12688, and comparing the level(s) of the metabolites in the sample to HMG CoA Lyase deficiency-positive and/or HMG CoA Lyase deficiency-negative reference levels of the metabolites.

Optionally, diagnosis of HMG CoA Lyase deficiency in a subject can be made or facilitated by analyzing the level(s) of one or more currently used diagnostic metabolites in combination with the foregoing novel metabolic biomarkers. Currently used diagnostic metabolites indicative of HMG CoA Lyase deficiency include 3-methylglutarylcarnitine (C6), 3-hydroxy-3-methyl-glutarate, 3-methylglutarate, and 3-hydroxyisovalerate. Accordingly, methods of diagnosing or facilitating diagnosis of HMG CoA Lyase deficiency may further include analyzing a biological sample obtained from the subject to determine the level of one or more additional metabolites including 3-methylglutarylcarnitine (C6), 3-hydroxy-3-methyl-glutarate, 3-methylglutarate, and 3-hydroxyisovalerate, and combinations thereof.

In one embodiment, one or more biomarkers selected from the group consisting of glutarylcarnitine, β-hydroxyisovalerylcarnitine, β-hydroxyisovalerate, 3-methylglutarylcarnitine, glutarate, hexadecanedioate, tetradecanedioate, octadecanedioate, dodecanedioate, 3-methylcrotonylglycine, 3-methylglutarylcarnitine, and adipate may be used in diagnosing or aiding in the diagnosis of HMG CoA Lyase deficiency in a subject.

Holocarboxylase

Novel metabolic biomarkers indicative of holocarboxylase include 3-methylcrotonylglycine, beta-hydroxyisovaleroylcarnitine (C5), propionylglycine (C3), 3-hydroxypropanoate, tigloylglycine, succinylcarnitine, 2-methylcitrate, 3-hydroxyisobutyrate, lactate, 3-hydroxy-2-ethylpropionate, isobutyrylglycine, alpha-hydroxyisovaleroyl carnitine, 3-methyl-2-oxobutyrate, 3-methyl-2-oxovalerate, 3-hydroxy-2-methylbutyrate, 4-methyl-2-oxopentanoate, malonylcarnitine, alpha-hydroxyisovalerate, 2-hydroxyl-3-methylvalerate, propionylcarnitine, tiglyl carnitine, isovalerylcarnitine, hydroxybutyrylcarnitine, succinate, 2-methylmalonylcarnitine, alpha-hydroxyisocaproate, biotin, and combinations thereof. Accordingly, diagnosis of holocarboxylase in a subject can be made or facilitated by analyzing a biological sample obtained from the subject to determine the level of one or more metabolites including 3-methylcrotonylglycine, beta-hydroxyisovaleroylcarnitine (C5), propionylglycine (C3), 3-hydroxypropanoate, tigloylglycine, succinylcarnitine, 2-methylcitrate, 3-hydroxyisobutyrate, lactate, 3-hydroxy-2-ethylpropionate, isobutyrylglycine, alpha-hydroxyisovaleroyl carnitine, 3-methyl-2-oxobutyrate, 3-methyl-2-oxovalerate, 3-hydroxy-2-methylbutyrate, 4-methyl-2-oxopentanoate, malonylcarnitine, alpha-hydroxyisovalerate, 2-hydroxyl-3-methylvalerate, propionylcarnitine, tiglyl carnitine, isovalerylcarnitine, hydroxybutyrylcarnitine, succinate, 2-methylmalonylcarnitine, and alpha-hydroxyisocaproate, biotin, and comparing the level(s) of the metabolites in the sample to holocarboxylase-positive and/or holocarboxylase-negative reference levels of the metabolites.

Optionally, diagnosis of holocarboxylase in a subject can be made or facilitated by analyzing the level(s) of one or more currently used diagnostic metabolites in combination with the foregoing novel metabolic biomarkers. Currently used diagnostic metabolites indicative of holocarboxylase include beta-hydroxyisovalerate. Accordingly, methods of diagnosing or facilitating diagnosis of holocarboxylase may further include analyzing a biological sample obtained from the subject to determine the level of one or more additional metabolites including beta-hydroxyisovalerate.

In one embodiment, one or more biomarkers selected from the group consisting of β-hydroxyisovalerylcarnitine, β-hydroxyisovalerate, 3-hydroxypropanoate, propionylglycine, tigloylglycine, 3-methylcrotonylglycine, succinylcarnitine may be used in diagnosing or aiding in the diagnosis of holocarboxylase in a subject.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of holocarboxylase in a subject can be made or facilitated by analyzing a biological sample derived from urine from the subject to determine the level of one or more metabolites including any of 2-methylcitrate, 3-hydroxyisobutyrate, lactate, 3-hydroxy-2-ethylpropionate, isobutyrylglycine, alpha-hydroxyisovaleroyl carnitine, 3-methyl-2-oxobutyrate, 3-methyl-2-oxovalerate, 3-hydroxy-2-methylbutyrate, 4-methyl-2-oxopentanoate, malonylcarnitine, alpha-hydroxyisovalerate, 2-hydroxyl-3-methylvalerate, propionylcarnitine, tiglyl carnitine, isovalerylcarnitine, hydroxybutyrylcarnitine, succinate, 2-methylmalonylcarnitine, alpha-hydroxyisocaproate, and combinations thereof.

Homocystinuria

Novel metabolic biomarkers indicative of Homocystinuriainclude gamma-glutamylmethionine, 5-methylthioadenosine (MTA), S-adenosylhomocysteine (SAH), N1-methyladenosine, glycylproline, 1-eicosenoylglycerophosphoethanolamine (20:1n9), 1-methylnicotinamide, N-acetyl-aspartyl-glutamate (NAAG), pyridoxal, 2-hydroxyisobutyrate, acisoga, carnosine, 3-methoxytyrosine, 2-hydroxydecanoate, delta-tocopherol, alpha-CEHC (2,5,7,8-tetramethyl-2-(2'-carboxyethyl)-6-hydroxychroman) sulfate (previously X-12435), N-acetyltryptophan, adenine, cortisol, X-19350, X-18965, X-15649, X-17303, X-18897, X-11564, X-18891, X-12748, X-18918, X-18905, X-18606, X-16574, X-18895, X-18907, X-19455, X-18909, X-19574, X-12110, X-20676, X-11360, X-18920, and combinations thereof. Accordingly, diagnosis of Homocystinuria in a subject can be made or facilitated by analyzing a biological sample obtained from the subject to determine the level of one or more metabolites including gamma-glutamylmethionine, 5-methylthioadenosine (MTA), S-adenosylhomocysteine (SAH), N1-methyladenosine, glycylproline, 1-eicosenoylglycerophosphoethanolamine (20:1n9), 1-methylnicotinamide, N-acetyl-aspartyl-glutamate (NAAG), pyridoxal, 2-hydroxyisobutyrate, acisoga, carnosine, 3-methoxytyrosine, 2-hydroxydecanoate, delta-tocopherol, alpha-CEHC (2,5,7,8-tetramethyl-2-(2'-carboxyethyl)-6-hydroxychroman) sulfate (previously X-12435), N-acetyltryptophan, adenine, cortisol, X-19350, X-18965, X-15649, X-17303, X-18897, X-11564, X-18891, X-12748, X-18918, X-18905, X-18606, X-16574, X-18895, X-18907, X-19455, X-18909, X-19574, X-12110, X-20676, X-11360, and X-18920, and comparing the level(s) of the metabolites in the sample to Homocystinuria-positive and/or Homocystinuria-negative reference levels of the metabolites.

Optionally, diagnosis of Homocystinuria in a subject can be made or facilitated by analyzing the level(s) of one or more currently used diagnostic metabolites in combination with the foregoing novel metabolic biomarkers. Currently used diagnostic metabolites indicative of Homocystinuria include homocysteine, cysteine, methionine, and other amino acids. Accordingly, methods of diagnosing or facilitating diagnosis of Homocystinuria may further include analyzing a biological sample obtained from the subject to determine the level of one or more additional metabolites including homocysteine, cysteine, methionine, other amino acids, and combinations thereof.

In one embodiment, one or more biomarkers selected from the group consisting of methionine, S-adenosylhomocystein (SAH), γ-glutamylmethionine, 5-methylthioadenosine (MTA), and N1-methyladenosine may be used in diagnosing or aiding in the diagnosis of Homocystinuria in a subject.

Isovaleric Acidemia

Novel metabolic biomarkers indicative of isovaleric acidemia include isovalerylglycine, isovalerylcarnitine (C5), valerate, valerylcarnitine, beta-hydroxyisovalerate, phenylcarnitine, beta-hydroxybutyrate, 3-methylcrotonylglycine, alpha-hydroxybutyrate, X-16577, X-14331, and combinations thereof. Accordingly, diagnosis of isovaleric acidemia in a subject can be made or facilitated by analyzing a biological sample obtained from the subject to determine the level of one or more metabolites including isovalerylglycine, isovalerylcarnitine (C5), valerate, valerylcarnitine, beta-hydroxyisovalerate, phenylcarnitine, beta-hydroxybutyrate, 3-methylcrotonylglycine, alpha-hydroxybutyrate, X-16577, and X-14331, and comparing the level(s) of the metabolites in the sample to isovaleric acidemia-positive and/or isovaleric acidemia-negative reference levels of the metabolites.

Optionally, diagnosis of isovaleric acidemia in a subject can be made or facilitated by analyzing the level(s) of one or more currently used diagnostic metabolites in combination with the foregoing novel metabolic biomarkers. Currently used diagnostic metabolites indicative of isovaleric acidemia include isovalerate (C5). Accordingly, methods of diagnosing or facilitating diagnosis of isovaleric acidemia may further include analyzing a biological sample obtained from the subject to determine the level of one or more additional metabolites including isovalerate (C5).

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In one embodiment, one or more biomarkers selected from the group consisting of isovalerylglycine, isovalerylcarnitine, isovalerate, lactate, 3-methylglutaroylcarnitine, glutaroylcarnitine, and beta-hydroxyisovalerate may be used in diagnosing or aiding in the diagnosis of isovaleric academia in a subject.

In some embodiments, a weighted combination of results from one or more aberrant small molecules measured in a sample in the form of a disease-specific composite score may be employed to aid in the diagnosis of isovaleric academia in a subject. In one embodiment, the weighted combination, or composite score, includes results regarding the metabolites 3-hydroxyisovalerate, isovalerylcarnitine, and isovalerate.

In some embodiments, the diagnosis of isovaleric acidemia in a subject can be made or facilitated by analyzing a biological sample derived from urine from the subject to determine the level of one or more metabolites including beta-hydroxybutyrate and alpha-hydroxybutyrate.

Lysinuric Protein Intolerance

Novel metabolic biomarkers indicative of Lysinuric protein intolerance include asparagine, N6-acetyllysine, glutamine, N2-acetyllysine, N-acetylarginine, gamma-glutamylglutamine, proline, S-methylcysteine, 2-hydroxydecanoate, 1-methylimidazoleacetate, 2-aminoheptanoate, 3-methyl-glutarylcarnitine, glutarylcarnitine, N6-trimethyllysine, 5-(galactosylhydroxy)-L-lysine, X-15636, 17654, X-12193, X-12425, and combinations thereof. Accordingly, diagnosis of Lysinuric protein intolerance in a subject can be made or facilitated by analyzing a biological sample obtained from the subject to determine the level of one or more metabolites including asparagine, N6-acetyllysine, glutamine, N2-acetyllysine, N-acetylarginine, gamma-glutamylglutamine, proline, S-methylcysteine, 2-hydroxydecanoate, 1-methylimidazoleacetate, -aminoheptanoate, 3-methylglutarylcarnitine, glutarylcarnitine, N6-trimethyllysine, 5-(galactosylhydroxy)-L-lysine, X-15636, 17654, X-12193, and X-12425, and comparing the level(s) of the metabolites in the sample to Lysinuric protein intolerance-positive and/or Lysinuric protein intolerance-negative reference levels of the metabolites.

Optionally, diagnosis of Lysinuric protein intolerance in a subject can be made or facilitated by analyzing the level(s) of one or more currently used diagnostic metabolites in combination with the foregoing novel metabolic biomarkers. Currently used diagnostic metabolites indicative of Lysinuric protein intolerance include ornithine, arginine, and lysine. Accordingly, methods of diagnosing or facilitating diagnosis of Lysinuric protein intolerance may further include analyzing a biological sample obtained from the subject to determine the level of one or more additional metabolites including ornithine, arginine, lysine, and combinations thereof.

In one embodiment, one or more biomarkers selected from the group consisting of N6-acetyllysine, glutamine, asparagine, arginine, ornithine, and lysine may be used in diagnosing or aiding in the diagnosis of Lysinuric protein intolerance in a subject.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of Lysinuric protein intolerance in a subject can be made or facilitated by analyzing a biological sample derived from urine from the subject to determine the level of one or more metabolites including any of 2-aminoheptanoate, 3-methylglutarylcarnitine, glutarylcarnitine, N6-trimethyllysine, 5-(galactosylhydroxy)-L-lysine, and combinations thereof.

Medium Chain Acyl CoA Dehydrogenase Deficiency

Novel metabolic biomarkers indicative of medium chain acyl CoA dehydrogenase deficiency include N-octanoylglycine, caproate (6:0), caprylate (8:0), heptanoate (7:0), dodecanedioate, O-methylcatechol sulfate, 1-stearoylglycerophosphocholine (18:0), 1-margaroylglycerophosphocholine (17:0), 1-docosapentaenoylglycerophosphocholine (22:5n3), N-palmitoyltaurine, pelargonate (9:0), deoxycarnitine, heptanoyl glycine, 3-methyladipate, 2-hydroxyglutarate, alpha-CEHC (2,5,7,8-tetramethyl-2-(2'-carboxyethyl)-6-hydroxychroman) sulfate (previously X-12435), methylhexanoylglutamine (previously X-12637), X-11521 (probable empirical formula: $C_{15}H_{27}NO_4$ and structure: 2-octenoylcarnitine), X-15646, X-12802, X-11478, X-11440 (probable hydroxypregnen-diol disulfate or pregnanolone-diol disulfate), X-15486, X-18913, X-13837, X-18946, X-11861, X-18888, X-18922, X-17438, X-18916, X-16674, X-12824, and combinations thereof. Accordingly, diagnosis of medium chain acyl CoA dehydrogenase deficiency in a subject can be made or facilitated by analyzing a biological sample obtained from the subject to determine the level of one or more metabolites including N-octanoylglycine, caproate (6:0), caprylate (8:0), heptanoate (7:0), dodecanedioate, O-methylcatechol sulfate, 1-stearoylglycerophosphocholine (18:0), 1-margaroylglycerophosphocholine (17:0), 1-docosapentaenoylglycerophosphocholine (22:5n3), N-palmitoyltaurine, pelargonate (9:0), deoxycarnitine, heptanoyl glycine, 3-methyladipate, 2-hydroxyglutarate, alpha-CEHC (2,5,7,8-tetramethyl-2-(2'-carboxyethyl)-6-hydroxychroman) sulfate (previously X-12435), methylhexanoylglutamine (previously X-12637), X-11521 (probable empirical formula: $C_{15}H_{27}NO_4$ and structure: 2-octenoylcarnitine), X-15646, X-12802, X-11478, X-11440 (probable hydroxypregnen-diol disulfate or pregnanolone-diol disulfate), X-15486, X-18913, X-13837, X-18946, X-11861, X-18888, X-18922, X-17438, X-18916, X-16674, and X-12824, and comparing the level(s) of the metabolites in the sample to medium chain acyl CoA dehydrogenase deficiency-positive and/or medium chain acyl CoA dehydrogenase deficiency-negative reference levels of the metabolites.

Optionally, diagnosis of medium chain acyl CoA dehydrogenase deficiency in a subject can be made or facilitated by analyzing the level(s) of one or more currently used diagnostic metabolites in combination with the foregoing novel metabolic biomarkers. Currently used diagnostic metabolites indicative of medium chain acyl CoA dehydrogenase deficiency include acylcarnitines, carnitine, 4-octenedioate, adipate, and organic acids (including e.g., hexanoylglycine (C6), octanoylcarnitine (C8), hexanoylcarnitine (C6), cis-4-decenoyl carnitine, 5-hydroxyhexanoate, suberate (octanedioate), sebacate (decanedioate), decanoylcarnitine, 3-hydroxydecanoate). Accordingly, methods of diagnosing or facilitating diagnosis of medium chain acyl CoA dehydrogenase deficiency may further include analyzing a biological sample obtained from the subject to determine the level of one or more additional metabolites including acylcarnitines, carnitine, 4-octenedioate, adipate, organic acids, and combinations thereof.

In one embodiment, one or more biomarkers selected from the group consisting of caproate, hexanoylglycine, octanoycarnitine, hexanoycarnitine, N-octanoyglycine, cis-4-decenoyl carnitine, deoxycarnitine, caprylate, 5-hydroxyhexanoate, decanoylcarnitine, suberate (octanedioate), N-palmitoyltaurine, and heptanoate may be used in diagnosing or aiding in the diagnosis of medium chain acyl CoA dehydrogenase deficiency in a subject.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of medium chain acyl CoA dehydrogenase deficiency in a subject can be made or facilitated by analyzing a biological sample derived from urine from the subject to determine the level of one or more metabolites including any of heptanoyl glycine, 3-methyladipate, 2-hydroxyglutarate, and combinations thereof.

Methylmalonic Acidemia

Novel metabolic biomarkers indicative of methylmalonic acidemia include 2-methylmalonyl carnitine, propionylcarnitine (C3), tiglyl carnitine, 2-methylbutyrylcarnitine (C5), 2-methylcitrate, succinylcarnitine, propionylglycine, 3-hydroxypropanoate, valerylcarnitine, isovalerylcarnitine, succinate, tigloylglycine, beta-hydroxyisovaleroylcarnitine, beta-hydroxyisovalerate, isobutyrylcarnitine, 3-hydroxy-2-ethylpropionate, butyrylcarnitine, 3-methylglutarylcarnitine, methylsuccinate, 3-methyl-2-oxovalerate, 3-methyl-2-oxobutyrate, X-12749, X-17564, X-12114, and combinations thereof. Accordingly, diagnosis of methylmalonic acidemia in a subject can be made or facilitated by analyzing a biological sample obtained from the subject to determine the level of one or more metabolites including 2-methylmalonyl carnitine, propionylcarnitine (C3), tiglyl carnitine, 2-methylbutyrylcarnitine (C5), 2-methylcitrate, succinylcarnitine, propionylglycine, 3-hydroxypropanoate, valerylcarnitine, isovalerylcarnitine, succinate, tigloylglycine, beta-hydroxyisovaleroylcarnitine, beta-hydroxyisovalerate, isobutyrylcarnitine, 3-hydroxy-2-ethylpropionate, butyrylcarnitine, 3-methylglutarylcarnitine, methylsuccinate, 3-methyl-2-oxovalerate, 3-methyl-2-oxobutyrate, X-12749, X-17564, and X-12114, and comparing the level(s) of the metabolites in the sample to methylmalonic acidemia-positive and/or methylmalonic acidemia-negative reference levels of the metabolites.

Optionally, diagnosis of methylmalonic acidemia in a subject can be made or facilitated by analyzing the level(s) of one or more currently used diagnostic metabolites in combination with the foregoing novel metabolic biomarkers. Currently used diagnostic metabolites indicative of methylmalonic acidemia include methylmalonate and methylmalonyl CoA. Accordingly, methods of diagnosing or facilitating diagnosis of methylmalonic acidemia may further include analyzing a biological sample obtained from the subject to determine the level of one or more additional metabolites including methylmalonate, methylmalonyl CoA, and combinations thereof.

In one embodiment, one or more biomarkers selected from the group consisting of propionylcarnitine, 2-methylmalonylcarnitine, 2-methylbutyrylcarnitine, valerylcarnitine, propionylglycine, 3-hydroxypropanoate, tigloylglycine, tiglyl carnitine, succinylcarnitine, succinate, isovalerylcarnitine, and 2-methylcitrate may be used in diagnosing or aiding in the diagnosis of methylmalonic academia in a subject.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of methylmalonic acidemia in a subject can be made or facilitated by analyzing a biological sample derived from urine from the subject to determine the level of one or more metabolites including any of 3-methylglutarylcarnitine, methylsuccinate, and combinations thereof.

Molybdenum Cofactor or Sulfite Oxidase Deficiency

Novel metabolic biomarkers indicative of molybdenum cofactor or sulfite oxidase deficiency include 5-HETE, leukotriene B4, 13-HODE+9-HODE, 12-HETE, urate, and combinations thereof. Accordingly, diagnosis of molybdenum cofactor or sulfite oxidase deficiency in a subject can be made or facilitated by analyzing a biological sample obtained from the subject to determine the level of one or more metabolites including 5-HETE, leukotriene B4, 13-HODE+9-HODE, 12-HETE, and urate, and comparing the level(s) of the metabolites in the sample to molybdenum cofactor or sulfite oxidase deficiency-positive and/or molybdenum cofactor or sulfite oxidase deficiency-negative reference levels of the metabolites.

Optionally, diagnosis of molybdenum cofactor or sulfite oxidase deficiency in a subject can be made or facilitated by analyzing the level(s) of one or more currently used diagnostic metabolites in combination with the foregoing novel metabolic biomarkers. Currently used diagnostic metabolites indicative of molybdenum cofactor or sulfite oxidase deficiency include xanthine, S-sulfocysteine, and thiosulfate. Accordingly, methods of diagnosing or facilitating diagnosis of molybdenum cofactor or sulfite oxidase deficiency may further include analyzing a biological sample obtained from the subject to determine the level of one or more additional metabolites including xanthine, S-sulfocysteine, thiosulfate, and combinations thereof.

In one embodiment, one or more biomarkers selected from the group consisting of 5-HETE, leukotriene B4, 13-HODE+9-HODE, and 12-HETE may be used in diagnosing or aiding in the diagnosis of molybdenum cofactor or sulfite oxidase deficiency in a subject.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of molybdenum cofactor or sulfite oxidase deficiency in a subject can be made or facilitated by analyzing a biological sample derived from urine from the subject to determine the level of one or more metabolites including any of urate, xanthine, S-sulfocysteine, and combinations thereof.

Maple Syrup Urine Disease

Novel metabolic biomarkers indicative of Maple syrup urine disease include 2-hydroxy-3-methylvalerate, alpha-hydroxyisovalerate, isovalerylcarnitine, 2-aminoheptanoate, 4-methyl-2-oxopentanoate, 1-linolenoylglycerophosphocholine (18:3n3), 2-linolenoylglycerophosphocholine (18:3n3), 1-myristoylglycerophosphocholine (14:0), 2-myristoylglycerophosphocholine, 5alpha-androstan-3alpha, 17beta-diol disulfate, 3-methyl-2-oxobutyrate, isovalerate, isobutyrylcarnitine, 3-hydroxyisobutyrate, 2-methylbutyrylcarnitine, beta-hydroxyisovaleroylcarnitine, allo-isoleucine, 3-methyl-2-oxovalerate, beta-hydroxyisovalerate, succinate, acetylcarnitine, 2-methylcitrate, tigloylglycine, tiglyl carnitine, hydroxybutyrylcarnitine, alpha-hydroxyisocaproate, X-13581, X-17690, X-13689 (glucuronide conjugate), and combinations thereof. Accordingly, diagnosis of Maple syrup urine disease in a subject can be made or facilitated by analyzing a biological sample obtained from the subject to determine the level of one or more metabolites including 2-hydroxy-3-methylvalerate, alpha-hydroxyisovalerate, isovalerylcarnitine, 2-aminoheptanoate, 4-methyl-2-oxopentanoate, 1-linolenoylglycerophosphocholine (18:3n3), 2-linolenoylglycerophosphocholine(18:3n3), 1-myristoylglycerophosphocholine (14:0), 2-myristoylglycerophosphocholine, 5alpha-androstan-3alpha, 17beta-diol disulfate, 3-methyl-2-oxobutyrate, isovalerate, isobutyrylcarnitine, 3-hydroxyisobutyrate, 2-methylbutyrylcarnitine, beta-hydroxyisovaleroylcarnitine, allo-isoleucine, 3-methyl-2-oxovalerate, beta-hydroxyisovalerate, succinate, acetylcarnitine, 2-methylcitrate, tigloylglycine, tiglyl carnitine, hydroxybutyrylcarnitine, alpha-hydroxyisocaproate, X-13581, X-17690, and X-13689 (glucuronide conjugate), and comparing the level(s) of the metabolites in the sample to Maple syrup urine disease-positive and/or Maple syrup urine disease-negative reference levels of the metabolites.

Optionally, diagnosis of Maple syrup urine disease in a subject can be made or facilitated by analyzing the level(s) of one or more currently used diagnostic metabolites in combination with the foregoing novel metabolic biomarkers. Currently used diagnostic metabolites indicative of Maple syrup urine disease include leucine, isoleucine, and valine. Accordingly, methods of diagnosing or facilitating diagnosis of Maple syrup urine disease may further include analyzing a biological sample obtained from the subject to determine the level of one or more additional metabolites including leucine, isoleucine, valine, and combinations thereof.

In one embodiment, one or more biomarkers selected from the group consisting of allo-isoleucine, a-hydroxyisovalerate, 2-hydroxy-3-methylvalerate, 4-methyl-2-oxopentanoate, leucine, 3-Methyl-2-Oxovalerate, Isoleucine, Isovalerate, 3-Methyl-2-Oxobutyrate, Valine, 3-hydroxyisobutyrate, isobutyrylcarnitine, isovalerylcarnitine, β-hydroxyisovaleroylcarnitine, and 2-methylbutyrylcarnitine may be used in diagnosing or aiding in the diagnosis of Maple syrup urine disease in a subject.

Ornithine Transcarbamylase Deficiency (OTC Deficiency)

Novel metabolic biomarkers indicative of OTC deficiency include phenylacetylglutamine, stearidonate (18:4n3), 3-ureidopropionate, 2-methylhippurate, 2-hydroxyphenylacetate, phenylcarnitine, hippurate, phenylpropionylglycine, benzoate, methyl-4-hydroxybenzoate, 4-phenylbutyrate, 2-pentanamido-3-phenylpropanoic acid, phenylacetate, phenylacetylglycine, trans-4-hydroxyproline, pro-hydroxy-pro, urea, phenyllactate (PLA), guanidinosuccinate, ornithine, X-20598, X-20588, and combinations thereof. Accordingly, diagnosis of OTC deficiency in a subject can be made or facilitated by analyzing a biological sample obtained from the subject to determine the level of one or more metabolites including phenylacetylglutamine, stearidonate (18:4n3), 3-ureidopropionate, 2-methylhippurate, 2-hydroxyphenylacetate, phenylcarnitine, hippurate, phenylpropionylglycine, benzoate, methyl-4-hydroxybenzoate, 4-phenylbutyrate, 2-pentanamido-3-phenylpropanoic acid, phenylacetate, phenylacetylglycine, trans-4-hydroxyproline, pro-hydroxy-pro, urea, phenyllactate (PLA), guanidinosuccinate, ornithine, X-20598, and X-20588, and comparing the level(s) of the metabolites in the sample to OTC deficiency-positive and/or OTC deficiency-negative reference levels of the metabolites.

Optionally, diagnosis of OTC deficiency in a subject can be made or facilitated by analyzing the level(s) of one or more currently used diagnostic metabolites in combination with the foregoing novel metabolic biomarkers. Currently used diagnostic metabolites indicative of OTC deficiency include orotate, citrulline, and arginine. Accordingly, methods of diagnosing or facilitating diagnosis of OTC deficiency may further include analyzing a biological sample obtained from the subject to determine the level of one or more additional metabolites including orotate, citrulline, arginine, and combinations thereof.

In one embodiment, one or more biomarkers selected from the group consisting of phenylacetylglutamine, phenylcarnitine, phenyulacetate, hippurate, glutamine, phenylacetylglyicne, orotate, creatinine, and urea may be used in diagnosing or aiding in the diagnosis of OTC deficiency in a subject.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of OTC deficiency in a subject can be made or facilitated by analyzing a biological sample derived from urine from the subject to determine the level of one or more metabolites including any of 2-methylhippurate, 2-hydroxyphenylacetate, phenylpropionylglycine, benzoate, methyl-4-hydroxybenzoate, 4-phenylbutyrate, 2-pentanamido-3-phenylpropanoic acid, and combinations thereof.

Propionic Acidemia

Novel metabolic biomarkers indicative of propionic acidemia include propionylglycine (C3), 2-methylcitrate, 3-hydroxypropanoate, propionylcarnitine (C3), 1-pentadecanoylglycerophosphocholine (15:0), tigloylglycine, succinylcarnitine, glutarylcarnitine (C5), 3-methylglutarylcarnitine (C6), tiglylcarnitine, butyrylcarnitine, 2-methylmalonyl carnitine, beta-hydroxyisovalerate, X-12819, and combinations thereof. Accordingly, diagnosis of propionic acidemia in a subject can be made or facilitated by analyzing a biological sample obtained from the subject to determine the level of one or more metabolites including propionylglycine (C3), 2-methylcitrate, 3-hydroxypropanoate, propionylcarnitine (C3), 1-pentadecanoylglycerophosphocholine (15:0), tigloylglycine, succinylcarnitine, glutarylcarnitine (C5), 3-methylglutarylcarnitine (C6), tiglylcarnitine, butyrylcarnitine, 2-methylmalonyl carnitine, beta-hydroxyisovalerate, and X-12819, and comparing the level(s) of the metabolites in the sample to propionic acidemia-positive and/or propionic acidemia-negative reference levels of the metabolites.

Optionally, diagnosis of propionic acidemia in a subject can be made or facilitated by analyzing the level(s) of one or more currently used diagnostic metabolites in combination with the foregoing novel metabolic biomarkers. Currently used diagnostic metabolites indicative of propionic acidemia include propionate. Accordingly, methods of diagnosing or facilitating diagnosis of propionic acidemia may further include analyzing a biological sample obtained from the subject to determine the level of one or more additionalmetabolites including propionate.

In one embodiment, one or more biomarkers selected from the group consisting of 2-methylcitrate, 3-hydroxypropanoate, propionylcarnitine, propionylglycine, tigloylglycine, and succinylcarnitine may be used in diagnosing or aiding in the diagnosis of propionic acidemia in a subject.

Phenylketonuria (PKU)

Novel metabolic biomarkers indicative of PKU include gamma-glutamylphenylalanine, phenyllactate, N-acetylphenylalanine, phenylpyruvate, gamma-glutamyltyrosine, 3-methoxytyrosine, 4-hydroxyphenylpyruvate, p-cresol sulfate, catechol sulfate, phenylacetylglutamine, o-cresol sulfate, phenylacetylglycine, phenylalanine-containing dipeptides (e.g., phenylalanylarginine, valylphenylalanine, histidylphenylalanine, phenylalanylserine, leucylphenylalanine, threonylphenylalanine, phenylalanylalanine, phenylalanylglycine, phenylalanylglutamate, phenylalanylphenylalanine, aspartylphenylalanine, tryptophylphenylalanine, phenylalanylisoleucine, glycylphenylalanine, phenylalanylleucine, phenylalanylaspartate), X-16283, X-15497, and combinations thereof. Accordingly, diagnosis of PKU in a subject can be made or facilitated by analyzing a biological sample obtained from the subject to determine the level of one or more metabolites including gamma-glutamylphenylalanine, phenyllactate, N-acetylphenylalanine, phenylpyruvate, gamma-glutamyltyrosine, 3-methoxytyrosine, 4-hydroxyphenylpyruvate, p-cresol sulfate, catechol sulfate, phenylacetylglutamine, o-cresol sulfate, phenylacetylglycine, phenylalanine-containing dipeptides (e.g., phenylalanylarginine, valylphenylalanine, histidylphenylalanine, phenylalanylserine, leucylphenylalanine, threonylphenylalanine, phenylalanylalanine, phenylalanylglycine, phenylalanylglutamate, phenylalanylphenylalanine, aspartylphenylalanine, tryptophylphenylalanine, phenylalanylisoleucine, glycylphenylalanine, phenylalanylleucine, phenylalanylaspartate), X-16283, and X-15497, and comparing the level(s) of the metabolites in the sample to PKU-positive and/or PKU-negative reference levels of the metabolites.

Optionally, diagnosis of PKU in a subject can be made or facilitated by analyzing the level(s) of one or more currently used diagnostic metabolites in combination with the foregoing novel metabolic biomarkers. Currently used diagnostic metabolites indicative of PKU include phenylalanine. Accordingly, methods of diagnosing or facilitating diagnosis of PKU may further include analyzing a biological sample obtained from the subject to determine the level of one or more additional metabolites including phenylalanine.

In one embodiment, one or more biomarkers selected from the group consisting of phenylalanine, phenyllactate, γ-glutamylphenylalanine, N-acetylphenylalanine, phenylpyruvate, phenylalanine-containing dipeptides, 4-hydroxyphenylpyruvate, 3-methoxytyrosine, cyclo(L-phe-L-pro), γ-glutamyltyrosine, cyclo(L-phe-D-pro), p-cresol sulfate, and catechol sulfate may be used in diagnosing or aiding in the diagnosis of PKU in a subject.

Succinic Semialdehyde Dehydrogenase Deficiency

Novel metabolic biomarkers indicative of succinic semialdehyde dehydrogenase deficiency include succinimide. Accordingly, diagnosis of succinic semialdehyde dehydrogenase deficiency in a subject can be made or facilitated by analyzing a biological sample obtained from the subject to determine the level of one or more metabolites including succinimide, and comparing the level(s) of the metabolites in the sample to succinic semialdehyde dehydrogenase deficiency-positive and/or succinic semialdehyde dehydrogenase deficiency-negative reference levels of the metabolites.

Optionally, diagnosis of succinic semialdehyde dehydrogenase deficiency in a subject can be made or facilitated by analyzing the level(s) of one or more currently used diagnostic metabolites in combination with the foregoing novel metabolic biomarkers. Currently used diagnostic metabolites indicative of succinic semialdehyde dehydrogenase deficiency include gamma-aminobutyrate (GABA). Accordingly, methods of diagnosing or facilitating diagnosis of succinic semialdehyde dehydrogenase deficiency may further include analyzing a biological sample obtained from the subject to determine the level of one or more additional metabolites including gamma-aminobutyrate (GABA).

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of succinic semialdehyde dehydrogenase deficiency in a subject can be made or facilitated by analyzing a biological sample derived from urine from the subject.

Succinyladenosine Lyase Deficiency

Novel metabolic biomarkers indicative of succinyladenosine lyase deficiency include xanthosine, 2'-deoxyguanosine, 2'-deoxyinosine, adenine, and combinations thereof. Accordingly, diagnosis of succinyladenosine lyase deficiency in a subject can be made or facilitated by analyzing a biological sample obtained from the subject to determine the level of one or more metabolites including xanthosine, 2'-deoxyguanosine, 2'-deoxyinosine, and adenine, and comparing the level(s) of the metabolites in the sample to succinyladenosine lyase deficiency-positive and/or succinyladenosine lyase deficiency-negative reference levels of the metabolites.

Optionally, diagnosis of succinyladenosine lyase deficiency in a subject can be made or facilitated by analyzing the level(s) of one or more currently used diagnostic metabolites in combination with the foregoing novel metabolic biomarkers. Currently used diagnostic metabolites indicative of succinyladenosine lyase deficiency include N6-succinyladenosine. Accordingly, methods of diagnosing or facilitating diagnosis of succinyladenosine lyase deficiency may further include analyzing a biological sample obtained from the subject to determine the level of one or more additional metabolites including N6-succinyladenosine.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of succinyladenosine lyase deficiency in a subject can be made or facilitated by analyzing a biological sample derived from urine from the subject.

Thymidine Phosphorylase Deficiency

Novel metabolic biomarkers indicative of Thymidine phosphorylase deficiency include 2'-deoxyuridine; 5,6-dihydrothymine, 5-methyluridine (ribothymidine), hippurate, 2-linoleoylglycerophosphocholine, 4-methylcatechol sulfate, 1-arachidoylglycerophosphocholine (20:0), taurolithocholate 3-sulfate, glycolithocholate sulfate, imidazole propionate, X-13862, X-19330, X-20620, X-12170, and combinations thereof. Accordingly, diagnosis of Thymidine phosphorylase deficiency in a subject can be made or facilitated by analyzing a biological sample obtained from the subject to determine the level of one or more metabolites including 2'-deoxyuridine, 5,6-dihydrothymine, 5-methyluridine (ribothymidine), hippurate, 2-linoleoylglycerophosphocholine, 4-methylcatechol sulfate, 1-arachidoylglycerophosphocholine (20:0), taurolithocholate 3-sulfate, glycolithocholate sulfate, imidazole propionate, X-13862, X-19330, X-20620, and X-12170, and comparing the level(s) of the metabolites in the sample to Thymidine phosphorylase deficiency-positive and/or Thymidine phosphorylase deficiency-negative reference levels of the metabolites.

Optionally, diagnosis of Thymidine phosphorylase deficiency in a subject can be made or facilitated by analyzing the level(s) of one or more currently used diagnostic metabolites in combination with the foregoing novel metabolic biomarkers. Currently used diagnostic metabolites indicative of Thymidine phosphorylase deficiency include thymidine. Accordingly, methods of diagnosing or facilitating diagnosis of Thymidine phosphorylase deficiency may further include analyzing a biological sample obtained from the subject to determine the level of one or more additional metabolites including thymidine.

In one embodiment, one or more biomarkers selected from the group consisting of thymidine, 2'-deoxyuridine, and thymine may be used in diagnosing or aiding in the diagnosis of Thymidine phosphorylase deficiency in a subject.

Trimethylysine Hydroxylase Epsilon Deficiency

Novel metabolic biomarkers indicative of trimethylysine hydroxylase epsilon deficiency include 1-arachidonoylglyercophosphate, X-16574, X-12822, X-15136, and combinations thereof. Accordingly, diagnosis of trimethylysine hydroxylase epsilon deficiency in a subject can be made or facilitated by analyzing a biological sample obtained from the subject to determine the level of one or more metabolites including 1-arachidonoylglyercophosphate, X-16574, X-12822, and X-15136, and comparing the level(s) of the metabolites in the sample to trimethylysine hydroxylase epsilon deficiency-positive and/or trimethylysine hydroxylase epsilon deficiency-negative reference levels of the metabolites.

Optionally, diagnosis of trimethylysine hydroxylase epsilon deficiency in a subject can be made or facilitated by analyzing the level(s) of one or more currently used diagnostic metabolites in combination with the foregoing novel metabolic biomarkers. Currently used diagnostic metabolites indicative of trimethylysine hydroxylase epsilon deficiency include N-6-trimethyllysine. Accordingly, methods of diagnosing or facilitating diagnosis of trimethylysine hydroxylase epsilon deficiency may further include analyzing a biological sample obtained from the subject to determine the level of one or more additional metabolites including N-6-trimethyllysine.

In one embodiment, the biomarker N6-trimethyllysine may be used in diagnosing or aiding in the diagnosis of trimethylysine hydroxylase epsilon deficiency in a subject.

Tyrosinemia

Novel metabolic biomarkers indicative of tyrosinemia include 3-(4-hydroxyphenyl)lactate, 4-hydroxyphenylpyruvate, 3-(3-hydroxyphenyl)propionate, 4-hydroxyphenylacetate, phenyllactate (PLA), X-13581, and combinations thereof. Accordingly, diagnosis of tyrosinemia in a subject can be made or facilitated by analyzing a biological sample obtained from the subject to determine the level of one or more metabolites including 3-(4-hydroxyphenyl)lactate, 4-hydroxyphenylpyruvate, 3-(3-hydroxyphenyl)propionate, 4-hydroxyphenylacetate, phenyllactate (PLA), and X-13581, and comparing the level(s) of the metabolites in the sample to tyrosinemia-positive and/or tyrosinemia-negative reference levels of the metabolites.

Optionally, diagnosis of tyrosinemia in a subject can be made or facilitated by analyzing the level(s) of one or more currently used diagnostic metabolites in combination with the foregoing novel metabolic biomarkers. Currently used diagnostic metabolites indicative of tyrosinemia include tyrosine. Accordingly, methods of diagnosing or facilitating diagnosis of tyrosinemia may further include analyzing a biological sample obtained from the subject to determine the level of one or more additional metabolites including tyrosine.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of tyrosinemia in a subject can be made or facilitated by analyzing a biological sample derived from urine from the subject.

Very Long Chain Acyl CoA Dehydrogenase Deficiency

Novel metabolic biomarkers indicative of very long chain acyl CoA dehydrogenase deficiency include 9-methyluric acid, xylulose, arachidonate (20:4n6), docosahexaenoate (DHA;22:6n3), eicosapentanoic acid (EPA), 5,8-tetradecadienoic acid (previously X-12442), 1-docosahexaenoyl-GPC (22:6; DHA-GPC), X-18739 (probable isomer of 2-tetradecenoylcarnitine), and combinations thereof. Accordingly, diagnosis of very long chain acyl CoA dehydrogenase deficiency in a subject can be made or facilitated by analyzing a biological sample obtained from the subject to determine the level of one or more metabolites including 9-methyluric acid, xylulose, arachidonate (20:4n6), docosahexaenoate (DHA;22:6n3), eicosapentanoic acid (EPA), 5,8-tetradecadienoic acid (previously X-12442), 1-docosahexaenoyl-GPC (22:6; DHA-GPC), and X-18739 (probable isomer of 2-tetradecenoylcarnitine), and comparing the level(s) of the metabolites in the sample to very long chain acyl CoA dehydrogenase deficiency-positive and/or very long chain acyl CoA dehydrogenase deficiency-negative reference levels of the metabolites.

Optionally, diagnosis of very long chain acyl CoA dehydrogenase deficiency in a subject can be made or facilitated by analyzing the level(s) of one or more currently used diagnostic metabolites in combination with the foregoing novel metabolic biomarkers. Currently used diagnostic metabolites indicative of very long chain acyl CoA dehydrogenase deficiency include myristoylcarnitine, stearoylcarnitine (C18), palmitoylcarnitine (C16), oleoylcarnitine (C18), myristoleate (14:1n5), myristoleoylcarnitine, and linoleoylcarnitine. Accordingly, methods of diagnosing or facilitating diagnosis of very long chain acyl CoA dehydrogenase deficiency may further include analyzing a biological sample obtained from the subject to determine the level of one or more additional metabolites including myristoylcarnitine, stearoylcarnitine (C18), palmitoylcarnitine (C16), oleoylcarnitine (C18), myristoleate (14:1n5), myristoleoylcarnitine, linoleoylcarnitine, and combinations thereof.

In one embodiment, one or more biomarkers selected from the group consisting of myristoylcarnitine, myristoleate, stearoylcarnitine, palmitoylcarnitine, laurylcarnitine, eicosapentanenoate, arachidonate, oleoylcarnitine, docosahexaenoate, docosapentaenoate, and X-12442 may be used in diagnosing or aiding in the diagnosis of very long chain acyl CoA dehydrogenase deficiency in a subject.

Xanthinuria

Novel metabolic biomarkers indicative of xanthinuria include hypoxanthine, xanthosine, 2'-deoxyinosine, inosine, N2-methylguanosine, creatinine, and combinations thereof. Accordingly, diagnosis of xanthinuria in a subject can be made or facilitated by analyzing a biological sample obtained from the subject to determine the level of one or more metabolites including hypoxanthine, xanthosine, 2'-deoxyinosine, inosine, N2-methylguanosine, and creatinine, and comparing the level(s) of the metabolites in the sample to xanthinuria-positive and/or xanthinuria-negative reference levels of the metabolites.

Optionally, diagnosis of xanthinuria in a subject can be made or facilitated by analyzing the level(s) of one or more currently used diagnostic metabolites in combination with the foregoing novel metabolic biomarkers. Currently used diagnostic metabolites indicative of xanthinuria include xanthine, urate, and creatine. Accordingly, methods of diagnosing or facilitating diagnosis of xanthinuria may further include analyzing a biological sample obtained from the subject to determine the level of one or more additional metabolites including xanthine, urate, and creatine.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of xanthinuria in a subject can be made or facilitated by analyzing a biological sample derived from urine from the subject.

X-Linked Creatine Transporter

Novel metabolic biomarkers indicative of X-linked creatine transporter include glycylleucine, 2-hydroxyoctanoate, 1,6-anhydroglucose, X-11483, X-18943, X-17422, X-17761, X-17335, and combinations thereof. Accordingly, diagnosis of X-linked creatine transporter in a subject can be made or facilitated by analyzing a biological sample obtained from the subject to determine the level of one or more metabolites including glycylleucine, 2-hydroxyoctanoate, 1,6-anhydroglucose, X-11483, X-18943, X-17422, X-17761, and X-17335, and comparing the level(s) of the metabolites in the sample to X-linked creatine transporter-positive and/or X-linked creatine transporter-negative reference levels of the metabolites.

Optionally, diagnosis of X-linked creatine transporter in a subject can be made or facilitated by analyzing the level(s) of one or more currently used diagnostic metabolites in combination with the foregoing novel metabolic biomarkers. Currently used diagnostic metabolites indicative of X-linked creatine transporter include creatine. Accordingly, methods of diagnosing or facilitating diagnosis of X-linked creatine transporter may further include analyzing a biological sample obtained from the subject to determine the level of one or more additional metabolites including creatine.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of X-linked creatine transporter in a subject can be made or facilitated by analyzing a biological sample derived from urine from the subject.

Sarcosinemia

Novel metabolic biomarkers indicative of Sarcosinemia include choline, betaine, glycine, dimethylglycine, and combinations thereof. Accordingly, diagnosis of Sarcosinemia in a subject can be made or facilitated by analyzing a biological sample obtained from the subject to determine the level of one or more metabolites including choline, betaine, glycine, and dimethylglycine, and comparing the level(s) of the metabolites in the sample to Sarcosinemia-positive and/or Sarcosinemia-negative reference levels of the metabolites.

Optionally, diagnosis of Sarcosinemia in a subject can be made or facilitated by analyzing the level(s) of one or more currently used diagnostic metabolites in combination with the foregoing novel metabolic biomarkers. Currently used diagnostic metabolites indicative of Sarcosinemia include sarcosine. Accordingly, methods of diagnosing or facilitating diagnosis of Sarcosinemia may further include analyzing a biological sample obtained from the subject to determine the level of one or more additional metabolites including sarcosine.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

Citrate Transporter Deficiency

Novel metabolic biomarkers indicative of Citrate Transporter Deficiency include alpha-ketoglutarate, succinate, fumarate, malate, glutamate, and combinations thereof. Accordingly, diagnosis of Citrate Transporter Deficiency in a subject can be made or facilitated by analyzing a biological sample obtained from the subject to determine the level of one or more metabolites including alpha-ketoglutarate, succinate, fumarate, malate, and glutamate, and comparing the level(s) of the metabolites in the sample to Citrate Transporter Deficiency-positive and/or Citrate Transporter Deficiency-negative reference levels of the metabolites.

Optionally, diagnosis of Citrate Transporter Deficiency in a subject can be made or facilitated by analyzing the level(s) of one or more currently used diagnostic metabolites in combination with the foregoing novel metabolic biomarkers. Currently used diagnostic metabolites indicative of Citrate Transporter Deficiency include citrate. Accordingly, methods of diagnosing or facilitating diagnosis of Citrate Transporter Deficiency may further include analyzing a biological sample obtained from the subject to determine the level of one or more additional metabolites including citrate.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of Citrate Transporter Deficiency in a subject can be made or facilitated by analyzing a biological sample derived from plasma, CSF, or urine from the subject.

Pyruvate Dehydrogenase Deficiency

Diagnosis of Pyruvate Dehydrogenase Deficiency in a subject can be made or facilitated by analyzing the level(s) of one or more currently used diagnostic metabolites. Currently used diagnostic metabolites indicative of Pyruvate Dehydrogenase Deficiency include pyruvate and lactate. Accordingly, methods of diagnosing or facilitating diagnosis of Pyruvate Dehydrogenase Deficiency may further include analyzing a biological sample obtained from the subject to determine the level of one or more additional metabolites including pyruvate and lactate.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

Hyperornithinemia-Homocitrullinemia-Hyperammonemia

Novel metabolic biomarkers indicative of Hyperornithinemia-Homocitrullinemia-Hyperammonemia include uracil, 3-ureidopropionate, orotate, glutamine, N-acetyl-beta-alanine, uridine, N-acetylaspartate (NAA), dimethylarginine (SDMA+ADMA), 5-methylthioadenosine (MTA), beta-alanine, 4-ureidobutyrate, and combinations thereof. Accordingly, diagnosis of Hyperornithinemia-Homocitrullinemia-Hyperammonemia in a subject can be made or facilitated by analyzing a biological sample obtained from the subject to determine the level of one or more metabolites including uracil, 3-ureidopropionate, orotate, glutamine, N-acetyl-beta-alanine, uridine, N-acetylaspartate (NAA), dimethyl-arginine (SDMA+ADMA), 5-methylthioadenosine (MTA), beta-alanine, and 4-ureidobutyrate, and comparing the level (s) of the metabolites in the sample to Hyperornithinemia-Homocitrullinemia-Hyperammonemia-positive and/or Hyperornithinemia-Homocitrullinemia-Hyperammonemia-negative reference levels of the metabolites.

Optionally, diagnosis of Hyperornithinemia-Homocitrullinemia-Hyperammonemia in a subject can be made or facilitated by analyzing the level(s) of one or more currently used diagnostic metabolites in combination with the foregoing novel metabolic biomarkers. Currently used diagnostic metabolites indicative of Hyperornithinemia-Homocitrullinemia-Hyperammonemia include ornithine, homocitrulline, spermine, and spermidine. Accordingly, methods of diagnosing or facilitating diagnosis of Hyperornithinemia-Homocitrullinemia-Hyperammonemia may further include analyzing a biological sample obtained from the subject to determine the level of one or more additional metabolites including ornithine, homocitrulline, spermine, and spermidine.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

Aromatic Amino Acid Decarboxylase (AAAD) Deficiency

Novel metabolic biomarkers indicative of Aromatic Amino Acid Decarboxylase (AAAD) Deficiency include tyrosine, phenylalanine, tryptophan, and combinations thereof. Accordingly, diagnosis of AAAD Deficiency in a subject can be made or facilitated by analyzing a biological sample obtained from the subject to determine the level of one or more metabolites including tyrosine, phenylalanine, and tryptophan, and comparing the level(s) of the metabolites in the sample to AAAD Deficiency-positive and/or AAAD Deficiency-negative reference levels of the metabolites.

Optionally, diagnosis of AAAD Deficiency in a subject can be made or facilitated by analyzing the level(s) of one or more currently used diagnostic metabolites in combination with the foregoing novel metabolic biomarkers. Currently used diagnostic metabolites indicative of AAAD Deficiency include L-dopa, 3-methoxytyrosine, 5-hydroxytryptophan, homovanillate, 5-hydroxyindoleacetate, and vanillactic acid. Accordingly, methods of diagnosing or facilitating diagnosis of AAAD Deficiency may further include analyzing a biological sample obtained from the subject to determine the level of one or more additional metabolites including L-dopa, 3-methoxytyrosine, 5-hydroxytryptophan, homovanillate, 5-hydroxyindoleacetate, and vanillactic acid.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples. In some embodiments, the diagnosis of AAAD Deficiency in a subject can be made or facilitated by analyzing a biological sample derived from plasma from the subject.

Smith-Lemli-Opitz Syndrome

Novel metabolic biomarkers indicative of Smith-Lemli-Opitz Syndrome include cholestanol. Accordingly, diagnosis of Smith-Lemli-Opitz Syndrome in a subject can be made or facilitated by analyzing a biological sample obtained from the subject to determine the level of one or more metabolites including cholestanol and comparing the level(s) of the metabolites in the sample to Smith-Lemli-Opitz Syndrome-positive and/or Smith-Lemli-Opitz Syndrome-negative reference levels of the metabolites.

Optionally, diagnosis of Smith-Lemli-Opitz Syndrome in a subject can be made or facilitated by analyzing the level(s) of one or more currently used diagnostic metabolites in combination with the foregoing novel metabolic biomarkers. Currently used diagnostic metabolites indicative of Smith-Lemli-Opitz Syndrome include 7-dehydrocholesterol. Accordingly, methods of diagnosing or facilitating diagnosis of Smith-Lemli-Opitz Syndrome may further include analyzing a biological sample obtained from the subject to determine the level of one or more additional metabolites including 7-dehydrocholesterol.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

Primary Carnitine Deficiency

Novel metabolic biomarkers indicative of Primary carnitine deficiency include N6-trimethyllysine. Accordingly, diagnosis of Primary carnitine deficiency in a subject can be made or facilitated by analyzing a biological sample obtained from the subject to determine the level of one or more metabolites including N6-trimethyllysine, and comparing the level(s) of the metabolites in the sample to Primary carnitine deficiency-positive and/or Primary carnitine deficiency-negative reference levels of the metabolites.

Optionally, diagnosis of Primary carnitine deficiency in a subject can be made or facilitated by analyzing the level(s) of one or more currently used diagnostic metabolites in combination with the foregoing novel metabolic biomarkers. Currently used diagnostic metabolites indicative of Primary carnitine deficiency include carnitine and acylcarnitine. Accordingly, methods of diagnosing or facilitating diagnosis of Primary carnitine deficiency may further include analyzing a biological sample obtained from the subject to determine the level of one or more additional metabolites including carnitine and acylcarnitine.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

Citrin Deficiency

Novel metabolic biomarkers indicative of Citrin Deficiency include orotate. Accordingly, diagnosis of Citrin Deficiency in a subject can be made or facilitated by analyzing a biological sample obtained from the subject to determine the level of one or more metabolites including orotate, and comparing the level(s) of the metabolites in the sample to Citrin Deficiency-positive and/or Citrin Deficiency-negative reference levels of the metabolites.

Optionally, diagnosis of Citrin Deficiency in a subject can be made or facilitated by analyzing the level(s) of one or more currently used diagnostic metabolites in combination with novel metabolic biomarkers. Currently used diagnostic metabolites indicative of Citrin Deficiency include citrulline, arginine, threonine, serine, methionine, phenylalanine, and tyrosine. Accordingly, methods of diagnosing or facilitating diagnosis of Citrin Deficiency may further include analyzing a biological sample obtained from the subject to determine the level of one or more additional metabolites including citrulline, arginine, threonine, serine, methionine, phenylalanine, and tyrosine.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

4-Aminobutyrate Aminotransferase (ABAT) Deficiency

Novel metabolic biomarkers indicative of ABAT Deficiency include 2-pyrrolidone. Accordingly, diagnosis of ABAT Deficiency in a subject can be made or facilitated by analyzing a biological sample obtained from the subject to determine the level of one or more metabolites including 2-pyrrolidone, and comparing the level(s) of the metabolites in the sample to ABAT Deficiency-positive and/or ABAT Deficiency-negative reference levels of the metabolites.

Optionally, diagnosis of ABAT Deficiency in a subject can be made or facilitated by analyzing the level(s) of one or more currently used diagnostic metabolites in combination with novel metabolic biomarkers. Currently used diagnostic metabolites indicative of ABAT Deficiency include GABA. Accordingly, methods of diagnosing or facilitating diagnosis of ABAT Deficiency may further include analyzing a biological sample obtained from the subject to determine the level of one or more additional metabolites including GABA.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of ABAT Deficiency in a subject can be made or facilitated by analyzing a biological sample derived from plasma or urine from the subject.

GLUT1 Deficiency (SLC2A1 Deficiency)

Novel metabolic biomarkers indicative of GLUT1 Deficiency include fructose, mannose, prolylhydroxyproline, hydroxyproline, glycylproline, N-acetylneuraminate, dimethylarginine (ADMA+SDMA), glutamine, gamma-glutamylglutamine, N-acetyl-aspartyl-glutamate (NAAG), N-acetylglutamine, ethylmalonate, creatine, and combinations thereof. Accordingly, diagnosis of GLUT1 Deficiency in a subject can be made or facilitated by analyzing a biological sample obtained from the subject to determine the level of one or more metabolites including fructose, mannose, prolylhydroxyproline, hydroxyproline, glycylproline, N-acetylneuraminate, dimethylarginine (ADMA+SDMA), glutamine, gamma-glutamylglutamine, N-acetyl-aspartyl-glutamate (NAAG), N-acetylglutamine, ethylmalonate, and creatine, and comparing the level(s) of the metabolites in the sample to GLUT1 Deficiency-positive and/or GLUT1 Deficiency-negative reference levels of the metabolites.

Optionally, diagnosis of GLUT1 Deficiency in a subject can be made or facilitated by analyzing the level(s) of one or more currently used diagnostic metabolites in combination with novel metabolic biomarkers. Currently used diagnostic metabolites indicative of GLUT1 Deficiency include glucose. Accordingly, methods of diagnosing or facilitating diagnosis of GLUT1 Deficiency may further include analyzing a biological sample obtained from the subject to determine the level of one or more additional metabolites including glucose.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of GLUT1 Deficiency in a subject can be made or facilitated by analyzing a biological sample derived from CSF from the subject.

3-Methylglutaconic Aciduria (MGA)

Novel metabolic biomarkers indicative of MGA include 3-methylglutarylcarnitine. Accordingly, diagnosis of MGA in a subject can be made or facilitated by analyzing a biological sample obtained from the subject to determine the level of one or more metabolites including 3-methylglutarylcarnitine, and comparing the level(s) of the metabolites in the sample to MGA-positive and/or MGA-negative reference levels of the metabolites.

Optionally, diagnosis of MGA in a subject can be made or facilitated by analyzing the level(s) of one or more currently used diagnostic metabolites in combination with novel metabolic biomarkers. Currently used diagnostic metabolites indicative of MGA include 3-methylglutaconic acid and 3-methylglutaric acid. Accordingly, methods of diagnosing or facilitating diagnosis of MGA may further include analyzing a biological sample obtained from the subject to determine the level of one or more additional metabolites including 3-methylglutaconic acid and 3-methylglutaric acid.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of MGA in a subject can be made or facilitated by analyzing a biological sample derived from plasma from the subject.

Short Chain Acyl-CoA Decarboxylase (SCAD) Deficiency

Novel metabolic biomarkers indicative of SCAD Deficiency include butyrylglycine. Accordingly, diagnosis of SCAD Deficiency in a subject can be made or facilitated by analyzing a biological sample obtained from the subject to determine the level of one or more metabolites including butyrylglycine, and comparing the level(s) of the metabolites in the sample to SCAD Deficiency-positive and/or SCAD Deficiency-negative reference levels of the metabolites.

Optionally, diagnosis of SCAD Deficiency in a subject can be made or facilitated by analyzing the level(s) of one or more currently used diagnostic metabolites in combination with novel metabolic biomarkers. Currently used diagnostic metabolites indicative of SCAD Deficiency include ethylmalonate, butyrylcarnitine, and methylsuccinate. Accordingly, methods of diagnosing or facilitating diagnosis of SCAD Deficiency may further include analyzing a biological sample obtained from the subject to determine the level of one or more additional metabolites including ethylmalonate, butyrylcarnitine, and methylsuccinate.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

Urocanase Deficiency

Diagnosis of urocanase deficiency in a subject can be made or facilitated by analyzing the level(s) of one or more currently used diagnostic metabolites in combination with novel metabolic biomarkers. Currently used diagnostic metabolites indicative of urocanase deficiency include cis-urocanate, trans-urocanate, and imidazole propionate. Accordingly, methods of diagnosing or facilitating diagnosis of urocanase deficiency may further include analyzing a biological sample obtained from the subject to determine the level of one or more additional metabolites including cis-urocanate, trans-urocanate, and imidazole propionate.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of urocanase deficiency in a subject can be made or facilitated by analyzing a biological sample derived from plasma from the subject.

3-Hydroxyisobutyryl-CoA Hydrolase Deficiency

Novel metabolic biomarkers indicative of 3-hydroxyisobutyryl-CoA hydrolase deficiency include 3-hydroxyisobutyrate, isobutyrylglycine, and combinations thereof. Accordingly, diagnosis of 3-hydroxyisobutyryl-CoA hydrolase deficiency in a subject can be made or facilitated by analyzing a biological sample obtained from the subject to determine the level of one or more metabolites including 3-hydroxyisobutyrate, isobutyrylglycine, and combinations thereof, and comparing the level(s) of the metabolites in the sample to 3-hydroxyisobutyryl-CoA hydrolase deficiency-positive and/or 3-hydroxyisobutyryl-CoA hydrolase deficiency-negative reference levels of the metabolites.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

Hyperoxaluria

Diagnosis of hyperoxaluria in a subject can be made or facilitated by analyzing the level(s) of one or more currently used diagnostic metabolites in combination with novel metabolic biomarkers. Currently used diagnostic metabolites indicative of hyperoxaluria include oxalate and glycolate. Accordingly, methods of diagnosing or facilitating diagnosis of hyperoxaluria may further include analyzing a biological sample obtained from the subject to determine the level of one or more additional metabolites including oxalate and glycolate.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of hyperoxaluria in a subject can be made or facilitated by analyzing a biological sample derived from urine from the subject.

γ-Butyrobetaine Hydroxylase Deficiency (BBOX Deficiency)

Novel metabolic biomarkers indicative of BBOX Deficiency include hexadecanedioate (C16), docosadioate, eicosanodioate, octadecanedioate (C18), dodecanedioate (C12), 2-aminooctanoate, 2-aminoheptanoate, alpha-hydroxyisocaproate, isovalerate (C5), decanoylcarnitine (C10), cis-4-decenoyl carnitine, palmitoylcarnitine (C16), oleoylcarnitine (C18), laurylcarnitine (C12), myristoleoylcarnitine, myristoylcarnitine, glycerol, 3-hydroxymyristate, 2-hydroxydecanoate, 3-hydroxylaurate, 3-hydroxysebacate, 3-hydroxyoctanoate, 3-hydroxydecanoate, pelargonate (9:0), caproate (6:0), and combinations thereof. Accordingly, diagnosis of BBOX Deficiency in a subject can be made or facilitated by analyzing a biological sample obtained from the subject to determine the level of one or more metabolites including hexadecanedioate (C16), docosadioate, eicosanodioate, octadecanedioate (C18), dodecanedioate (C12), 2-aminooctanoate, 2-aminoheptanoate, alpha-hydroxyisocaproate, isovalerate (C5), decanoylcarnitine (C10), cis-4-decenoyl carnitine, palmitoylcarnitine (C16), oleoylcarnitine (C18), laurylcarnitine (C12), myristoleoylcarnitine, myristoylcarnitine, glycerol, 3-hydroxymyristate, 2-hydroxydecanoate, 3-hydroxylaurate, 3-hydroxysebacate, 3-hydroxyoctanoate, 3-hydroxydecanoate, pelargonate (9:0), caproate (6:0), and combinations thereof, and comparing the level(s) of the metabolites in the sample to BBOX Deficiency-positive and/or BBOX Deficiency-negative reference levels of the metabolites.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

Disorders of Amino Acid Metabolism and Transport (Including Urea Cycle Disorders and Organic Acidemias)

Metabolic biomarkers indicative of disorders of amino acid metabolism and transport (including urea cycle disorders and organic acidemias) include N-acetylalanine, aspartate, glutarate (pentanedioate), glutarylcarnitine (C5), 3-hydroxyglutarate, glutaconate, phenylalanine, N-acetylphenylalanine, phenylpyruvate, phenyllactate (PLA), phenylacetate, phenylacetylglycine, phenylacetylglutamine, 4-hydroxyphenylpyruvate, 3-(4-hydroxyphenyl) lactate, p-cresol sulfate, o-cresol sulfate, 3-methoxytyrosine, leucine, 4-methyl-2-oxopentanoate, isovalerate, isovalerylglycine, isovalerylcarnitine (C5), 3-methylcrotonylglycine, beta-hydroxyisovalerate, beta-hydroxyisovaleroylcarnitine, 3-methylglutarylcarnitine (C6), alpha-hydroxyisovalerate, isoleucine, allo-isoleucine, 3-methyl-2-oxovalerate, 2-methylbutyrylcarnitine (C5), tiglyl carnitine, tigloylglycine, 2-hydroxy-3-methylvalerate, 3-hydroxy-2-ethylpropionate, valine, 3-methyl-2-oxobutyrate, isobutyrylcarnitine, 3-hydroxyisobutyrate, alpha-hydroxyisocaproate, homocysteine, cystathionine, arginine, urea, ornithine, proline, citrulline, argininosuccinate, homoarginine, homocitrulline, N-acetylarginine, N-delta-acetylornithine, trans-4-hydroxyproline, pro-hydroxy-pro, creatine, creatinine, 4-guanidinobutanoate, guanidinosuccinate, gamma-glutamylphenylalanine, gamma-glutamyltyrosine, alanylalanine, arginylprolineaspartylphenylalanine, glycylphenylalanine, histidylphenylalanine, isoleucylaspartate, leucylphenylalanine, phenylalanylalanine, phenylalanylarginine, phenylalanylaspartate, phenylalanylglutamate, phenylalanylglycine, phenylalanylisoleucine, phenylalanylleucine phenylalanylphenylalanine, phenylalanylserine, pyroglutamylvaline, threonylphenylalanine, tryptophylphenylalanine, valylphenylalanine, fructose, sorbose, succinylcarnitine, succinate, 2-methylcitrate, valerate, stearidonate (18:4n3), adipate, dodecanedioate (C12), tetradecanedioate (C14), hexadecanedioate (C16), octadecanedioate (C18), 2-aminoheptanoate, 2-linolenoylglycerophosphocholine (18:3n3), 2-methylmalonyl carnitine, butyrylcarnitine, propionylcarnitine (C3), propionylglycine (C3), methylmalonyl CoA, methylmalonic acid, acetylcarnitine, hydroxybutyrylcarnitine, valerylcarnitine, hexanoylcarnitine, myristoylcarnitine, palmitoylcarnitine (C16), hexenedioylcarnitine (previously X-17001), 3-hydroxypropanoate, 1-myristoylglycerophosphocholine (14:0), 2-myristoylglycerophosphocholine, 1-pentadecanoylglycerophosphocholine (15:0), 1-linolenoylglycerophosphocholine (18:3n3), 1-stearoylglycerophosphoethanolamine, 1,3-dipalmitoylglycerol, 5alpha-androstan-3 alpha, 17beta-diol disulfate, orotate, uridine, uracil, 3-ureidopropionate, hippurate, catechol sulfate, phenylcarnitine, propionate, 5-hydroxytryptophan, 5-methylthioadenosine (MTA), beta-alanine, dimethylarginine (SDMA+ADMA), glutamine, N-acetylaspartate (NAA), N-acetyl-beta-alanine, tryptophan, tyrosine, 2-pyrrolidone, gamma-glutamylleucine, O-sulfo-L-tyrosine, palmitoyl-sphingomyelin, gamma-glutamylisoleucine, cysteine s-sulfate, 2-aminoadipate, phenylacetylglutamine, 3,4-dihydroxyphenylacetate, phenylpropionylglycine, 2-pentanamido-3-phenylpropanoic acid, 2-hydroxyphenylacetate, N-acetylleucine, methylsuccinate, ethylmalonate, guanidinoacetate, beta-hydroxybutyrate, N-carbamoylaspartate, 4-ureidobutyrate, hippurate, 2-methylhippurate, benzoate, methyl-4-hydroxybenzoate, 4-phenylbutyrate, and combinations thereof. Accordingly, diagnosis of disorders of amino acid metabolism and transport (including urea cycle disorders and organic acidemias) in a subject can be made or facilitated by analyzing a biological sample obtained from the subject to determine the level of one or more metabolites listed above, and comparing the level(s) of the metabolites in the sample to disease or disorder-positive and/or disease or disorder-negative reference levels of the metabolites.

Optionally, diagnosis of disorders of amino acid metabolism and transport (including urea cycle disorders and organic acidemias) in a subject can be made or facilitated by analyzing the level(s) of one or more currently used diagnostic metabolites in combination with the foregoing metabolic biomarkers.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of disorders of amino acid metabolism and transport in a subject can be made or facilitated by analyzing a biological sample derived from urine from the subject to determine the level of one or more metablolites including any of 2-aminoadipate, phenylacetylglutamine, 3,4-dihydroxyphenylacetate, phenylpropionylglycine, 2-pentanamido-3-phenylpropanoic acid, 2-hydroxyphenylacetate, N-acetylleucine, methylsuccinate, ethylmalonate, guanidinoacetate, beta-hydroxybutyrate, N-carbamoylaspartate, 4-ureidobutyrate, hippurate, 2-methylhippurate, benzoate, methyl-4-hydroxybenzoate, 4-phenylbutyrate, and combinations thereof.

Fatty Acid Oxidation Disorders

Metabolic biomarkers indicative of fatty acid oxidation disorders include xylulose, caproate (6:0), heptanoate (7:0), caprylate (C8), pelargonate (9:0), caprate (C10), myristoleate (14:1n5), eicosapentanoic acid (EPA), docosahexaenoate (DHA;22:6n3), arachidonate (20:4n6), suberate (octanedioate), sebacate (C8), dodecanedioate (C12), hexanoylglycine (C6), N-octanoylglycine, hexanoylcarnitine, octanoylcarnitine, decanoylcarnitine, cis-4-decenoyl carnitine, myristoylcarnitine, palmitoylcarnitine (C16), stearoylcarnitine (C18), oleoylcarnitine (C18), deoxycarnitine, carnitine, 3-hydroxydecanoate, 5-hydroxyhexanoate, N-palmitoyltaurine, 1-margaroylglycerophosphocholine (17:0), 1-stearoylglycerophosphocholine (18:0), 1-docosapentaenoylglycerophosphocholine (22:5n3), 9-methyluric acid, alpha-CEHC (2,5,7,8-tetramethyl-2-(2'-carboxyethyl)-6-hydroxychroman) sulfate (previously X-12435), O-methylcatechol sulfate, 5,8-tetradecadienoic acid (previously X-12442), methylhexanoylglutamine (previously X-12637), 7-dehydrocholesterol, cholestanol, N6-trimethyllysine, butyrylglycine, 1-docosahexaenoyl-GPC (22:6; DHA-GPC), 2-hydroxyglutarate, 3-methyladipate, 4-octenedioate, heptanoyl glycine, and combinations thereof. Accordingly, diagnosis of fatty acid oxidation disorders in a subject can be made or facilitated by analyzing a biological sample obtained from the subject to determine the level of one or more foregoing metabolic biomarkers, and comparing the level(s) of the metabolites in the sample to disease or disorder-positive and/or disease or disorder-negative reference levels of the metabolites.

Optionally, diagnosis of fatty acid oxidation disorders in a subject can be made or facilitated by analyzing the level(s) of one or more currently used diagnostic metabolites in combination with the foregoing metabolic biomarkers.

As explained above, the biological sample from the subject can be isolated from any suitable biological source, e.g., blood, blood plasma, serum, skin, epidermal tissue, adipose tissue, aortic tissue, liver tissue, urine, cerebral spinal fluid, crevicular fluid, or cell samples.

In some embodiments, the diagnosis of disorders of amino acid metabolism and transport in a subject can be made or facilitated by analyzing a biological sample derived from urine from the subject to determine the level of one or more metabolites including any of 2-hydroxyglutarate, 3-methyladipate, 4-octenedioate, heptanoyl glycine, and combinations thereof.

EXAMPLES

I. General Methods

A. Metabolomic Profiling

The metabolomic platforms consisted of three independent methods: ultrahigh performance liquid chromatography/tandem mass spectrometry (UHLC/MS/MS$^2$) optimized for basic species, UHLC/MS/MS$^2$ optimized for acidic species, and gas chromatography/mass spectrometry (GC/MS).

B. Sample Preparation

Plasma and urine samples were stored at −80° C. until needed and then thawed on ice just prior to extraction. Extraction was executed using an automated liquid handling robot (MicroLab Star, Hamilton Robotics, Reno, NV), where 450 µl methanol was added to 100 µl of each sample to precipitate proteins. The methanol contained four recovery standards to allow confirmation of extraction efficiency. Each solution was then mixed on a Geno/Grinder 2000 (Glen Mills Inc., Clifton, NJ) at 675 strokes per minute and then centrifuged for 5 minutes at 2000 rpm. Four 110 µl aliquots of the supernatant of each sample were taken and dried under nitrogen and then under vacuum overnight. The following day, one aliquot was reconstituted in 50 µL of 6.5 mM ammonium bicarbonate in water at (pH 8) and one aliquot was reconstituted using 50 µL 0.1% formic acid in water. Both reconstitution solvents contained sets of instrument internal standards for marking an LC retention index and evaluating LC-MS instrument performance. A third 110 µl aliquot was derivatized by treatment with 50 µL of a mixture of N,O-bis trimethylsilyltrifluoroacetamide and 1% trimethylchlorosilane in cyclohexane:dichloromethane:acetonitrile (5:4:1) plus 5% triethylamine, with internal standards added for marking a GC retention index and for assessment of the recovery from the derivatization process. This mixture was then dried overnight under vacuum and the dried extracts were then capped, shaken for five minutes and then heated at 60° C. for one hour. The samples were allowed to cool and spun briefly to pellet any residue prior to being analyzed by GC-MS. The remaining aliquot was sealed after drying and stored at −80° C. to be used as backup samples, if necessary. The extracts were analyzed on three separate mass spectrometers: one UPLC-MS system employing ultra-performance liquid chromatography-mass spectrometry for detecting positive ions, one UPLC-MS system detecting negative ions, and one Trace GC Ultra Gas Chromatograph-DSQ gas chromatography-mass spectrometry (GC-MS) system (Thermo Scientific, Waltham, MA).

C. UPLC Method

All reconstituted aliquots analyzed by LC-MS were separated using a Waters Acquity UPLC (Waters Corp., Milford, MA). The aliquots reconstituted in 0.1% formic acid used mobile phase solvents consisting of 0.1% formic acid in water (A) and 0.1% formic acid in methanol (B). Aliquots reconstituted in 6.5 mM ammonium bicarbonate used mobile phase solvents consisting of 6.5 mM ammonium bicarbonate in water, pH 8 (A) and 6.5 mM ammonium bicarbonate in 95/5 methanol/water. The gradient profile utilized for both the formic acid reconstituted extracts and the ammonium bicarbonate reconstituted extracts was from 0.5% B to 70% B in 4 minutes, from 70% B to 98% B in 0.5 minutes, and hold at 98% B for 0.9 minutes before returning to 0.5% B in 0.2 minutes. The flow rate was 350 µL/min. The sample injection volume was 5 µL and 2× needle loop overfill was used. Liquid chromatography separations were made at 40° C. on separate acid or base-dedicated 2.1 mm×100 mm Waters BEH C18 1.7 μm particle size columns.

D. UPLC-MS Methods

In Example 1, a linear trap quadrupole mass spectrometer (LTQ, Thermo Scientific, Waltham, MA) was used. In Example 4, a Q-Exactive high resolution/accurate mass orbitrap mass spectrometer (Q-Exactive, ThermoFisher Scientific, Waltham, MA) operated at 35,000 mass resolution was used. In all other examples, an OrbitrapElite (OrbiElite Thermo Scientific, Waltham, MA) mass spectrometer was used. The Q-Exactive and OrbiElite mass spectrometers utilized a HESI-II source with sheath gas set to 80, auxiliary gas at 12, and voltage set to 4.2 kV for positive mode. Settings for negative mode had sheath gas at 75, auxiliary gas at 15 and voltage was set to 2.75 kV. The source heater temperature for both modes was 430° C. and the capillary temperature was 350° C. The mass range was 99-1000 m/z with a scan speed of 4.6 total scans per second also alternating one full scan and one MS/MS scan and the resolution was set to 30,000. The Fourier Transform Mass Spectroscopy (FTMS) full scan automatic gain control (AGC) target was set to $5\times10^5$ with a cutoff time of 500 ms. The AGC target for the ion trap MS/MS was $3\times10^3$ with a maximum fill time of 100 ms. Normalized collision energy for positive mode was set to 32 arbitrary units and negative mode was set to 30. For both methods activation Q was 0.35 and activation time was 30 ms, again with a 3 m/z isolation mass window. The dynamic exclusion setting with 3.5 second duration was enabled for the OrbiElite. Calibration was performed weekly using an infusion of Pierce™ LTQ Velos Electrospray Ionization (ESI) Positive Ion Calibration Solution or Pierce™ ESI Negative Ion Calibration Solution.

E. GC-MS Method

Derivatized samples were analyzed by GC-MS. A sample volume of 1.0 μl was injected in split mode with a 20:1 split ratio on to a diphenyl dimethyl polysiloxane stationary phase, thin film fused silica column, Crossbond RTX-5Si1, 0.18 mm i.d.×20 m with a film thickness of 20 μm (Restek, Bellefonte, PA). The compounds were eluted with helium as the carrier gas and a temperature gradient that consisted of the initial temperature held at 60° C. for 1 minute; then increased to 220° C. at a rate of 17.1° C./minute; followed by an increase to 340° C. at a rate of 30° C./minute and then held at this temperature for 3.67 minutes. The temperature was then allowed to decrease and stabilize to 60° C. for a subsequent injection. The mass spectrometer was operated using electron impact ionization with a scan range of 50-750 mass units at 4 scans per second, 3077 amu/sec. The dual stage quadrupole (DSQ) was set with an ion source temperature of 290° C. and a multiplier voltage of 1865 V. The MS transfer line was held at 300° C. Tuning and calibration of the DSQ was performed daily to ensure optimal performance.

F. Data Processing and Analysis

For each biological matrix data set on each instrument, relative standard deviations (RSDs) of peak area were calculated for each internal standard to confirm extraction efficiency, instrument performance, column integrity, chromatography, and mass calibration. Several of these internal standards serve as retention index (RI) markers and were checked for retention time and alignment. Modified versions of the software accompanying the UPLC-MS and GC-MS systems were used for peak detection and integration. The output from this processing generated a list of m/z ratios, retention times and area under the curve values. Software specified criteria for peak detection including thresholds for signal to noise ratio, height and width.

The biological data sets, including QC samples, were chromatographically aligned based on a retention index that utilizes internal standards assigned a fixed RI value. The RI of the experimental peak is determined by assuming a linear fit between flanking RI markers whose values do not change. The benefit of the RI is that it corrects for retention time drifts that are caused by systematic errors such as sample pH and column age. Each compound's RI was designated based on the elution relationship with its two lateral retention markers. Using an in-house software package, integrated, aligned peaks were matched against an in-house library (a chemical library) of authentic standards and routinely detected unknown compounds, which is specific to the positive, negative or GC-MS data collection method employed. Matches were based on retention index values within 150 RI units of the prospective identification and experimental precursor mass match to the library authentic standard within 0.4 m/z for the LTQ and DSQ data. The experimental MS/MS was compared to the library spectra for the authentic standard and assigned forward and reverse scores. A perfect forward score would indicate that all ions in the experimental spectra were found in the library for the authentic standard at the correct ratios and a perfect reverse score would indicate that all authentic standard library ions were present in the experimental spectra and at correct ratios. The forward and reverse scores were compared and a MS/MS fragmentation spectral score was given for the proposed match. All matches were then manually reviewed by an analyst that approved or rejected each call based on the criteria above. However, manual review by an analyst is not required. In some embodiments the matching process is completely automated.

Further details regarding a chemical library, a method for matching integrated aligned peaks for identification of named compounds and routinely detected unknown compounds, and computer-readable code for identifying small molecules in a sample may be found in U.S. Pat. No. 7,561,975, which is incorporated by reference herein in its entirety.

G. Quality Control

From the samples of plasma or urine, aliquots of each of the individual samples were combined to make technical replicates, which were extracted as described above. Extracts of this pooled plasma or urine sample were injected six times for each data set on each instrument to assess process variability. As an additional quality control, five water aliquots were also extracted as part of the sample set on each instrument to serve as process blanks for artifact identification. All QC samples included the instrument internal standards to assess extraction efficiency, and instrument performance and to serve as retention index markers for ion identification. The standards were isotopically labeled or otherwise exogenous molecules chosen so as not to obstruct detection of intrinsic ions.

H. Statistical Analysis

The goal of the statistical analysis was to identify "extreme" values (outliers) in each of the metabolites detected in the sample. A two-step process was performed based on the percent fill (the percentage of samples for which a value was detected in the metabolites). When the fill was less than or equal 10%, samples in which a value is detected were flagged. When the fill was greater than 10%, the missing values were imputed with a random normal variable with mean equal to the observed minimum and standard deviation equal to 1. The data was then Log transformed, and the Inter Quartile Range (IQR), defined as the difference between the 3rd and 1st quartiles, was calculated. Values that were greater than 1.5*IQR above the 3rd quartile or 1.5*IQR below the 1st quartile were then flagged. The log transformed data were also analyzed to calculate the Z-score for each metabolite in each individual. The Z-score of the metabolite for an individual represents the number of standard deviations above the mean for the given metabolite. A positive Z-score means the metabolite level is above the mean and a negative Z-score means the metabolite level is below the mean.

The results obtained were useful for diagnosing and/or aiding in the diagnosis of more than thirty disorders as described in the examples below using a single small volume sample from the subject and without requiring a priori knowledge of the disorder or disease. In fact, in some cases the individual was treated for a genetic disorder that the metabolomics data indicated was not penetrant, thus the patient did not require treatment, and in other cases the metabolomics analysis indicated presence of a disorder for which the genetic mutation uncovered by exome sequencing was regarded as insignificant. Additional types of diagnostic results that were obtained using the methods described below.

For some subjects, clinically diagnostic biomarkers were determined to be aberrant and additional aberrant biochemicals, some of which were biochemically related to the clinical diagnostic metabolite, were also shown to be aberrant. For some subjects, the clinically diagnostic metabolite was not detected; however, novel biochemicals, at least some of which are related to the diagnostic metabolite, were shown to be aberrant which enabled the diagnosis. For some subjects, clinically diagnostic metabolites were determined as aberrant in a different sample type than is currently used clinically (e.g., a urine marker was detected in plasma), which enabled the diagnosis with a novel sample type. For certain disorders clinically diagnostic metabolites are not available, but the analysis revealed novel biochemicals that were useful to make a clinical diagnosis.

Example 1: Assessment of Individuals with Disease in Pilot Study

To evaluate the ability to diagnose or aid in the diagnosis of disease, the method was performed on a cohort comprised of 100 symptomatic individuals, 56 for whom a diagnosis was known (as a positive "control" for the method, N=56) and 44 for whom a diagnosis had not been determined ("test" individuals, N=44). Plasma samples were obtained from each individual and small molecules were extracted from an aliquot (typically 50-100 uL) of the plasma sample. Each sample aliquot was surveyed across a biochemical library of 7000+ biochemicals to detect biochemicals present in the sample. At the time of analysis, all samples were blinded as to diagnosis. A total of 923 biochemicals, 523 named and 400 unnamed, were detected. Named biochemicals represent molecules for which there is an authentic chemical standard available and that authentic chemical standard has been run on an equivalent platform and the "ion fragmentation signature" for that standard has been identified and captured in the in-house chemical library. Unnamed biochemicals represent entities for which the "ion fragmentation signature" has been established but for which no known standard is available in the chemical library. The unnamed biochemicals have been sufficiently characterized by analytical techniques for unique identification. The unnamed biochemicals are designated herein by the nomenclature "X-" followed by a specific five digit number. Identifying analytical information for the unnamed biochemical small molecules appears below in Table 4.

For each of the 100 symptomatic individuals, the data were automatically statistically analyzed using IQR to identify outliers in the biochemicals surveyed. Rare biochemicals and missing biochemicals were also analyzed for each individual. The metabolites in the sample were automatically mapped to subpathways and super-pathways and a visualization of the data was generated. The results of the analysis of the 100 symptomatic subjects are summarized in Table 1. The diagnosis for each individual subject, the number of metabolites that were determined to be outliers based on 1.5*IQR, 3.0*IQR and the total number of outliers (i.e., for 1.5*IQR and for 3.0*IQR) are presented.

At the time of the analysis performed using the methods herein, the diagnoses were blinded to the analysts. Following analysis, the clinical diagnoses were made available to compare the findings and determine if the results were consistent with the diagnosis. Based on the IQR data and missing metabolites data aberrant metabolites were identified in the samples from the subjects and using this information diagnoses were proposed for five subjects. When the diagnosis information was unblinded, it was shown that the diagnosis based on the aberrant metabolites was consistent with the clinical diagnosis. For example, aberrant metabolites phenylalanine and phenyllactate were used to diagnose phenylketonuria (PKU) in one individual. In another example, aberrant metabolites sebacate (decanedioate), 2-hydroxyglutarate, azelate (nonanedioate), caprylate (8:0), hexanoylcarnitine, and octanoylcarnitine were used to diagnose medium chain acyl CoA dehydrogenase deficiency (MCAD deficiency) in an individual. In another example, aberrant metabolites isoleucine, valine, 3-methyl-2-oxobutyrate, 3-methyl-2-oxovalerate, and alpha-hydroxyisovalerate, were used to diagnose maple syrup urine disease in an individual. In another example, aberrant metabolite isovalerylcarnitine was used to diagnose isovaleric acidemia in one individual. In another example, a subject was diagnosed with thymidine phosphorylase deficiency. Thymidine was identified in the sample from the subject as a rare biochemical (a biochemical not normally detected in reference samples) consistent with a diagnosis of thymidine phosphorylase deficiency.

TABLE 1

Experimental Results to Identify Aberrant Biochemicals for Initial Analysis of Diagnosis of Disease or Disorder

| | | Number of Metabolites | | |
|---|---|---|---|---|
| Subject No. | Diagnosis | 1.5* IQR | 3.0* IQR | Total Outliers |
| 1 | 3-methylcrotonyl CoA carboxylase deficiency | 3 | 1 | 4 |
| 2 | Argininemia | 1 | 4 | 5 |
| 3 | Argininemia | 4 | 1 | 5 |

TABLE 1-continued

Experimental Results to Identify Aberrant Biochemicals for Initial Analysis of Diagnosis of Disease or Disorder

| Subject No. | Diagnosis | Number of Metabolites 1.5* IQR | 3.0* IQR | Total Outliers |
|---|---|---|---|---|
| 4 | argininosuccinic acid lyase deficiency | 3 | 0 | 3 |
| 5 | biotinidase deficiency | 2 | 1 | 3 |
| 6 | biotinidase deficiency | 21 | 4 | 25 |
| 7 | borderline XCrt finding | 24 | 7 | 31 |
| 8 | cbl a | 29 | 5 | 34 |
| 9 | cbl c | 2 | 1 | 3 |
| 10 | cbl c | 6 | 6 | 12 |
| 11 | Citrullinemia | 13 | 18 | 31 |
| 12 | Citrullinemia | 9 | 3 | 12 |
| 13 | Citrullinemia | 23 | 26 | 49 |
| 14 | Citrullinemia | 11 | 15 | 26 |
| 15 | Citrullinemia | 30 | 48 | 78 |
| 16 | Cystinosis | 33 | 12 | 45 |
| 17 | cytogenetic abnormality: 47, XXX | 2 | 3 | 5 |
| 18 | Dravet syndrome (not a metabolic disorder) | 2 | 1 | 3 |
| 19 | glutaric aciduria type 1 | 0 | 0 | 0 |
| 20 | guanidinoacetate methyl transferase deficiency | 8 | 0 | 8 |
| 21 | guanidinoacetate methyl transferase deficiency | 6 | 2 | 8 |
| 22 | isovaleric acidemia | 6 | 1 | 7 |
| 23 | Lysinuric protein intolerance | 12 | 3 | 15 |
| 24 | Lysinuric protein intolerance | 11 | 3 | 14 |
| 25 | Maple syrup urine disease | 6 | 0 | 6 |
| 26 | Maple syrup urine disease | 31 | 36 | 67 |
| 27 | Maple syrup urine disease | 4 | 2 | 6 |
| 28 | medium chain acyl CoA dehydrogenase deficiency | 44 | 6 | 50 |
| 29 | methylmalonic acidemia | 23 | 9 | 32 |
| 30 | methylmalonic acidemia | 43 | 12 | 55 |
| 31 | methylmalonic acidemia | 12 | 8 | 20 |
| 32 | molybdenum cofactor or sulfite oxidase deficiency | 16 | 9 | 25 |
| 33 | ornithine transcarbamoylase deficiency | 11 | 5 | 16 |
| 34 | ornithine transcarbamoylase deficiency | 7 | 1 | 8 |
| 35 | ornithine transcarbamoylase deficiency | 11 | 5 | 16 |
| 36 | ornithine transcarbamoylase deficiency | 13 | 4 | 17 |
| 37 | ornithine transcarbamoylase deficiency | 6 | 3 | 9 |
| 38 | ornithine transcarbamoylase deficiency | 5 | 0 | 5 |
| 39 | ornithine transcarbamoylase deficiency | 2 | 2 | 4 |
| 40 | ornithine transcarbamoylase deficiency | 0 | 0 | 0 |
| 41 | ornithine transcarbamoylase deficiency | 2 | 0 | 2 |
| 42 | ornithine transcarbamoylase deficiency | 10 | 2 | 12 |
| 43 | ornithine transcarbamoylase deficiency (carrier) | 3 | 1 | 4 |
| 44 | PKU | 11 | 4 | 15 |
| 45 | PKU | 2 | 4 | 6 |
| 46 | PKU | 3 | 1 | 4 |
| 47 | PKU | 1 | 0 | 1 |
| 48 | suspected cbl disorder | 15 | 0 | 15 |
| 49 | Thymidine phosphorylase | 9 | 1 | 10 |
| 50 | trimethylysine hydroxylase epsilon deficiency | 6 | 0 | 6 |
| 51 | trimethylysine hydroxylase epsilon deficiency | 57 | 15 | 72 |
| 52 | trimethylysine hydroxylase epsilon deficiency | 5 | 4 | 9 |
| 53 | very long chain acyl CoA dehydrogenase deficiency | 6 | 6 | 12 |
| 54 | X-linked creatine transporter | 1 | 0 | 1 |
| 55 | X-linked creatine transporter | 1 | 0 | 1 |
| 56 | X-linked creatine transporter | 4 | 0 | 4 |
| 57 | undiagnosed | 6 | 0 | 6 |
| 58 | undiagnosed | 8 | 3 | 11 |
| 59 | undiagnosed | 3 | 3 | 6 |
| 60 | undiagnosed | 1 | 1 | 2 |
| 61 | undiagnosed | 14 | 2 | 16 |
| 62 | undiagnosed | 1 | 0 | 1 |
| 63 | undiagnosed | 9 | 2 | 11 |
| 64 | undiagnosed | 18 | 25 | 43 |
| 65 | undiagnosed | 3 | 0 | 3 |
| 66 | undiagnosed | 4 | 3 | 7 |
| 67 | undiagnosed | 2 | 1 | 3 |
| 68 | undiagnosed | 4 | 0 | 4 |
| 69 | undiagnosed | 29 | 4 | 33 |
| 70 | undiagnosed | 0 | 0 | 0 |
| 71 | undiagnosed | 1 | 0 | 1 |
| 72 | undiagnosed | 5 | 4 | 9 |
| 73 | undiagnosed | 0 | 0 | 0 |
| 74 | undiagnosed | 15 | 2 | 17 |
| 75 | undiagnosed | 12 | 3 | 15 |

TABLE 1-continued

Experimental Results to Identify Aberrant Biochemicals for Initial Analysis of Diagnosis of Disease or Disorder

| Subject No. | Diagnosis | Number of Metabolites 1.5* IQR | 3.0* IQR | Total Outliers |
|---|---|---|---|---|
| 76 | undiagnosed | 6 | 0 | 6 |
| 77 | undiagnosed | 3 | 1 | 4 |
| 78 | undiagnosed | 5 | 0 | 5 |
| 79 | undiagnosed | 1 | 0 | 1 |
| 80 | undiagnosed | 4 | 4 | 8 |
| 81 | undiagnosed | 0 | 0 | 0 |
| 82 | undiagnosed | 3 | 1 | 4 |
| 83 | undiagnosed | 0 | 1 | 1 |
| 84 | undiagnosed | 2 | 0 | 2 |
| 85 | undiagnosed | 17 | 0 | 17 |
| 86 | undiagnosed | 4 | 1 | 5 |
| 87 | undiagnosed | 1 | 0 | 1 |
| 88 | undiagnosed | 4 | 0 | 4 |
| 89 | undiagnosed | 2 | 0 | 2 |
| 90 | undiagnosed | 9 | 4 | 13 |
| 91 | undiagnosed | 3 | 0 | 3 |
| 92 | undiagnosed | 1 | 0 | 1 |
| 93 | undiagnosed | 32 | 8 | 40 |
| 94 | undiagnosed | 7 | 3 | 10 |
| 95 | undiagnosed | 9 | 12 | 21 |
| 96 | undiagnosed | 9 | 3 | 12 |
| 97 | undiagnosed | 4 | 1 | 5 |
| 98 | undiagnosed | 5 | 0 | 5 |
| 99 | undiagnosed | 4 | 0 | 4 |
| 100 | undiagnosed | 1 | 0 | 1 |

Example 2: Clinical Assessment of Individuals with Disease in Expanded Study

In another example, the method described herein was used to evaluate plasma samples from 200 individuals. The 200 samples consisted of the cohort of 100 samples described in Example 1 plus 100 samples from a new cohort of symptomatic individuals. All 200 samples included in this study had been analyzed using one or more targeted panels of analytes in a quantitative analysis performed in a clinical diagnostic laboratory. The most common targeted tests completed were panel assays for amino acids or acylcarnitines (108 and 26 patients, respectively). Of the 200 subjects in the combined cohort, 132 subjects were positively diagnosed for an inborn error of metabolism (IEM) by a treating physician; for 68 subjects, no clinical diagnosis could be determined.

Using the OrbiElite mass spectrometer in the LC-MS analysis method, each sample was surveyed across the entire 7000+ biochemical library to measure biochemicals detected within that sample. From each sample, an aliquot was removed and the small molecules (biochemicals) were extracted and analyzed; the biochemicals detected in the samples were identified and aberrant levels were determined to obtain diagnostic information (e.g., Table 2) which was stored in a database. A total of 1292 biochemicals, 706 named and 586 unnamed, were detected. These biochemicals include small peptides (e.g., di-, tri-) and small molecules that represent many classes of biomarkers, including amino acids (140), peptides (94), carbohydrates (26), lipids (243), cofactors (29), energy metabolites (11), nucleotides (32), and xenobiotics (131).

For each of the 200 symptomatic individuals, the data was automatically statistically analyzed using IQR and Z-scores to identify outliers in the biochemicals surveyed. Rare biochemicals and missing biochemicals were also analyzed for each individual. Unlike targeted diagnostic analysis, metabolomic diagnostic findings were not confined to a single class of analytes. Instead, metabolites from multiple biochemical pathways, including, for example, amino acids, nucleotides, and lipids, as well as carnitine and glycine conjugated adducts, were detected and used in the analysis. The metabolites detected in the sample were automatically mapped to subpathways and super-pathways. All detected biochemicals were automatically classified into 41 biochemical subpathways. An automated visualization of the data, including the aberrant biochemicals and the abnormal biochemical super and subpathways to which the aberrant biochemical were mapped was generated. Example graphic illustrations of the visualizations are presented in FIGS. 4-14 and described in detail below.

Aberrant biochemicals were identified and abnormal pathways were determined as follows. Aberrant biochemicals included missing biochemicals, rare biochemicals and outliers. Aberrant biochemicals in the form of outliers were identified based on either 1.5*IQR or 3.0*IQR using the log transformed data. To accommodate missing values, compounds present in ≤10% of all samples were automatically reported as rare compounds. Missing values were imputed with a random normal variable centered around the observed minimum for compounds present in >10% of all samples. Aberrant biochemicals were also identified by determining a Z-score for each metabolite. In this example the metabolites with Z-scores <−1.5 or >1.5 were determined as aberrant.

To identify abnormal pathways, the data for each biochemical was log transformed, centered (i.e., the mean was set to have mean=0) and standardized (sd=1). Observed values were next squared and then summed across all compounds in the pathway. Missing values were imputed with the observed minimum prior to transformation. Pathways were classified as either typical for a given population or abnormal, meaning that the biochemical distance for that pathway for the individual was among the highest 10% of all samples for a given pathway. Abnormal classification was calculated using Euclidean distances from the geometric mean of each pathway. Each super-pathway is comprised of multiple subpathways as described below.

Prior to analysis, all of the diagnoses were blinded to the analysts. Following analysis, the clinical diagnoses were made available for comparison with the clinical findings to determine if the results of the analysis were consistent with the clinical diagnoses. In addition, the 100 previously analyzed samples from Example 1 served as anchor samples that allowed comparison of the data from the subjects described and analyzed in Example 1 with data obtained in the repeat analysis and with data from the 100 new subjects. Inclusion of the previously analyzed samples as anchor samples in runs with samples from the 100 new subjects enabled correction of run to run variability. The results of the analysis of the 100 anchor samples from the 100 symptomatic subjects that were previously analyzed were compared to the results obtained from the first run in Example 1 to assess reproducibility of the data. Importantly, the metabolites identified as aberrant (including rare biochemicals or missing biochemicals) were consistent between the two analyses.

The data and visualizations were evaluated by a clinician to determine if the results obtained using the methods described were consistent with the clinically determined diagnosis. The diagnostic results based upon the analysis and the clinical diagnosis are summarized in Table 2. Column 1 of Table 2 lists the disorder, including synonyms. Column 2 shows the number of individuals with each diagnosis, Column 3 lists the Sensitivity, Column 4 lists the Specificity for the diagnosis of the disorder, (Note: Sensitivity and Specificity were based on the results of the analysis methods described herein), Column 5 lists metabolites that are currently used in the clinic to diagnose the disorder. The analysis results are presented in Columns 6 and 7. Column 6 lists clinically used metabolites that were found to be aberrant using the methods disclosed herein. Column 7 labeled "Analysis results: Novel metabolites, aberrant in diagnosed subjects" lists metabolites not currently used for clinical diagnosis that were identified as aberrant based on the results of the methods used herein in the subjects having that clinical diagnosis; some of these metabolites are biochemically related to the clinically used diagnostic metabolite.

In some individuals the clinically diagnostic metabolite was not observed. However, other metabolites, at least some of which were biochemically related to the diagnostic metabolite, were aberrant which aided in diagnosis of that disorder. Thus, the methods herein aided in the diagnosis of disorders that were not diagnosed using the current clinical methods. These novel results are indicated for the disorders described in the examples below and summarized in Table 2 above. It should be emphasized that the metabolites were measured in each sample and each sample was assayed for all diseases reported simultaneously. Thus, in a single, small volume (≤100 ul) sample a plurality of metabolites were measured to identify aberrant metabolites which were automatically mapped to biochemical pathways to aid in the diagnosis of all of the diseases and disorders described below.

As noted above, additional aberrant metabolites that may be useful to diagnose or aid in diagnosis of disease were identified from analysis of the data for the 200 subjects. These metabolites can serve as biomarkers to supplement currently used clinical diagnostic assays, to provide surrogate biomarkers, and/or to provide additional pathway information that may be informative for diagnosis or aiding in diagnosis. Such markers can be combined with the current clinically used metabolites to generate a panel of metabolites that form a metabolite signature of the disease or disorder. Such markers can be used alone or in combination with current clinically used metabolites to aid in the diagnosis of the disease and the results may be visually displayed. In some embodiments, a disease or disorder-specific predictive composite score based on one or more relevant metabolites can be used to aid in the diagnosis of the disease. In addition, such markers can aid in diagnosis when the clinically used metabolite is not detected or the measured level of said metabolite is equivocal. Said signatures can be stored in a database and used to diagnose or aid in the diagnosis of the disease or disorder.

TABLE 2

Experimental Results of Diagnosis of Disease or Disorder

| Disease or Disorder/ Synonym(s) for Disorder | No. of Diagnosed Subjects | Sensitivity | Specificity | Currently used diagnostic metabolite(s) | Currently used diagnostic metabolite(s) identified as aberrant in our analysis | Analysis Results: Novel metabolites, aberrant in diagnosed subjects |
|---|---|---|---|---|---|---|
| 3-methylcrotonyl CoA carboxylase deficiency/3-MCC deficiency, 3-methylcrotonylglycinuria, MCC deficiency | 4 | 100% | 100% | 3-methylcrotonylglycine, beta-hydroxyisovalerate | 3-methylcrotonylglycine, beta-hydroxyisovalerate | beta-hydroxyisovaleroylcarnitine, glutarylcarnitine (C5), 3-methylcrotonylglycine, adipate, glutarate (pentanedioate), octadecanedioate (C18), hexadecanedioate (C16), tetradecanedioate (C14), dodecanedioate (C12), isovalerate, leucine, isovalerylglycine, alpha-hydroxyisovalerate, succinylcarnitine, 3-methylglutarylcarnitine, isovalerylcarnitine, alanylalanine, pyroglutamylvaline, X-12007, X-12814 |

TABLE 2-continued

Experimental Results of Diagnosis of Disease or Disorder

| Disease or Disorder/ Synonym(s) for Disorder | No. of Diagnosed Subjects | Sensi-tivity | Specificity | Currently used diagnostic metabolite(s) | Currently used diagnostic metabolite(s) identified as aberrant in our analysis | Analysis Results: Novel metabolites, aberrant in diagnosed subjects |
|---|---|---|---|---|---|---|
| argininosuccinic acid lyase deficiency/ Argininosuccinic aciduria, ASA Deficiency, ASL Deficiency | 2 | 100% | 100% | argininosuccinate | argininosuccinate as a rare compound | N-delta-acetylornithine, citrulline, isoleucylaspartate, uracil, arginine, aspartate, ornithine, uridine, homocitrulline, orotate, homoarginine, sorbose, fructose, methyl-4-hydroxybenzoate, O-sulfo-L-tyrosine, palmitoyl sphingomyelin, X-15245, X-15664, X-13507, X-15454 |
| Argininemia/ Arginase deficiency, hyperargininemia | 4 | 100% | 100% | arginine, 4-guanidinobutanoate | arginine, 4-guanidinobutanoate | homoarginine, N-acetylarginine, ornithine, urea, homocitrulline, uracil, aspartate, argininosuccinate, creatine, proline, orotate, creatinine, uridine, 3-ureidopropionate, betaine, leucine, isoleucine, gamma-glutamylleucine, X-12339, X-12681 |
| biotinidase deficiency/Bioton deficiency, BTD deficiency, Late-onset multiple carboxylase deficiency | 2 | 0% | 100% | none | none | biotin, xylitol, 3-methylcrotonylglycine, propionylcarnitine (C3) |
| Cbl (cobalamin deficiency) | 2 | 100% | 100% | methylmalonic acid, homocysteine, 2-methylcitrate, cystathionine | none | 2-methylmalonyl carnitine, propionylcarnitine, X-12749 |
| Cbl A | 1 | 100% | 100% | methylmalonic acid, homocysteine, 2-methylcitrate, cystathionine | 2-methylcitrate | 2-methylmalonyl carnitine, tiglyl carnitine, 2-methylbutyrylcarnitine, propionylcarnitine, X-12749 |
| Cbl C | 4 | 100% | 50% | methylmalonic acid, homocysteine, 2-methylcitrate, cystathionine | none | 2-methylmalonyl carnitine, propionylcarnitine, X-17677, X-12749 |
| Citrullinemia/ Argininosuccinate synthetase deficiency, ASS deficiency, CTLN1 | 9 | 100% | 100% | citrulline, argininosuccinic acid | citrulline | homocitrulline, 3-ureidopropionate, phenylacetylglutamine, phenylacetylglycine, homoarginine, urea, guanidinosuccinate, phenylacetate, N-acetylalanine, gamma-glutamylphenylalanine, gamma-glutamylisoleucine, tryptophan, 1,5-anhydroglucitol (1,5-AG), N-acetyl-citrulline (previously X-12386), X-19684, X-12681, X-20598, X-18446, X-20588 |
| CPTII/Carnitine palmitoyltransferase 2 deficiency | 1 | 100% | 100% | carnitine, acylcarnitines | decanoylcarnitine (C10) | N-octanoylglycine (C8 ester), sebacate(C8), caprate (C10), caprylate(C8), octanoylcarnitine, and hexanoylcarnitine |
| Cystinosis/Cystine diathesis, Cystine disease | 3 | 0% | 100% | cystine | none | cys-gly (oxidized), 1,5-anhydroglucitol (1,5-AG), glycocholenate sulfate, 4-acetylphenol sulfate, cresol glucuronide (X-11837), erythritol, vanillylmandelate, N2,N2-dimethyl-guanosine, |

TABLE 2-continued

Experimental Results of Diagnosis of Disease or Disorder

| Disease or Disorder/ Synonym(s) for Disorder | No. of Diagnosed Subjects | Sensi-tivity | Specificity | Currently used diagnostic metabolite(s) | Currently used diagnostic metabolite(s) identified as aberrant in our analysis | Analysis Results: Novel metabolites, aberrant in diagnosed subjects |
|---|---|---|---|---|---|---|
| | | | | | | phenylacetylglutamine, X-12846, X-12303, X-19145, X-12216, X-17717, X-15667, X-12119, X-11315, X-12731, X-12705, X-17685, X-18371 |
| glutaric aciduria type 1/ Dicarboxylic amionaciduria, GAI, Glutaricacidemia I, Glutaryl-CoA, dehydrogenase deficiency | 5 | 100% | 100% | glutarate (pentanedioate), glutarylcarnitine (C5), 3-hydroxyglutarate, glutaconate | glutarate (pentanedioate), glutarylcarnitine (C5) | X-12364, X-15674 |
| guanidinoacetate methyl transferase deficiency/GAMT deficiency | 8 | 0% | 100% | none | none | creatine, 3-(4-hydroxyphenyl)lactate, 1,3-dipalmitoylglycerol, guanidinoacetate, cysteine s-sulfate, X-19602, X-12906, X-13007, X-10458 |
| HMG CoA Lyase Deficiency/3-hydroxy-3-methylglutaric aciduria, HL deficiency | 2 | 100% | 100% | 3-methylglutarylcarnitine (C6), 3-hydroxy-3-methyl-glutarate, 3-methylglutarate, 3-hydroxyisovalerate | 3-methylglutarylcarnitine (C6), 3-hydroxy-3-methyl-glutarate, 3-methylglutarate, 3-hydroxyisovalerate | beta-hydroxyisovalerate, beta-hydroxyisovaleroylcarnitine, glutarylcarnitine (C5), 3-methylcrotonylglycine, adipate, glutarate (pentanedioate), octadecanedioate (C18), hexadecanedioate (C16), tetradecanedioate (C14), dodecanedioate (C12), isovalerate, arginylproline, 1-stearoylglycerophosphoethanolamine, o-cresol sulfate, acetylcarnitine, palmitoylcarnitine, hexanoylcarnitine, myristoylcarnitine, hexenedioylcarnitine (X-17001), X-17715, X-12741, X-16134, X-10593, X-12688 |
| Holocarboxylase/ Holocarboxylase synthetase deficiency | 1 | 100% | 100% | beta-hydroxyisovalerate | beta-hydroxyisovalerate | 3-methylcrotonylglycine, beta-hydroxyisovaleroylcarnitine (C5), propionylglycine (C3), 3-hydroxypropanoate, tigloylglycine, succinylcarnitine, biotin |
| Homocystinuria/ Cystathionine beta-synthase deficiency | 2 | 100% | 100% | homocysteine, cysteine, methionine, other amino acids | methionine | gamma-glutamylmethionine, 5-methylthioadenosine (MTA), S-adenosylhomocysteine (SAH), N1-methyladenosine, glycylproline, 1-eicosenoylglycerophosphoethanolamine (20:1n9), 1-methylnicotinamide, N-acetyl-aspartyl-glutamate (NAAG), pyridoxal, 2-hydroxyisobutyrate, acisoga, carnosine, 3-methoxytyrosine, 2-hydroxydecanoate, delta-tocopherol, alpha-CEHC sulfate (X-12435), N-acetyltryptophan, adenine, cortisol, X-19350, X-18965, X-15649, X-17303, X-18897, X-11564, X-18891, X-12748, X-18918, X-18905, X-18606, X-16574, X- |

TABLE 2-continued

Experimental Results of Diagnosis of Disease or Disorder

| Disease or Disorder/ Synonym(s) for Disorder | No. of Diagnosed Subjects | Sensi-tivity | Specificity | Currently used diagnostic metabolite(s) | Currently used diagnostic metabolite(s) identified as aberrant in our analysis | Analysis Results: Novel metabolites, aberrant in diagnosed subjects |
|---|---|---|---|---|---|---|
| | | | | | | 18895, X-18907, X-19455, X-18909, X-19574, X-12110, X-20676, X-11360, X-18920 |
| isovaleric acidemia/ Isovaleric acid CoA dehydrogenase deficiency, IVA, IVD deficiency | 2 | 100% | 100% | isovalerate (C5) | isovalerate (C5) | isovalerylglycine, isovalerylcarnitine (C5), valerate, valerylcarnitine, beta-hydroxyisovalerate, 3-methylcrotonylglycine, phenylcarnitine, X-16577, X-14331 |
| Lysinuric protein intolerance/ Dibasicamino aciduria II, LPI | 2 | 100% | 100% | ornithine, arginine, lysine | ornithine, arginine, lysine | asparagine, N6-acetyllysine, Glutamine, N2-acetyllysine, N-acetylarginine, gamma-glutamylglutamine, proline, S-methylcysteine, 2-hydroxydecanoate, 1-methylimidazoleacetate, X-15636, X-17654, X-12193, X-12425 |
| medium chain acyl CoA dehydrogenase deficiency/MCAD deficiency, MCADD, ACADM deficiency, Acyl-CoA dehydrogenase medium chain deficiency | 2 | 100% | 100% | acylcarnitines, carnitine, organic acids | hexanoylglycine (C6), octanoylcarnitine (C8), hexanoylcarnitine (C6), cis-4-decenoyl carnitine, 5-hydroxyhexanoate, suberate (octanedioate), sebacate (decanedioate), decanoylcarnitine, 3-hydroxydecanoate | N-octanoylglycine, caproate (6:0), caprylate (8:0), heptanoate (7:0), dodecanedioate, N-palmitoyltaurine, pelargonate (9:0), deoxycarnitine, O-methylcatechol sulfate, 1-stearoylglycerophosphocholine (18:0), 1-margaroylglycerophosphocholine (17:0), 1-docosapentaenoylglycerophos phocholine (22:5n3), alpha-CEHC sulfate (X-12435), methylhexanoylglutamine (X-12637), X-11521, X-15646, X-12802, X-11478, X-11440, X-15486, X-18913, X-13837, X-18946, X-11861, X-18888, X-18922, X-17438, X-18916, X-16674, X-12824 |
| methylmalonic acidemia | 9 | 100% | 100% | methylmalonate, methylmalonyl CoA | none | 2-methylmalonyl carnitine, propionylcarnitine (C3), tiglyl carnitine, 2-methylbutyrylcarnitine (C5), 2-methylcitrate, succinylcarnitine, propionylglycine, 3-hydroxypropanoate, valerylcarnitine, isovalerylcarnitine, succinate, tigloylglycine, beta-hydroxyisovaleroylcarnitine, beta-hydroxyisovalerate, isobutyrylcarnitine, 3-hydroxy-2-ethylpropionate, butyrylcarnitine, 3-methyl-2-oxovalerate, 3-methyl-2-oxobutyrate, X-12749, X-17564, X-12114 |
| molybdenum cofactor or sulfite oxidase deficiency/ MOCD | 1 | 0% | 100% | xanthine, S-sulfocysteine, thiosulfate | none | 5-HETE, leukotriene B4, 13-HODE + 9-HODE, 12-HETE |
| Maple syrup urine disease/BCKD deficiency, Branched Chain Ketonuria I | 18 | 100% | 100% | leucine, isoleucine, valine | isoleucine, leucine, valine | 2-hydroxy-3-methylvalerate, alpha-hydroxyisovalerate, isovalerylcarnitine, 3-methyl-2-oxobutyrate, isovalerate, isobutyrylcarnitine, 3-hydroxyisobutyrate, 2-methylbutyrylcarnitine, beta- |

TABLE 2-continued

| Experimental Results of Diagnosis of Disease or Disorder | | | | | | |
|---|---|---|---|---|---|---|
| Disease or Disorder/ Synonym(s) for Disorder | No. of Diagnosed Subjects | Sensi-tivity | Specificity | Currently used diagnostic metabolite(s) | Currently used diagnostic metabolite(s) identified as aberrant in our analysis | Analysis Results: Novel metabolites, aberrant in diagnosed subjects |
| | | | | | | hydroxyisovaleroylcarnitine, allo-isoleucine, 3-methyl-2-oxovalerate, beta-hydroxyisovalerate, succinate, acetylcarnitine, 2-methylcitrate, tigloylglycine, tiglyl carnitine, hydroxybutyrylcarnitine, alpha-hydroxyisocaproate, 2-aminoheptanoate, 4-methyl-2-oxopentanoate, 1-linolenoylglycerophosphocholine (18:3n3), 2-linolenoylglycerophosphocholine (18:3n3), 1-myristoylglycerophosphocholine (14:0), 2-myristoylglycerophosphocholine, 5alpha-androstan-3alpha, 17beta-diol disulfate, X-13581, X-17690, X-13689 |
| ornithine transcarbamylase deficiency/OTC deficiency, OTCD, Ornithine carbamoyltransferase deficiency | 17 | 100% | 100% | orotate, citrulline, arginine | orotate | phenylacetylglutamine, 3-ureidopropionate, phenylacetate, phenylcarnitine, phenylacetylglycine, trans-4-hydroxyproline, pro-hydroxy-pro, urea, phenyllactate (PLA), guanidinosuccinate, hippurate, ornithine, stearidonate (18:4n3), X-20598, X-20588 |
| propionic acidemia/ Propionyl CoA carboxylase deficiency, PCC deficiency, Hyperglycinemia with ketoacidosis and lactic acidosis, Ketotic glycinemia | 9 | 100% | 100% | propionate | none | propionylglycine (C3), 2-methylcitrate, 3-hydroxypropanoate, propionylcarnitine (C3), tigloylglycine, succinylcarnitine, glutarylcarnitine (C5), 3-methylglutarylcarnitine (C6), 2-methylmalonyl carnitine, tiglylcarnitine, beta-hydroxyisovalerate, 1-pentadecanoylglycerophosphocholine (15:0), butyrylcarnitine, X-12819 |
| PKU/ Phenylketonuria, hyperphenylalanemia | 8 | 100% | 100% | phenylalanine | phenylalanine | gamma-glutamylphenylalanine, phenyllactate, N-acetylphenylalanine, phenylpyruvate, gamma-glutamyltyrosine, 3-methoxytyrosine, 4-hydroxyphenylpyruvate, p-cresol sulfate, catechol sulfate, o-cresol sulfate, phenylacetylglutamine, phenylalanylarginine, valylphenylalanine, histidylphenylalanine, phenylalanylserine, leucylphenylalanine, threonylphenylalanine, phenylalanylalanine, phenylalanylglycine, phenylalanylglutamate, phenylalanylphenylalanine, aspartylphenylalanine, tryptophylphenylalanine, phenylalanylisoleucine, glycylphenylalanine, |

TABLE 2-continued

Experimental Results of Diagnosis of Disease or Disorder

| Disease or Disorder/ Synonym(s) for Disorder | No. of Diagnosed Subjects | Sensi-tivity | Specificity | Currently used diagnostic metabolite(s) | Currently used diagnostic metabolite(s) identified as aberrant in our analysis | Analysis Results: Novel metabolites, aberrant in diagnosed subjects |
|---|---|---|---|---|---|---|
| | | | | | | phenylalanylleucine, phenylalanylaspartate, phenylacetylglycine, X-16283, X-15497 |
| Thymidine phosphorylase deficiency/ Mitochondrial neurogastrointestinal encephalopathy syndrome, MNGIE, OGIMD | 2 | 100% | 100% | thymidine | thymidine as a rare compound | 2'-deoxyuridine, 5,6-dihydrothymine, 5-methyluridine (ribothymidine), hippurate, 2-linoleoylglycerophosphocholine, 4-methylcatechol sulfate, 1-arachidoylglycerophosphocholine (20:0), taurolithocholate 3-sulfate, glycolithocholate sulfate, imidazole propionate, X-13862, X-19330, X-20620, X-12170 |
| trimethylysine hydroxylase epsilon deficiency | 4 | 100% | 99% | N6-trimethyllysine | N6-trimethyllysine | 1-arachidonoylglyercophosphate, X-16574, X-12822, X-15136 |
| very long chain acyl CoA dehydrogenase deficiency (VLCAD) | 2 | 50% | 100% | myristoylcarnitine, stearoylcarnitine (C18), palmitoylcarnitine (C16), oleoylcarnitine (C18), myristoleate (14:1n5), linoleoylcarnitine, myristoleoylcarnitine | myristoylcarnitine, stearoylcarnitine (C18), palmitoylcarnitine (C16), oleoylcarnitine (C18), myristoleate (14:1n5), linoleoylcarnitine, myristoleoylcarnitine | arachidonate (20:4n6), docosahexaenoate (DHA;22:6n3), eicosapentanoic acid (EPA), 9-methyluric acid, xylulose, 5,8-tetradecadienoic acid (X-12442), docosahexaenoate-glycerophosphocholine, X-18739 |
| X-linked creatine transporter/ X-linked creatine deficiency | 3 | 0% | 100% | none | none | glycylleucine, 2-hydroxyoctanoate, 1,6-anhydroglucose, X-11483, X-18943, X-17422, X-17761, X-17335 |
| Sarcosinemia | 1 | 100% | 100% | sarcosine | sarcosine | dimethylglycine, betaine, choline, glycine |
| Citrate transporter deficiency | 5 | 100% | 100% | citrate | citrate | alpha-ketoglutarate, succinate, fumarate, malate |
| Pyruvate dehydrogenase deficiency | 1 | 100% | 100% | Pyruvate, lactate | none | none |
| Hyperornithinemia-Homocitrullinemia-Hyperammonemia (HHH) | 1 | 100% | 100% | homocitrulline, ornithine, spermine, spermidine | homocitrulline, ornithine | uracil, 3-ureidopropionate, orotate, glutamine, N-acetyl-beta-alanine, uridine, N-acetylaspartate (NAA), dimethylarginine (SDMA + ADMA), 5-methylthioadenosine (MTA), beta-alanine, 4-ureidobutyrate |
| Aromatic amino acid decarboxylase deficiency | 1 | 100% | 100% | L-dopa, 3-methoxytyrosine, 5-hydroxytryptophan, homovanillate, 5-hydroxyindoleacetate, and vanillactic acid (currently used for urine and CSF samples) | 3-methoxytyrosine, 5-hydroxytryptophan | Tyrosine, phenylalanine, tryptophan |
| Smith-Lemli-Opitz syndrome | 1 | 100% | 100% | 7-dehydrocholesterol | 7-dehydrocholesterol | cholestanol |
| Primary carnitine deficiency | 1 | 100% | 100% | carnitine, acylcarnitine | carnitine | N6-trimethyllysine |
| Citrin deficiency | 1 | 100% | 100% | citrulline, arginine, | citrulline | Orotate |

TABLE 2-continued

Experimental Results of Diagnosis of Disease or Disorder

| Disease or Disorder/ Synonym(s) for Disorder | No. of Diagnosed Subjects | Sensi-tivity | Specificity | Currently used diagnostic metabolite(s) | Currently used diagnostic metabolite(s) identified as aberrant in our analysis | Analysis Results: Novel metabolites, aberrant in diagnosed subjects |
|---|---|---|---|---|---|---|
| | | | | threonine, serine, methionine, phenylalanine, and tyrosine | | |
| 4-aminobutyrate aminotransferase (ABAT) Deficiency | 2 | 100% | 100% | GABA | GABA | 2-pyrrolidone |
| 3-methylglutaconic aciduria (MGA) | 1 | 100% | 100% | 3-methylglutaconic acid, 3-methylglutaric acid | none | 3-methylglutarylcarnitine |
| Short chain acyl-CoA decarboxylase (SCAD) deficiency/ butyryl-CoA dehydrogenase deficiency | 1 | 100% | 100% | ethylmalonate, butyrylcarnitine, methylsuccinate | ethylmalonate, butyrylcarnitine, methylsuccinate | butyrylglycine |
| Urocanase deficiency | 1 | 100% | 100% | cis-urocanate, trans-urocanate, imidazole propionate | cis-urocanate, trans-urocanate, imidazole propionate | none |
| 3-hydroxyisobutyryl-CoA hydrolase deficiency/ methacrylic aciduria | 2 | 0% | 50% | none | none | 3-hydroxyisobutyrate, isobutyrylglycine |
| γ-Butyrobetaine Hydroxylase Deficiency, BBOX Deficiency | 1 | 100% | 100% | none | none | hexadecanedioate (C16), docosadioate, eicosanodioate, octadecanedioate (C18), dodecanedioate (C12), 2-aminooctanoate, 2-aminoheptanoate, alpha-hydroxyisocaproate, isovalerate (C5), decanoylcarnitine (C10), cis-4-decenoyl carnitine, palmitoylcarnitine (C16), oleoylcarnitine (C18), laurylcarnitine (C12), myristoleoylcarnitine, myristoylcarnitine, glycerol, 3-hydroxymyristate, 2-hydroxydecanoate, 3-hydroxylaurate, 3-hydroxysebacate, 3-hydroxyoctanoate, 3-hydroxydecanoate, pelargonate (9:0), caproate (6:0) |

Figure 4:
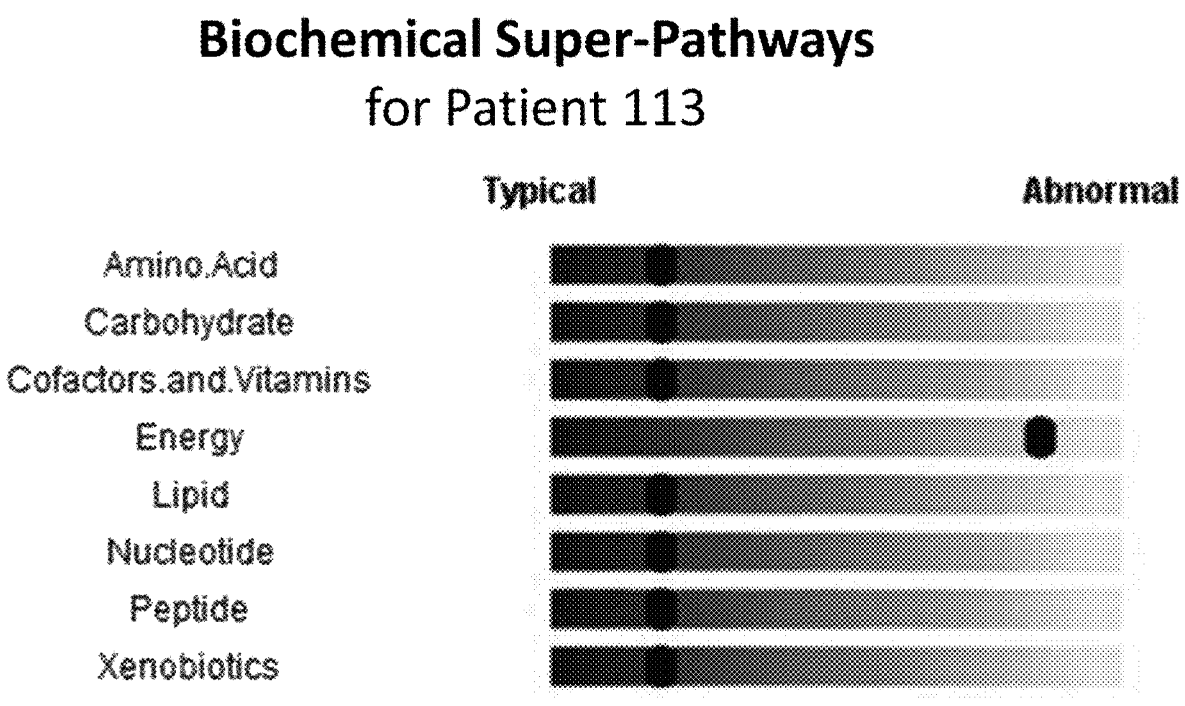
FIG. 4 is an illustration of a visual display of eight biochemical super-pathways and the classification status of each pathway for patient 113.
Figure 5:
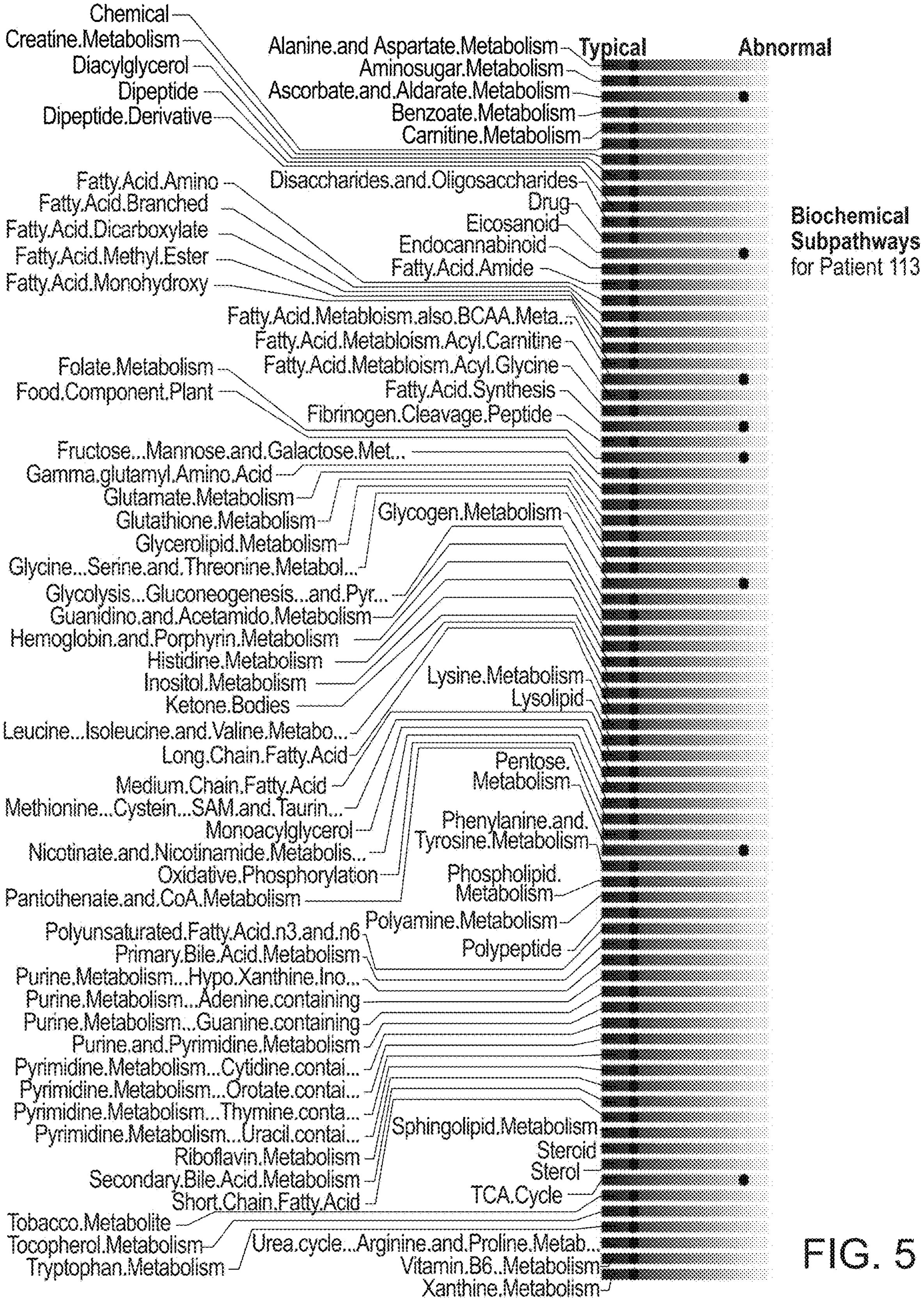
FIG. 5 is an example visual display of the status of all biochemical subpathways for patient 113.
Figure 6:
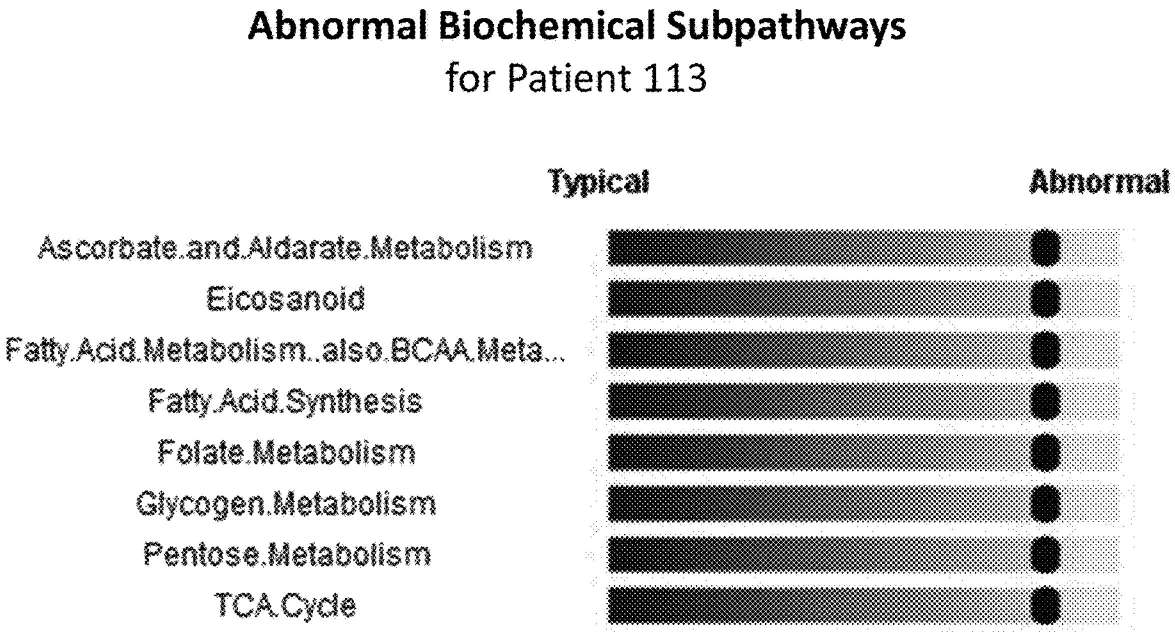
FIG. 6 is an illustration of a visual display of abnormal biochemical subpathways for patient 113.
Figure 8:
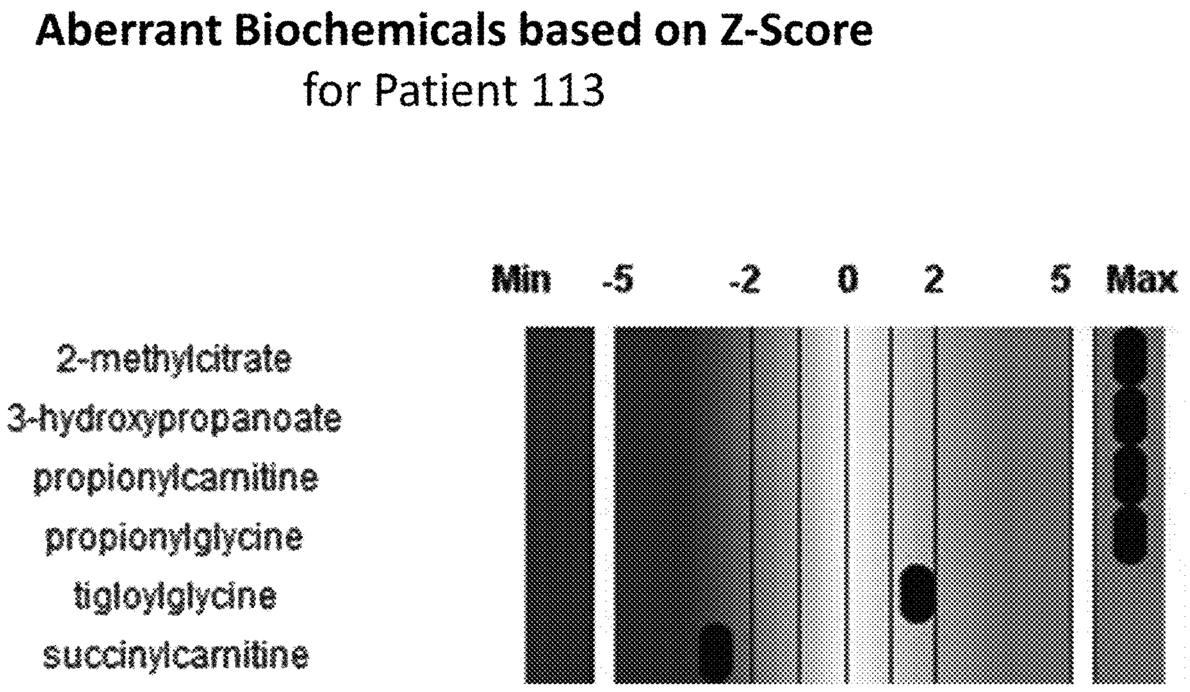
FIG. 8 is an example of a visual display of individual aberrant biochemicals for patient 113 based on Z-score analysis that are diagnostic for the disorder or biochemically related to the diagnostic biochemical.
Figure 9:
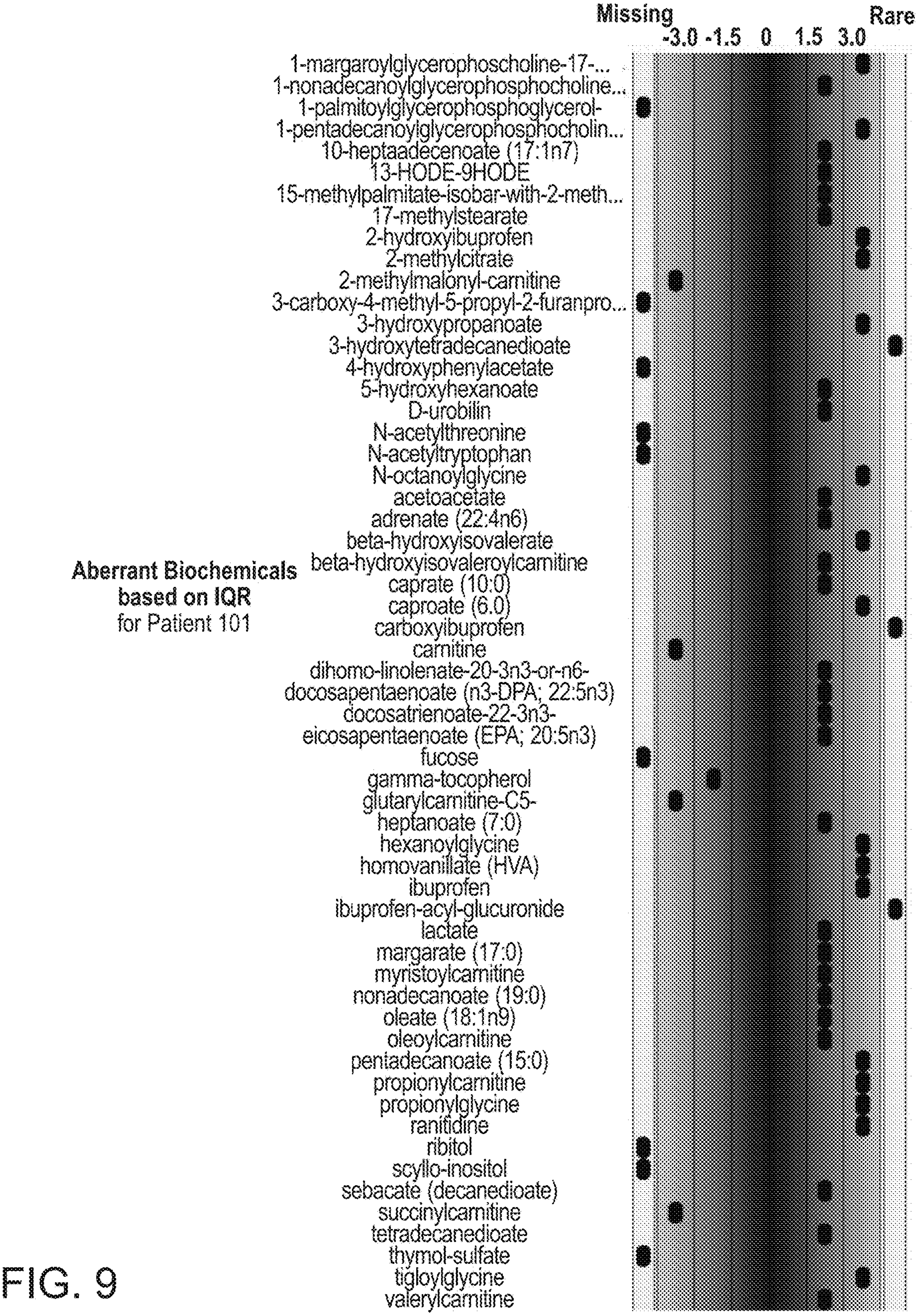
FIG. 9 is an example of a visual display of individual aberrant biochemicals for patient 101.
Figure 10:
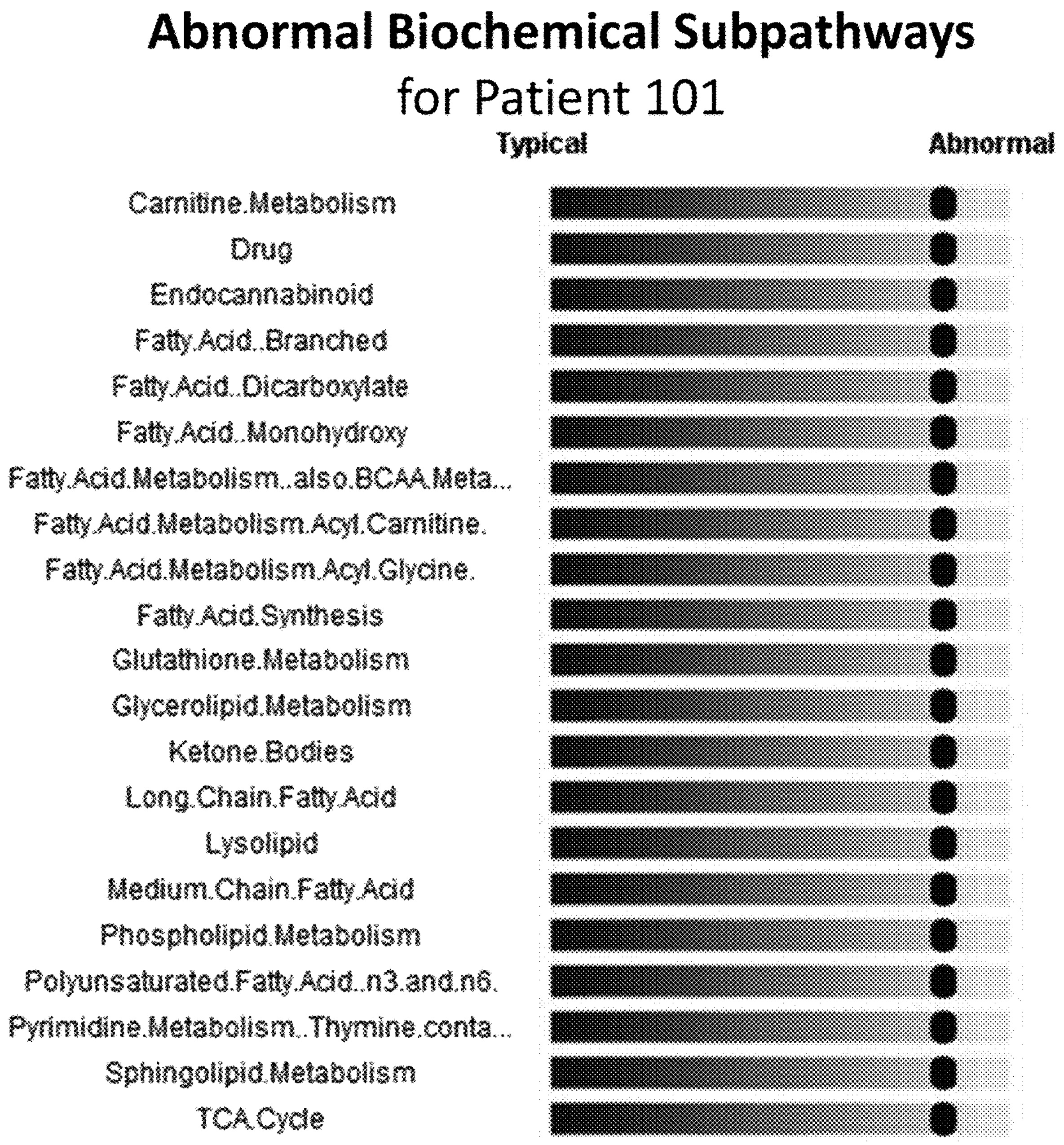
FIG. 10 is an illustration of a visual display of biochemical subpathways determined to be abnormal for patient 101.

Non-limiting examples showing graphic illustrations of the automated visualization of the biochemical super-pathways are presented in FIG. 4, the biochemical subpathways are presented in FIGS. 5, 6, and 10, and the biochemicals are presented in FIGS. 7-9 and 11-14. An example graphic illustration of the visualization of biochemical super-pathways for one patient is presented in FIG. 4. The biochemical super-pathways are listed on the left. The black dots indicate the pathway as being typical or abnormal for that subject. Using the methods described herein, the energy pathway was determined to be abnormal for this patient. The biochemical subpathways visualization for the patient is exemplified in FIG. 5. The biochemical subpathways ascorbate and aldarate metabolism; eicosanoid metabolism; fatty acid metabolism (branched chain amino acid (BCAA) metabolism); fatty acid synthesis; folate metabolism; glycogen metabolism; pentose metabolism, and TCA (tricarboxylic acid) cycle are indicated as abnormal. An example of the visualization of the abnormal subpathways is illustrated in FIG. 6.

Figure 7:
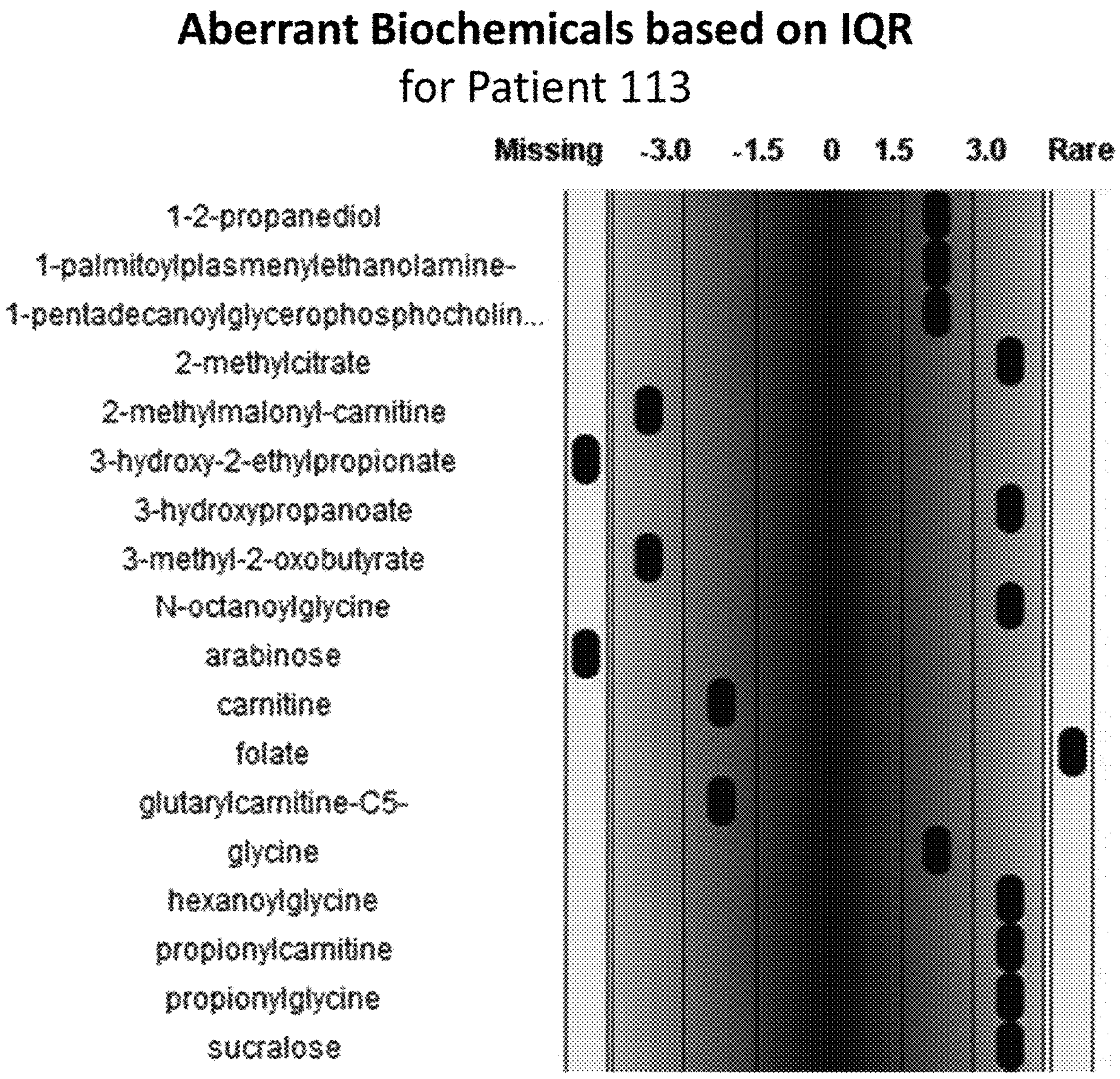
FIG. 7 is an example visual display of individual aberrant biochemicals for patient 113.

Examples of the automated visual display of aberrant biochemicals as determined by IQR or Z-score analysis are graphically illustrated in FIGS. 7 & 8, respectively. These results are consistent with the clinical diagnosis for this patient. Additional, non-limiting examples described below were produced using these methods to generate the following results for the indicated disorders from plasma samples collected from the 200 participants.

Propionic Acidemia.

Levels of propionylglycine were elevated 3.0*IQR in the sample from a propionic acidemia patient. It was also apparent from the automated visual display of biochemicals that other metabolites related to propionylglycine (e.g., 2-methylcitrate, 3-hydroxypropanoate and propionylcarnitine) were aberrant. The visual display is graphically illustrated in FIG. 7. The ability to identify these related metabolites increased the confidence in the diagnosis of propionic acidemia. As shown in the display of FIG. 7, the biochemical folate was a rare biochemical, and the biochemicals 3-hydroxy-2-ethylpropionate and arabinose were missing; 2-methylmalonyl-carnitine and 3-methyl-2-oxobutyrate were present at levels that were reduced by at least 3.0*IQR; carnitine and glutarylcarnitine (C5) were present at levels that were reduced by at least 1.5*IQR; 1,2-propanediol, 1-palmitoylglycerophosphocholine (16:0), and 1-pentadecanoylglycerophosphocholine (15:0) were present at levels that were elevated by at least 1.5*IQR; and 2-methylcitrate, 3-hydroxypropanoate, N-octanoylglycine, hexanoylglycine, propionylcarnitine, propionylglycine, and sucralose were present at levels that were elevated by at least 3.0*IQR. The data were also statistically analyzed by calculating a Z-score for each metabolite to identify statistically aberrant biochemicals. An example of the Z-score visualization is graphically illustrated in FIG. 8. Z-scores for all metabolites were calculated for the 9 patients diagnosed with propionic acidemia (PAA). Propionylglycine and related metabolites (e.g., 2-methylcitrate, 3-hydroxypropanoate and propionylcarnitine) all had Z-score values of greater than 2. In another patient with propionic acidemia the levels of tigloylglycine, propionyl carnitine (C3), propionylglycine, 2-methylcitrate, and 3-hydroxypropanoate were elevated 3.0*IQR, while 2-methylmalonyl carnitine (C3), and succinylcarnitine were reduced 3.0*IQR. An automated visual display of the data is illustrated in FIG. 9. The aberrant biochemicals were automatically mapped to biochemical pathways. An automated visual display of mapping aberrant biochemicals to biochemical pathways is exemplified in FIG. 10. In another example, the clinical diagnostic metabolite propionate was not detected in some of the patients with propionic acidemia. However, the biochemically related metabolites 2-methylcitrate, 3-hydroxypropanoate, and propionylcarnitine (C3) were elevated in all 9 patents and the Z-score values for said metabolites were at least 2. Additional metabolites propionylglycine (C3), 1-pentadecanoylglycerophosphocholine (15:0), tigloylglycine, succinylcarnitine, glutarylcarnitine (C5), 3-methylglutarylcarnitine (C6), tiglylcarnitine, butyrylcarnitine, 2-methylmalonyl carnitine, beta-hydroxyisovalerate, and X-12819 were aberrant based on Z-scores. The observed aberrant levels of these metabolites aided in the diagnosis indicating the utility of these compounds as novel biomarkers of propionic acidemia.

Figure 11:
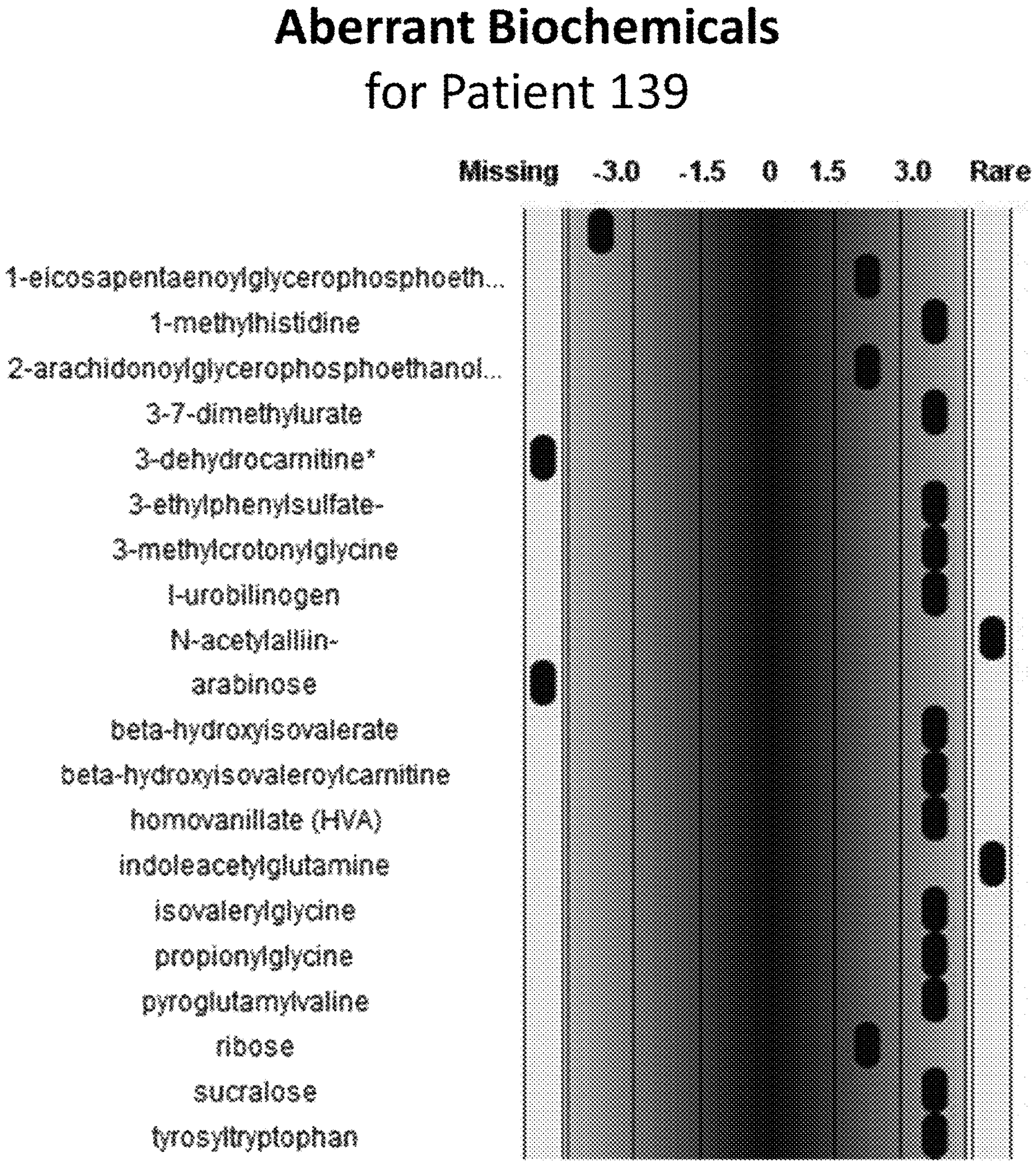
FIG. 11 is an illustration of a visual display of individual aberrant biochemicals for patient 139.

3-methylcrotonyl CoA carboxylase deficiency. The level of 3-methylcrotonylglycine measured in a patient with 3-methylcrotonyl CoA carboxylase deficiency was elevated 3.0*IQR. It was apparent from the visual display of the biochemicals that not only were levels of 3-methylcrotonylglycine aberrant but additional metabolites were aberrant also. A graphic illustration of the visual display of the data is shown in FIG. 11. In a further example, in patients diagnosed with 3-methylcrotonyl CoA carboxylase deficiency, the Z-score for the clinical diagnostic metabolites 3-methylcrotonylglycine, beta-hydroxyisovalerate was greater than 2. In addition, the metabolites beta-hydroxyisovaleroylcarnitine, glutarylcarnitine (C5), 3-methylcrotonylglycine, adipate, glutarate (pentanedioate), octadecanedioate (C18), hexadecanedioate (C16), tetradecanedioate (C14), dodecanedioate (C12), isovalerylglycine, leucine, isovalerate, alanylalanine, pyroglutamylvaline, leucine, isovalerate, alanylalanine, alpha-hydroxyisovalerate, succinylcarnitine, 3-methylglutarylcarnitine, isovalerylcarnitine, X-12007, and X-12814 were aberrant based on the Z-scores.

Figure 12:
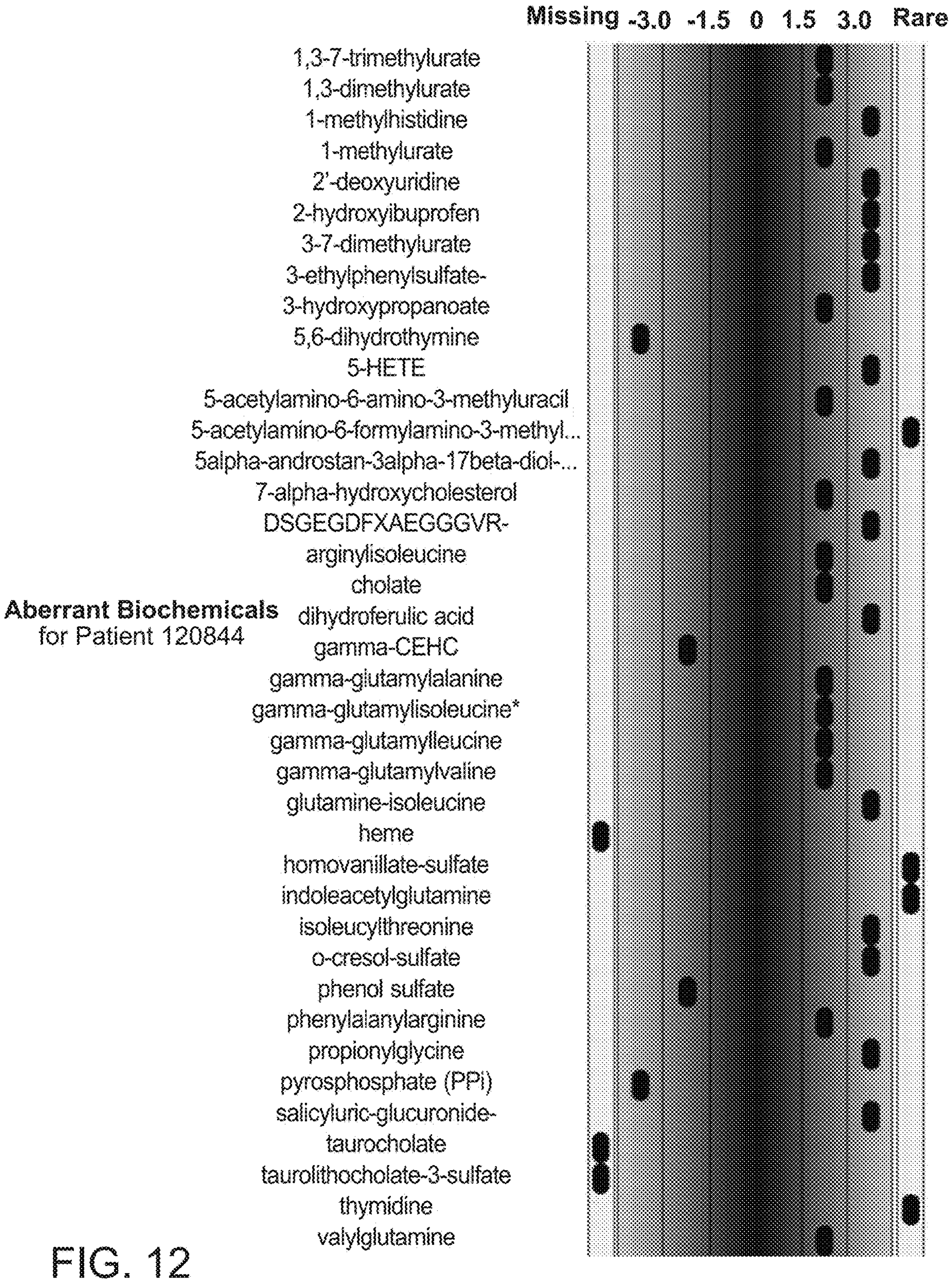
FIG. 12 is an example of a visual display of individual aberrant biochemicals for patient 120844.

Thymidine phosphorylase deficiency. Thymidine is rarely present in plasma samples. Automated visual displays of the data indicated that thymidine was observed in samples from patients determined to have thymidine phosphorylase deficiency. These results are indicated by the black dot in the "Rare" column for thymidine in the example graphic illustration of the visual display for one patient which is shown in FIG. 12. The identification of thymidine as a biochemical present in the plasma sample from this patient aided in the diagnosis of thymidine phosphorylase deficiency.

In another example, in patients with Thymidine phosphorylase deficiency, the clinical metabolite thymidine was identified as a rare compound. In addition, the biochemicals 2'-deoxyuridine, 5-methyluridine (ribothymidine), 5,6-dihydrothymine, hippurate, 2-linoleoylglycerophosphocholine, 4-methylcatechol sulfate, 1-arachidoylglycerophosphocholine (20:0), taurolithocholate 3-sulfate, glycolithocholate sulfate, imidazole propionate, X-13862, X-19330, X-20620, and X-12170 were aberrant in both patients based on Z-score analysis.

Figure 13:
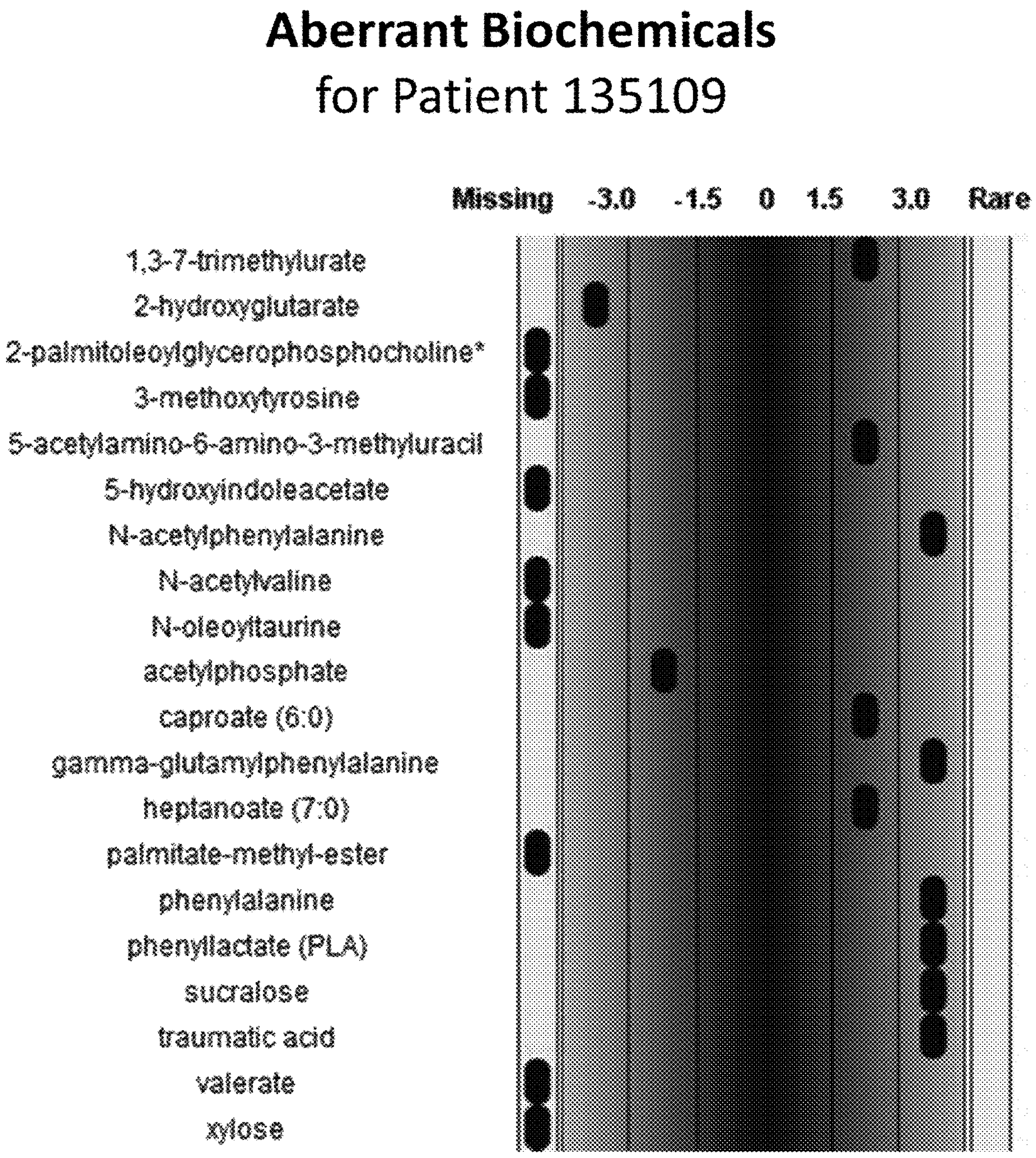
FIG. 13 is an example visual display of individual aberrant biochemicals for patient 135109.

Phenylketonuria (PKU). Levels of phenylalanine were elevated 3.0*IQR in samples from a PKU patients. Additional metabolites were also aberrant. A graphic illustration of the automated visual display of the statistical analysis of the biochemicals for one patient is shown in FIG. 13. The visual display shows that not only was phenylalanine aberrant but that other biochemicals related to phenylalanine (e.g., gamma-glutamylphenylalanine and phenyllactate (PLA) were aberrant also. In another example, in the patients diagnosed with PKU the Z-score was greater than 2 for the clinical diagnostic metabolite phenylalanine. In addition, the biochemically related metabolites phenyllactate, gamma-glutamylphenylalanine, N-acetylphenylalanine, phenylpyruvate, gamma-glutamyltyrosine, 3-methoxytyrosine, 4-hydroxyphenylpyruvate, p-cresol sulfate, catechol sulfate, o-cresol sulfate, phenylacetylglycine, and the additional metabolites phenylacetylglutamine, phenylalanine-containing dipeptides (e.g., phenylalanylarginine, valylphenylalanine, histidylphenylalanine, phenylalanylserine, leucylphenylalanine, threonylphenylalanine, phenylalanylalanine, phenylalanylglycine, phenylalanylglutamate, phenylalanylphenylalanine, aspartylphenylalanine, tryptophylphenylalanine, phenylalanylisoleucine, glycylphenylalanine, phenylalanylleucine, phenylalanylaspartate), X-15497 and X-16283 were aberrant based on Z-scores.

Figure 14:
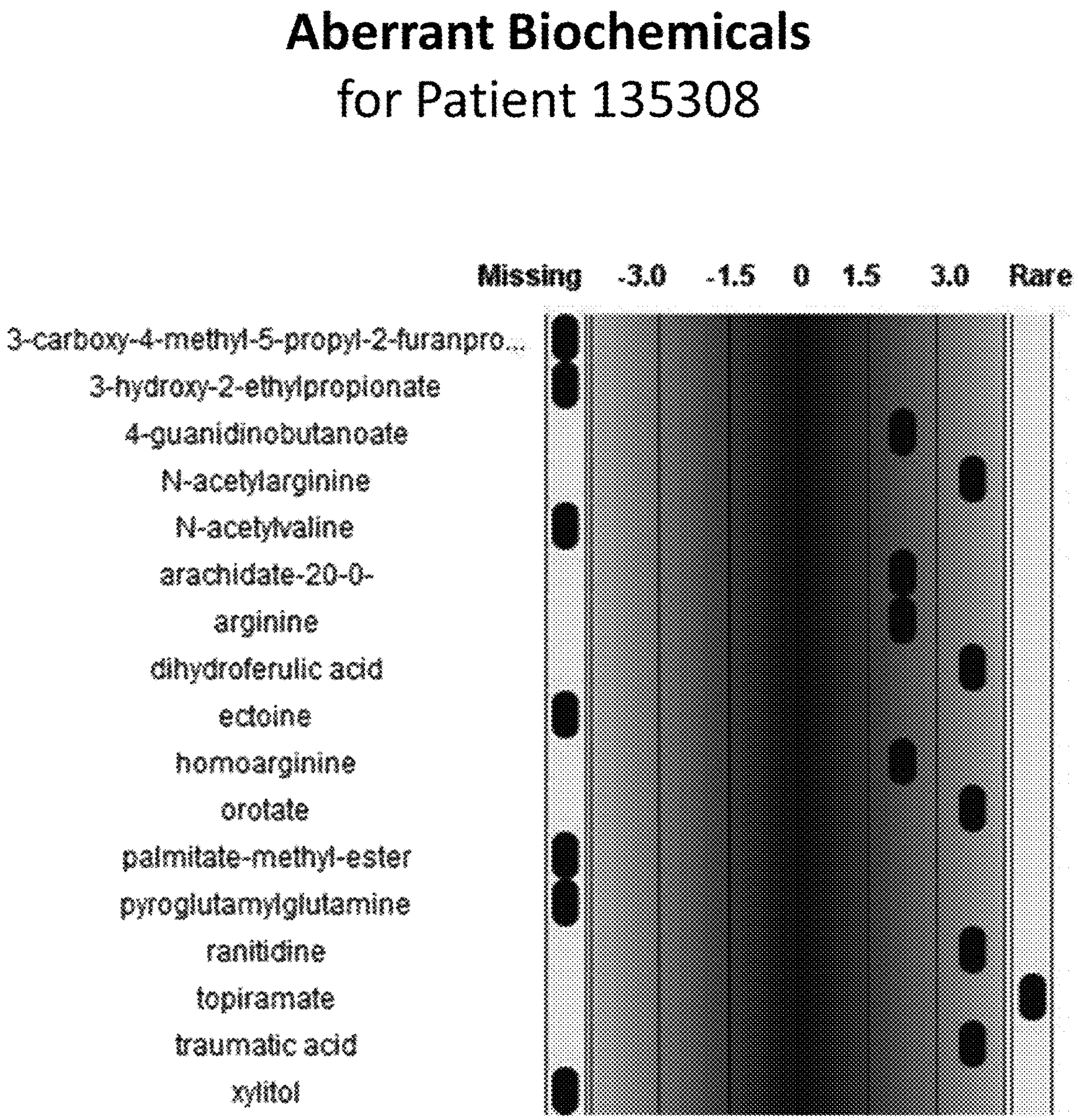
FIG. 14 is an illustration of a visual display of individual aberrant biochemicals for patient 135308.

Argininemia. Levels of arginine, 4-guanidinobutanoate, and homoarginine were elevated 1.5*IQR and levels of N-acetylarginine were elevated 3.0*IQR in a patient with Argininemia. The automated visual display of biochemicals shows that not only were the levels of arginine, homoarginine and N-acetylarginine aberrant but it revealed additional metabolites that were aberrant also. An example graphic illustration of the visual display of the IQR data is shown in FIG. 14. In a further analysis based on Z-scores the clinical metabolites arginine, and 4-guanidinobutanoate, and additional metabolites homoarginine, N-acetylarginine, ornithine, urea, homocitrulline, uracil, aspartate, argininosuccinate, proline, orotate, creatinine, uridine, 3-ureidopropionate, creatine, betaine, leucine, isoleucine, gamma-glutamylleucine, X-12339, and X-12681 were aberrant.

Figure 15:
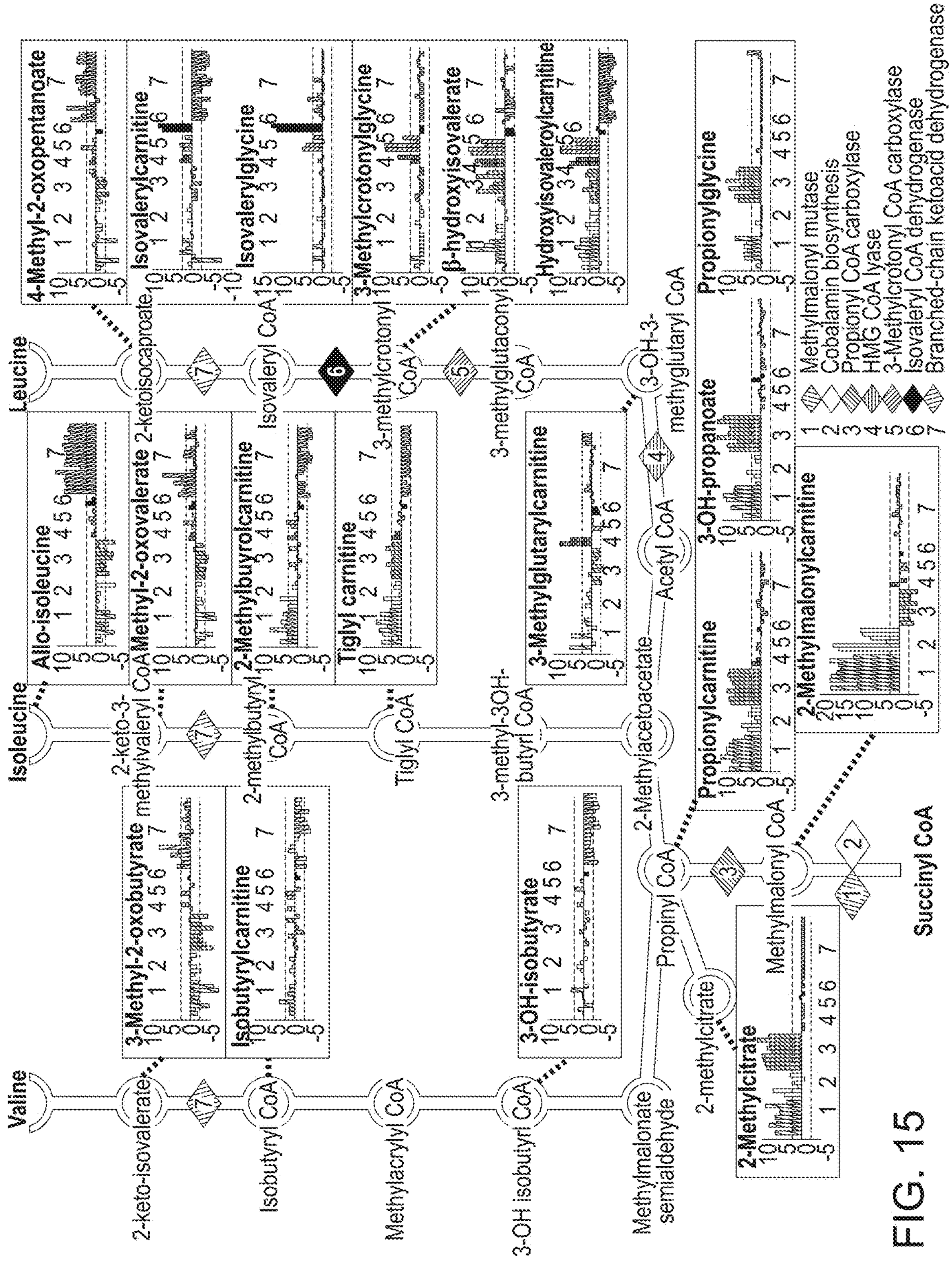
FIG. 15 is an example of a visual display of branched chain amino acid (BCAA) biochemical pathways with aberrant metabolites from 51 patients with disorders of BCAA metabolism mapped to the pathways. The disorders are indicated by numbers 1-7. Diamond shapes indicate known disruptions in the biochemical pathway for the given disorder.

BCAA metabolism. The current clinical practice to diagnose disorders of BCAA metabolism is performed by organic acid extraction of a number of organic acids from urine samples, including 3-methyl-2-oxobutyrate, 3-methyl-2-oxovalerate, β-hydroxyisovalerate, and tiglyglycine. However, using the described method these disorders may be diagnosed in a plasma sample, thereby facilitating the multi-plexed screening for many disorders simultaneously from a single sample type. For example, using the plasma samples described in Example 2, the aberrant metabolites detected in the samples of 51 patients with disorders of BCAA metabolism (e.g., methylmalonic acidemia, cobalamin deficiency, propionic acidemia, HMG CoA lyase deficiency, 3-methylcrotonyl CoA carboxylase deficiency, Isovaleric acidemia, maple syrup urine disease), were automatically mapped to the BCAA metabolism biochemical pathway. The results indicated that the valine, leucine, and isoleucine pathways were abnormal in subjects with the indicated diseases. The levels of the aberrant metabolites measured in the valine, isoleucine, and leucine (BCAA metabolism) biochemical pathways that were abnormal is illustrated in FIG. 15.

Methylmalonic acidemia. In one example, the clinical diagnostic metabolites methylmalonate and methylmalonyl CoA were not detected in some of the patients diagnosed with methylmalonic acidemia. However, the biochemically related metabolites 2-methylmalonyl carnitine, propionylcarnitine (C3), tiglyl carnitine, 2-methylbutyrylcarnitine (C5), 2-methylcitrate, succinylcarnitine, propionylglycine, 3-hydroxypropanoate, valerylcarnitine, isovalerylcarnitine, succinate, tigloylglycine, and the additional metabolites beta-hydroxyisovaleroylcarnitine, beta-hydroxyisovalerate, isobutyrylcarnitine, 3-hydroxy-2-ethylpropionate, butyrylcarnitine, 3-methyl-2-oxovalerate, 3-methyl-2-oxobutyrate, X-12749, X-17564, and X-12114 were aberrant based on the Z-scores.

Biotinidase deficiency. In another example, there are no clinical metabolites useful for diagnosis of biotinidase deficiency. However, analysis of samples collected from these subjects revealed that the metabolites 3-methylcrotonylglycine, propionylcarnitine (C3), biotin and xylitol were aberrant based on Z-score analysis. Thus, a biochemical signature for biotinidase deficiency was observed in plasma samples using the methods described herein.

Cystinosis. In another example, the clinical metabolite cystine was not detected in patients diagnosed with cystinosis. For cystinosis, there are no described pathogenomic abnormalities in unreduced plasma, and this disorder is routinely diagnosed using white blood cell lysates. However, the biochemicals cys-gly (oxidized), 1,5-anhydroglucitol (1,5-AG), glycocholenate sulfate, 4-acetylphenol sulfate, cresol glucuronide (previously X-11837), erythritol, vanillylmandelate, N2,N2-dimethyl-guanosine, phenylacetylglutamine, X-12846, X-12303, X-19145, X-12216, X-17717, X-15667, X-12119, X-11315, X-12731, X-12705, X-17685, and X-18371 were aberrant based on Z-score analysis. Thus, a biochemical signature was observed in plasma samples using the methods described herein.

Guanidinoacetate methyl transferase (GAMT) deficiency. In another example, there are no clinical metabolites useful for diagnosis of guanidinoacetate methyl transferase (GAMT) deficiency. However, the metabolites creatine, 3-(4-hydroxyphenyl)lactate, 1,3-dipalmitoylglycerol, guanidinoacetate, cysteine s-sulfate, X-19602, X-12906, X-13007, and X-10458 were aberrant based on Z-score analysis. The observed aberrant levels of these metabolites indicate the utility of these compounds as novel biomarkers of GAMT deficiency.

Molybdenum cofactor deficiency. In another example, there are no described pathogenomic abnormalities for molybdenum cofactor deficiency in unreduced plasma, and this disorder is routinely diagnosed using reductant-treated plasma. In patients diagnosed with molybdenum cofactor deficiency (MOCD), the clinical metabolites observed in reductant-treated plasma: xanthine; thiosulfate; and S-sulfocysteine; were not detected in plasma. In addition, the biochemicals 5-HETE, leukotriene B4, 13-HODE+9-HODE, and 12-HETE were aberrant based on Z-score analysis. The observed aberrant levels of these metabolites indicate the utility of these compounds as novel biomarkers of molybdenum cofactor deficiency.

X-linked creatine transporter. In another example, there are no described pathogenomic abnormalities in unreduced plasma for X-linked creatine transporter and the disorder is routinely diagnosed using urine. In our analysis of plasma samples from patients with X-linked creatine transporter, the clinical metabolite in urine, creatine, was not detected. However, the biochemicals glycylleucine, 2-hydroxyoctanoate, 1,6-anhydroglucose, X-11483, X-18943, X-17422, X-17761, and X-17335 were aberrant in plasma based on Z-score analysis. While there are no clinically diagnostic metabolites described for plasma for this disorder, the observed aberrant levels of these metabolites indicate the utility of these compounds as novel biomarkers of X-linked creatine transporter in plasma.

Argininosuccinic acid lyase deficiency. In another example the clinical metabolite argininosuccinate was an aberrant biochemical (i.e., rare compound) in the patients diagnosed with argininosuccinic acid lyase deficiency; the additional metabolites uracil, arginine, aspartate, N-delta-acetylornithine, citrulline, isoleucylaspartate, ornithine, uridine, homocitrulline, orotate, homoarginine, sorbose, fructose, methyl-4-hydroxybenzoate, O-sulfo-L-tyrosine, palmitoyl sphingomyelin, X-13507, X-15245, X-15664, and X-15454, were also aberrant based on Z-score analysis. The observed aberrant levels of these metabolites indicate the utility of these compounds as novel biomarkers of argininosuccinic acid lyase deficiency.

Cobalamin deficiency. In another example, in the patients diagnosed with cobalamin deficiency, the clinical metabolites methylmalonic acid, homocysteine, 2-methylcitrate, and cystathionine were not detected. However, the additional metabolites 2-methylmalonyl carnitine, propionylcarnitine, and X-12749 were aberrant based on Z-score analysis.

Cbl a. In another example, in the patient diagnosed with cbl a, the biochemical 2-methylcitrate, a clinical metabolite useful for diagnosis, was aberrant. The additional metabolites 2-methylmalonyl carnitine, tiglyl carnitine, 2-methylbutyrylcarnitine, propionylcarnitine, and X-12749 were also aberrant based on Z-score analysis.

Cbl c. In another example, in the patients diagnosed with cbl c, the clinical metabolites methylmalonic acid, homocysteine, 2-methylcitrate, and cystathionine were not detected. However, the additional metabolites 2-methylmalonyl carnitine, propionylcarnitine, X-12749, and X-17677 were aberrant based on Z-score analysis.

Citrullinemia. In another example, in the patients diagnosed with Citrullinemia, the clinically used diagnostic metabolite, citrulline was aberrant. The additional metabolites homocitrulline, 3-ureidopropionate, N-acetylalanine, phenylacetylglutamine, phenylacetate, phenylacetylglycine, homoarginine, urea, guanidinosuccinate, gamma-glutamylphenylalanine, gamma-glutamylisoleucine, tryptophan, 1,5-anhydroglucitol (1,5-AG), N-acetyl-citrulline (previously X-12386), X-19684, X-12681, X-20598, X-18446, and X-20588 were aberrant based on Z-score analysis.

CPTII. In another example, the patient with CPTII had aberrant levels of the clinically used diagnostic metabolite, decanoylcarnitine (C10) and the levels of sebacate (C8), caprate (C10), caprylate (C8), and N-octanoylglycine (C8 ester), octanoylcarnitine, and hexanoylcarnitine were aberrant based on Z-score analysis.

Glutaric aciduria type 1. In another example, in the patients with glutaric aciduria type 1, the clinical metabolites glutarate (pentanedioate) and glutarylcarnitine (C5) and the biochemicals X-12364 and X-15674 were aberrant based on Z-score analysis.

HMG CoA Lyase deficiency. In another example, in the patients with HMG CoA Lyase deficiency, the clinical metabolites 3-methylglutarylcarnitine, 3-hydroxy-3-methylglutarate, 3-methylglutarate, and 3-hydroxyisovalerate were aberrant. The biochemicals beta-hydroxyisovalerate, beta-hydroxyisovaleroylcarnitine, glutarylcarnitine (C5), arginylproline, 1-stearoylglycerophosphoethanolamine, o-cresol sulfate, 3-methylcrotonylglycine, adipate, glutarate (pentanedioate), octadecanedioate (C18), hexadecanedioate (C16), tetradecanedioate (C14), dodecanedioate (C12), isovalerate, acetylcarnitine, palmitoylcarnitine, hexanoylcarnitine, myristoylcarnitine, hexenedioylcarnitine (previously X-17001), X-17715, X-12741, X-16134, X-10593, and X-12688 were also aberrant in both patients based on Z-score analysis.

Holocarboxylase synthetase deficiency. In another example, the patients diagnosed with Holocarboxylase synthetase deficiency had aberrant levels of the clinical metabolite beta-hydroxyisovalerate. The biochemicals 3-methylcrotonylglycine, beta-hydroxyisovaleroylcarnitine (C5), propionylglycine (C3), 3-hydroxypropanoate, tigloylglycine, succinylcarnitine, and biotin, were also aberrant based on Z-score analysis.

Homocystinuria. In another example, in the patients diagnosed with Homocystinuria, the clinical metabolite methionine was aberrant. The biochemicals gamma-glutamylmethionine, 5-methylthioadenosine (MTA), S-adenosylhomocysteine (SAH), N1-methyladenosine, glycylproline, 1-eicosenoylglycerophosphoethanolamine (20:1n9), 1-methylnicotinamide, N-acetyl-aspartyl-glutamate (NAAG), pyridoxal, 2-hydroxyisobutyrate, acisoga, carnosine, 3-methoxytyrosine, 2-hydroxydecanoate, delta-tocopherol, alpha-CEHC (2,5,7,8-tetramethyl-2-(2'-carboxyethyl)-6-hydroxychroman) sulfate (previously X-12435), N-acetyltryptophan, adenine, cortisol, X-19350, X-18965, X-15649, X-17303, X-18897, X-11564, X-18891, X-12748, X-18918, X-18905, X-18606, X-16574, X-18895, X-18907, X-19455, X-18909, X-19574, X-12110, X-20676, X-11360, and X-18920 were also aberrant in both subjects based on Z-score analysis.

Isovaleric acidemia. In another example, in the patients with isovaleric acidemia, the clinical metabolite isovalerate was aberrant. The biochemicals isovalerylglycine, isovalerylcarnitine (C5), valerate, phenylcarnitine, valerylcarnitine, beta-hydroxyisovalerate, 3-methylcrotonylglycine, X-16577, and X-14331 were also aberrant in both patients based on Z-score analysis.

Lysinuric protein intolerance. In another example, in the patients with Lysinuric protein intolerance, the clinical metabolites ornithine, arginine, and lysine were aberrant. The biochemicals asparagine, N6-acetyllysine, glutamine, N2-acetyllysine, N-acetylarginine, gamma-glutamylglutamine, proline, S-methylcysteine, 2-hydroxydecanoate, 1-methylimidazoleacetate, X-15636, X-17654, X-12193, and X-12425 were also aberrant based on Z-score analysis.

Medium chain acyl CoA dehydrogenase (MCAD) deficiency. In another example, in the patients with medium chain acyl CoA dehydrogenase (MCAD) deficiency, the clinical metabolites hexanoylglycine (C6), octanoylcarnitine (C8), hexanoylcarnitine (C6), cis-4-decenoyl carnitine, 5-hydroxyhexanoate, suberate (octanedioate), sebacate (decanedioate), decanoylcarnitine, and 3-hydroxydecanoate were aberrant. The biochemicals N-octanoylglycine, caproate (6:0), caprylate (8:0), heptanoate (7:0), dodecanedioate, 1-docosapentaenoylglycerophosphocholine (22:5n3), O-methylcatechol sulfate, 1-stearoylglycerophosphocholine (18:0), 1-margaroylglycerophosphocholine (17:0), N-palmitoyltaurine, pelargonate (9:0), deoxycarnitine, alpha-CEHC (2,5,7,8-tetramethyl-2-(2'-carboxyethyl)-6-hydroxychroman) sulfate (previously X-12435), X-11521 (probable empirical formula: $C_{15}H_{27}NO_4$ and structure: 2-octenoylcarnitine), X-11440 (probable hydroxypregnendiol disulfate or pregnanolone-diol disulfate), methylhexanoylglutamine (previously X-12637), X-15646, X-12802, X-11478, X-15486, X-18913, X-13837, X-18946, X-11861, X-18888, X-18922, X-17438, X-18916, X-16674, and X-12824 were also aberrant based on Z-score analysis.

Maple Syrup Urine Disease. In another example, in the patients with Maple Syrup Urine Disease, the clinical metabolites isoleucine and leucine were aberrant, and the biochemicals 2-hydroxy-3-methylvalerate, alpha-hydroxyisovalerate, isovalerylcarnitine, 2-aminoheptanoate, 4-methyl-2-oxopentanoate, 1-linolenoylglycerophosphocholine (18:3n3), 2-linolenoylglycerophosphocholine (18:3n3), 1-myristoylglycerophosphocholine (14:0), 2-myristoylglycerophosphocholine, 5alpha-androstan-3alpha, 17beta-diol disulfate, valine, 3-methyl-2-oxobutyrate, isovalerate, isobutyrylcarnitine, 3-hydroxyisobutyrate, 2-methylbutyrylcarnitine, beta-hydroxyisovaleroylcarnitine, allo-isoleucine, 3-methyl-2-oxovalerate, beta-hydroxyisovalerate, succinate, acetylcarnitine, 2-methylcitrate, tigloylglycine, tiglyl carnitine, hydroxybutyrylcarnitine, alpha-hydroxyisocaproate, X-13689 (glucuronide conjugate), X-13581, X-17690, and were aberrant in at least 10 of the 18 patients based on Z-score analysis.

Ornithine transcarbamylase deficiency. In another example, in the patients with ornithine transcarbamylase deficiency, the clinical metabolites citrulline, and arginine were not detected. However, the clinical metabolite orotate, and the biochemicals phenylacetylglutamine, stearidonate (18:4n3), 3-ureidopropionate, phenylacetate, phenylcarnitine, phenylacetylglycine, trans-4-hydroxyproline, pro-hydroxy-pro, urea, phenyllactate (PLA), guanidinosuccinate, hippurate, ornithine, X-20598, and X-20588 were aberrant based on Z-score analysis.

Trimethyllysine hydroxylase epsilon deficiency. In another example, in the patients with trimethyllysine hydroxylase epsilon deficiency, the clinical metabolite N-6-trimethyllysine was aberrant. The biochemicals 1-arachidonoylglyercophosphate, X-16574, X-12822, and X-15136 were aberrant in at least three of the four patients based on Z-score analysis.

Very long chain acyl CoA dehydrogenase deficiency. In another example, in the patients with very long chain acyl CoA dehydrogenase deficiency, the clinical metabolites myristoylcarnitine, stearoylcarnitine (C18), palmitoylcarnitine (C16), oleoylcarnitine (C18), myristoleate (14:1n5), and linoleoylcarnitine were aberrant. The biochemicals 9-methyluric acid, xylulose, arachidonate (20:4n6), docosahexaenoate (DHA;22:6n3), eicosapentanoic acid (EPA), 5,8-tetradecadienoic acid (previously X-12442), 1-docosahexaenoyl-GPC (22:6; DHA-GPC), and X-18739 (probable isomer of 2-tetradecenoylcarnitine) were also aberrant based on Z-score analysis.

Sarcosinemia. In another example, in the patient with Sarcosinemia, the clinical metabolite sarcosine was aberrant. The biochemicals dimethylglycine, betaine, choline, and glycine were also aberrant based on Z-score analysis.

Citrate Transporter Deficiency. In another example, in the patients with Citrate Transporter Deficiency, the clinical metabolite citrate was aberrant. The biochemicals alpha-ketoglutarate, succinate, fumarate, and malate were also aberrant based on Z-score analysis. Currently, there is no diagnostic test available for Citrate Transporter Deficiency, and thus there is no preferred sample type for the diagnosis. As described herein, metabolites aberrant in Citrate Transporter Deficiency were identified in plasma, urine, and CSF samples.

Hyperornithinemia-Homocitrullinemia-Hyperammonemia (HHH). In another example, in the patient with Hyperornithinemia-Homocitrullinemia-Hyperammonemia, the clinical metabolites homocitrulline and ornithine were aberrant. The biochemicals uracil, 3-ureidopropionate, orotate, glutamine, N-acetyl-beta-alanine, uridine, N-acetylaspartate (NAA), dimethylarginine (SDMA+ADMA), 5-methylthioadenosine (MTA), beta-alanine, and 4-ureidobutyrate were also aberrant based on Z-score analysis.

Aromatic amino acid decarboxylase deficiency. In another example, the clinical metabolites L-dopa, homovanillate, 5-hydroxyindoleacetate, and vanillactic acid were not detected in patients diagnosed with Aromatic amino acid decarboxylase deficiency. For Aromatic amino acid decarboxylase deficiency, the disorder is routinely diagnosed using CSF samples. However, in plasma samples, the clinical metabolites 3-methoxytyrosine and 5-hydroxytryptophan, and the biochemicals tyrosine, phenylalanine, and tryptophan were aberrant based on Z-score analysis. Thus, a biochemical signature was observed in plasma samples using the methods described herein.

Smith-Lemli-Opitz syndrome. In another example, in the patient with Smith-Lemli-Opitz syndrome, the clinical metabolite 7-dehydrocholesterol was aberrant. The biochemical cholestanol was also aberrant based on Z-score analysis.

Primary carnitine deficiency. In another example, in the patient with Primary carnitine deficiency, the clinical metabolite carnitine was aberrant. The biochemical N6-trimethyllysine was also aberrant based on Z-score analysis.

Citrin deficiency. In another example, in the patient with Citrin deficiency, the clinical metabolite citrulline was aberrant. The biochemical orotate was also aberrant based on Z-score analysis.

ABAT deficiency. In another example, in the patients with ABAT deficiency, the clinical metabolite GABA was aberrant. The biochemical 2-pyrrolidone was also aberrant based on Z-score analysis.

3-methylglutaconic aciduria (MGA). In another example, in the patient with MGA, the clinical metabolites 3-methylglutaconic acid and 3-methylglutaric acid were not detected. For MGA, the disorder is routinely detected using urine samples. However, in plasma samples, the biochemical butyrylglycine was aberrant based on Z-score analysis.

SCAD deficiency. In another example, in the patient with SCAD deficiency, the clinical metabolites ethylmalonate, butyrylcarnitine, and methylsuccinate were aberrant. The biochemical butyrylglycine was also aberrant based on Z-score analysis.

Urocanase deficiency. In another example, in the patient with urocanase deficiency, the clinical metabolites routinely detected in urine, cis-urocanate, trans-urocanate, and imidazole propionate were also aberrant in plasma samples based on Z-score analysis.

3-hydroxyisobutyryl-CoA hydrolase deficiency. In another example, there are no clinical metabolites useful for diagnosis of 3-hydroxyisobutyryl-CoA hydrolase deficiency. 3-hydroxyisobutyryl-CoA hydroxylase deficiency in a subject results from mutations in the HIBCH gene, which encodes the enzyme for hydroxylysis of hydroxyisobutyryl-CoA and hydroxypropionyl-CoA. This enzyme is important for valine metabolism. In one of the two subjects diagnosed with 3-hydroxyisobutyryl-CoA hydroxylase deficiency, two metabolites in valine metabolism, specifically, 3-hydroxyisobutyrate and isobutyrylglycine, were aberrant based on Z-score analysis. Both individuals also showed aberrant levels of several metabolites of leucine metabolism, a pathway not directly affected by the mutation, but possibly the result of medication or nutritional intervention. Thus, it is likely that both individuals were being treated for 3-hydroxyisobutyryl-CoA hydroxylase deficiency which may have masked the metabolic signature of the disease in the one patient. However, the observed aberrant levels of the metabolites 3-hydroxyisobutyrate and isobutyrylglycine indicate the utility of these compounds as novel biomarkers of 3-hydroxyisobutyryl-CoA hydrolase deficiency.

γ-Butyrobetaine Hydroxylase Deficiency (BBOX Deficiency). In another example, there are no clinical metabolites useful for diagnosis of BBOX deficiency. However, the metabolites hexadecanedioate (C16), docosadioate, eicosanodioate, octadecanedioate (C18), dodecanedioate (C12), 2-aminooctanoate, 2-aminoheptanoate, alpha-hydroxyisocaproate, isovalerate (C5), decanoylcarnitine (C10), cis-4-decenoyl carnitine, palmitoylcarnitine (C16), oleoylcarnitine (C18), laurylcarnitine (C12), myristoleoylcarnitine, myristoylcarnitine, glycerol, 3-hydroxymyristate, 2-hydroxydecanoate, 3-hydroxylaurate, 3-hydroxysebacate, 3-hydroxyoctanoate, 3-hydroxydecanoate, pelargonate (9:0), and caproate (6:0) were aberrant based on Z-score analysis. The observed aberrant levels of these metabolites indicate the utility of these compounds as novel biomarkers of BBOX deficiency.

Disorders of amino acid metabolism and transport (including urea cycle disorders and organic acidemias). In another example, in patients with disorders of amino acid metabolism and transport (including urea cycle disorders and organic acidemias), the metabolites N-acetylalanine, aspartate, glutarate (pentanedioate), glutarylcarnitine (C5), 3-hydroxyglutarate, glutaconate, phenylalanine, N-acetylphenylalanine, phenylpyruvate, phenyllactate (PLA), phenylacetate, phenylacetylglycine, phenylacetylglutamine, 4-hydroxyphenylpyruvate, 3-(4-hydroxyphenyl) lactate, p-cresol sulfate, o-cresol sulfate, 3-methoxytyrosine, leucine, 4-methyl-2-oxopentanoate, isovalerate, isovalerylglycine, isovalerylcarnitine (C5), 3-methylcrotonylglycine, beta-hydroxyisovalerate, beta-hydroxyisovaleroylcarnitine, 3-methylglutarylcarnitine (C6), alpha-hydroxyisovalerate, isoleucine, allo-isoleucine, 3-methyl-2-oxovalerate, 2-methylbutyrylcarnitine (C5), tiglyl carnitine, tigloylglycine, 2-hydroxy-3-methylvalerate, 3-hydroxy-2-ethylpropionate, valine, 3-methyl-2-oxobutyrate, isobutyrylcarnitine, 3-hydroxyisobutyrate, alpha-hydroxyisocaproate, homocysteine, cystathionine, arginine, urea, ornithine, proline, citrulline, argininosuccinate, homoarginine, homocitrulline, N-acetylarginine, N-delta-acetylornithine, trans-4-hydroxyproline, pro-hydroxy-pro, creatine, creatinine, 4-guanidinobutanoate, guanidinosuccinate, gamma-glutamylphenylalanine, gamma-glutamyltyrosine, alanylalanine, arginylprolineaspartylphenylalanine, glycylphenylalanine, histidylphenylalanine, isoleucylaspartate, leucylphenylalanine, phenylalanylalanine, phenylalanylarginine, phenylalanylaspartate, phenylalanylglutamate, phenylalanylglycine, phenylalanylisoleucine, phenylalanylleucine phenylalanylphenylalanine, phenylalanylserine, pyroglutamylvaline, threonylphenylalanine, tryptophylphenylalanine, valylphenylalanine, fructose, sorbose, succinylcarnitine, succinate, 2-methylcitrate, valerate, stearidonate (18:4n3), adipate, dodecanedioate (C12), tetradecanedioate (C14), hexadecanedioate (C16), octadecanedioate (C18), 2-aminoheptanoate, 2-linolenoylglycerophosphocholine (18:3n3), 2-methylmalonyl carnitine, butyrylcarnitine, propionylcarnitine (C3), propionylglycine (C3), methylmalonyl CoA, methylmalonic acid, acetylcarnitine, hydroxybutyrylcarnitine, valerylcarnitine, hexanoylcarnitine, myristoylcarnitine, palmitoylcarnitine (C16), hexenedioylcarnitine (previously X-17001), 3-hydroxypropanoate, 1-myristoylglycerophosphocholine (14:0), 2-myristoylglycerophosphocholine, 1-pentadecanoylglycerophosphocholine (15:0), 1-linolenoylglycerophosphocholine (18:3n3), 1-stearoylglycerophosphoethanolamine, 1,3-dipalmitoylglycerol, 5alpha-androstan-3 alpha, 17beta-diol disulfate, orotate, uridine, uracil, 3-ureidopropionate, hippurate, catechol sulfate, phenylcarnitine, propionate, 5-hydroxytryptophan, 5-methylthioadenosine (MTA), beta-alanine, dimethylarginine (SDMA+ADMA), glutamine, N-acetylaspartate (NAA), N-acetyl-beta-alanine, tryptophan, tyrosine, 2-pyrrolidone, gamma-glutamylleucine, O-sulfo-L-tyrosine, palmitoyl-sphingomyelin, gamma-glutamylisoleucine, cysteine s-sulfate, were aberrant based on Z-score analysis.

Fatty acid oxidation disorders. In another example, in patients with fatty acid oxidation disorders, the metabolites xylulose, caproate (6:0), heptanoate (7:0), caprylate (C8), pelargonate (9:0), caprate (C10), myristoleate (14:1n5), eicosapentanoic acid (EPA), docosahexaenoate (DHA;22:6n3), arachidonate (20:4n6), suberate (octanedioate), sebacate (C8), dodecanedioate (C12), hexanoylglycine (C6), N-octanoylglycine, hexanoylcarnitine, octanoylcarnitine, decanoylcarnitine, cis-4-decenoyl carnitine, myristoylcarnitine, palmitoylcarnitine (C16), stearoylcarnitine (C18), oleoylcarnitine (C18), deoxycarnitine, carnitine, 3-hydroxydecanoate, 5-hydroxyhexanoate, N-palmitoyltaurine, 1-margaroylglycerophosphocholine (17:0), 1-stearoylglycerophosphocholine (18:0), 1-docosapentaenoylglycerophosphocholine (22:5n3), 9-methyluric acid, alpha-CEHC (2,5,7,8-tetramethyl-2-(2'-carboxyethyl)-6-hydroxychroman) sulfate (previously X-12435), O-methylcatechol sulfate, 5,8-tetradecadienoic acid (previously X-12442), methylhexanoylglutamine (previously X-12637), 7-dehydrocholesterol, cholestanol, N6-trimethyllysine, butyrylglycine, and 1-docosahexaenoyl-GPC (22:6; DHA-GPC), were aberrant based on Z-score analysis.

Example 3: Clinical Assessment of Individuals with Disease (Urine)

In another example, urine samples from 100 symptomatic individuals were analyzed as described in Example 2 to diagnose or aid in the diagnosis of disease. All samples included in this study had been analyzed using one or more targeted panels of analytes in a quantitative analysis performed in a clinical diagnostic laboratory. Of the 100 subjects in the cohort, 33 subjects were positively diagnosed by a treating physician; for 67 subjects, no clinical diagnosis could be determined. At the time of analysis, the diagnostic information associated with the sample was blinded to the analysts. A total of 1201 biochemicals, 663 named and 538 unnamed, were detected. As with the plasma samples described in Example 2, after analysis of the samples, the resulting data and visualizations were evaluated by a clinician to determine if the results obtained using the methods of the invention were consistent with the clinically determined diagnosis. The diagnostic results of the analysis are summarized in Table 3. Column 1 lists the disorder including synonyms, Column 2 lists the number of diagnosed subjects, Column 3 lists the Sensitivity, and Column 4 lists the Specificity for the diagnosis of the disorder. Column 5 lists metabolites that are currently used in the clinic to diagnose the disorder. Column 6 lists clinically used metabolites that were found to be aberrant using the methods disclosed herein. Column 7 lists metabolites not currently used for clinical diagnosis that were identified as aberrant based on the results of the methods used herein in the subjects having that clinical diagnosis; some of these metabolites are biochemically related to the clinically used diagnostic metabolite. In some individuals the clinically diagnostic metabolite was not observed; however, other biochemically related metabolites were aberrant which aided in diagnosis of that disorder. These results are indicated for the disorders described in the examples below.

TABLE 3

Experimental Results of Diagnosis of Disease or Disorder (Urine)

| Disease or Disorder/ Synonym(s) for Disorder | No. of Diagnosed Subjects | Sensitivity | Specificity | Currently used diagnostic metabolite(s) | Currently used diagnostic metabolite(s) identified as aberrant in our analysis | Analysis Results: Novel metabolites, aberrant in diagnosed subjects |
|---|---|---|---|---|---|---|
| 3-methylcrotonyl CoA carboxylase deficiency/ 3-MCC deficiency, 3-methylcrotonylglycin uria, MCC deficiency | 1 | 100% | 100% | 3-methylcrotonyl glycine, beta-hydroxyisovalerate | 3-methylcrotonyl glycine, beta-hydroxyisovalerate | beta-hydroxyisovaleroylcarnitine, ethylmalonate, N-acetylleucine |
| Adenosine deaminase deficiency/ ADA deficiency, | 1 | 100% | 100% | deoxyadenosine, S-adenosylhomocysteine | 2'-deoxyadenosine | 2'-deoxyinosine, adenine, N2-methylguanosine, 2'-deoxyguanosine, urate, N1- |

TABLE 3-continued

| Disease or Disorder/ Synonym(s) for Disorder | No. of Diagnosed Subjects | Sensi-tivity | Specificity | Currently used diagnostic metabolite(s) | Currently used diagnostic metabolite(s) identified as aberrant in our analysis | Analysis Results: Novel metabolites, aberrant in diagnosed subjects |
|---|---|---|---|---|---|---|
| ADA-SCID | | | | | | methyladenosine, adenosine, allantoin, xanthine, guanosine, hypoxanthine, N2,N2-dimethylguanosine, 7-methylguanosine |
| Citrullinemia/ Argininosuccinate synthetase deficiency, ASS deficiency, CTLN1 | 3 | 100% | 100% | citrulline, argininosuccinic acid | citrulline | 4-ureidobutyrate, homocitrulline, 3-ureidopropionate, phenylacetylglutamine, N-carbamoylaspartate, guanidinoacetate, urea, 4-guanidinobutanoate, N-acetylarginine, hippurate, ornithine, 2-methylhippurate, phenylacetylglycine, 4-phenylbutyrate, creatinine, orotate, 3,4-dihydroxyphenylacetate |
| Dihydropyrimidine dehydrogenase deficiency | 1 | 100% | 100% | uracil, thymine | uracil, thymine | cytidine, 5,6-dihydrouracil, 4-ureidobutyrate, 3-ureidopropionate, uridine, orotate, N-carbamoylaspartate |
| glutaric aciduria type 1/ Dicarboxylic amionaciduria, GAI, Glutaricacidemia I, Glutaryl-CoA, dehydrogenase deficiency | 1 | 100% | 100% | glutarate (pentanedioate), glutarylcarnitine (C5), 3-hydroxyglutarate, glutaconate | glutarate (pentanedioate), glutarylcarnitine (C5) | 3-methylglutarylcarnitine, 2-aminoadipate |
| guanidinoacetate methyl transferase deficiency/ GAMT deficiency | 4 | 0% | 0% | none | none | creatinine, guanidinoacetate |
| Holocarboxylase/ Holocarboxylase synthetase deficiency | 3 | 100% | 100% | beta-hydroxyisovalerate | beta-hydroxyisovalerate | 3-methylcrotonylglycine, beta-hydroxyisovaleroylcarnitine, propionylglycine (C3), 3-hydroxypropanoate, 2-methylcitrate, 3-hydroxyisobutyrate, lactate, 3-hydroxy-2-ethylpropionate, isobutyrylglycine, alpha-hydroxyisovaleroyl carnitine, 3-methyl-2-oxobutyrate, 3-methyl-2-oxovalerate, 3-hydroxy-2-methylbutyrate, 4-methyl-2-oxopentanoate, succinylcarnitine, malonylcarnitine, alpha-hydroxyisovalerate, 2-hydroxy-3-methylvalerate, propionylcarnitine, tiglylcarnitine, isovalerylcarnitine, hydroxybutyrylcarnitine, succinate, 2-methylmalonylcarnitine, alpha-hydroxyisocaproate |
| isovaleric acidemia/ Isovaleric acid CoA dehydrogenase deficiency, IVA, IVD deficiency | 1 | 100% | 100% | isovalerate (C5) | isovalerate (C5) | isovalerylglycine, isovalerylcarnitine (C5), beta-hydroxybutyrate, alpha-hydroxybutyrate |
| Lysinuric Protein Intolerance | 1 | 0% | 100% | ornithine, arginine, lysine | none | 2-aminoheptanoate, N6-acetyllysine, N2-acetyllysine, 3-methylglutarylcarnitine, |

Experimental Results of Diagnosis of Disease or Disorder (Urine)

TABLE 3-continued

Experimental Results of Diagnosis of Disease or Disorder (Urine)

| Disease or Disorder/ Synonym(s) for Disorder | No. of Diagnosed Subjects | Sensi-tivity | Specificity | Currently used diagnostic metabolite(s) | Currently used diagnostic metabolite(s) identified as aberrant in our analysis | Analysis Results: Novel metabolites, aberrant in diagnosed subjects |
|---|---|---|---|---|---|---|
| | | | | | | glutarylcarnitine, N6-trimethyllysine, 5-(galactosylhydroxy)-L-lysine |
| medium chain acyl CoA dehydrogenase deficiency/ MCAD deficiency, MCADD, ACADM deficiency, Acyl-CoA dehydrogenase medium chain deficiency | 2 | 100% | 100% | acylcarnitines, carnitine, organic acids | hexanoylglycine (C6), 5-hydroxyhexanoate, octanoylcarnitine (C8), suberate (octanedioate), 4-octenedioate, adipate, hexanoylcarnitine (C6), decanoylcarnitine | N-octanoylglycine, heptanoyl glycine, 3-methyladipate, 2-hydroxyglutarate |
| methylmalonic acidemia | 2 | 100% | 100% | methylmalonate, methylmalonyl CoA | methylmalonate | 2-methylmalonyl carnitine, 2-methylcitrate, 3-methylglytarylcarnitine, propionylcarnitine (C3), succinylcarnitine, propionylglycine, beta-hydroxyisovaleroylcarnitine, beta-hydroxyisovalerate, 3-hydroxy-2-ethylpropionate, methylsuccinate |
| molybdenum cofactor or sulfite oxidase deficiency/ MOCD | 1 | 100% | 100% | xanthine, S-sulfocysteine, thiosulfate (currently used only for samples from blood, e.g., reductant-treated plasma) | xanthine, S-sulfocysteine | urate |
| ornithine transcarbamylase deficiency/ OTC deficiency, OTCD, Ornithine carbamoyltransferase deficiency | 2 | 0% | 100% | orotate, citrulline, arginine | none | phenylacetylglutamine, 2-methylhippurate, 2-hydroxyphenylacetate, phenylcarnitine, hippurate, phenylpropionylglycine, benzoate, methyl-4-hydroxybenzoate, 4-phenylbutyrate, 2-pentamido-3-phenylpropanoic acid |
| Succinic semialdehyde dehydrogenase deficiency | 1 | 100% | 100% | gamma-aminobutyrate (GABA) | gamma-aminobutyrate (GABA) | succinimide |
| Succinyladenosine lyase deficiency | 2 | 100% | 100% | N6-succinyladenosine | N6-succinyladenosine | xanthosine, 2'-deoxyguanosine, 2'-deoxyinosine, adenine |
| Tyrosinemia | 2 | 100% | 100% | tyrosine | tyrosine | 3-(4-hydroxyphenyl)lactate, 4-hydroxyphenylpyruvate, 3-(3-hydroxyphenyl)propionate, 4-hydroxyphenylacetate, phenyllactate (PLA), X-13581 |
| Xanthinuria/ Lesche Nyhan | 1 | 100% | 100% | xanthine, urate, creatine | urate, creatine | hypoxanthine, xanthosine, 2'-deoxyinosine, inosine, N2-methylguanosine, creatinine |
| X-linked creatine transporter/ X-linked creatine deficiency | 4 | 100% | 100% | creatine | creatine | none |
| Citrate transport deficiency | 4 | 100% | 100% | Citrate | Citrate | none |

TABLE 3-continued

Experimental Results of Diagnosis of Disease or Disorder (Urine)

| Disease or Disorder/ Synonym(s) for Disorder | No. of Diagnosed Subjects | Sensi-tivity | Specificity | Currently used diagnostic metabolite(s) | Currently used diagnostic metabolite(s) identified as aberrant in our analysis | Analysis Results: Novel metabolites, aberrant in diagnosed subjects |
|---|---|---|---|---|---|---|
| 4-Aminobutyrate aminotransferase (ABAT) deficiency | 2 | 100% | 100% | GABA | GABA | 2-pyrrolidone |
| Hyperoxaluria | 10 | 50% | 50% | oxalate, glycolate, glyoxylate | oxalate, glycolate | none |

Adenosine deaminase deficiency. In an example, the Z-score was greater than 2 for the clinical diagnostic metabolite 2'-deoxyadenosine in the patient diagnosed with adenosine deaminase deficiency. In addition, the biochemically related metabolites 2'-deoxyinosine, adenine, N2-methylguanosine, 2'-deoxyguanosine, urate, N1-methyladenosine, adenosine, allantoin, xanthine, guanosine, hypoxanthine, N2,N2-dimethylguanosine, and 7-methylguanosine, were aberrant based on the Z-scores. The observed aberrant levels of these metabolites indicate the utility of these compounds as novel biomarkers of adenosine deaminase deficiency.

Dihydropyrimidine dehydrogenase deficiency. In another example, in the patients diagnosed with dihydropyrimidine dehydrogenase deficiency, the clinical metabolites uracil and thymine and the additional metabolites cytidine, 5,6-dihydrouracil, 4-ureidobutyrate, 3-ureidopropionate, uridine, orotate, and N-carbamoylaspartate were aberrant based on Z-score analysis.

Succinic semialdehyde dehydrogenase deficiency. In another example, in the patient with succinic semialdehyde dehydrogenase deficiency, the clinical metabolite gamma-aminobutyrate (GABA) and the biochemically related metabolite succinimide were aberrant based on Z-score analysis.

Succinyladenosine lyase deficiency. In another example, in the patients with succinyladenosine lyase deficiency, the clinical metabolite N6-succinyladenosine and the biochemically related metabolites xanthosine, 2'-deoxyguanosine, 2'-deoxyinosine, and adenine were aberrant based on Z-score analysis.

Tyrosinemia. In another example, in the patients with tyrosinemia, the clinical metabolite tyrosine and the additional metabolites 3-(4-hydroxyphenyl) lactate, 4-hydroxyphenylpyruvate, 3-(3-hydroxyphenyl)propionate, 4-hydroxyphenylacetate, phenyllactate (PLA), and X-13581, were aberrant based on Z-score analysis.

Xanthinuria. In another example, in the patient with xanthinuria, the clinical metabolite xanthine was not detected. However, the clinical metabolites urate, and creatine and the biochemically related metabolites hypoxanthine, xanthosine, 2'-deoxyinosine, inosine, N2-methylguanosine, and creatinine were aberrant based on Z-score analysis.

3-methylcrotonyl CoA carboxylase deficiency. In another example, in patients diagnosed with 3-methylcrotonyl CoA carboxylase deficiency, the clinical diagnostic metabolites 3-methylcrotonylglycine and beta-hydroxyisovalerate were aberrant. In addition, the metabolites beta-hydroxyisovaleroylcarnitine, ethylmalonate, and N-acetylleucine were aberrant based on the Z-scores.

Citrullinemia. In another example, in the patients diagnosed with Citrullinemia, the clinically used diagnostic metabolite, citrulline was aberrant. The additional metabolites 4-ureidobutyrate, homocitrulline, 3-ureidopropionate, phenylacetylglutamine, N-carbamoylaspartate, guanidinoacetate, urea, 4-guanidinobutanoate, N-acetylarginine, hippurate, ornithine, 2-methylhippurate, phenylacetylglycine, 4-phenylbutyrate, creatinine, orotate, and 3,4-dihydroxyphenylacetate were aberrant based on Z-score analysis.

Glutaric aciduria type 1. In another example, in the patients with glutaric aciduria type 1, the clinical metabolites glutarate (pentanedioate) and glutarylcarnitine (C5) and the biochemicals 3-methylglutarylcarnitine and 2-aminoadipate were aberrant based on Z-score analysis.

Guanidinoacetate methyl transferase (GAMT) deficiency. In another example, there are no clinical metabolites useful for diagnosis of guanidinoacetate methyl transferase (GAMT) deficiency. However, in the patients with GAMT deficiency, the biochemicals creatinine and guanidinoacetate were aberrant based on Z-score analysis. The observed aberrant levels of these metabolites indicate the utility of these compounds as novel biomarkers of GAMT deficiency.

Holocarboxylase synthetase deficiency. In another example, the patients diagnosed with Holocarboxylase synthetase deficiency had aberrant levels of the clinical metabolite beta-hydroxyisovalerate. The biochemicals 3-methylcrotonylglycine, beta-hydroxyisovaleroylcarnitine, propionylglycine (C3), 3-hydroxypropanoate, 2-methylcitrate, 3-hydroxyisobutyrate, lactate, 3-hydroxy-2-ethylpropionate, isobutyrylglycine, alpha-hydroxyisovaleroyl carnitine, 3-methyl-2-oxobutyrate, 3-methyl-2-oxovalerate, 3-hydroxy-2-methylbutyrate, 4-methyl-2-oxopentanoate, succinylcarnitine, malonylcarnitine, alpha-hydroxyisovalerate, 2-hydroxy-3-methylvalerate, propionylcarnitine, tiglyl carnitine, isovalerylcarnitine, hydroxybutyrylcarnitine, succinate, 2-methylmalonylcarnitine, and alpha-hydroxyisocaproate were also aberrant based on Z-score analysis.

Isovaleric acidemia. In another example, in the patient with isovaleric acidemia, the clinical metabolite isovalerate was aberrant. The biochemicals isovalerylglycine, isovalerylcarnitine (C5), beta-hydroxybutyrate, and alpha-hydroxybutyrate were also aberrant in both patients based on Z-score analysis.

Lysinuric protein intolerance. In another example, in the patient with Lysinuric protein intolerance, the clinical metabolites ornithine, arginine, and lysine were not detected. The biochemicals 2-aminoheptanoate, N6-acetyllysine, N2-acetyllysine, 3-methylglutarylcarnitine, glutarylcarnitine, N6-trimethyllysine, and 5-(galactosylhydroxy)-L-lysine were aberrant based on Z-score analysis.

Medium chain acyl CoA dehydrogenase (MCAD) deficiency. In another example, in the patients with medium chain acyl CoA dehydrogenase (MCAD) deficiency, the clinical metabolites hexanoylglycine (C6), 5-hydroxyhexanoate, octanoylcarnitine (C8), suberate (octanedioate), 4-octenedioate, adipate, hexanoylcarnitine (C6), and decanoylcarnitine were aberrant. The biochemicals N-octanoylglycine, heptanoyl glycine, 3-methyladipate, and 2-hydroxyglutarate were also aberrant based on Z-score analysis.

Methylmalonic acidemia. In another example, the clinical diagnostic metabolite methylmalonyl CoA was not detected the patients diagnosed with methylmalonic acidemia. However, the clinical metabolite methylmalonate and additional metabolites 2-methylmalonyl carnitine, 2-methylcitrate, 3-methylglytarylcarnitine, propionylcarnitine (C3), succinylcarnitine, propionylglycine, beta-hydroxyisovaleroylcarnitine, beta-hydroxyisovalerate, 3-hydroxy-2-ethylpropionate, and methylsuccinate were aberrant based on the Z-scores.

Molybdenum cofactor deficiency. In another example, there are no described pathogenomic abnormalities for molybdenum cofactor deficiency in urine, and this disorder is routinely diagnosed using reductant-treated plasma. In patients diagnosed with molybdenum cofactor deficiency (MOCD), the clinical metabolites, xanthine and S-sulfocysteine, observed in reductant-treated plasma, were aberrant in urine samples; the clinical metabolite thiosulfate was not detected. In addition, the biochemical urate was aberrant based on Z-score analysis. The observed aberrant levels of these metabolites indicate the utility of these compounds as novel biomarkers of molybdenum cofactor deficiency.

Ornithine transcarbamylase deficiency. In another example, in the patients with ornithine transcarbamylase deficiency, the clinical metabolites citrulline, and arginine were not detected. However, the clinical metabolite orotate, and the biochemicals phenylacetylglutamine, 2-methylhippurate, 2-hydroxyphenylacetate, phenylcarnitine, hippurate, phenylpropionylglycine, benzoate, methyl-4-hydroxybenzoate, 4-phenylbutyrate, and 2-pentamido-3-phenylpropanoic acid were aberrant based on Z-score analysis.

Citrate transporter deficiency. In another example, in the patients with citrate transporter deficiency, the clinical metabolite citrate was aberrant based on Z-score analysis.

ABAT deficiency. In another example, in the patients with ABAT deficiency, the clinical metabolite GABA and the biochemical 2-pyrrolidone were aberrant based on Z-score analysis.

Hyperoxaluria. In another example, in the patients with hyperoxaluria, the clinical metabolites oxalate and glycolate were aberrant based on Z-score analysis.

In another example, in patients with disorders of amino acid metabolism and transport (including urea cycle disorders and organic acidemias), the metabolites 2-aminoadipate, phenylacetylglutamine, 3,4-dihydroxyphenylacetate, phenylpropionylglycine, 2-pentanamido-3-phenylpropanoic acid, 2-hydroxyphenylacetate, N-acetylleucine, methylsuccinate, ethylmalonate, guanidinoacetate, beta-hydroxybutyrate, N-carbamoylaspartate, 4-ureidobutyrate, hippurate, 2-methylhippurate, benzoate, methyl-4-hydroxybenzoate, 4-phenylbutyrate, glutarate (pentanedioate), glutarylcarnitine (C5), 3-hydroxyglutarate, glutaconate, phenylacetylglycine, isovalerate, isovalerylglycine, isovalerylcarnitine (C5), 3-methylcrotonylglycine, beta-hydroxyisovalerate, beta-hydroxyisovaleroylcarnitine, 3-methylglutarylcarnitine (C6), 3-hydroxy-2-ethylpropionate, arginine, urea, ornithine, citrulline, argininosuccinate, homocitrulline, N-acetylarginine, creatine, 4-guanidinobutanoate, succinylcarnitine, 2-methylcitrate, 2-methylmalonyl carnitine, propionylcarnitine (C3), propionylglycine (C3), methylmalonyl CoA, methylmalonic acid, orotate, 3-ureidopropionate, phenylcarnitine, and 2-pyrrolidone were aberrant based on Z-score analysis.

Fatty acid oxidation disorders. In another example, in patients with fatty acid oxidation disorders, the metabolites 2-hydroxyglutarate, 3-methyladipate, 4-octenedioate, heptanoyl glycine, adipate, suberate (octanedioate), hexanoylglycine (C6), N-octanoylglycine, hexanoylcarnitine, octanoylcarnitine, decanoylcarnitine, carnitine, and 5-hydroxyhexanoate were aberrant based on Z-score analysis.

Figure 16A:
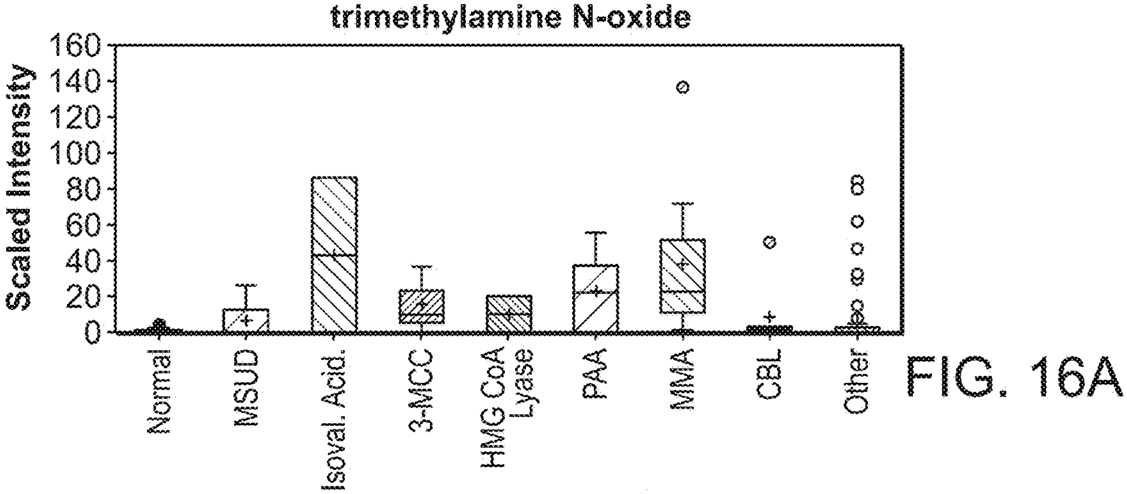
FIGS. 16A-16C are plots in an example visual display of metabolites altered as a result of supplemental therapy of patients in Example 4.
Figure 16B:
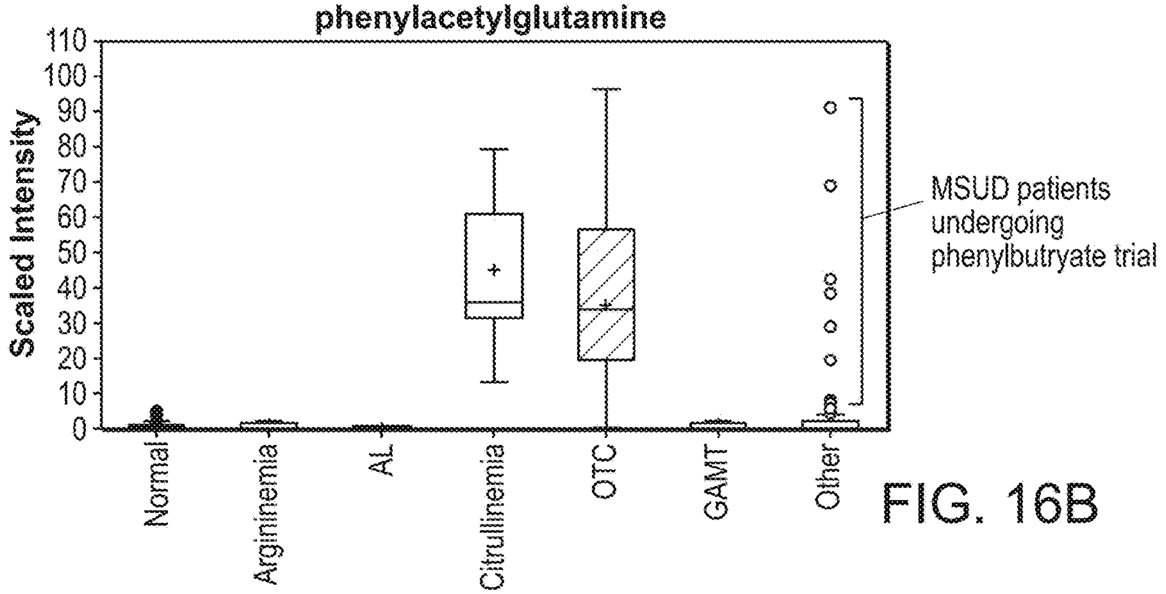
Figure 16C:
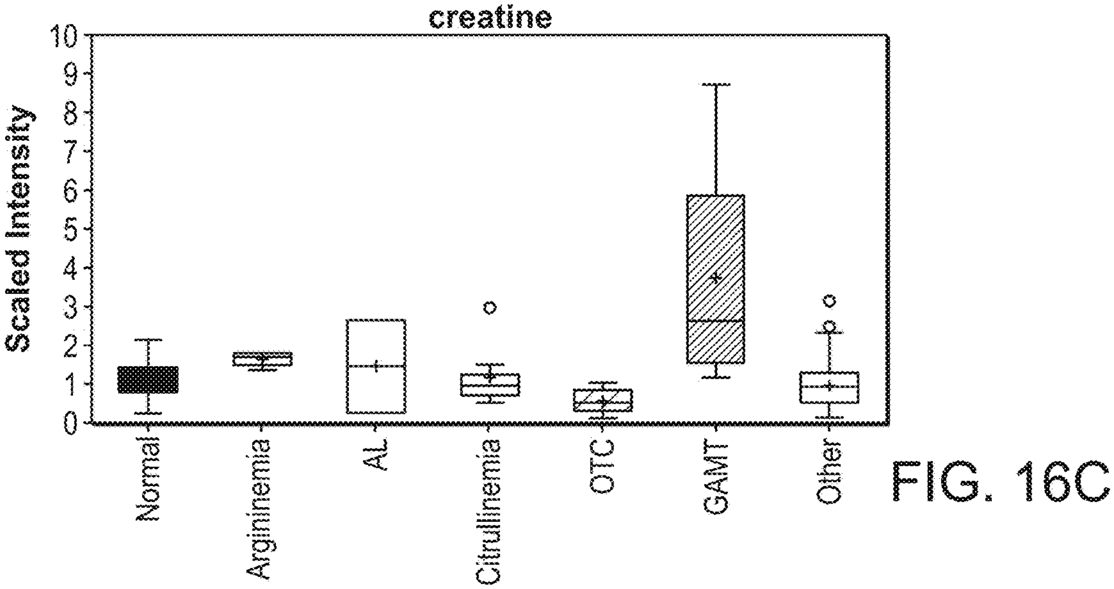

Example 4: Clinical Assessment of Individuals with Disease: Determining and Monitoring Effect of Treatment and/or Disease Severity In another example, the results of the methods described herein for the samples from Example 2 were used to evaluate the effectiveness of therapeutic intervention and biochemical changes in response to clinical management of disease in diagnosed individuals which aids in the clinical monitoring of the patient to determine therapeutic efficacy and treatment compliance. For example, in a patient with very long chain acyl CoA dehydrogenase deficiency (VLCAD) undergoing treatment with a medium chain triglyceride formula, the effects of treatment were observed; the levels of short and medium chain length fatty acids were aberrant in the plasma sample of the patient by Z-score analysis, and the biochemical 7-hydroxyoctanoate was aberrant as a rare biochemical (a metabolite rarely detected in plasma samples). In another example, in several patients with ornithine transcarbamoylase (OTC) deficiency, a combination of dietary intervention and phenylbutyrate treatment masked the metabolic disturbances associated with OTC deficiency (i.e., the diagnostic metabolites were at normal levels). In OTC deficiency, citrullinemia, and MSUD patients who were undergoing a phenylbutyrate trial the phenylbutyrate metabolite, phenylacetylglutamine, was elevated as illustrated in FIG. 16B. In another example, the metabolite trimethylamine N-oxide, was elevated in patients receiving supplemental carnitine for treatment of isovaleric acidemia, propionic acidemia (PAA), and methylmalonic acidemia (MMA) as shown in FIG. 16A. In another example, supplemental creatine is directly measurable in plasma collected from patients diagnosed with argininosuccinic acid lyase deficiency (AL) or GAMT as illustrated in FIG. 16C. In another example, in a patient diagnosed with pyruvate dehydrogenase E1 alpha deficiency, the diagnostic metabolites lactate and pyruvate were identified in the sample but were not aberrant because the patient was receiving medical and nutritional treatment. In another example, a patient diagnosed with Smith-Lemli-Opitz syndrome was on cholesterol supplementation therapy. The subject did not show aberrant levels of cholesterol, but the biomarker cholestanol, a reduced form of cholesterol, was identified as a rare metabolite in the sample.

Figure 17:
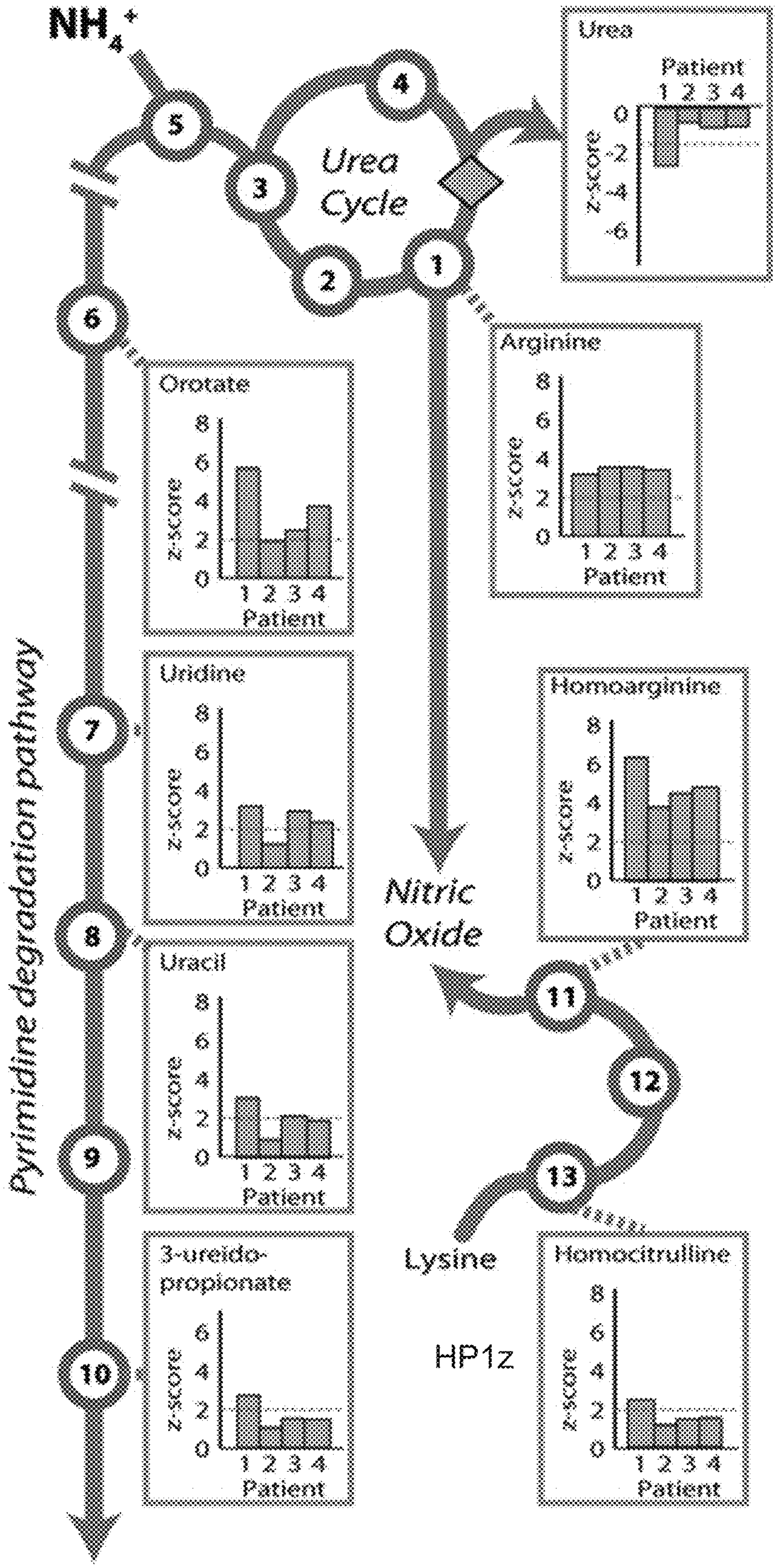
FIG. 17 is an example visual display of biochemical pathways related to argininemia with aberrant metabolites mapped to the pathways. The patients are indicated by numbers 1-4. The diamond indicates the location of the deficient enzyme in argininemia. Values are given as z-scores (y-axis), and dashed gray lines indicate z-scores of >2 or <−2. Pathway intermediates are indicated by numbered circles, (1) arginine, (2) argininosuccinate, (3) citrulline, (4) ornithine, (5) carbamoylphosphate, (6) orotate, (7) uridine, (8) uracil, (9) dihydrouracil, (10) 3-ureidopropionate, (11) homoarginine, (12) homoargininosuccinate, and (13) homocitrulline.

In another example, the methods described herein were used to determine disease severity and can be used to monitor changes in disease severity. For example, argininemia is caused by autosomal recessive mutations affecting the urea cycle enzyme arginase, and this disorder is diagnosed clinically based on measured plasma arginine levels. The aberrant biochemicals determined in four argininemia patients were automatically mapped to the disease-associated biochemical pathways. Aberrantly elevated levels of arginine, as well as aberrant levels of multiple analytes located more distal to the primary enzymatic defect (e.g., orotate, uridine, uracil, 3-ureidopropionate, urea, ornithine, N-acetylarginine, 4-guanidinobutanoate, creatinine, and homoarginine) were observed. An illustration of said biochemical pathways overlayed with the data showing the levels of the biochemicals in each patient is presented in FIG. 17. Patient 1 had higher levels of multiple metabolites compared to the other argininemia cases, suggesting that clinical symptoms were more severe in patient 1. Indeed, in the three months prior to sampling, patient 1 was admitted to the hospital on three separate occasions for acute decompensation associated with hyperammonemic events. Conversely, patients 2-4 had no acute events leading to hospitalization in the months prior to or immediately following sample submission. Importantly, arginine levels were similarly elevated across all argininemia patients, and differences in clinical status were only be predicted by looking at novel diagnostic biomarkers. In FIG. 17, the patents were numbered 1 to 4 merely for convenience and these numbers do not correspond to the patient numbers used in Table 1.

Example 5: Clinical Assessment of Individuals in the Control Cohort

In another example, aberrant metabolites were uncovered in some of the 68 control samples (i.e., samples from patients with normal biochemical genetics testing) from Example 2 that were analyzed using the methods described herein, indicating the presence of a disorder for which the patient was currently asymptomatic. For example, in patient 1165, trimethyllysine was identified as aberrant; levels were higher than in any other control sample, and the elevated levels were consistent with those of other patients having confirmed trimethyllysine hydroxylase epsilon deficiency. Thus, based on the results of the analysis, trimethyllysine hydroxylase epsilon deficiency was suspected and follow-up testing was recommended.

In another example, in patient 1169, slight elevations of C14, C14.1, and C14.2 were observed from the clinical acylcarnitine analysis, raising suspicion for VLCAD. Additional clinical molecular testing (DNA sequencing) of ACADVL did not detect deleterious mutations in the gene sequence. However, the results of the analysis using the methods described herein revealed (i) aberrant levels (elevated) of C14/C16 fatty acids, (ii) aberrant levels (elevated) of acetoacetate, and (iii) normal levels of C14/C16 acylcarnitine conjugates. Both the elevated ketone production and the relatively normal acylcarnitine levels in the face of extreme C14/C16 fatty acid elevations indicated a very low likelihood of VLCAD deficiency. This fuller metabolic picture obtained using the methods described herein aided in the diagnosis of this individual. Further, the aberrant metabolite levels and abnormal pathway mapping analysis suggested that the metabolic alterations in patient 1169 were most likely explained by fasting. With this information in hand, ACADVL gene sequencing would have been unnecessary.

In another example, the methods used herein were useful to determine the importance of base-pair changes detected using whole exome sequencing (WES) and aided in diagnosis (i.e., to 'rule-in' or 'rule-out' a disorder). For example, the results of the methods described herein ruled out disorders in patients for whom WES reported a variant of unknown significance (VUS). In one example, a VUS [c.673G>T(p.G225W)] was reported within GLYCTK—the gene affected in glyceric aciduria. However, using the methods described herein the levels of glycerate in this were patient determined to be normal. In another example in a patient with a VUS [c.730G>A(p.G244R)] in SLC25A15, which is the gene affected in hyperornithinemia-hyperammonemia-homocitrullinemia syndrome, normal levels of ornithine, glutamine, and homocitrulline were determined, thereby ruling out the disorder. In another example, the results of the methods described herein helped support the pathogenicity of molecular results. For example, WES results for patient 1186 revealed a heterozygous VUS [c.455G>A (p.G152D)] in SARDH, which is the gene deficient in sarcosinemia. Using the methods described herein, significant elevations of choline, betaine, dimethylglycine, and sarcosine were determined. These elevated levels are consistent with sarcosinemia, a metabolic disorder for which the existence of clinical symptoms is debated.

Example 6: mPROFILE Clinical Assessment of Individuals in a Healthy Cohort

Figure 18:
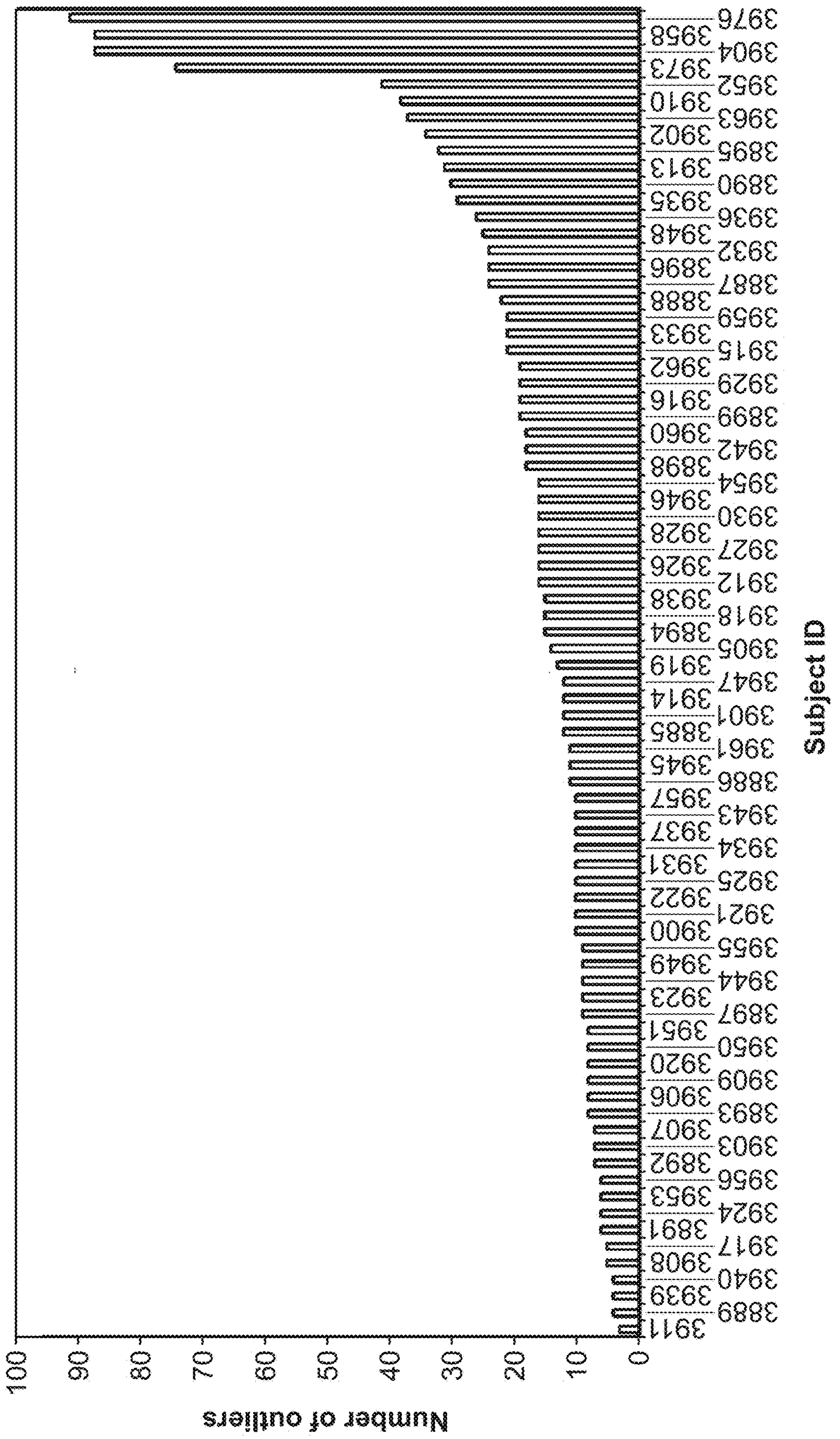
FIG. 18 is a graphical representation ranking of the total number of metabolite outliers for each subject.

Using a metabolomics platform consisting of three independent mass spectrometry methods, we surveyed samples of plasma from 80 subjects for biochemicals in 8 pathways and their associated 41 sub-pathways and measured a total of 575 metabolites of known structures. It was found that the individual metabolites exhibited a substantial range of variation across the 80 subjects. On the basis that this cohort was generally healthy, we took the assumption that for any given metabolite, the inter quartile of its values in the cohort may represent the dynamic range of a healthy metabolic state. For each subject, we applied statistical analysis to identify metabolites with levels significantly deviating from the inter quartile range of the population (outliers), which may indicate metabolic abnormalities that warrant further investigation. FIG. 18 is a rank of the total number of metabolite outliers associated with each subject. We further examined metabolites sharing the same chemical pathways and biological functions as the outliers. These analyses led to the identification of various subjects with biochemical signatures that provide insights on early indications of disease conditions.

A. Sensitivity to Acetaminophen-Induced Toxicity

Figure 19:
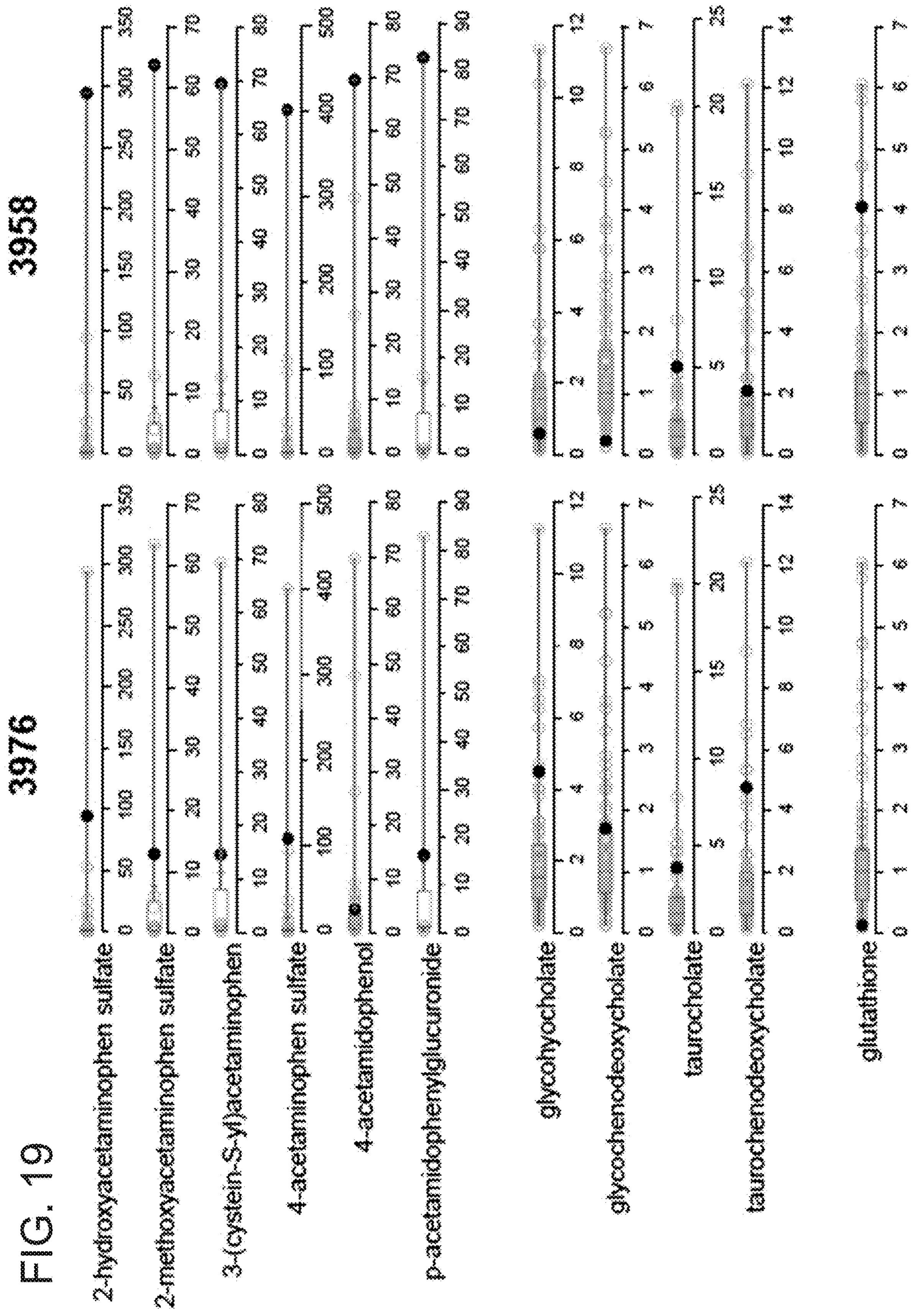
FIG. 19 shows an example visual display of dot plots showing data distribution in the cohort for the acetaminophen metabolites, four primary bile acids, and glutathione. The black dots show the metabolite level for either 3976 or 3958. The open dots show the data distribution for the rest of the cohort. The box represents the middle 50% of the distribution, and left and right "whiskers" represent the entire spread of the data. The vertical line refers to the median and the plus sign represents the mean.

Acetaminophen overdose is a leading cause of acute liver failure. In the liver, acetaminophen is converted to a reactive metabolite that depletes cellular glutathione (GSH), thus leading to oxidative stress and cell death. Due to acetaminophen's frequent and chronic use for pain and fever, the identification of at risk populations could improve therapeutic options for individual patient and prevent adverse clinical outcome. In this cohort, the highest levels of acetaminophen metabolites were detected in subject 3958 and subject 3976 (FIG. 19). Subject 3976 also displayed elevated levels of primary bile acids (FIG. 19), suggesting impaired liver function. The elevated plasma primary bile acids have been found to be early biomarkers for drug induced liver injury in rats (Yamazaki, M. et al. Perturbation of bile acid homeostasis is an early pathogenesis event of drug induced liver injury in rats. *Toxicol Appl Pharmacol* 268, 79-89 (2013)). Coincidently, subject 3976 also exhibited the lowest glutathione in this cohort (FIG. 19). In contrast, subject 3958 showed normal bile acid levels with the exception of elevated taurocholate. Subject 3958 also had elevated glutathione (FIG. 19). Collectively, these observations may suggest that subject 3976 was sensitive to acetaminophen-induced liver injury while subject 3958 can tolerate acetaminophen well. This may relate to their cellular capability to maintain glutathione levels in response to acetaminophen.

B. Early Indications of Diabetes

Figure 20:
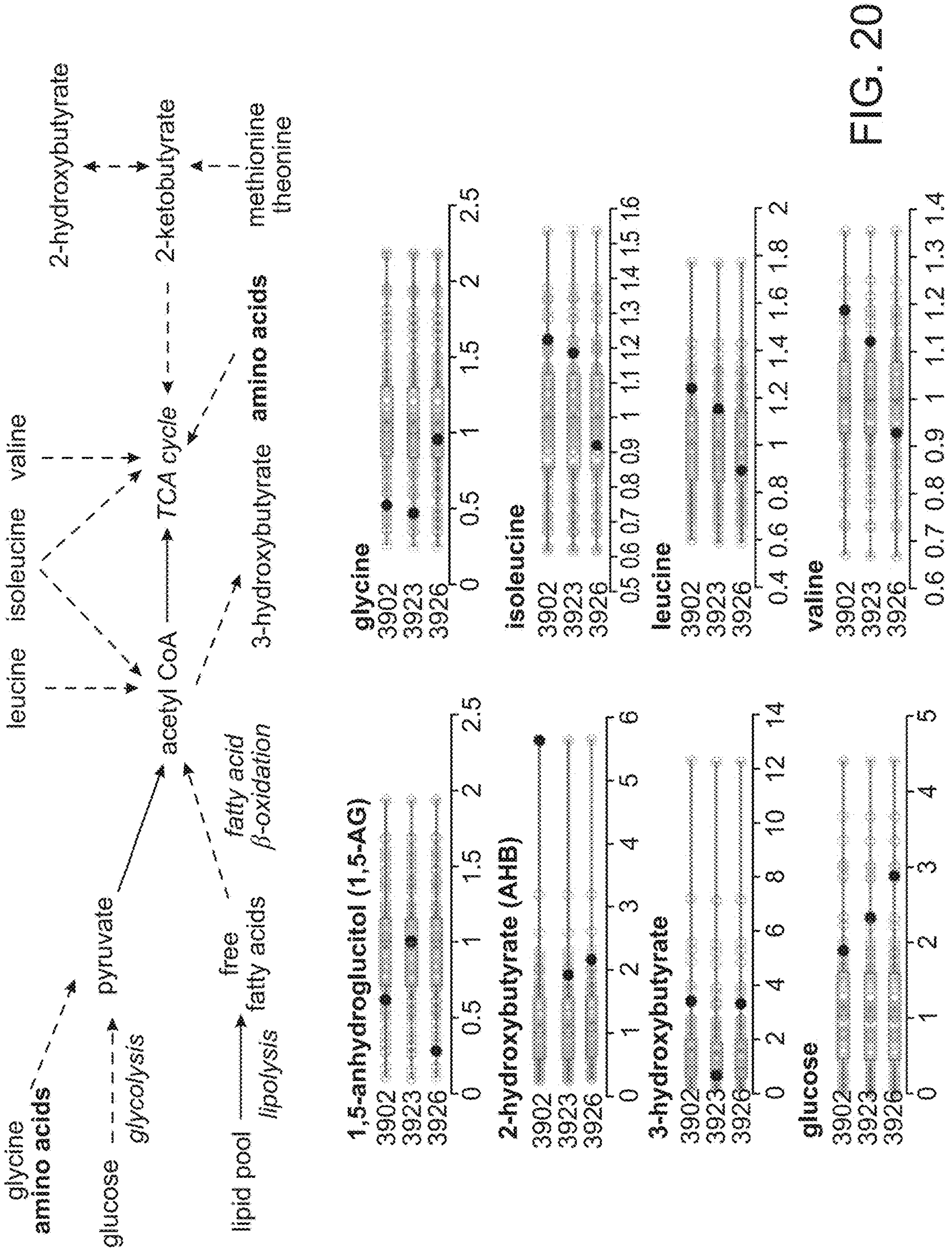
FIG. 20 shows an example visual display of condensed metabolic schemes for energy metabolism and dot plots showing data distribution in the cohort for the key metabolites with known association with type II diabetes. The black dots show the metabolite level for the specific subjects as labeled next to the plots. The open dots show the data distribution for the rest of the cohort. The box represents the middle 50% of the distribution, and left and right "whiskers" represent the entire spread of the data. The vertical line refers to the median and the plus sign refers to the mean.

One of the early hallmarks of metabolic diseases is mitochondrial dysfunction. A number of biochemical pathways originating from key mitochondrial functions, such as energy homeostasis and redox balance, can be readily observed in the metabolomics data. Additionally, metabolites with known associations to insulin resistance and type II diabetes, including α-hydroxybutyrate (α-HB) (Ferrannini, E. et al. Early metabolic markers of the development of dysglycemia and type 2 diabetes and their physiological significance. *Diabetes* 62, 1730-1737 (2013)), 1,5-anhydroglucitol (1,5-AG) (Yamanouchi, T. et al. Clinical usefulness of serum 1,5-anhydroglucitol in monitoring glycemic control. *Lancet* 347, 1514-1518 (1996)), branched chain amino acids (BCAAs) (Newgard, C. B. et al. A branched-chain amino acid-related metabolic signature that differentiates obese and lean humans and contributes to insulin resistance. *Cell Metab* 9, 311-326 (2009)), and glycine (Perseghin, G., Ghosh, S., Gerow, K. & Shulman, G. I. Metabolic defects in lean nondiabetic offspring of NIDDM parents: a cross-sectional study. *Diabetes* 46, 1001-1009 (1997)), may provide insights on the disease condition. Subject 3902 exhibited elevated α-HB, decreased 1,5-AG, decreased glycine, and slightly elevated BCAAs (FIG. 20). In addition, increased glucose and 3-hydroxybutyrate (a product of fatty acid β-oxidation and BCAA catabolism) suggested altered energy metabolism consistent with disrupted glycolysis and increased lipolysis (FIG. 20). Collectively these biochemical signatures suggested early indications of diabetes. Subjects 3926 and 3923 displayed similar signatures albeit more subtle (FIG. 20).

C. Liver Dysfunction

Figure 21:
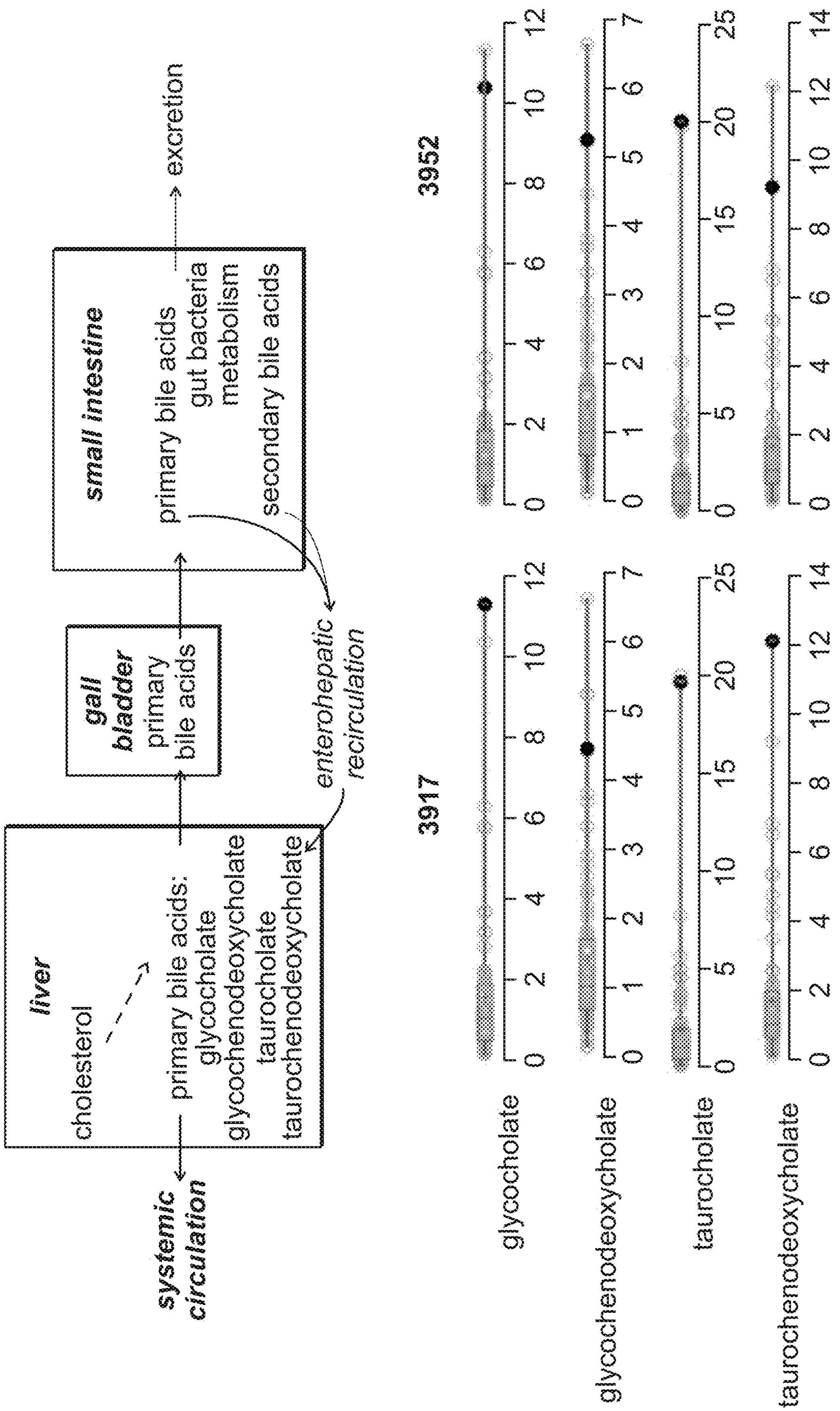
FIG. 21 shows an illustration of a visual display of bile acid circulation and dot plots showing data distribution in the cohort for the four primary bile acids. The black dots show the metabolite level for either 3917 or 3952. The open dots show the data distribution for the rest of the cohort. The box represents the middle 50% of the distribution, and left and right "whiskers" represent the entire spread of the data. The vertical line refers to the median and the plus sign refers to the mean.

The primary bile acids (glycocholate, glycochenodeoxycholate, taurocholate, and taurochenodeoxycholate) are synthesized in the liver, stored in gall bladder, and subsequently released into the gut for digestion (FIG. 21). In the ileum, the bile acids are actively transported by enterohepatic circulation to be reabsorbed by the liver. In healthy conditions, the liver is very efficient in removing bile acids from the circulation, but liver diseases have been known to elevate total bile acid levels in the general circulation (Barnes, S., Gallo, G. A., Trash, D. B. & Morris, J. S. Diagnostic value of serum bile acid estimations in liver disease. J Clin Pathol 28, 506-509 (1975)). In subjects 3917 and 3952, the primary bile acids were substantially elevated (FIG. 21), suggesting that these two subjects may have impaired liver function.

D. Metabolic Disease

Figure 23:
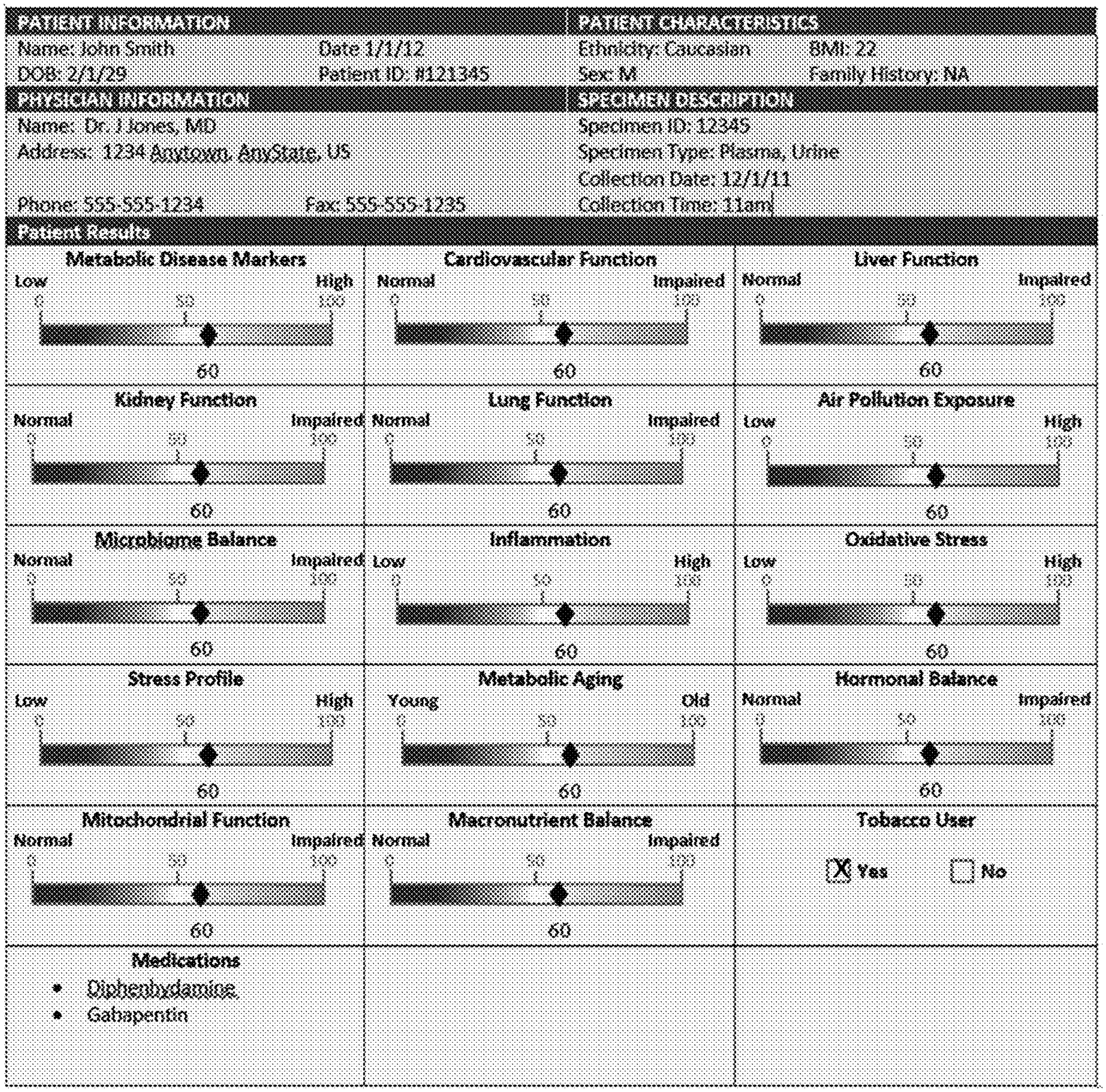
FIG. 23 is an example report showing the results of analysis of an individual and reporting the clinical status of the individual, including disease risk scores, in accordance with an embodiment.

Metabolites reflective of energy utilization, storage and mitochondrial function were measured in biological samples (plasma, urine) from a subject. The metabolites measured were 1,5-anhdroglucitol (1,5AG), 1-linoleoyleglycerophosphocholine (18:2n6, LGCP), 2-hydroxybutyrate (AHB), 3-hydroxybutyrate (BHBA), 3-hydroxyisobutyrate, 3-methyl-2-oxobutyrate, 3-methyl-2-oxobalerate, 4-methyl-2-oxopentanoate, alanine, fructose, glucose, glutamate, glycine, isollelucine, leucine, mannose, oleate (18:1n9), palmlitoylcarnitine, phenylalanine, serine, tyrosine, and valine. The analytical measurements are used to generate a metabolic disease risk score (scale 0-100). Results of such analysis are summarized in a report. An example report is illustrated in FIG. 23.

E. Cardiovascular Function

Metabolites indicative of cardiovascular health were measured in biological samples (plasma, urine) from a subject. The metabolites measured were adenosine, azelate, cholesterol, creatinine, dodecanedioate, hexadecanedioate, histidine, octadecanedioate, phenylalanine, sebacate, tetradecanedioate, and urate. The analytical measurements are used to generate a cardiovascular disease risk score (scale 0-100). Results of such analysis are summarized in a report. An example report is illustrated in FIG. 23.

F. Kidney Function

Metabolites indicative of the kidney filtration status were measured in biological samples (plasma, urine) from a subject. The metabolites measured were 3-indoxyl sulfate, 3-methylhitidine, 4-acetamidobutanoate, arabitol, C-glycosyltryptophan, creatinine, erthritol, indolelacetate, kynurenine, lathosterol, myo-inositol, N2,N2-dimethylguanosine, N-acetylalanine, N-acetylserine, N-acetylthreonine, N-formylmethionine, phylacethylglutamine, pseudouridine, succinylcarnitine, trans-4-hydroxyproline, tryptophan, and urea. The analytical measurements are used to generate a Kidney Function Score (scale 0-100). Results of such analysis are summarized in a report. An example report is illustrated in FIG. 23.

G. Lung Function

Metabolites indicative of lung function were measured in biological samples (plasma, urine) from a subject. The metabolites measured were 3-carboxy-4-methyl-5-propyl-2-furanopropanoate, 3-phylpropionate (hydrocinnamate), alpha-tocopherol, asparagine, benzoate, bilirubin (Z,Z), butyrylcarnitine, gamma-glutamylvaline, glycerate, glycine, indoepropionate, N-acetylglycine, proline, pseudouridine, pyridoxate, serine, succinylcarnitine, and threonate. The analytical measurements are used to generate a lung function score (scale 0-100). Results of such analysis are summarized in a report. An example report is illustrated in FIG. 23.

H. Inflammation

Metabolites indicative of inflammation were measured in biological samples (plasma, urine) from a subject. The metabolites measured were 13-HODE+9-HODE, arachidonate (20:4n6), cortisol, docosahexaenoate (DHA, 22:6n3), eicosapentaenoate (EPA, 20:5n3), kynurenate, kynurenine, and quinolinate. The analytical measurements are used to generate an inflammation score (scale 0-100). Results of such analysis are summarized in a report. An example report is illustrated in FIG. 23.

I. Hormonal Balance

Metabolites indicative of hormonal balance were measured in biological samples (plasma, urine) from a subject. The metabolites measured were pregnenolone sulfate, 21-hydroxypregnenolone monosulfate, 21-hydroxypregnenolone disulfate, 5-pregnen-3b, 17-diol-20-one 3-sulfate, 5alpha-pregnan-3beta, 20alpha-diol monosulfate, 5alpha-pregnan-3beta,20alpha-diol disulfate, pregnanediol-3-glucuronide, cortisol, corticosterone, 11-dehydrocorticosterone, cortisone, dehydroisoandrosterone sulfate (DHEA-S), 16a-hydroxy DHEA 3-sulfate, epiandrosterone sulfate, androsterone sulfate, 5alpha-androstan-3alpha,17alpha-diol monosulfate, 5alpha-androstan-3alpha,17alpha-diol disulfate, etiocholanolone glucuronide, 11-ketoetiocholanolone glucuronide, 4-androsten-3beta,17beta-diol monosulfate, 4-androsten-3beta,17beta-diol disulfate, testosterone sulfate, 5alpha-androstan-3alpha,17beta-diol mono sulfate, 5alpha-androstan-3alpha,17beta-diol disulfate, 5alpha-androstan-3beta,17beta-diol monosulfate, 5alpha-androstan-3beta, 17beta-diol disulfate, estrone 3-sulfate, and thyroxin. The analytical measurements are used to generate a hormonal balance score (scale 0-100). Results of such analysis are summarized in a report. An example report is illustrated in FIG. 23.

J. Oxidative Stress

Metabolites indicative of oxidative stress were measured in biological samples (plasma, urine) from a subject. These metabolites give indications of the oxidative stress status and capacity to combat reactive oxygen status. Low levels of antioxidants and high levels of terminal electron acceptors are associated with increased oxidative stress. The metabolites measured were 13-HODE+9-HODE, 5-oxoproline, alantoin, alpha-tocopherol, anserine, bilirubin (Z,Z), biliverdin, cys-gly,oxidized, cysteine-glutathione disulfide, cysteine, gamma-tocopherol, hypoxanthine, methionine sulfone, methionine sulfoxide, threonate, and urate. The analytical measurements are used to generate an oxidative stress score (scale 0-100). Results of such analysis are summarized in a report. An example report is illustrated in FIG. 23.

K. Mitochondrial Function

Metabolites indicative of mitochondrial function were measured in biological samples (plasma, urine) from a subject. The metabolites measured were homocitrulline, leucine, 4-methyl-2-oxopentanoate, isovalerate, isovalerylglycine, isovalerylcarnitine, beta-hydroxyisovalerate, beta-hydroxyisovaleroylcarnitine, alpha-hydroxyisovaleroyl carnitine, 3-methylglutaconate, alpha-hydroxyisovalerate, methylsuccinate, isoleucine, 3-methyl-2-oxovalerate, 2-methylbutyrylcarnitine (C5), tiglyl Carnitine, tigloylglycine, 2-hydroxy-3-methylvalerate, 3-hydroxy-2-ethylpropionate, ethylmalonate, valine, 3-methyl-2-oxobutyrate, isobutyrylcarnitine, isobutyrylglycine, 3-hydroxyisobutyrate, alpha-hydroxyisocaproate, azelate (nonanedioate), sebacate (decanedioate), dodecanedioate, tetradecanedioate, hexadecanedioate, octadecanedioate, formylmethioine, alanine, lactate, citrate, alpha-ketoglutarate, succinylcarnitine, succinate, fumarate, malate, palmitoylcarnitine, stearoylcarnitine, oleoylcarnitine, and BHBA. The analytical measurements are used to generate a mitochondrial function score (scale 0-100). Results of such analysis are summarized in a report. An example report is illustrated in FIG. 23.

L. Stress Profile

Metabolites indicative of stress response were measured in biological samples (plasma, urine) from a subject. The metabolites measured were cortisol, cortisone, glucose and thyroxine. The analytical measurements are used to generate a stress score (scale 0-100). Results of such analysis are summarized in a report. An example report is illustrated in FIG. 23.

M. Metabolic Aging

Metabolites indicative of metabolic aging were measured in biological samples (plasma, urine) from a subject. The metabolites measured were 3-carboxy-4-methyl-5-propyl-2-furanoproanoate, C-glycosyltryptophan, citrate, citrulline, creatinine, dehydroisoandrosterone sulfate (DHEA-S), eicosapenaenoate (EPA, 20:5n3), erythritol, glucose, glutamate, glycine, leucine, myo-inositol, palmitoleoyl sphingomyelin, p-cresol sulfate, phenylacetylgutamine, and psuedouridine. The analytical measurements are used to generate a metabolic age score (scale 0-100), where the value indicates the metabolic age of the subject and in relation to chronological age gives an indication of the overall metabolic health. Results of such analysis are summarized in a report. An example report is illustrated in FIG. 23.

N. Microbiome Balance

Metabolites indicative of microbiome activity that can be used to determine microbiome balance were measured in biological samples (plasma, urine) from a subject. The metabolites measured were 3-(3-hydroxyphenyl)propionate, 3-(4-hydroxyphenyl) lactate, 3-(4-hydroxyphenyl)propionate, 3-(3-(sulfooxy)phenyl)propanoic acid, 3-hydroxyhippurate, 3-indoxyl sulfate, 3-phenylpropionate (hydrocinnamate), 4-ethylphenylsulfate, 4-hydroxyhippurate, 4-hydroxyphenylpyruvate, 4-vinylphenol sulfate, 5-hydroxyindoleacetate, chenodeoxycholate, cholate, deoxycholate, glycocholenate sulfate, glcodeoxycholate, glycohocholate, glycolitocholate, glycolithocholate sulfate, glycoursodeoxycholate, hippurate, hyodeoxycholate, indoleacetate, indoleacetylglutamine, indolebutyrate, indolelacte, indoleproionate, p-creosol sulfate, o-creosol sulfate, p-cresol-glucuronide, phenol sulfate, phenylacetate, phenylacetylgutamine, phenyllactate (PLA), taurocholenate sulfate, taurodeoxycholate, taurolithocholate 3-sulfate, tauroursodeoxycholate, and ursodeoxycholate. The analytical measurements are used to generate a microbiome profile score (scale 0-100). Results of such analysis are summarized in a report. An example report is illustrated in FIG. 23.

O. Macronutrient Balance

Metabolites indicative of macronutrient balance were measured in biological samples (plasma, urine) from a subject. The metabolites measured were histidine, isoleucine, leucine, valine, lysine, methionine, phenylalamine, tryptophan, threonine, alanine, arginine, aspartate, cysteine, glutamate, glutamine, glycine, proline, serine, tyrosine, asparagine, choline, linolenate [alpha or gamma; (18:3n3 or 6)], and linoleate (18:2n6). The analytical measurements are used to generate a macronutrient balance score (scale 0-100). Results of such analysis are summarized in a report. An example report is illustrated in FIG. 23.

P. Air Pollution Exposure

Metabolites indicative of exposure to air pollution were measured in biological samples (plasma, urine) from a subject. The metabolites measured were alpha-tocopherol, asparagine, benzoate, glycerate, glycine, N-acetylglycine, serine, and threonate. The analytical measurements are used to generate an air pollution score (scale 0-100). Results of such analysis are summarized in a report. An example report is illustrated in FIG. 23.

Q. Medications/Xenobiotics

Medications are detected using the methods described herein and the levels measured in biological samples (plasma, urine) from a subject are reported. Other xenobiotics are also detected using the methods described herein and the levels measured, if any, in biological samples from a subject are also reported.

Example 7: Disease or Disorder-Specific Predictive Composite Scores Based on One or More Aberrant Small Molecules The measured value for one or more aberrant small molecules detected in each sample may be used in one or more mathematical (statistical) models to generate a disease or disorder-specific predictive composite score. The score is useful for facilitating the automated determination of the disease status of the individual subject from whom the sample was collected. In one example, a composite score was generated based on the z-score obtained for aberrant small molecules using a regression algorithm as follows: To obtain the composite score, do coef1*(z-score for metabolite 1)+coef2*(z-score for metabolite 2)+ . . . +coefp*(z-score for metabolite p) for the p-metabolites in the panel, where coef1 means "coefficient one", coef2 means "coefficient two" and so on for each small molecule included in the composite score. The data from the 200 patients was used to determine the coefficients for generating disease or disorder-specific composite scores for multiple different diseases or disorders. Disease or disorder-predictive composite scoring methods based on the z-score obtained for relevant aberrant small molecules using the regression algorithm above have been developed for more than 30 diseases so far. After the coefficients are determined based on data from a group of patients, the coefficients can be used for generation of disease or disorder-specific composite scores for additional individual patients and for additional groups of patients. These composite scoring methods are presented in Table 4. For some diseases or disorders two methods of scording were derived. In these diseases or disorders "rare" metabolites are among the aberrant small molecules included in the scoring method and these "rare" small molecules may not be detected in an anchor sample set. In such diseases or disorders, a second scoring method was developed that does not include the "rare" small molecule and allows the sample set to be compared, through the use of anchor samples, to prior samples. The results of composite scoring methods for two different disorders are exemplified below for non-limiting illustration.

TABLE 4

Composite scoring methods for aiding in the diagnosis of disease

| Disease | Disease or Disorder-Specific Composite Scoring Method |
|---|---|
| 3-methylcrotonyl CoA carboxylase deficiency | Disease Score = A (beta-hydroxyisovalerate) + B (beta-hydroxyisovaleroylcarnitine)<br>OR<br>Disease Score = A (3-methylcrotonylglycine) + B (beta-hydroxyisovalerate) + C (beta-hydroxyisovaleroylcarnitine) |
| argininosuccinic acid lyase deficiency | Disease Score = −A (aspartate) + B (citrulline) + C (uracil) − D (urea)<br>OR<br>Disease Score = A (argininosuccinate) − B (aspartate) + C (citrulline) + D (uracil) − E (urea) |
| Argininemia | Disease Score = A (4-guanidinobutanoate) + B (arginine) − C (aspartate) + D (homocitrulline) + E (N-acetylarginine) − F (ornithine) + G (orotate) − H (urea) + I (uridine) |
| Cbl (cobalamin deficiency) | Disease Score = A (2-methylmalonyl carnitine) + B (methylmalonate (MMA)) + C (propionylcarnitine) |
| Citrullinemia | Disease Score = A (3-ureidopropionate) + B (citrulline) + C (homocitrulline) + D (N-acetyl-citrulline (X-12386))<br>OR<br>Disease Score = A (3-ureidopropionate) + B (citrulline) + C (homocitrulline) + D (phenylacetate) + E (phenylacetylglutamine)+ F (N-acetyl-citrulline (X-12386)) |
| Carnitine palmitoyltransferase 2 deficiency | Disease Score = A (caprate (10:0)) + B (caprylate (8:0)) + C (decanoylcarnitine) + D (hexanoylcarnitine) + E (N-octanoylglycine) + F (octanoylcarnitine) + G (sebacate (decanedioate)) |
| Glutaric aciduria type 1 | Disease Score = A (glutarate (pentanedioate)) + B (glutarylcarnitine (C5)) |
| guanidinoacetate methyl transferase deficiency/GAMT deficiency | Disease Score = A (creatine) + B (guanidinoacetate) |
| HMG CoA Lyase Deficiency | Disease Score = A (3-hydroxy-3-methylglutarate) + B(beta-hydroxyisovalerate) + C (glutarate (pentanedioate)) + D (glutarylcarnitine (C5)) + E (tetradecanedioate) |
| Holocarboxylase/ Holocarboxylase synthetase deficiency | Disease Score = A (3-hydroxypropanoate) + B (beta-hydroxyisovalerate) + C (propionylcarnitine) + D (propionylglycine) − E (succinylcarnitine) |
| Homocystinuria/Cystathionine beta-synthase deficiency | Disease Score = A (5-methylthioadenosine (MTA)) + B(gamma-glutamylmethionine) + C (methionine) + D(N1-methyladenosine) + E (S-adenosylhomocysteine (SAH)) |
| Isovaleric acidemia | Disease Score = A (isovalerate) + B (isovalerylcarnitine) + C (isovalerylglycine) − D (beta-hydroxyisovalerate) |
| Lysinuric protein intolerance | Disease Score = −A (arginine) + B (asparagine) + C (glutamine) − D (lysine) + E (N6-acetyllysine) − F (ornithine) |
| medium chain acyl CoA dehydrogenase deficiency/ MCAD deficiency | Disease Score = A (5-hydroxyhexanoate) + B (caproate (6:0)) + C (caprylate (8:0)) + D (hexanoylcarnitine) + E (hexanoylglycine) + F (N-octanoylglycine) + G (octanoylcarnitine) + H (suberate (octanedioate)) |
| methylmalonic acidemia | Disease Score = A (2-methylmalonyl carnitine) + B (3-hydroxypropanoate) + C (methylmalonate (MMA)) + D (propionylcarnitine) + E (propionylglycine) + F (tiglyl carnitine) |
| molybdenum cofactor or sulfite oxidase deficiency | Disease Score = A (12-HETE) + B (13-HODE + 9-HODE) + C (leukotriene B4) |
| Maple syrup urine disease | Disease Score = A (4-methyl-2-oxopentanoate) + B (allo-isoleucine) + C (alpha-hydroxyisovalerate) − D (3-hydroxyisobutyrate) − E (isovalerylcarnitine) |
| ornithine transcarbamylase deficiency | Disease Score = A (phenylacetate) + B (phenylacetylglutamine) − C (urea) |
| propionic acidemia | Disease Score = A (3-hydroxypropanoate) + B (propionylcarnitine) + C (propionylglycine) − D (succinylcarnitine) |
| PKU | Disease Score = A (gamma-glutamylphenylalanine) + B (N-acetylphenylalanine) + C (phenylacetate) + D (phenylalanine) + E (phenylpyruvate) |
| Thymidine phosphorylase deficiency | Disease Score = A (2'-deoxyuridine) + B (thymine)<br>OR<br>Disease Score = A (2'-deoxyuridine) + B (thymine) + C (thymidine) |

TABLE 4-continued

Composite scoring methods for aiding in the diagnosis of disease

| Disease | Disease or Disorder-Specific Composite Scoring Method |
|---|---|
| trimethylysine hydroxylase epsilon deficiency | Disease Score = A (N6-trimethyllysine) |
| very long chain acyl CoA dehydrogenase deficiency | Disease Score = A (1-docosahexaenoyl-GPC (22:6)) + B (docosahexaenoate (DHA; 22:6n3)) + C (eicosapentaenoate (EPA; 20:5n3)) + D (linoleoylcarnitine) + E (myristoleoylcarnitine) + F (myristoylcarnitine) + G (oleoylcarnitine) + H (palmitoylcarnitine) + (stearoylcarnitine) |
| Sarcosinemia | Disease Score = A (betaine) + B (choline) + C (dimethylglycine) + D (sarcosine (N-Methylglycine)) |
| Citrate transporter deficiency | Disease Score = −A (alpha-ketoglutarate) + B (citrate) − C (fumarate) − D (malate) − E (succinate) |
| Hyperornithinemia-Homocitrullinemia-Hyperammonemia (HHH) | Disease Score = A (3-ureidopropionate) + B (homocitrulline) + C (ornithine) + D (uracil) |
| Aromatic amino acid decarboxylase deficiency | Disease Score = A (3-methoxytyrosine) + B (phenylalanine) + C (tryptophan) + D (tyrosine) |
| 4-aminobutyrate aminotransferase (ABAT) Deficiency | Disease Score = A (2-pyrrolidinone) |
| 3-methylglutaconic aciduria (MGA) | Disease Score = A (3-methylglutarylcarnitine) |
| Short chain acyl-CoA decarboxylase (SCAD) deficiency | Disease Score = A (butyrylcarnitine) + B (ethylmalonate) |
| Urocanase deficiency | Disease Score = A (imidazole propionate) + B (trans-urocanate) OR Disease Score = A (cis-urocanate) + B (imidazole propionate) + C (trans-urocanate) |
| γ-Butyrobetaine Hydroxylase Deficiency (BBOX Deficiency) | Disease Score = A (deoxycarnitine) |

Figure 24:
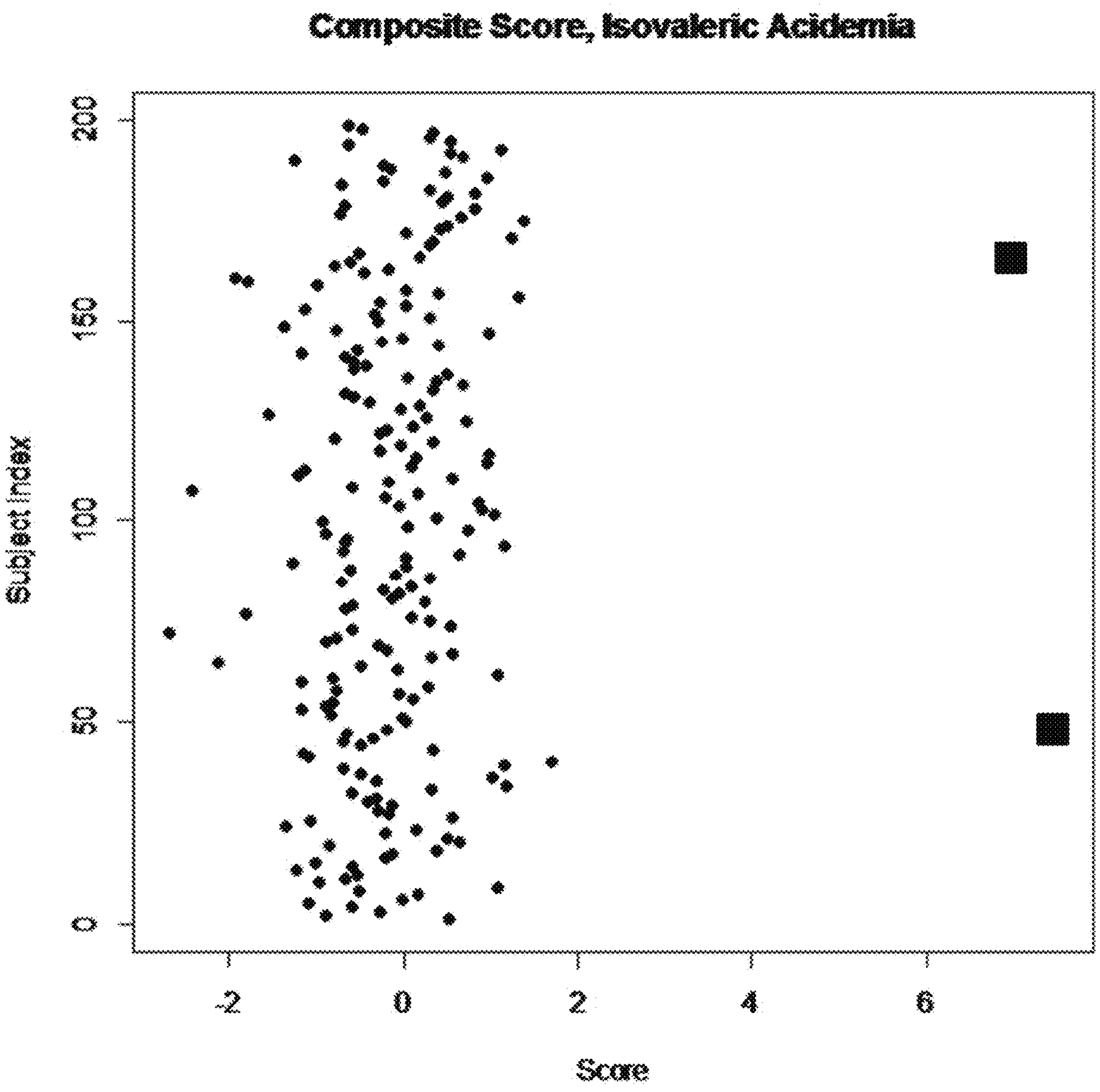
FIG. 24 shows an illustration of a visual display for the scores of an exemplary disease or disorder-specific composite scoring method to aid in the diagnosis of isovlaeric academia in a subject. The composite scores for 200 patient samples are shown. Composite scores for the two subjects with isovaleric academia are shown by black squares.

In one example, the biochemicals 3-hydroxyisovalerate, isovalerlcarnitine, isovalerylglycine, and isovalerate were used to generate composite scores to aid in the diagnosis of isovaleric academia in a subject. The composite scores obtained for two of the 200 subjects in the cohort based on the following scoring method: 0.22*(z-score for isovalerate)+0.26*(z-score for isovalerylcarnitine)+0.36*(z-score for isovalerylglycine)−0.15*(z-score for beta-hydroxyisovalerate) predicted isovaleric acidemia. The composite scores calculated for the two individuals compared to the subjects that do not have isovaleric acidemia are presented in the graphic illustration of the prediction in FIG. 24. The two patients with isovaleric academia (shown by black squares) can be distinguished from the rest of the cohort using the described predictive scoring method.

Figure 25:
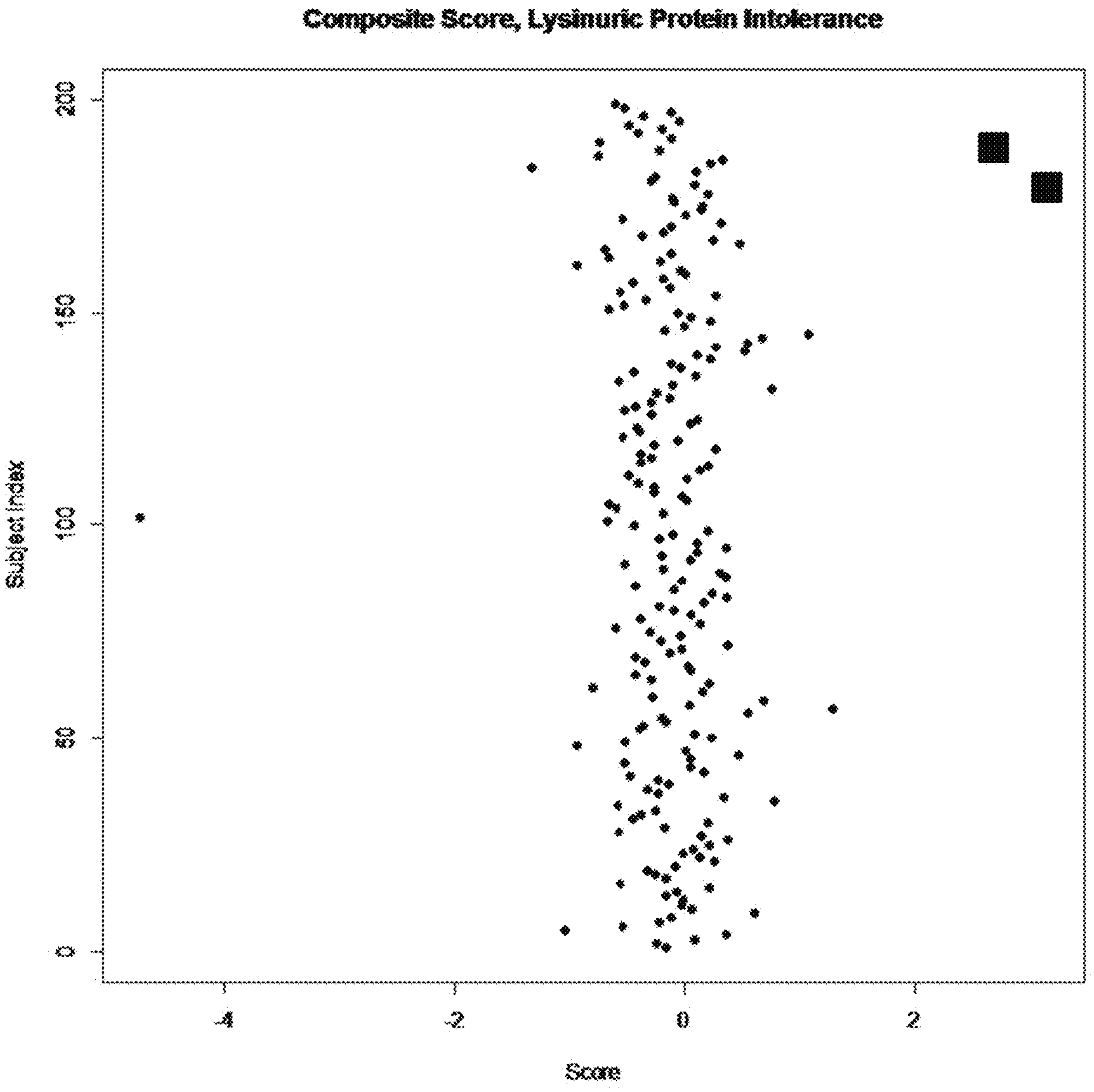
FIG. 25 shows an illustration of a visual display for the scores of an exemplary disease or disorder-specific composite scoring method to aid in the diagnosis of lysinuric protein intolerance in a subject. The composite scores for 200 patient samples are shown. Composite scores for the two subjects with lysinuric protein intolerance are shown by black squares.

In another example, the biochemicals N6-acetyllysine, glutamine, asparagine, lysine, arginine, and ornithine were used to generate composite scores to aid in the diagnosis of Lysinuric protein intolerance in a subject. The composite scores obtained for two of the 200 subjects in the cohort based on the following scoring method: 0.2*(z-score for N6-acetyllysine)+0.2*(z-score for glutamine)+0.2*(z-score for asparagine)−0.2*(z-score for lysine)−0.1*(z-score for arginine)−0.1*(z-score for ornithine) predicted lysinuric protein intolerance. The composite scores calculated for the two individuals compared to the subjects that do not have Lysinuric protein intolerance are presented in the graphic illustration of the prediction in FIG. 25. The two patients with lysinuric protein intolerance (shown by black squares) can be distinguished from the rest of the cohort using the described predictive scoring method.

Example 8: Analytical Characterization of Unnamed Small Molecules

Samples were collected from a cohort of patients as described in Example 2. Metabolites were extracted and proteins were precipitated from the samples (100 μl) by the addition of 450 μL of methanol. Two separate UPLC methods were utilized, one in acidic conditions and the other in basic conditions. The precipitated extract was split into four aliquots and dried under nitrogen and then in vacuo. One aliquot was reconstituted in 50 μl of 0.1% formic acid in water (for use in the acidic method), and another aliquot was reconstituted in 50 μl of 6.5 mM ammonium bicarbonate in water, pH 8 (for use in the basic method).

Both methods used chromatography which was performed on 2.1 mm×100 mm Acquity 1.7 um C18 BEH columns (Waters Corp., Milford, MA, USA) using an Acquity UPLC system. The mobile phase, at a flow rate of 350 μL/min, used solvent A, 0.1% formic acid in water, and solvent B, 0.1% formic acid in methanol (gradient profile: 0% B to 70% B in 4 min, 70 to 98% B in 0.5 min, 98% B for 0.9 min), for the acidic method. Sample aliquots processed for the basic method were gradient-eluted at a flow rate of 350 μL/min using solvent A, 6.5 mM ammonium bicarbonate in water, pH 8, and solvent B, 6.5 mM ammonium bicarbonate in 95/5 methanol/water (gradient profile: 0% B to 70% B in 4 min, 70 to 98% B in 0.5 min, 98% B for 0.9 min).

The sample eluents were analyzed using an OrbiElite mass spectrometer (MS) (ThermoFisher Corporation) using heated electrospray ionization (HESI). The acidic method monitored for positive ions and the basic method monitored for negative ions in independent injections using separate acid/base dedicated columns heated to 40° C. The MS interface capillary was maintained at 350° C., the source heater at 430° C., with a sheath gas flow of 80 and 75 (arbitrary units) for the positive and negative ion injections, respectively, and an aux gas flow of 15 and 12 (arbitrary units) for both negative and positive injections, respectively. The spray voltage for the positive ion injection was 4.0 kV and 3.0 kV for the negative ion injection. The instrument scanned 80-1000 m/z and alternated between a high resolution accurate mass MS scan (resolution 30,000) and unit mass resolution MS/MS scans. The scan speed was approximately 6 scans/sec (3 MS and 3 MS/MS scans). MS/MS normalized collision energy was set to 28 and 32 for positive and negative ion injections, respectively, and activation Q 0.25, and activation time 30 ms, with a 3 m/z isolation window for both injections. MS/MS scans were collected using dynamic exclusion with an exclusion time of 3.5 sec. Isotoptically labeled compounds were spiked into every sample and were used to assess instrument performance and suitability, including retention time, mass and sensitivity stability over the course of the run (usually 20 hours). In addition, a quality control sample, which consisted of a pooled aliquot from all samples, was analyzed every 8 injections to ensure technical reproducibility.

Software using standard industry approaches for MS peak detection was used for the detection and integration of MS peaks. Briefly, extracted ion chromatograms were binned by mass in a given range, baseline noise was determined, peak areas were calculated, and various user-defined peak thresholds including minimum height, signal-to-noise, width, symmetry, and area were applied to detected MS peaks. MS peaks passing above threshold criteria were assembled into lists that were then inserted into a relational database for storage and further analysis. Finally, individual MS peaks were grouped based on peak apex retention time for ease of viewing similarly retained ion features. All samples were aligned based on retention time (RT) markers present throughout the chromatogram using a retention index (RI). The retention index of a sample component is a number, obtained by interpolation (usually logarithmic), relating the adjusted retention volume (time) or the retention factor of the sample component to the adjusted retention volumes (times) of two standards eluted before and after the peak of the sample component.

The resulting data were searched against a chemical library generated specifically for each method (e.g. UPLC positive ion data was searched against a library specific for UPLC positive ion mode). Biochemical identifications were based on three criteria: retention index within 75 RI units of the proposed identification (or approximately 5 s), experimental precursor mass match to the library within 0.4 m/z, and the MS/MS forward and reverse scores. The MS/MS scores were based on a comparison of the ions present in the experimental spectrum to the ions present in the library spectrum. Biochemical identification was performed by a software program, and the computer generated identification was verified by a human analyst.

Computer software checked all ions that were not assigned to any library entry across a set of injections and within a specified chromatographic time window. By correlating ions across multiple injections, the natural biological variability of biochemicals was used to identify possible new authentic biochemicals that were not already included as an entry as part of the library. Any biochemicals that did not have a library match but were determined to be bona fide biochemicals based on the recurrent nature of the spectral pattern for that biochemical were added to the library so that the biochemical, although unnamed, could be tracked in current and future studies. Thus, although the biochemical was not identified (because an authentic chemical standard was not available in the library), the properties or behavior of the biochemical that were obtained from the analysis method were indicated, without indicating the specific chemical composition or structure of the biochemical (referred to as unnamed biochemicals).

Table 5 below includes analytical characteristics of each of the unnamed metabolites listed in Table 2 above. Table 5 includes, for each listed biomarker metabolite, the Identifier used to refer to the metabolite (Identifier), the number used to identify the metabolite in the chemical library of authentic standards database (Comp ID), the retention time (RT), retention index (RI), quant mass (Mass), and polarity obtained using the analytical methods described above. "Mass" refers to the mass of the C12 isotope of the parent ion used in quantification of the compound. The analytical method used for quantification is indicated in column three (Platform); "202" indicates LC-MS/MS' using the method optimized for acidic species and "203" indicates LC-MS/MS' optimized for basic species. "Polarity" indicates the polarity of the quantitative ion as being either positive (+) or negative (−).

TABLE 5

Analytical Characteristics of Unnamed Small Molecules

| Identifier | Comp ID | Platform | RT | RI | Mass | Polarity |
|---|---|---|---|---|---|---|
| X-10593 | 33066 | 202 | 1.24 | 1256 | 172.09692 | +i |
| X-11315 | 32632 | 202 | 1.19 | 1210 | 130.08647 | +i |
| X-11360 | 32677 | 202 | 1.84 | 1880 | 245.14949 | +i |
| X-11440 | 32757 | 203 | 3.58 | 3571 | 246.07449 | −i |
| X-11478 | 32795 | 203 | 4.3 | 4286 | 165.0917 | −i |
| X-11483 | 32800 | 203 | 4.45 | 4443 | 505.20716 | −i |
| X-11521 | 32838 | 202 | 3.71 | 3650 | 286.20172 | +i |
| X-11564 | 32881 | 203 | 1.2 | 1188 | 177.02234 | −i |
| X-11837 | 33248 | 203 | 2.53 | 2484 | 283.08252 | −i |
| X-11861 | 33206 | 203 | 4.63 | 4617 | 229.1446 | −i |
| X-12007 | 33353 | 203 | 1.35 | 1376 | 222.99134 | −i |
| X-12110 | 33525 | 202 | 1.1 | 1147 | 286.13965 | +i |
| X-12114 | 33529 | 202 | 1.47 | 1517 | 365.17397 | +i |
| X-12119 | 33534 | 202 | 1.54 | 1582 | 208.06379 | +i |
| X-12170 | 33590 | 202 | 2.45 | 2534 | 181.06078 | +i |
| X-12193 | 35760 | 203 | 2.32 | 2343 | 201.1133 | −i |
| X-12216 | 33637 | 203 | 1.68 | 1701 | 227.99676 | −i |
| X-12303 | 33725 | 203 | 2.01 | 2034 | 176.98576 | −i |
| X-12339 | 33764 | 202 | 1.02 | 1055 | 174.08732 | +i |
| X-12364 | 33792 | 202 | 1.79 | 1800 | 204.08662 | +i |
| X-12386 | 33787 | 202 | 1.42 | 1451 | 218.11339 | +i |
| X-12425 | 33854 | 203 | 0.73 | 732 | 307.15155 | −i |
| X-12435 | 33877 | 203 | 3.18 | 3174 | 357.10175 | −i |
| X-12442 | 33884 | 203 | 5.28 | 5286 | 223.17091 | −i |
| X-12637 | 34236 | 203 | 3.45 | 3430 | 257.15072 | −i |
| X-12681 | 34290 | 202 | 0.92 | 931 | 176.10296 | +i |
| X-12688 | 34297 | 202 | 1.2 | 1210 | 203.13919 | +i |
| X-12705 | 34315 | 203 | 1.24 | 1245 | 324.07291 | −i |
| X-12731 | 34341 | 203 | 2.09 | 2073 | 238.96905 | −i |
| X-12741 | 34351 | 203 | 2.55 | 2485 | 294.055 | −i |
| X-12748 | 37939 | 203 | 0.55 | 558 | 320.06249 | −i |
| X-12749 | 34359 | 202 | 1.51 | 1562 | 262.12879 | +i |
| X-12802 | 34485 | 202 | 2.72 | 2731 | 318.19151 | +i |
| X-12814 | 34497 | 203 | 2.59 | 2597 | 405.17576 | −i |
| X-12819 | 34502 | 203 | 2.7 | 2702 | 170.08223 | −i |
| X-12822 | 34505 | 203 | 2.78 | 2786 | 389.09131 | −i |
| X-12824 | 40821 | 202 | 3.33 | 3380.1 | 245.14916 | +i |
| X-12846 | 34529 | 203 | 4.17 | 4218 | 481.24353 | −i |
| X-13507 | 35281 | 202 | 1.37 | 1443 | 158.09239 | +i |
| X-13581 | 35359 | 203 | 5.2 | 5150 | 257.176 | −i |
| X-13689 | 35498 | 203 | 3.62 | 3696 | 495.22383 | −i |
| X-13837 | 35732 | 203 | 0.99 | 1002 | 299.12489 | −i |
| X-13862 | 35757 | 203 | 2.24 | 2263 | 250.07221 | −i |
| X-14331 | 36257 | 202 | 2.51 | 2560 | 393.22303 | +i |
| X-15136 | 37277 | 202 | 4.03 | 4063 | 243.0871 | +i |
| X-15245 | 37387 | 203 | 0.59 | 581 | 233.03069 | −i |
| X-15454 | 37702 | 202 | 1.04 | 1079 | 246.10831 | +i |
| X-15486 | 37734 | 203 | 3.65 | 3638 | 269.15012 | −i |
| X-15497 | 37745 | 203 | 2.89 | 2877 | 236.0921 | −i |
| X-15636 | 37885 | 203 | 3.69 | 3814 | 243.03282 | −i |
| X-15646 | 37895 | 203 | 2.85 | 2888 | 343.08602 | −i |
| X-15649 | 37898 | 203 | 3.95 | 4039 | 277.14368 | −i |
| X-15664 | 37913 | 203 | 3.62 | 3695 | 469.17077 | −i |
| X-15667 | 37916 | 202 | 2.25 | 2330 | 202.08654 | +i |
| X-15674 | 37923 | 203 | 1.3 | 1325 | 187.02512 | −i |

TABLE 5-continued

Analytical Characteristics of Unnamed Small Molecules

| Identifier | Comp ID | Platform | RT | RI | Mass | Polarity |
|---|---|---|---|---|---|---|
| X-16134 | 38581 | 202 | 3.05 | 3151.9 | 603.79217 | +i |
| X-16283 | 38852 | 203 | 2.28 | 2338.1 | 192.0668 | −i |
| X-16574 | 39147 | 203 | 4.25 | 4357.6 | 263.00147 | −i |
| X-16577 | 39150 | 203 | 4.56 | 4639.3 | 169.12376 | −i |
| X-16674 | 39250 | 203 | 1.31 | 1361.5 | 217.1082 | −i |
| X-17001 | 39632 | 202 | 1.73 | 1729.5 | 288.1441 | +i |
| X-17303 | 40101 | 202 | 1.9 | 1916.8 | 176.07035 | +i |
| X-17335 | 40133 | 202 | 4.46 | 4521.7 | 248.1674 | +i |
| X-17422 | 40247 | 202 | 3.6 | 3684.5 | 471.19641 | +i |
| X-17438 | 40267 | 203 | 1.95 | 1986.1 | 245.1396 | −i |
| X-17564 | 40395 | 202 | 1.35 | 1441 | 247.1286 | +i |
| X-17654 | 40596 | 203 | 5.23 | 5204.6 | 365.26892 | −i |
| X-17677 | 40774 | 203 | 1.57 | 1552.2 | 204.98109 | −i |
| X-17685 | 40782 | 203 | 2.59 | 2592.6 | 233.01212 | −i |
| X-17690 | 40787 | 203 | 2.87 | 2882.4 | 245.04848 | −i |
| X-17715 | 40815 | 202 | 2.33 | 2364.4 | 330.08139 | +i |
| X-17717 | 40817 | 202 | 2.57 | 2593 | 304.14981 | +i |
| X-17761 | 40863 | 202 | 4.92 | 4910.6 | 274.18301 | +i |
| X-18371 | 41590 | 202 | 1.81 | 1846 | 265.08508 | +i |
| X-18446 | 41672 | 202 | 2.58 | 2683.5 | 280.15366 | +i |
| X-18606 | 41840 | 203 | 3.79 | 3940.3 | 429.177 | −i |
| X-18739 | 42076 | 202 | 5.04 | 5076.6 | 370.2944 | +i |
| X-18888 | 42273 | 203 | 2.44 | 2539.8 | 267.12421 | −i |
| X-18891 | 42276 | 203 | 2.76 | 2867.1 | 399.1491 | −i |
| X-18895 | 42280 | 203 | 3.35 | 3472 | 231.05161 | −i |
| X-18897 | 42282 | 203 | 3.38 | 3499.7 | 221.0842 | −i |
| X-18905 | 42290 | 203 | 3.81 | 3938 | 427.18021 | −i |
| X-18907 | 42292 | 203 | 3.94 | 4066.7 | 222.092 | −i |
| X-18909 | 42294 | 203 | 4.08 | 4210.2 | 221.084 | −i |
| X-18913 | 42298 | 203 | 4.44 | 4550.4 | 185.11856 | −i |
| X-18916 | 42301 | 203 | 4.5 | 4610.9 | 297.1707 | −i |
| X-18918 | 42303 | 203 | 4.54 | 4646.8 | 427.18 | −i |
| X-18920 | 42305 | 203 | 4.76 | 4841.8 | 429.196 | −i |
| X-18922 | 42307 | 203 | 4.83 | 4907.9 | 299.18643 | −i |
| X-18943 | 42330 | 203 | 2.52 | 2624.9 | 279.09836 | −i |
| X-18946 | 42333 | 203 | 2.63 | 2740.4 | 269.13965 | −i |
| X-18965 | 42352 | 203 | 4.62 | 4727 | 442.1905 | −i |
| X-19145 | 42552 | 203 | 3.98 | 4170.5 | 417.21176 | −i |
| X-19330 | 42806 | 202 | 2.62 | 2773 | 202.04739 | +i |
| X-19350 | 42826 | 203 | 1.08 | 1149 | 394.12851 | −i |
| X-19455 | 42931 | 203 | 4.24 | 4385.7 | 261.0228 | −i |
| X-19574 | 43130 | 203 | 3.82 | 4045.7 | 307.0285 | −i |
| X-19602 | 43159 | 203 | 4.16 | 4375.2 | 410.13019 | −i |
| X-19684 | 43269 | 202 | 1.11 | 1227.3 | 177.08676 | +i |
| X-20588 | 45189 | 202 | 2.12 | 2263.9 | 274.11844 | +i |
| X-20598 | 45199 | 202 | 3.04 | 3208.6 | 266.10214 | +i |
| X-20620 | 45221 | 203 | 1.81 | 1874 | 231.12367 | −i |
| X-20676 | 45277 | 202 | 1.98 | 2120.3 | 359.19193 | +i |

What is claimed:

1. A mass spectrometry method of measuring levels of small molecules in a sample from an individual subject to determine small molecules having aberrant levels in the sample from the individual subject, the determination being relevant to screening for a plurality of diseases or disorders in the individual subject or relevant to facilitating diagnosis of one or more of a plurality of diseases or disorders in the individual subject, the method comprising:

A) for each of a plurality of reference samples from a corresponding plurality of reference subjects, determining, by mass spectrometry measurements, relative levels of small molecules in the reference sample from the reference subject for a plurality of small molecules during a first experimental run in which relative levels of small molecules are also measured in one or more anchor samples, the determining relative levels of small molecules in the reference sample from the reference subject for the plurality of small molecules during the first experimental run including obtaining experimental data during the first experimental run from one or more first matrix sample technical replicate(s), each including one or more instrument internal standards;

B) for each of the plurality of small molecules, determining a standard range for a level of the small molecule based on a statistical analysis of the measured relative levels of the small molecule in the reference samples from the plurality of reference subjects relative to a level or levels of the small molecule in the one or more anchor samples;

C) determining, by mass spectrometry measurements, relative levels of small molecules in the sample from the individual subject in a second experimental run that is separate from the first experimental run and in which relative levels of small molecules are also measured in one or more additional anchor samples before or after generation of the experimental data from the sample from the individual subject, wherein the one or more anchor samples and the one or more additional anchor samples comprise a mixture of samples from individuals different from the individual subject and different from any of the reference subjects, the determining relative levels of small molecules in the sample from the individual subject in a second experimental run including obtaining experimental data during the second experimental run from one or more second matrix technical replicate(s), each including one or more instrument internal standards;

D) determining a level of deviation of the measured relative level of the small molecule in the individual subject from the measured relative level or levels of the same small molecule in the one or more additional anchor samples for each of the plurality of small molecules in the sample from the individual subject for which a level was measured in at least one of the additional one or more anchor samples based on the measured relative levels of the small molecules in the sample from the individual subject and the measured relative levels of the small molecules from the additional one or more anchor samples from the separate second experimental run, wherein the one or more anchor samples and the one or more additional anchor samples do not include any internal standard, and wherein the one or more anchor samples and the one or more additional anchor samples are free from any sample from the individual subject and any sample from the reference subjects;

E) comparing the determined level of deviation of the measured relative level of the small molecule in the sample from the individual subject to the standard range for the level of the small molecule as determined from statistical analysis of the measurements of the plurality of reference samples from the corresponding plurality of reference subjects from the first experimental run to determine if any of the plurality of small molecules in the sample from the individual subject have aberrant levels, an aberrant level being determined if the determined level of deviation falls outside the standard range for the level of the small molecule;

F) for a sample from an individual subject having an aberrant level of any of the plurality of small molecules in the sample, identifying a subset of the small molecules, each having an aberrant level; and storing or transmitting information regarding the identified subset of small molecules having aberrant levels in the sample from the individual subject; and G) for a sample from an individual subject not having an aberrant level of any of the plurality of small molecules in the sample, identifying that no aberrant levels were detected; and storing or transmitting information indicating that no aberrant levels were detected in the sample from the individual subject.

2. The method of claim 1, wherein the method further comprises, for the sample from the individual subject having an aberrant level of any of the plurality of small molecules in the sample:

obtaining information from a database based on the aberrant levels of the identified subset of the small molecules; and identifying one or more abnormal biochemical pathways based on the aberrant levels of the identified subset of the small molecules and the obtained information, wherein a biochemical pathway is identified as abnormal if it is associated with any of the small molecules identified as having an aberrant level in the sample from the individual subject.

3. The method of claim 2, wherein the method further comprises generating a graphical representation of information representing the one or more abnormal biochemical pathways for the sample from the individual subject having an aberrant level of any of the plurality of small molecules in the sample.

4. The method of claim 2, wherein the stored or transmitted information regarding the one or more small molecules identified as having aberrant levels includes a graphical representation comprising a graphical association of each of the one or more small molecules having an aberrant level with a corresponding portion of the one or more identified abnormal biochemical pathways that includes, for each of the one or more small molecules identified as having aberrant levels associated with the identified one or more abnormal biochemical pathways, a graphical indication of a deviation of the level of the small molecule relative to the standard level for the small molecule.

5. The method of claim 2, wherein the stored or transmitted information regarding the one or more small molecules identified as having aberrant levels associated with the identified one or more abnormal biochemical pathways includes, for each of the one or more small molecules identified as having aberrant levels associated with the identified one or more abnormal biochemical pathways, a graphical representation comprising a graphical indication of an amount of deviation of the level of the small molecule from the standard level for the small molecule.

6. The method of claim 2, further comprising generating and storing a graphical representation of at least one of the identified one or more abnormal biochemical pathways, the graphical representation including an indication of one or more of the small molecules identified as having aberrant levels associated with the identified one or more abnormal biochemical pathways.

7. The method of claim 1, further comprising obtaining information from a database based on the identified subset of small molecules having aberrant levels, the obtained information including an identification of at least one recommended follow up test associated with the identified subset of the small molecules having aberrant levels.

8. The method of claim 1, wherein one or more of the small molecules in the sample from the individual subject are selected from the group consisting of endogenous, microbial, xenobiotic, and dietary small molecules present in the sample.

9. The method of claim 1, wherein an aberrant level of a small molecule in the sample from the individual subject includes a small molecule measured in one or more of the reference samples and absent from the small molecules of the sample from the individual subject, and/or wherein an aberrant level of the small molecule in the sample from the individual subject includes a small molecule present in the small molecules of the sample from the individual subject and rare in or absent from the plurality of reference samples.

10. The method of claim 1, wherein the standard range for at least some of the small molecules in the plurality of small molecules is determined based on an inter quartile range in the statistical analysis of the measured levels of the small molecule in the reference samples from the plurality of reference subjects from the first experimental run.

11. The method of claim 1, wherein the standard range for at least some of the small molecules in the plurality of small molecules is based on a range of a standard score in the statistical analysis of the measured relative levels of the small molecule in the reference samples from the plurality of reference subjects from the first experimental run.

12. The method of claim 1, wherein the sample from the individual subject comprises blood, blood plasma, serum, or urine.

13. The method of claim 1, wherein the plurality of small molecules each having a standard range includes between 200 and 25,000 small molecules.

14. The method of claim 1, wherein determining relative levels of small molecules in the sample from the individual subject during the second experimental run comprises performing liquid chromatography/mass spectrometry on the sample from the individual subject during the second experimental run.

15. The method of claim 1, wherein determining relative levels of small molecules in the sample from the individual subject during the second experimental run comprises detecting small molecules in the sample from the individual subject and identifying at least some of the detected small molecules by matching experimental detection data to stored information regarding named compounds.

16. The method of claim 1, wherein the method facilitates diagnosis of a disease or disorder in the individual subject; and wherein the method further comprises:

obtaining diagnostic information from a database based on the aberrant levels of the identified subset of the small molecules for the sample from the individual subject, the database including information associating an aberrant level of one or more small molecules of the plurality of small molecules with information regarding a disease or disorder for each of the plurality of diseases and disorders; and storing the obtained diagnostic information, the stored diagnostic information including one or more of: an identification of at least one biochemical pathway associated with the identified subset of the small molecules having aberrant levels, an identification of at least one disease or disorder associated with the identified subset of the small molecules having aberrant levels, and an identification of at least one recommended follow up test associated with the identified subset of the small molecules having aberrant levels;

thereby facilitating diagnosis of a disease or disorder in the individual subject.

17. The method of claim 16, wherein the stored diagnostic information associated with the identified subset of the small molecules having aberrant levels includes an identification of at least one recommended diagnostic test or procedure for confirming a diagnosis of a disease or disorder.

18. The method of claim 1, wherein the method screens the individual subject for the plurality of diseases or disorders; and wherein the method further comprises:

for a sample having an aberrant level of any of the plurality of small molecules in the sample, obtaining diagnostic information from a database based on the aberrant levels of the identified subset of the small molecules, the database including information associating an aberrant level of one or more small molecules of the plurality of small molecules with an information regarding a disease or disorder for each of a plurality of diseases and disorders;

for a sample having an aberrant level of any of the plurality of small molecules in the sample, storing the obtained diagnostic information, the stored diagnostic information including one or more of: an identification of at least one biochemical pathway associated with the identified subset of the small molecules having aberrant levels, an identification of at least one disease or disorder associated with the identified subset of the small molecules having aberrant levels, and an identification of at least one recommended follow up test associated with the identified subset of the small molecules having aberrant levels; and for a sample not having an aberrant level of any of the plurality of small molecules in the sample, storing information indicating that no aberrant levels were detected;

thereby screening the individual subject for the plurality of diseases and disorders.

19. The method of claim 18, wherein the plurality of diseases and disorders includes a rare disease or a rare disorder.

* * * * *